(12) United States Patent
Garcia Cordente et al.

(10) Patent No.: US 8,389,033 B2
(45) Date of Patent: Mar. 5, 2013

(54) MODIFIED INDUSTRIAL YEAST STRAINS

(75) Inventors: Antonio Felipe Garcia Cordente, Adelaide (AU); Jan Hendrik Swiegers, Fredensborg (DK)

(73) Assignees: The Australian Wine Research Institute Ltd, Urrbrae SA (AU); Mauri Yeast Australia Pty Ltd, Sydney (AU)

( * ) Notice: Subject to any disclaimer, the term of this patent is extended or adjusted under 35 U.S.C. 154(b) by 265 days.

(21) Appl. No.: 12/594,099

(22) PCT Filed: Oct. 8, 2008

(86) PCT No.: PCT/AU2008/001485
§ 371 (c)(1),
(2), (4) Date: Jan. 22, 2010

(87) PCT Pub. No.: WO2009/046485
PCT Pub. Date: Apr. 16, 2009

(65) Prior Publication Data
US 2011/0305794 A1    Dec. 15, 2011

(30) Foreign Application Priority Data
Oct. 9, 2007    (AU) .............................. 2007905528

(51) Int. Cl.
C12N 1/00 (2006.01)
C12C 11/00 (2006.01)
A21D 2/00 (2006.01)
A21D 8/02 (2006.01)
A23L 1/10 (2006.01)
C12G 1/022 (2006.01)
C12G 3/02 (2006.01)

(52) U.S. Cl. .......... 426/11; 435/254.21; 426/15; 426/18
(58) Field of Classification Search .................. None
See application file for complete search history.

(56) References Cited

U.S. PATENT DOCUMENTS
2010/0143536 A1* 6/2010 Bisson et al. ................... 426/11

FOREIGN PATENT DOCUMENTS
WO    WO-2008115759 A2    9/2008

OTHER PUBLICATIONS

Eglinton, JM and Henschke PA. *Saccharomyces cerevisiae* strains AWRI 838, Lalvin EC1118, and Maurivin PDM do not produce excessive sulfur dioxide in white wine fermentations. 1996. Australian Journal of Grape and Wine Research, 2, 77-83.*
Hosseini-Mazinani et al. "Cloning and Sequencing of Sulfite Reductase α Subunit from *Saccharomyces cerevisiae*." DNA Res. 2.1(1995):15-19.
Linderholm et al. "Allele Diversity Among Genes of the Sulfate Reduction Pathway in Wine Strains of *Saccharomyces cerevisiae*." Am. J. Enol. Viticul. 57.4(2006):431-440.
Spiropoulos et al. "*MET17* and Hydrogen Sulfide Formation in *Saccharomyces cerevisiae*." Appl. Environ. Microbiol. 66.10(2000):4421-4426.
Sutherland et al. "Subunit and Cofactor Binding of *Saccharomyces cerevisiae* Sulfite Reductase—Towards Developing Wine Yeast With Lowered Ability to Produce Hydrogen Sulfide." Aus. J. Grape Wine Res. 9.3(2003):186-193.
Thomas et al. "Physiological Analysis of Mutants of *Saccharomyces cerevisiae* Impaired in Sulphate Assimilation." J. Gen. Microbiol. 138.10(1992):2021-2028.

* cited by examiner

Primary Examiner — David J Steadman
Assistant Examiner — Paul Holland
(74) Attorney, Agent, or Firm — Occhiuti Rohlicek & Tsao LLP

(57) ABSTRACT

The present invention relates to modified industrial yeast strains that show reduced hydrogen sulfide production. In one embodiment the invention provides an industrial yeast strain comprising a modification in a MET5 gene and/or a MET10 gene which results in reduced hydrogen sulfide production when compared to the corresponding industrial yeast strain without the modification. The present invention also relates to methods of manufacturing these modified industrial yeast strains and their use in the production of fermented products.

14 Claims, 33 Drawing Sheets

```
S288C     ATGACTGCTTCTGACCTCTTGACGCTCCCACAATTGTTGGCGCAATATTCCTCTAGTGCT 60
PDM-2     ATGACTGCTTCTGACCTCTTGACGCTCCCACAATTGTTGGCGCAATATTCCTCTAGTGCT 60
EF058187  ATGACTGCTTCTGACCTCTTGACGCTCCCACAATTGTTGGCGCAATATTCCTCTAGTGCT 60
EF058185  ATGACTGCTTCTGACCTCTTGACGCTCCCACAATTGTTGGCGCAATATTCCTCTAGTGCT 60
EF058186  ATGACTGCTTCTGACCTCTTGACGCTCCCACAATTGTTGGCGCAATATTCCTCTAGTGCT 60
EF058188  ATGACTGCTTCTGACCTCTTGACGCTCCCACAATTGTTGGCGCAATATTCCTCTAGTGCT 60
PDM-1     ATGACTGCTTCTGACCTCTTGACGCTCCCACAATTGTTGGCGCAATATTCCTCTAGTGCT 60
          ************************************************************

S288C     CCCCAAAATAAAGTGTTCTACACTACTAGCACAAAAAATAGTCATTCATCCTTCAAAGGG 120
PDM-2     CCCCAAAATAAAGTGTTCTACACTACTAGCACAAAAAATAGTCATTCATCCTTCAAAGGG 120
EF058187  CCCCAAAATAAAGTGTTCTACACTACTAGCACAAAAAATAGTCATTCATCCTTCAAAGGG 120
EF058185  CCCCAAAATAAAGTGTTCTACACTACTAGCACAAAAAATAGTCATTCATCCTTCAAAGGG 120
EF058186  CCCCAAAATAAAGTGTTCTACACTACTAGCACAAAAAATAGTCATTCATCCTTCAAAGGG 120
EF058188  CCCCAAAATAAAGTGTTCTACACTACTAGCACAAAAAATAGTCATTCATCCTTCAAAGGG 120
PDM-1     CCCCAAAATAAAGTGTTCTACACTACTAGCACAAAAAATAGTCATTCATCCTTCAAAGGG 120
          ************************************************************

S288C     CTAGAATCTGTTGCCACAGATGCTACTCATCTATTGAACAATCAAGATCCATTGAATACC 180
PDM-2     CTAGAATCTGTTGCCACAGATGCTACTCATCTATTGAACAATCAAGATCCATTGAATACC 180
EF058187  CTAGAATCTGTTGCCACAGATGCTACTCATCTATTGAACAATCAAGATCCATTGAATACC 180
EF058185  CTAGAATCTGTTGCCACAGATGCTACTCATCTATTGAACAATCAAGATCCATTGAATACC 180
EF058186  CTAGAATCTGTTGCCACAGATGCTACTCATCTATTGAACAATCAAGATCCATTGAATACC 180
EF058188  CTAGAATCTGTTGCCACAGATGCTACTCATCTATTGAACAATCAAGATCCATTGAATACC 180
PDM-1     CTAGAATCTGTTGCCACAGATGCTACTCATCTATTGAACAATCAAGATCCATTGAATACC 180
          ************************************************************

S288C     ATCAAAGATCAACTCTCTAAGGACATTTTAACTACCGTTTTTACAGATGAAACTACTTTG 240
PDM-2     ATCAAAGATCAACTCTCTAAGGACATTTTAACTACCGTTTTTACAGATGAAACTACTTTG 240
EF058187  ATCAAAGATCAACTCTCTAAGGACATTTTAACTACCGTTTTTACAGATGAAACTACTTTG 240
EF058185  ATCAAAGATCAACTCTCTAAGGACATTTTAACTACCGTTTTTACAGATGAAACTACTTTG 240
EF058186  ATCAAAGATCAACTCTCTAAGGACATTTTAACTACCGTTTTTACAGATGAAACTACTTTG 240
EF058188  ATCAAAGATCAACTCTCTAAGGACATTTTAACTACCGTTTTTACAGATGAAACTACTTTG 240
PDM-1     ATCAAAGATCAACTCTCTAAGGACATTTTAACTACCGTTTTTACAGATGAAACTACTTTG 240
          ************************************************************

S288C     GTCAAATCCATCCACCATCTATATTCTCTTCCTAATAAACTTCCATTGGTGATTACAGTG 300
PDM-2     GTCAAATCCATCCACCATCTATATTCTCTTCCTAATAAACTTCCATTGGTGATTACAGTG 300
EF058187  GTCAAATCCATCCACCATCTATATTCTCTTCCTAATAAACTTCCATTGGTGATTACAGTG 300
EF058185  GTCAAATCCATCCACCATCTATATTCTCTTCCTAATAAACTTCCATTGGTGATTACAGTG 300
EF058186  GTCAAATCCATCCACCATCTATATTCTCTTCCTAATAAACTTCCATTGGTGATTACAGTG 300
EF058188  GTCAAATCCATCCACCATCTATATTCTCTTCCTAATAAACTTCCATTGGTGATTACAGTG 300
PDM-1     GTCAAATCCATCCACCATCTATATTCTCTTCCTAATAAACTTCCATTGGTGATTACAGTG 300
          ************************************************************

S288C     GATTTGAATTTGCAAGATTATTCCGCAATTCCTGCGTTAAAGGATCTTTCTTTCCCCATC 360
PDM-2     GATTTGAATTTGCAAGATTATTCCGCAATTCCTGCGTTAAAGGATCTTTCTTTCCCCATC 360
EF058187  GATTTGAATTTGCAAGATTATTCCGCAATTCCTGCGTTAAAGGATCTTTCTTTCCCCATC 360
EF058185  GATTTGAATTTGCAAGATTATTCCGCAATTCCTGCGTTAAAGGATCTTTCTTTCCCCATC 360
EF058186  GATTTGAATTTGCAAGATTATTCCGCAATTCCTGCGTTAAAGGATCTTTCTTTCCCCATC 360
EF058188  GATTTGAATTTGCAAGATTATTCCGCAATTCCTGCGTTAAAGGATCTTTCTTTCCCCATC 360
PDM-1     GATTTGAATTTGCAAGATTATTCCGCAATTCCTGCGTTAAAGGATCTTTCTTTCCCCATC 360
          ************************************************************

S288C     TTAATATCTTCTGATTTGCAAACTGCAATTTCAAACGCGGACTCTTCTTATAAGATTGCT 420
PDM-2     TTAATATCTTCTGATTTGCAAACTGCAATTTCAAACGCGGACTCTTCTTATAAGATTGCT 420
EF058187  TTAATATCTTCTGATTTGCAAACTGCAATTTCAAACGCGGACTCTTCTTATAAGATTGCT 420
EF058185  TTAATATCTTCTGATTTGCAAACTGCAATTTCAAACGCGGACTCTTCTTATAAGATTGCT 420
EF058186  TTAATATCTTCTGATTTGCAAACTGCAATTTCAAACGCGGACTCTTCTTATAAGATTGCT 420
EF058188  TTAATATCTTCTGATTTGCAAACTGCAATTTCAAACGCGGACTCTTCTTATAAGATTGCT 420
PDM-1     TTAATATCTTCTGATTTGCAAACTGCAATTTCAAACGCGGACTCTTCTTATAAGATTGCT 420
          ************************************************************
```

FIGURE 2

| | |
|---|---|
| S288C    | ACAAGTTCTCTGACCCCAGTTTTCCATTTTCTTAACTTGGAGAAAATTGGCACGAGTACA 480 |
| PDM-2    | ACAAGTTCTCTGACCCCAGTTTTCCATTTTCTTAACTTGGAGAAAATTGGCACGAGTACA 480 |
| EF058187 | ACAAGTTCTCTGACCCCAGTTTTCCATTTTCTTAACTTGGAGAAAATTGGCACGAGTACA 480 |
| EF058185 | ACAAGTTCTCTGACCCCAGTTTTCCATTTTCTTAACTTGGAGAAAATTGGCACGAGTACA 480 |
| EF058186 | ACAAGTTCTCTGACCCCAGTTTTCCATTTTCTTAACTTGGAGAAAATTGGCACGAGTACA 480 |
| EF058188 | ACAAGTTCTCTGACCCCAGTTTTCCATTTTCTTAACTTGGAGAAAATTGGCACGAGTACA 480 |
| PDM-1    | ACAAGTTCTCTGACCCCAGTTTTCCATTTTCTTAACTTGGAGAAAATTGGCACAAGTACA 480 |
|          | ***************************************************** ****** |

| | |
|---|---|
| S288C    | GCTATTGAACAAGACATCGACTTTCCTACCTTGGAGATTGCTAACGAAGAGACTAAAGTA 540 |
| PDM-2    | GCTATTGAACAAGACATCGACTTTCCTACCTTGGAGATTGCTAACGAAGAGACTAAAGTA 540 |
| EF058187 | GCTATTGAACAAGACATCGACTTTCCTACCTTGGAGATTGCTAACGAAGAGACTAAAGTA 540 |
| EF058185 | GCTATTGAACAAGACATCGACTTTCCTACCTTGGAGATTGCTAACGAAGAGACTAAAGTA 540 |
| EF058186 | GCTATTGAACAAGACATCGACTTTCCTACCTTGGAGATTGCTAACGAAGAGACTAAAGTA 540 |
| EF058188 | GCTATTGAACAAGACATCGACTTTCCTACCTTGGAGATTGCTAACGAAGAGACTAAAGTA 540 |
| PDM-1    | GCTATTGAACAAGACATCGACTTTCCTACCTTGGAGATTGCTAACGAAGAGACTAAAGTA 540 |
|          | ************************************************************ |

| | |
|---|---|
| S288C    | GCATTATCAGAAGCTACTGATTCATTGACAAATTTTGAACTGGTTAAAGGTAAAGAGTCA 600 |
| PDM-2    | GCATTATCAGAAGCTACTGATTCATTGACAAATTTTGAACTGGTTAAAGGTAAAGAGTCA 600 |
| EF058187 | GCATTATCAGAAGCTACTGATTCATTGACAAATTTTGAACTGGTTAAAGGTAAAGAGTCA 600 |
| EF058185 | GCATTATCAGAAGCTACTGATTCATTGACAAATTTTGAACTGGTTAAAGGTAAAGAGTCA 600 |
| EF058186 | GCATTATCAGAAGCTACTGATTCATTGACAAATTTTGAACTGGTTAAAGGTAAAGAGTCA 600 |
| EF058188 | GCATTATCAGAAGCTACTGATTCATTGACAAATTTTGAACTGGTTAAAGGTAAAGAGTCA 600 |
| PDM-1    | GCATTATCAGAAGCTACTGATTCATTGACAAATTTTGAACTGGTTAAAGGTAAAGAGTCA 600 |
|          | ************************************************************ |

| | |
|---|---|
| S288C    | ATTACCACTGTCATTGTTAACCTGTCACCATATGACGCGGAATTCAGTAGCGTATTGCCT 660 |
| PDM-2    | ATTACCACTGTCATTGTTAACCTGTCACCATATGACGCGGAATTCAGTAGCGTATTGCCT 660 |
| EF058187 | ATTACCACTGTCATTGTTAACCTGTCACCATATGACGCGGAATTCAGTAGCGTATTGCCT 660 |
| EF058185 | ATTACCACTGTCATTGTTAACCTGTCACCATATGACGCGGAATTCAGTAGCGTATTGCCT 660 |
| EF058186 | ATTACCACTGTCATTGTTAACCTGTCACCATATGACGCGGAATTCAGTAGCGTATTGCCT 660 |
| EF058188 | ATTACCACTGTCATTGTTAACCTGTCACCATATGACGCGGAATTCAGTAGCGTATTGCCT 660 |
| PDM-1    | ATTACCACTGTCATTGTTAACCTGTCACCATATGACGCGGAATTCAGTAGCGTATTGCCT 660 |
|          | ************************************************************ |

| | |
|---|---|
| S288C    | TCAAACGTAGGATTGATCAAGATTAGAGTATACAGACCATGGAATTTTTCCAAGTTCTTG 720 |
| PDM-2    | TCAAACGTAGGATTGATCAAGATTAGAGTATACAGACCATGGAATTTTTCCAAGTTCTTG 720 |
| EF058187 | TCAAACGTAGGATTGATCAAGATTAGAGTATACAGACCATGGAATTTTTCCAAGTTCTTG 720 |
| EF058185 | TCAAACGTAGGATTGATCAAGATTAGAGTATACAGACCATGGAATTTTTCCAAGTTCTTG 720 |
| EF058186 | TCAAACGTAGGATTGATCAAGATTAGAGTATACAGACCATGGAATTTTTCCAAGTTCTTG 720 |
| EF058188 | TCAAACGTAGGATTGATCAAGATTAGAGTATACAGACCATGGAATTTTTCCAAGTTCTTG 720 |
| PDM-1    | TCAAACGTAGGATTGATCAAGATTAGAGTATACAGACCATGGAATTTTTCCAAGTTCTTG 720 |
|          | ************************************************************ |

| | |
|---|---|
| S288C    | GAAATACTGCCATCTTCTGTTACCAAAATCGCCGTTTTACAGGGTGTCTCTAAGAAATCG 780 |
| PDM-2    | GAAATACTGCCATCTTCTGTTACCAAAATCGCCGTTTTACAGGGTGTCTCTAAGAAATCG 780 |
| EF058187 | GAAATACTGCCATCTTCTGTTACCAAAATCGCCGTTTTACAGGGTGTCTCTAAGAAATCG 780 |
| EF058185 | GAAATACTGCCATCTTCTGTTACCAAAATCGCCGTTTTACAGGGTGTCTCTAAGAAATCG 780 |
| EF058186 | GAAATACTGCCATCTTCTGTTACCAAAATCGCCGTTTTACAGGGTGTCTCTAAGAAATCG 780 |
| EF058188 | GAAATACTGCCATCTTCTGTTACCAAAATCGCCGTTTTACAGGGTGTCTCTAAGAAATCG 780 |
| PDM-1    | GAAATACTGCCATCTTCTGTTACCAAAATCGCCGTTTTACAGGGTGTCTCTAAGAAATCG 780 |
|          | ************************************************************ |

| | |
|---|---|
| S288C    | CAATCAAACGAATTTCAACCATTTCTTTTGGACTTCTTTGGCAATTTAATGAATTAGTT 840 |
| PDM-2    | CAATCAAACGAATTTCAACCATTTCTTTTGGACTTCTTTGGCAATTTAATGAATTAGTT 840 |
| EF058187 | CAATCAAACGAATTTCAACCATTTCTTTTGGACTTCTTTGGCAATTTAATGAATTAGTT 840 |
| EF058185 | CAATCAAACGAATTTCAACCATTTCTTTTGGACTTCTTTGGCAATTTAATGAATTAGTT 840 |
| EF058186 | CAATCAAACGAATTTCAACCATTTCTTTTGGACTTCTTTGGCAATTTAATGAATTAGTT 840 |
| EF058188 | CAATCAAACGAATTTCAACCATTTCTTTTGGACTTCTTTGGCAATTTAATGAATTAGTT 840 |
| PDM-1    | CAATCAAACGAATTTCAACCATTTCTTTTGGACTTCTTTGGCAATTTAATGAATTAGTT 840 |
|          | ************************************************************ |

FIGURE 2 (continued)

```
S288C       TCTAGGAACATCGAGCAGGTAGTGTTGACTAATATTGGTAATGTGAATGATTATGGCAAC 900
PDM-2       TCTAGGAACATCGAGCAG---GTGTTGACTAATATTGGTAATGTGAATGATTATGGCAAC 897
EF058187    TCTAGGAACATCGAGCAGGTAGTGTTGACTAATATTGGTAATGTGAATGATTATGGCAAC 900
EF058185    TCTAGGAACATCGAGCAGGTAGTGTTGACTAATATTGGTAATGTGAATGATTATGGCAAC 900
EF058186    TCTAGGAACATCGAGCAGGTAGTGTTGACTAATATTGGTAATGTGAATGATTATGGCAAC 900
EF058188    TCTAGGAACATCGAGCAGGTAGTGTTGACTAATATTGGTAATGTGAATGATTATGGCAAC 900
PDM-1       TCTAGGAACATCGAGCAGGTAGTGTTGACTAATATTGGTAATGTGAATGATTATGGCAAC 900
            *****************   ****************************************

S288C       GTTATCAACACCGTCATATCGAATATTAACAAGAAGGAACCAGATAATAACTTATTTTTA 960
PDM-2       GTTATCAACACCGTCATATCGAATATTAACAAGAAGGAACCAGATAATAACTTATTTTTA 957
EF058187    GTTATCAACACCGTCATATCGAATATTAACAAGAAGGAACCAGATAATAACTTATTTTTA 960
EF058185    GTTATCAACACCGTCATATCGAATATTAACAAGAAGGAACCAGATAATAACTTATTTTTA 960
EF058186    GTTATCAACACCGTCATATCGAATATTAACAAGAAGGAACCAGATAATAACTTATTTTTA 960
EF058188    GTTATCAACACCGTCATATCGAATATTAACAAGAAGGAACCAGATAATAACTTATTTTTA 960
PDM-1       GTTATCAACACCGTCATATCGAATATTAACAAGAAGGAACCAGATAATAACTTATTTTTA 960
            ************************************************************

S288C       GGTGAATCCAATGAAAAGGCTGAGGAACAAGCTGAAGTTACTCAACTTATTTCTTCTGTC 1020
PDM-2       GGTGAATCCAATGAAAAGGCTGAGGAACAAGCTGAAGTTACTCAACTTATTTCTTCTGTC 1017
EF058187    GGTGAATCCAATGAAAAGGCTGAGGAACAAGCTGAAGTTACTCAACTTATTTCTTCTGTC 1020
EF058185    GGTGAATCCAATGAAAAGGCTGAGGAACAAGCTGAAGTTACTCAACTTATTTCTTCTGTC 1020
EF058186    GGTGAATCCAATGAAAAGGCTGAGGAACAAGCTGAAGTTACTCAACTTATTTCTTCTGTC 1020
EF058188    GGTGAATCCAATGAAAAGGCTGAGGAACAAGCTGAAGTTACTCAACTTATTTCTTCTGTC 1020
PDM-1       GGTGAATCCAATGAAAAGGCTGAGGAACAAGCTGAAGTTACTCAACTTATTTCTTCTGTC 1020
            ************************************************************

S288C       AAAAAAGTTGTGAACTTAGAAGACGCCTATATCAAAGTGCTAAAACAGTTATTTTCATCA 1080
PDM-2       AAAAAAGTTGTGAACTTAGAAGACGCCTATATCAAAGTGCTAAAACAGTTATTTTCATCA 1077
EF058187    AAAAAAGTTGTGAACTTAGAAGACGCCTATATCAAAGTGCTAAAACAGTTATTTTCATCA 1080
EF058185    AAAAAAGTTGTGAACTTAGAAGACGCCTATATCAAAGTGCTAAAACAGTTATTTTCATCA 1080
EF058186    AAAAAAGTTGTGAACTTAGAAGACGCCTATATCAAAGTGCTAAAACAGTTATTTTCATCA 1080
EF058188    AAAAAAGTTGTGAACTTAGAAGACGCCTATATCAAAGTGCTAAAACAGTTATTTTCATCA 1080
PDM-1       AAAAAAGTTGTGAACTTAGAAGACGCCTATATCAAAGTGCTAAAACAGTTATTTTCATCA 1080
            ************************************************************

S288C       AATCTACAAATTTTGAATCAATTTTCCAGTGAGACAATTGAACCAAGTAATCCAGAATTT 1140
PDM-2       AATCTACAAATTTTGAATCAATTTTCCAGTGAGACAATTGAACCAAGTAATCCAGAATTT 1137
EF058187    AATCTACAAATTTTGAATCAATTTTCCAGTGAGACAATTGAACCAAGTAATCCAGAATTT 1140
EF058185    AATCTACAAATTTTGAATCAATTTTCCAGTGAGACAATTGAACCAAGTAATCCAGAATTT 1140
EF058186    AATCTACAAATTTTGAATCAATTTTCCAGTGAGACAATTGAACCAAGTAATCCAGAATTT 1140
EF058188    AATCTACAAATTTTGAATCAATTTTCCAGTGAGACAATTGAACCAAGTAATCCAGAATTT 1140
PDM-1       AATCTACAAATTTTGAATCAATTTTCCAGTGAGACAATTGAACCAAGTAATCCAGAATTT 1140
            ************************************************************

S288C       GGTTTTGGACGCTTTTTAAAACAAGAAGCCCAGCGTGAAGAATTGATCAGCTTAGCAAAA 1200
PDM-2       GGTTTTGGACGCTTTTTAAAACAAGAAGCCCAGCGTGAAGAATTGATCAGCTTAGCAAAA 1197
EF058187    GGTTTTGGACGCTTTTTAAAACAAGAAGCCCAGCGTGAAGAATTGATCAGCTTAGCAAAA 1200
EF058185    GGTTTTGGACGCTTTTTAAAACAAGAAGCCCAGCGTGAAGAATTGATCAGCTTAGCAAAA 1200
EF058186    GGTTTTGGACGCTTTTTAAAACAAGAAGCCCAGCGTGAAGAATTGATCAGCTTAGCAAAA 1200
EF058188    GGTTTTGGACGCTTTTTAAAACAAGAAGCCCAGCGTGAAGAATTGATCAGCTTAGCAAAA 1200
PDM-1       GGTTTTGGACGCTTTTTAAAACAAGAAGCCCAGCGTGAAGAATTGATCAGCTTAGCAAAA 1200
            ************************************************************

S288C       ACCTCTCTTGATCCAAGTCTTTACTTGTCCGAGGATGCAAATAAAATTGTTCAACTATTA 1260
PDM-2       ACCTCTCTTGATCCAAGTCTTTACTTGTCCGAGGATGCAAATAAAATTGTTCAACTATTA 1257
EF058187    ACCTCTCTTGATCCAAGTCTTTACTTGTCCGAGGATGCAAATAAAATTGTTCAACTATTA 1260
EF058185    ACCTCTCTTGATCCAAGTCTTTACTTGTCCGAGGATGCAAATAAAATTGTTCAACTATTA 1260
EF058186    ACCTCTCTTGATCCAAGTCTTTACTTGTCCGAGGATGCAAATAAAATTGTTCAACTATTA 1260
EF058188    ACCTCTCTTGATCCAAGTCTTTACTTGTCCGAGGATGCAAATAAAATTGTTCAACTATTA 1260
PDM-1       ACCTCTCTTTATCCAAGTCTTTACTTGTCCGAGGATGCAAATAAAATTGTTCAACTATTA 1260
            ********* **************************************************
```

FIGURE 2 (continued)

```
S288C      TCTAAATGGTTGTCATTCAATGGACGCGATCTTGACGAAGCTCAATTACAAGAGGCCAAT  1320
PDM-2      TCTAAATGGTTGTCATTCAATGGACGCGATCTTGACGAAGCTCAATTACAAGAGGCCAAT  1317
EF058187   TCTAAATGGTTGTCATTCAATGGACGCGATCTTGACGAAGCTCAATTACAAGAGGCCAAT  1320
EF058185   TCTAAATGGTTGTCATTCAATGGACGCGATCTTGACGAAGCTCAATTACAAGAGGCCAAT  1320
EF058186   TCTAAATGGTTGTCATTCAATGGACGCGATCTTGACGAAGCTCAATTACAAGAGGCCAAT  1320
EF058188   TCTAAATGGTTGTCATTCAATGGACGCGATCTTGACGAAGCTCAATTACAAGAGGCCAAT  1320
PDM-1      TCTAAATGGTTGTCATTCAATGGACGCGATCTTGACGAAGCTCAATTACAAGAGGCCAAT  1320
           ************************************************************

S288C      GCGACAGGTTTGGAAATATTTCAGTTATTACAATCTAATCAAGATTCCTCTACTGTCTTA  1380
PDM-2      GCGACAGGTTTGGAAATATTTCAGTTATTACAATCTAATCAAGATTCCTCTACTGTCTTA  1377
EF058187   GCGACAGGTTTGGAAATATTTCAGTTATTACAATCTAATCAAGATTCCTCTACTGTCTTA  1380
EF058185   GCGACAGGTTTGGAAATATTTCAGTTATTACAATCTAATCAAGATTCCTCTACTGTCTTA  1380
EF058186   GCGACAGGTTTGGAAATATTTCAGTTATTACAATCTAATCAAGATTCCTCTACTGTCTTA  1380
EF058188   GCGACAGGTTTGGAAATATTTCAGTTATTACAATCTAATCAAGATTCCTCTACTGTCTTA  1380
PDM-1      GCGACAGGTTTGGAAATATTTCAGTTATTACAATCTAATCAAGATTCCTCTACTGTCTTA  1380
           ************************************************************

S288C      AAATTCTTAAAAGATAGCTCCAACAAGCGATTCTTTTATTTTCAAATCAAGCTGGCTAATT  1440
PDM-2      AAATTCTTAAAGATAGCTCCAACAAGCGATTCTTTTATTTTCAAATCAAGCTGGCTAATT  1437
EF058187   AAATTCTTAAAAGATAGCTCCAACAAGCGATTCTTTTATTTTCAAATCAAGCTGGCTAATT  1440
EF058185   AAATTCTTAAMGATAGCTCCAACAAGCGATTCTTTTATTTTCAAATCAAGCTGGCTAATT  1440
EF058186   AAATTCTTAAAGATAGCTCCAACAAGCGATTCTTTTATTTTCAAATCAAGCTGGCTAATT  1440
EF058188   AAATTCTTAAAGATAGCTCCAACAAGCGATTCTTTTATTTTCAAATCAAGCTGGCTAATT  1440
PDM-1      AAATTCTTAAAGATAGCTCCAACAAGCGATTCTTTTATTTTCAAATCAAGCTGGCTAATT  1440
           *********  *************************************************

S288C      GGCTCCGATGCCTGGTCTTATGATTTGGGTCACTCAGGTATTCAACAGGTTTTATCCTCC  1500
PDM-2      GGCTCCGATGCCTGGTCTTATGATTTGGGTCACTCAGGTATTCAACAGGTTTTATCCTCC  1497
EF058187   GGCTCCGATGCCTGGTCTTATGATTTGGGTCACTCAGGTATTCAACAGGTTTTATCCTCC  1500
EF058185   GGCTCCGATGCCTGGTCTTATGATTTGGGTCACTCAGGTATTCAACAGGTTTTATCCTCC  1500
EF058186   GGCTCCGATGCCTGGTCTTATGATTTGGGTCACTCAGGTATTCAACAGGTTTTATCCTCC  1500
EF058188   GGCTCCGATGCCTGGTCTTATGATTTGGGTCACTCAGGTATTCAACAGGTTTTATCCTCC  1500
PDM-1      GGCTCCGATGCCTGGTCTTATGATTTGGGTCACTCAGGTATTCAACAGGTTTTATCCTCC  1500
           ************************************************************

S288C      CGTAAAAACATTAATGTTTTATTGATTGATTCAGAGCCATATGACCATAGAAAGCAAAAC  1560
PDM-2      CGTAAAAACATTAATGTTTTATTGATTGATTCAGAGCCATATGACCATAGAAAGCAAAAC  1557
EF058187   CGTAAAAACATTAATGTTTTATTGATTGATTCAGAGCCATATGACCATAGAAAGCAAAAC  1560
EF058185   CGTAAAAACATTAATGTTTTATTGATTGATTCAGAGCCATATGACCATAGAAAGCAAAAC  1560
EF058186   CGTAAAAACATTAATGTTTTATTGATTGATTCAGAGCCATATGACCATAGAAAGCAAAAC  1560
EF058188   CGTAAAAACATTAATGTTTTATTGATTGATTCAGAGCCATATGACCATAGAAAGCAAAAC  1560
PDM-1      CGTAAAAACATTAATGTTTTATTGATTGATTCAGAGCCATATGACCATAGAAAGCAAAAC  1560
           ************************************************************

S288C      CAGGATAGAAAGAAAGATGTTGGTTTGTACGCCATGAATTATTACAGTGCCTATGTTGCC  1620
PDM-2      CAGGATAGAAAGAAAGATGTTGGTTTGTACGCCATGAATTATTACAGTGCCTATGTTGCC  1617
EF058187   CAGGATAGAAAGAAAGATGTTGGTTTGTACGCCATGAATTATTACAGTGCCTATGTTGCC  1620
EF058185   CAGGATAGAAAGAAAGATGTTGGTTTGTACGCCATGAATTATTACAGTGCCTATGTTGCC  1620
EF058186   CAGGATAGAAAGAAAGATGTTGGTTTGTACGCCATGAATTATTACAGTGCCTATGTTGCC  1620
EF058188   CAGGATAGAAAGAAAGATGTTGGTTTGTACGCCATGAATTATTACAGTGCCTATGTTGCC  1620
PDM-1      CAGGATAGAAAGAAAGATGTTGGTTTGTACGCCATGAATTATTACAGTGCCTATGTTGCC  1620
           ************************************************************

S288C      TCTGTAGCAGTATATGCTTCTTACACCCAACTATTGACTGCAATAATAGAGGCATCTAAA  1680
PDM-2      TCTGTAGCAGTATATGCTTCTTACACCCAACTATTGACTGCAATAATAGAGGCATCTAAA  1677
EF058187   TCTGTAGCAGTATATGCTTCTTACACCCAACTATTGACTGCAATAATAGAGGCATCTAAA  1680
EF058185   TCTGTAGCAGTATATGCTTCTTACACCCAACTATTGACTGCAATAATAGAGGCATCTAAA  1680
EF058186   TCTGTAGCAGTATATGCTTCTTACACCCAACTATTGACTGCAATAATAGAGGCATCTAAA  1680
EF058188   TCTGTAGCAGTATATGCTTCTTACACCCAACTATTGACTGCAATAATAGAGGCATCTAAA  1680
PDM-1      TCTGTAGCAGTATATGCTTCTTACACCCAACTATTGACTGCAATAATAGAGGCATCTAAA  1680
           ************************************************************
```

FIGURE 2 (continued)

```
S288C      TACAATGGTCCTTCTATTGTCTTGGCTTATTTGCCGTATAATTCCGAAAATGATACTCCA 1740
PDM-2      TACAATGGTCCTTCTATTGTCTTGGCTTATTTGCCGTATAATTCCGAAAATGATACTCCA 1737
EF058187   TACAATGGTCCTTCTATTGTCTTGGCTTATTTGCCGTATAATTCCGAAAATGATACTCCA 1740
EF058185   TACAATGGTCCTTCTATTGTCTTGGCTTATTTGCCGTATAATTCCGAAAATGATACTCCA 1740
EF058186   TACAATGGTCCTTCTATTGTCTTGGCTTATTTGCCGTATAATTCCGAAAATGATACTCCA 1740
EF058188   TACAATGGTCCTTCTATTGTCTTGGCTTATTTGCCGTATAATTCCGAAAATGATACTCCA 1740
PDM-1      TACAATGGTCCTTCTATTGTCTTGGCTTATTTGCCGTATAATTCCGAAAATGATACTCCA 1740
           ************************************************************

S288C      TTAGAAGTCTTAAAGGAAACCAAAAACGCCGTTGAATCTGGTTACTGGCCATTGTATAGG 1800
PDM-2      TTAGAAGTCTTAAAGGAAACCAAAAACGCCGTTGAATCTGGTTACTGGCCATTGTATAGG 1797
EF058187   TTAGAAGTCTTAAAGGAAACCAAAAACGCCGTTGAATCTGGTTACTGGCCATTGTATAGG 1800
EF058185   TTAGAAGTCTTAAAGGAAACCAAAAACGCCGTTGAATCTGGTTACTGGCCATTGTATAGG 1800
EF058186   TTAGAAGTCTTAAAGGAAACCAAAAACGCCGTTGAATCTGGTTACTGGCCATTGTATAGG 1800
EF058188   TTAGAAGTCTTAAAGGAAACCAAAAACGCCGTTGAATCTGGTTACTGGCCATTGTATAGG 1800
PDM-1      TTAGAAGTCTTAAAGGAAACCAAAAACGCCGTTGAATCTGGTTACTGGCCATTGTATAGG 1800
           ************************************************************

S288C      TTTAATCCTGTTTATGACGATCCATCAACAGATAAGGAGGCATTTAGCTTGGATTCTTCG 1860
PDM-2      TTTAATCCTGTTTATGACGATCCATCAACAGATAAGGAGGCATTTAGCTTGGATTCTTCG 1857
EF058187   TTTAATCCTGTTTATGACGATCCATCAACAGATAAGGAGGCATTTAGCTTGGATTCTTCG 1860
EF058185   TTTAATCCTGTTTATGACGATCCATCAACAGATAAGGAGGCATTTAGCTTGGATTCTTCG 1860
EF058186   TTTAATCCTGTTTATGACGATCCATCAACAGATAAGGAGGCATTTAGCTTGGATTCTTCG 1860
EF058188   TTTAATCCTGTTTATGACGATCCATCAACAGATAAGGAGGCATTTAGCTTGGATTCTTCG 1860
PDM-1      TTTAATCCTGTTTATGACGATCCATCAACAGATAAGGAGGCATTTAGCTTGGATTCTTCG 1860
           ************************************************************

S288C      GTTATCAGAAAACAATTACAGGACTTCTTAGACCGTGAGAATAAGCTTACCCTATTAACC 1920
PDM-2      GTTATCAGAAAACAATTACAGGACTTCTTAGACCGTGAGAATAAGCTTACCCTATTAACC 1917
EF058187   GTTATCAGAAAACAATTACAGGACTTCTTAGACCGTGAGAATAAGCTTACCCTATTAACC 1920
EF058185   GTTATCAGAAAACAATTACAGGACTTCTTAGACCGTGAGAATAAGCTTACCCTATTAACC 1920
EF058186   GTTATCAGAAAACAATTACAGGACTTCTTAGACCGTGAGAATAAGCTTACCCTATTAACC 1920
EF058188   GTTATCAGAAAACAATTACAGGACTTCTTAGACCGTGAGAATAAGCTTACCCTATTAACC 1920
PDM-1      GTTATCAGAAAACAATTACAGGACTTCTTAGACCGTGAGAATAAGCTTACCCTATTAACC 1920
           ************************************************************

S288C      AGAAAAGATCCATCTTTGTCAAGAAATCTAAAGCAATCTGCTGGTGATGCGTTGACAAGG 1980
PDM-2      AGAAAAGATCCATCTTTGTCAAGAAATCTAAAGCAATCTGCTGGTGATGCGTTGACAAGG 1977
EF058187   AGAAAAGATCCATCTTTGTCAAGAAATCTAAAGCAATCTGCTGGTGATGCGTTGACAAGG 1980
EF058185   AGAAAAGATCCATCTTTGTCAAGAAATCTAAAGCAATCTGCTGGTGATGCGTTGACAAGG 1980
EF058186   AGAAAAGATCCATCTTTGTCAAGAAATCTAAAGCAATCTGCTGGTGATGCGTTGACAAGG 1980
EF058188   AGAAAAGATCCATCTTTGTCAAGAAATCTAAAGCAATCTGCTGGTGATGCGTTGACAAGG 1980
PDM-1      AGAAAAGATCCATCTTTGTCAAGAAATCTAAAGCAATCTGCTGGTGATGCGTTGACAAGG 1980
           ************************************************************

S288C      AAACAAGAAAAAGAAGCAAGGCTGCCTTCGATCAGTTATTGGAGGGTTTGTCCGGCCCA 2040
PDM-2      AAACAAGAAAAAGAAGCAAGGCTGCCTTCGATCAGTTATTGGAGGGTTTGTCCGGCCCA 2037
EF058187   AAACAAGAAAAAGAAGCAAGGCTGCCTTCGATCAGTTATTGGAGGGTTTGTCCGGCCCA 2040
EF058185   AAACAAGAAAAAGAAGCAAGGCTGCCTTCGATCAGTTATTGGAGGGTTTGTCCGGCCCA 2040
EF058186   AAACAAGAAAAAGAAGCAAGGCTGCCTTCGATCAGTTATTGGAGGGTTTGTCCGGCCCA 2040
EF058188   AAACAAGAAAAAGAAGCAAGGCTGCCTTCGATCAGTTATTGGAGGGTTTGTCCGGCCCA 2040
PDM-1      AAACAAGAAAAAGAAGCAAGGCTGCCTTCGATCAGTTATTGGAGGGTTTGTCCGGCCCA 2040
           ************************************************************

S288C      CCGCTACACGTCTATTATGCTTCTGACGGTGGTAATGCTGCAAACTTGGCAAAGAGACTA 2100
PDM-2      CCGCTACACGTCTATTATGCTTCTGACGGTGGTAATGCTGCAAACTTGGCAAAGAGACTA 2097
EF058187   CCGCTACACGTCTATTATGCTTCTGACGGTGGTAATGCTGCAAACTTGGCAAAGAGACTA 2100
EF058185   CCGCTACACGTCTATTATGCTTCTGACGGTGGTAATGCTGCAAACTTGGCAAAGAGACTA 2100
EF058186   CCGCTACACGTCTATTATGCTTCTGACGGTGGTAATGCTGCAAACTTGGCAAAGAGACTA 2100
EF058188   CCGCTACACGTCTATTATGCTTCTGACGGTGGTAATGCTGCAAACTTGGCAAAGAGACTA 2100
PDM-1      CCGCTACACGTCTATTATGCTTCTGACGGTGGTAATGCTGCAAACTTGGCAAAGAGACTA 2100
           ************************************************************
```

FIGURE 2 (continued)

```
S288C      GCAGCAAGGGCATCTGCAAGAGGTTTAAAGGCTACTGTTCTGTCCATGGATGACATTATT 2160
PDM-2      GCAGCAAGGGCATCTGCAAGAGGTTTAAAGGCTACTGTTCTGTCCATGGATGACATTATT 2157
EF058187   GCAGCAAGGGCATCTGCAAGAGGTTTAAAGGCTACTGTTCTGTCCATGGATGACATTATT 2160
EF058185   GCAGCAAGGGCATCTGCAAGAGGTTTAAAGGCTACTGTTCTGTCCATGGATGACATTATT 2160
EF058186   GCAGCAAGGGCATCTGCAAGAGGTTTAAAGGCTACTGTTCTGTCCATGGATGACATTATT 2160
EF058188   GCAGCAAGGGCATCTGCAAGAGGTTTAAAGGCTACTGTTCTGTCCATGGATGACATTATT 2160
PDM-1      GCAGCAAGGGCATCTGCAAGAGGTTTAAAGGCTACTGTTCTGTCCATGGATGACATTATT 2160
           ************************************************************

S288C      TTGGAAGAATTACCTGGTGAAGAGAATGTAGTTTTCATTACTTCCACGGCTGGGCAAGGT 2220
PDM-2      TTGGAAGAATTACCTGGTGAAGAGAATGTAGTTTTCATTACTTCCACGGCTGGGCAAGGT 2217
EF058187   TTGGAAGAATTACCTGGTGAAGAGAATGTAGTTTTCATTACTTCCACGGCTGGGCAAGGT 2220
EF058185   TTGGAAGAATTACCTGGTGAAGAGAATGTAGTTTTCATTACTTCCACGGCTGGGCAAGGT 2220
EF058186   TTGGAAGAATTACCTGGTGAAGAGAATGTAGTCTTCATTACTTCCACGGCTGGGCAAGGT 2220
EF058188   TTGGAAGAATTACCTGGTGAAGAGAATGTAGTTTTCATTACTTCCACGGCTGGGCAAGGT 2220
PDM-1      TTGGAAGAATTACCTGGTGAAGAGAATGTAGTTTTCATTACTTCCACGGCTGGGCAAGGT 2220
           ******************************** ***************************

S288C      GAATTCCCCCAAGACGGTAAGTCTTTCTGGGAAGCTCTGAAAAATGACACCGACTTGGAT 2280
PDM-2      GAATTCCCCCAAGACGGTAAGTCTTTCTGGGAAGCTCTGAAAAATGACACCGACTTGGAT 2277
EF058187   GAATTCCCCCAAGACGGTAAGTCTTTCTGGGAAGCTCTGAAAAATGACACCGACTTGGAT 2280
EF058185   GAATTCCCCCAAGACGGTAAGTCTTTCTGGGAAGCTCTGAAAAATGACACCGACTTGGAT 2280
EF058186   GAATTCCCCCAAGACGGTAAGTCTTTCTGGGAAGCTCTGAAAAATGACACCGACTTGGAT 2280
EF058188   GAATTCCCCCAAGACGGTAAGTCTTTCTGGGAAGCTCTGAAAAATGACACCGACTTGGAT 2280
PDM-1      GAATTCCCCCAAGACGGTAAGTCTTTCTGGGAAGCTCTGAAAAATGACACCGACTTGGAT 2280
           ************************************************************

S288C      TTAGCTAGTTTGAATGTTGCTGTTTTTGGTCTCGGTGATTCTGAGTATTGGCCACGTAAA 2340
PDM-2      TTAGCTAGTTTGAATGTTGCTGTTTTTGGTCTCGGTGATTCTGAGTATTGGCCACGTAAA 2337
EF058187   TTAGCTAGTTTGAATGTTGCTGTTTTTGGTCTCGGTGATTCTGAGTATTGGCCACGTAAA 2340
EF058185   TTAGCTAGTTTGAATGTTGCTGTTTTTGGTCTCGGTGATTCTGAGTATTGGCCACGTAAA 2340
EF058186   TTAGCTAGTTTGAATGTTGCTGTTTTTGGTCTCGGTGATTCTGAGTATTGGCCACGTAAA 2340
EF058188   TTAGCTAGTTTGAATGTTGCTGTTTTTGGTCTCGGTGATTCTGAGTATTGGCCACGTAAA 2340
PDM-1      TTAGCTAGTTTGAATGTTGCTGTTTTTGGTCTCGGTGATTCTGAGTATTGGCCACGTAAA 2340
           ************************************************************

S288C      GAAGATAAACATTATTTTAACAAGCCTTCACAGGATTTATTTAAGCGCTTGGAATTATTG 2400
PDM-2      GAAGATAAACATTATTTTAACAAGCCTTCACAGGATTTATTTAAGCGCTTGGAATTATTG 2397
EF058187   GAAGATAAACATTATTTTAACAAGCCTTCACAGGATTTATTTAAGCGCTTGGAATTATTG 2400
EF058185   GAAGATAAACATTATTTTAACAAGCCTTCACAGGATTTATTTAAGCGCTTGGAATTATTG 2400
EF058186   GAAGATAAACATTATTTTAACAAGCCTTCACAGGATTTATTTAAGCGCTTGGAATTATTG 2400
EF058188   GAAGATAAACATTATTTTAACAAGCCTTCACAGGATTTATTTAAGCGCTTGGAATTATTG 2400
PDM-1      GAAGATAAACATTATTTTAACAAGCCTTCACAGGATTTATTTAAGCGCTTGGAATTATTG 2400
           ************************************************************

S288C      AGTGCCAAAGCCCTAATTCCCTTGGGACTGGGTGATGATCAAGATGCTGATGGTTTCCAA 2460
PDM-2      AGTGCCAAAGCCCTAATTCCCTTGGGACTGGGTGATGATCAAGATGCTGATGGTTTCCAA 2457
EF058187   AGTGCCAAAGCCCTAATTCCCTTGGGACTGGGTGATGATCAAGATGCTGATGGTTTCCAA 2460
EF058185   AGTGCCAAAGCCCTAATTCCCTTGGGACTGGGTGATGATCAAGATGCTGATGGTTTCCAA 2460
EF058186   AGTGCCAAAGCCCTAATTCCCTTGGGACTGGGTGATGATCAAGATGCTGATGGTTTCCAA 2460
EF058188   AGTGCCAAAGCCCTAATTCCCTTGGGACTGGGTGATGATCAAGATGCTGATGGTTTCCAA 2460
PDM-1      AGTGCCAAAGCCCTAATTCCCTTGGGACTGGGTGATGATCAAGATGCTGATGGTTTCCAA 2460
           ************************************************************

S288C      ACTGCTTATTCTGAGTGGGAACCTAAATTATGGGAAGCTCTTGGTGTTTCCGGCGCTGCT 2520
PDM-2      ACTGCTTATTCTGAGTGGGAACCTAAATTATGGGAAGCTCTTGGTGTTTCCGGCGCTGCT 2517
EF058187   ACTGCTTATTCTGAGTGGGAACCTAAATTATGGGAAGCTCTTGGTGTTTCCGGCGCTGCT 2520
EF058185   ACTGCTTATTCTGAGTGGGAACCTAAATTATGGGAAGCTCTTGGTGTTTCCGGCGCTGCT 2520
EF058186   ACTGCTTATTCTGAGTGGGAACCTAAATTATGGGAAGCTCTTGGTGTTTCCGGCGCTGCT 2520
EF058188   ACTGCTTATTCTGAGTGGGAACCTAAATTATGGGAAGCTCTTGGTGTTTCCGGCGCTGCT 2520
PDM-1      ACTGCTTATTCTGAGTGGGAACCTAAATTATGGGAAGCTCTTGGTGTTTCCGGCGCTGCT 2520
           ************************************************************
```

FIGURE 2 (continued)

```
S288C      GTTGATGATGAGCCAAAACCTGTTACAAACGAGGATATTAAGAGAGAATCTAATTTCTTG 2580
PDM-2      GTTGATGATGAGCCAAAACCTGTTACAAACGAGGATATTAAGAGAGAATCTAATTTCTTG 2577
EF058187   GTTGATGATGAGCCAAAACCTGTTACAAACGAGGATATTAAGAGAGAATCTAATTTCTTG 2580
EF058185   GTTGATGATGAGCCAAAACCTGTTACAAACGAGGATATTAAGAGAGAATCTAATTTCTTG 2580
EF058186   GTTGATGATGAGCCAAAACCTGTTACAAACGAGGATATTAAGAGAGAATCTAATTTCTTG 2580
EF058188   GTTGATGATGAGCCAAAACCTGTTACAAACGAGGATATTAAGAGAGAATCTAATTTCTTG 2580
PDM-1      GTTGATGATGAGCCAAAACCTGTTACAAACGAGGATATTAAGAGAGAATCTAATTTCTTG 2580
           ************************************************************

S288C      AGAGGTACTATCAGTGAGAACTTAAAGGATACTTCTTCAGGTGGTGTTACTCACGCTAAT 2640
PDM-2      AGAGGTACTATCAGTGAGAACTTAAAGGATACTTCTTCAGGTGGTGTTACTCACGCTAAT 2637
EF058187   AGAGGTACTATCAGTGAGAACTTAAAGGATACTTCTTCAGGTGGTGTTACTCACGCTAAT 2640
EF058185   AGAGGTACTATCAGTGAGAACTTAAAGGATACTTCTTCAGGTGGTGTTACTCACGCTAAT 2640
EF058186   AGAGGTACTATCAGTGAGAACTTAAAGGATACTTCTTCAGGTGGTGTTACTCACGCTAAT 2640
EF058188   AGAGGTACTATCAGTGAGAACTTAAAGGATACTTCTTCAGGTGGTGTTACTCACGCTAAT 2640
PDM-1      AGAGGTACTATCAGTGAGAACTTAAAGGATACTTCTTCAGGTGGTGTTACTCACGCTAAT 2640
           ************************************************************

S288C      GAACAATTAATGAAATTTCACGGTATTTACACCCAAGACGATCGTGACATTAGAGAAATA 2700
PDM-2      GAACAATTAATGAAATTTCACGGTATTTACACCCAAGACGATCGTGACATTAGAGAAATA 2697
EF058187   GAACAATTAATGAAATTTCACGGTATTTACACCCAAGACGATCGTGACATTAGAGAAATA 2700
EF058185   GAACAATTAATGAAATTTCACGGTATTTACACCCAAGACGATCGTGACATTAGAGAAATA 2700
EF058186   GAACAATTAATGAAATTTCACGGTATTTACACCCAAGACGATCGTGACATTAGAGAAATA 2700
EF058188   GAACAATTAATGAAATTTCACGGTATTTACACCCAAGACGATCGTGACATTAGAGAAATA 2700
PDM-1      GAACAATTAATGAAATTTCACGGTATTTACACCCAAGACGATCGTGACATTAGAGAAATA 2700
           ************************************************************

S288C      CGTAAGTCACAAGGCTTAGAGCCATACTATATGTTTATGGCAAGAGCTCGTTTACCAGGT 2760
PDM-2      CGTAAGTCACAAGGCTTAGAGCCATACTATATGTTTATGGCAAGAGCTCGTTTACCAGGT 2757
EF058187   CGTAAGTCACAAGGCTTAGAGCCATACTATATGTTTATGGCAAGAGCTCGTTTACCAGGT 2760
EF058185   CGTAAGTCACAAGGCTTAGAGCCATACTATATGTTTATGGCAAGAGCTCGTTTACCAGGT 2760
EF058186   CGTAAGTCACAAGGCTTAGAGCCATACTATATGTTTATGGCAAGAGCTCGTTTACCAGGT 2760
EF058188   CGTAAGTCACAAGGCTTAGAGCCATACTATATGTTTATGGCAAGAGCTCGTTTACCAGGT 2760
PDM-1      CGTAAGTCACAAGGCTTAGAGCCATACTATATGTTTATGGCAAGAGCTCGTTTACCAGGT 2760
           ************************************************************

S288C      GGTAAGACCACTCCACAACAATGGCTTGCTCTGGATCACTTATCTGATACTTCAGGCAAT 2820
PDM-2      GGTAAGACCACTCCACAACAATGGCTTGCTCTGGATCACTTATCTGATACTTCAGGCAAT 2817
EF058187   GGTAAGACCACTCCACAACAATGGCTTGCTCTGGATCACTTATCTGATACTTCAGGCAAT 2820
EF058185   GGTAAGACCACTCCACAACAATGGCTTGCTCTGGATCACTTATCTGATACTTCAGGCAAT 2820
EF058186   GGTAAGACCACTCCACAACAATGGCTTGCTCTGGATCACTTATCTGATACTTCAGGCAAT 2820
EF058188   GGTAAGACCACTCCACAACAATGGCTTGCTCTGGATCACTTATCTGATACTTCAGGCAAT 2820
PDM-1      GGTAAGACCACTCCACAACAATGGCTTGCTCTGGATCACTTATCTGATACTTCAGGCAAT 2820
           ************************************************************

S288C      GGTACCCTGAAATTAACAACAAGGGCAACCTTCCAGATTCATGGTGTGCTAAAGAAGAAC 2880
PDM-2      GGTACCCTGAAATTAACAACAAGGGCAACCTTCCAGATTCATGGTGTGCTAAAGAAGAAC 2877
EF058187   GGTACCCTGAAATTAACAACAAGGGCAACCTTCCAGATTCATGGTGTGCTAAAGAAGAAC 2880
EF058185   GGTACCCTGAAATTAACAACAAGGGCAACCTTCCAGATTCATGGTGTGCTAAAGAAGAAC 2880
EF058186   GGTACCCTGAAATTAACAACAAGGGCAACCTTCCAGATTCATGGTGTGCTAAAGAAGAAC 2880
EF058188   GGTACCCTGAAATTAACAACAAGGGCAACCTTCCAGATTCATGGTGTGCTAAAGAAGAAC 2880
PDM-1      GGTACCCTGAAATTAACAACAAGGGCAACCTTCCAGATTCATGGTGTGCTAAAGAAGAAC 2880
           ************************************************************

S288C      TTGAAACACACATTGAGAGGAATGAATGCAGTTCTTATGGATACATTAGCTGCTGCAGGT 2940
PDM-2      TTGAAACACACATTGAGAGGAATGAATGCAGTTCTTATGGATACATTAGCTGCTGCAGGT 2937
EF058187   TTGAAACACACATTGAGAGGAATGAATGCAGTTCTTATGGATACATTAGCTGCTGCAGGT 2940
EF058185   TTGAAACACACATTGAGAGGAATGAATGCAGTTCTTATGGATACATTAGCTGCTGCAGGT 2940
EF058186   TTGAAACACACATTGAGAGGAATGAATGCAGTTCTTATGGATACATTAGCTGCTGCAGGT 2940
EF058188   TTGAAACACACATTGAGAGGAATGAATGCAGTTCTTATGGATACATTAGCTGCTGCAGGT 2940
PDM-1      TTGAAACACACATTGAGAGGAATGAATGCAGTTCTTATGGATACATTAGCTGCTGCAGGT 2940
           ************************************************************
```

FIGURE 2 (continued)

```
S288C     GACGTGAACAGAAATGTCATGGTTTCTGCTCTACCAACCAATGCCAAGGTTCACCAACAA 3000
PDM-2     GACGTGAACAGAAATGTCATGGTTTCTGCTCTACCAACCAATGCCAAGGTTCACCAACAA 2997
EF058187  GACGTGAACAGAAATGTCATGGTTTCTGCTCTACCAACCAATGCCAAGGTTCACCAACAA 3000
EF058185  GACGTGAACAGAAATGTCATGGTTTCTGCTCTACCAACCAATGCCAAGGTTCACCAACAA 3000
EF058186  GACGTGAACAGAAATGTCATGGTTTCTGCTCTACCAACCAATGCCAAGGTTCACCAACAA 3000
EF058188  GACGTGAACAGAAATGTCATGGTTTCTGCTCTACCAACCAATGCCAAGGTTCACCAACAA 3000
PDM-1     GACGTGAACAGAAATGTCATGGTTTCTGCTCTACCAACCAATGCCAAGGTTCACCAACAA 3000
          ************************************************************

S288C     ATCGCTGATATGGGAAAATTGATTTCTGATCATTTCTTACCAAAGACTACGGCCTACCAC 3060
PDM-2     ATCGCTGATATGGGAAAATTGATTTCTGATCATTTCTTACCAAAGACTACGGCCTACCAC 3057
EF058187  ATCGCTGATATGGGAAAATTGATTTCTGATCATTTCTTACCAAAGACTACGGCCTACCAC 3060
EF058185  ATCGCTGATATGGGAAAATTGATTTCTGATCATTTCTTACCAAAGACTACGGCCTACCAC 3060
EF058186  ATCGCTGATATGGGAAAATTGATTTCTGATCATTTCTTACCAAAGACTACGGCCTACCAC 3060
EF058188  ATCGCTGATATGGGAAAATTGATTTCTGATCATTTCTTACCAAAGACTACGGCCTACCAC 3060
PDM-1     ATCGCTGATATGGGAAAATTGATTTCTGATCATTTCTTACCAAAGACTACGGCCTACCAC 3060
          ************************************************************

S288C     GAAGTTTGGCTGGAGGGCCCAGAAGAACAGGACGATGATCCATCCTGGCCATCTATTTTT 3120
PDM-2     GAAGTTTGGCTGGAGGGCCCAGAAGAACAGGACGATGATCCATCCTGGCCATCTATTTTT 3117
EF058187  GAAGTTTGGCTGGAGGGCCCAGAAGAACAGGACGATGATCCATCCTGGCCATCTATTTTT 3120
EF058185  GAAGTTTGGCTGGAGGGCCCAGAAGAACAGGACGATGATCCATCCTGGCCATCTATTTTT 3120
EF058186  GAAGTTTGGCTGGAGGGCCCAGAAGAACAGGACGATGATCCATCCTGGCCATCTATTTTT 3120
EF058188  GAAGTTTGGCTGGAGGGCCCAGAAGAACAGGACGATGATCCATCCTGGCCATCTATTTTT 3120
PDM-1     GAAGTTTGGCTGGAGGGCCCAGAAGAACAGGACGATGATCCATCCTGGCCATCTATTTTT 3120
          ************************************************************

S288C     GAAAACAGAAAAGATGGTCCAAGAAAAAAGAAGACTCTAGTTAGCGGTAACGCTTTGGTC 3180
PDM-2     GAAAACAGAAAAGATGGTCCAAGAAAAAAGAAGACTCTAGTTAGCGGTAACGCTTTGGTC 3177
EF058187  GAAAACAGAAAAGATGGTCCAAGAAAAAAGAAGACTCTAGTTAGCGGTAACGCTTTGGTC 3180
EF058185  GAAAACAGAAAAGATGGTCCAAGAAAAAAGAAGACTCTAGTTAGCGGTAACGCTTTGGTC 3180
EF058186  GAAAACAGAAAAGATGGTCCAAGAAAAAAGAAGACTCTAGTTAGCGGTAACGCTTTGGTC 3180
EF058188  GAAAACAGAAAAGATGGTCCAAGAAAAAAGAAGACTCTAGTTAGCGGTAACGCTTTGGTC 3180
PDM-1     GAAAACAGAAAAGATGGTCCAAGAAAAAAGAAGACTCTAGTTAGCGGTAACGCTTTGGTC 3180
          ************************************************************

S288C     GATATTGAACCAATTTACGGTCCAACTTATCTGCCAAGAAAGTTTAAATTCAACATCGCC 3240
PDM-2     GATATTGAACCAATTTACGGTCCAACTTATCTGCCAAGAAAGTTTAAATTCAACATCGCC 3237
EF058187  GATATTGAACCAATTTACGGTCCAACTTATCTGCCAAGAAAGTTTAAATTCAACATCGCC 3240
EF058185  GATATTGAACCAATTTACGGTCCAACTTATCTGCCAAGAAAGTTTAAATTCAACATCGCC 3240
EF058186  GATATTGAACCAATTTACGGTCCAACTTATCTGCCAAGAAAGTTTAAATTCAACATCGCC 3240
EF058188  GATATTGAACCAATTTACGGTCCAACTTATCTGCCAAGAAAGTTTAAATTCAACATCGCC 3240
PDM-1     GATATTGAACCAATTTACGGTCCAACTTATCTGCCAAGAAAGTTTAAATTCAACATCGCC 3240
          ************************************************************

S288C     GTTCCTCCATATAACGATGTGGATGTATTATCTATCGATGTCGGTTTAGTTGCTATAGTT 3300
PDM-2     GTTCCTCCATATAACGATGTGGATGTATTATCTATCGATGTCGGTTTAGTTGCTATAGTT 3297
EF058187  GTTCCTCCATATAACGATGTGGATGTATTATCTATCGATGTCGGTTTAGTTGCTATAGTT 3300
EF058185  GTTCCTCCATATAACGATGTGGATGTATTATCTATCGATGTCGGTTTAGTTGCTATAGTT 3300
EF058186  GTTCCTCCATATAACGATGTGGATGTATTATCTAGCGATGTCGGTTTAGTTGCTATAGTT 3300
EF058188  GTTCCTCCATATAACGATGTGGATGTATTATCTATCGATGTCGGTTTAGTTGCTATAGTT 3300
PDM-1     GTTCCTCCATATAACGATGTGGATGTATTATCTATCGATGTCGGTTTAGTTGCTATAGTT 3300
          ********************************** *************************

S288C     AACCCAGAAACTCAAATCGTGGAGGGTTATAATGTTTTGTTGGTGGTGGTATGGGTACC 3360
PDM-2     AACCCAGAAACTCAAATCGTGGAGGGTTATAATGTTTTGTTGGTGGTGGTATGGGTACC 3357
EF058187  AACCCAGAAACTCAAATCGTGGAGGGTTATAATGTTTTGTTGGTGGTGGTATGGGTACC 3360
EF058185  AACCCAGAAACTCAAATCGTGGAGGGTTATAATGTTTTGTTGGTGGTGGTATGGGTACC 3360
EF058186  AACCCAGAAACTCAAATCGTGGAGGGTTATAATGTTTTGTTGGTGGTGGTATGGGTACC 3360
EF058188  AACCCAGAAACTCAAATCGTGGAGGGTTATAATGTTTTGTTGGTGGTGGTATGGGTACC 3360
PDM-1     AACCCAAAACTCAAATCGTGGAGGGTTATAATGTTTTGTTGGTGGTGGTATGGGTACC 3360
          ****** ****************************************************
```

FIGURE 2 (continued)

```
S288C     ACTCATAACAACAAGAAAACTTACCCAAGATTAGGGTCATGCTTAGGTTTTGTTAAAACT 3420
PDM-2     ACTCATAACAACAAGAAAACTTACCCAAGATTAGGGTCATGCTTAGGTTTTGTTAAAACT 3417
EF058187  ACTCATAACAACAAGAAAACTTACCCAAGATTAGGGTCATGCTTAGGTTTTGTTAAAACT 3420
EF058185  ACTCATAACAACAAGAAAACTTACCCAAGATTAGGGTCATGCTTAGGTTTTGTTAAAACT 3420
EF058186  ACTCATAACAACAAGAAAACTTACCCAAGATTAGGGTCATGCTTAGGTTTTGTTAAAACT 3420
EF058188  ACTCATAACAACAAGAAAACTTACCCAAGATTAGGGTCATGCTTAGGTTTTGTTAAAACT 3420
PDM-1     ACTCATAACAACAAGAAAACTTACCCAAGATTAGGGTCATGCTTAGGTTTTGTTAAAACT 3420
          ************************************************************

S288C     GAAGACATTATTCCACCACTTGAAGGTATCGTTATTGTCCAAAGAGATCACGGTGACCGT 3480
PDM-2     GAAGACATTATTCCACCACTTGAAGGTATCGTTATTGTCCAAAGAGATCACGGTGACCGT 3477
EF058187  GAAGACATTATTCCACCACTTGAAGGTATCGTTATTGTCCAAAGAGATCACGGTGACCGT 3480
EF058185  GAAGACATTATTCCACCACTTGAAGGTATCGTTATTGTCCAAAGAGATCACGGTGACCGT 3480
EF058186  GAAGACATTATTCCACCACTTGAAGGTATCGTTATTGTCCAAAGAGATCACGGTGACCGT 3480
EF058188  GAAGACATTATTCCACCACTTGAAGGTATCGTTATTGTCCAAAGAGATCACGGTGACCGT 3480
PDM-1     GAAGACATTATTCCACCACTTGAAGGTATCGTTATTGTCCAAAGAGATCACGGTGACCGT 3480
          ************************************************************

S288C     AAAGACCGTAAGCATGCTCGTTTAAAGTATACTGTAGATGATATGGGTGTCGAAGGCTTC 3540
PDM-2     AAAGACCGTAAGCATGCTCGTTTAAAGTATACTGTAGATGATATGGGTGTCGAAGGCTTC 3537
EF058187  AAAGACCGTAAGCATGCTCGTTTAAAGTATACTGTAGATGATATGGGTGTCGAAGGCTTC 3540
EF058185  AAAGACCGTAAGCATGCTCGTTTAAAGTATACTGTAGATGATATGGGTGTCGAAGGCTTC 3540
EF058186  AAAGACCGTAAGCATGCTCGTTTAAAGTATACTGTAGATGATATGGGTGTCGAAGGCTTC 3540
EF058188  AAAGACCGTAAGCATGCTCGTTTAAAGTATACTGTAGATGATATGGGTGTCGAAGGCTTC 3540
PDM-1     AAAGACCGTAAGCATGCTCGTTTAAAGTATACTGTAGATGATATGGGTGTCGAAGGCTTC 3540
          ************************************************************

S288C     AAGCAAAAAGTGGAGGAATACTGGGGTAAGAAATTCGAGCCTGAGAGACCATTTGAGTTT 3600
PDM-2     AAGCAAAAAGTGGAGGAATACTGGGGTAAGAAATTCGAGCCTGAGAGACCATTTGAGTTT 3597
EF058187  AAGCAAAAAGTGGAGGAATACTGGGGTAAGAAATTCGAGCCTGAGAGACCATTTGAGTTT 3600
EF058185  AAGCAAAAAGTGGAGGAATACTGGGGTAAGAAATTCGAGCCTGAGAGACCATTTGAGTTT 3600
EF058186  AAGCAAAAAGTGGAGGAATACTGGGGTAAGAAATTCGAGCCTGAGAGACCATTTGAGTTT 3600
EF058188  AAGCAAAAAGTGGAGGAATACTGGGGTAAGAAATTCGAGCCTGAGAGACCATTTGAGTTT 3600
PDM-1     AAGCAAAAAGTGGAGGAATACTGGGGTAAGAAATTCGAGCCTGAGAGACCATTTGAGTTT 3600
          ************************************************************

S288C     AAATCTAATATTGATTACTTTGGATGGATTAAAGATGAAACTGGGTTAAACCACTTTACC 3660
PDM-2     AAATCTAATATTGATTACTTTGGATGGATTAAAGATGAAACTGGGTTAAACCACTTTACC 3657
EF058187  AAATCTAATATTGATTACTTTGGATGGATTAAAGATGAAACTGGGTTAAACCACTTTACC 3660
EF058185  AAATCTAATATTGATTACTTTGGATGGATTAAAGATGAAACTGGGTTAAACCACTTTACC 3660
EF058186  AAATCTAATATTGATTACTTTGGATGGATTAAAGATGAAACTGGGTTAAACCACTTTACC 3660
EF058188  AAATCTAATATTGATTACTTTGGATGGATTAAAGATGAAACTGGGTTAAACCACTTTACC 3660
PDM-1     AAATCTAATATTGATTACTTTGGATGGATTAAAGATGAAACTGGGTTAAACCACTTTACC 3660
          ************************************************************

S288C     GCATTTATTGAAAATGGTAGGGTTGAAGATACACCAGATTTGCCTCAAAAGACAGGTATT 3720
PDM-2     GCATTTATTGAAAATGGTAGGGTTGAAGATACACCAGATTTGCCTCAAAAGACAGGTATT 3717
EF058187  GCACTTATTGAAAATGGTAGGGTTGAAGATACACCAGATTTGCCTCAAAAGACAGGTATT 3720
EF058185  GCATTTATTGAAAATGGTAGGGTTGAAGATACACCAGATTTGCCTCAAAAGACAGGTATT 3720
EF058186  GCATTTATTGAAAATGGTAGGGTTGAAGATACACCAGATTTGCCTCAAAAGACAGGTATT 3720
EF058188  GCATTTATTGAAAATGGTARGGTTGAAGATACACCAGATTTGCCTCAAAAGACAGGTATT 3720
PDM-1     GCATTTATTGAAAATGGTAGGGTTGAAGATACACCAGATTTGCCTCAAAAGACAGGTATT 3720
          *** ************** *****************************************

S288C     AGAAAGGTTGCTGAATACATGCTTAAGACTAATTCTGGTCATTTCAGATTGACTGGTAAT 3780
PDM-2     AGAAAGGTTGCTGAATACATGCTTAAGACTAATTCTGGTCATTTCAGATTGACTGGTAAT 3777
EF058187  AGAAAGGTTGCTGAATACATGCTTAAGACTAATTCTGGTCATTTCAGATTGACTGGTAAT 3780
EF058185  AGAAAGGTTGCTGAATACATGCTTAAGACTAATTCTGGTCATTTCAGATTGACTGGTAAT 3780
EF058186  AGAAAGGTTGCTGAATACATGCTTAAGACTAATTCTGGTCATTTCAGATTGACTGGTAAT 3780
EF058188  AGAAAGGTTGCTGAATACATGCTTAAGACTAATTCTGGTCATTTCAGATTGACTGGTAAT 3780
PDM-1     AGAAAGGTTGCTGAATACATGCTTAAGACTAATTCTGGTCATTTCAGATTGACTGGTAAT 3780
          ************************************************************
```

FIGURE 2 (continued)

```
S288C     CAACATTTGGTTATCTCTAATATTACAGATGAACATGTTGCTGGAATAAAATCTATTTTA 3840
PDM-2     CAACATTTGGTTATCTCTAATATTACAGATGAACATGTTGCTGGAATAAAATCTATTTTA 3837
EF058187  CAACATTTGGTTATCTCTAATATTACAGATGAACATGTTGCTGGAATAAAATCTATTTTA 3840
EF058185  CAACATTTGGTTATCTCTAATATTACAGATGAACATGTTGCTGGAATAAAATCTATTTTA 3840
EF058186  CAACATTTGGTTATCTCTAATATTACAGATGAACATGTTGCTGGAATAAAATCTATTTTA 3840
EF058188  CAACATTTGGTTATCTCTAATATTACAGATGAACATGTTGCTGGAATAAAATCTATTTTA 3840
PDM-1     CAACATTTGGTTATCTCTAATATTACAGATGAACATGTTGCTGGAATAAAATCTATTTTA 3840
          ************************************************************

S288C     AAGACCTATAAATTGGATAACACCGATTTCAGCGGTTTGAGATTATCTTCATCTTCCTGT 3900
PDM-2     AAGACCTATAAATTGGATAACACCGATTTCAGCGGTTTGAGATTATCTTCATCTTCCTGT 3897
EF058187  AAGACCTATAAATTGGATAACACCGATTTCAGCGGTTTGAGATTATCTTCATCTTCCTGT 3900
EF058185  AAGACCTATAAATTGGATAACACCGATTTCAGCGGTTTGAGATTATCTTCATCTTCCTGT 3900
EF058186  AAGACCTATAAATTGGATAACACCGATTTCAGCGGTTTGAGATTATCTTCATCTTCCTGT 3900
EF058188  AAGACCTATAAATTGGATAACACCGATTTCAGCGGTTTGAGATTATCTTCATCTTCCTGT 3900
PDM-1     AAGACCTATAAATTGGATAACACCGATTTCAGCGGTTTGAGATTATCTTCATCTTCCTGT 3900
          ************************************************************

S288C     GTTGGTTTGCCAACATGTGGTTTAGCGTTTGCCGAATCTGAACGTTTCCTACCTGACATT 3960
PDM-2     GTTGGTTTGCCAACATGTGGTTTAGCGTTTGCCGAATCTGAACGTTTCCTACCTGACATT 3957
EF058187  GTTGGTTTGCCAACATGTGGTTTAGCGTTTGCCGAATCTGAACGTTTCCTACCTGACATT 3960
EF058185  GTTGGTTTGCCAACATGTGGTTTAGCGTTTGCCGAATCTGAACGTTTCCTACCTGACATT 3960
EF058186  GTTGGTTTGCCAACATGTGGTTTAGCGTTTGCCGAATCTGAACGTTTCCTACCTGACATT 3960
EF058188  GTTGGTTTGCCAACATGTGGTTTAGCGTTTGCCGAATCTGAACGTTTCCTACCTGACATT 3960
PDM-1     GTTGGTTTGCCAACATGTGGTTTAGCGTTTGCCGAATCTGAACGTTTCCTACCTGACATT 3960
          ************************************************************

S288C     ATTACTCAGTTGGAAGATTGTTTAGAAGAGTATGGTTTACGCCATGATTCCATTATTATG 4020
PDM-2     ATTACTCAGTTGGAAGATTGTTTAGAAGAGTATGGTTTACGCCATGATTCCATTATTATG 4017
EF058187  ATTACTCAGTTGGAAGATTGTTTAGAAGAGTATGGTTTACGCCATGATTCCATTATTATG 4020
EF058185  ATTACTCAGTTGGAAGATTGTTTAGAAGAGTATGGTTTACGCCATGATTCCATTATTATG 4020
EF058186  ATTACTCAGTTGGAAGATTGTTTAGAAGAGTATGGTTTACGCCATGATTCCATTATTATG 4020
EF058188  ATTACTCAGTTGGAAGATTGTTTAGAAGAGTATGGTTTACGCCATGATTCCATTATTATG 4020
PDM-1     ATTACTCAGTTGGAAGATTGTTTAGAAGAGTATGGTTTACGCCATGATTCCATTATTATG 4020
          ************************************************************

S288C     AGAATGACTGGTTGCCCTAACGGTTGTTCTCGTCCATGGCTAGGTGAATTAGCTCTTGTT 4080
PDM-2     AGAATGACTGGTTGCCCTAACGGTTGTTCTCGTCCATGGTTAGGTGAATTAGCTCTTGTT 4077
EF058187  AGAATGACTGGTTGCCCTAACGGTTGTTCTCGTCCATGGCTAGGTGAATTAGCTCTTGTT 4080
EF058185  AGAATGACTGGTTGCCCTAACGGTTGTTCTCGTCCATGGCTAGGTGAATTAGCTCTTGTT 4080
EF058186  AGAATGACTGGTTGCCCTAACGGTTGTTCTCGTCCATGGCTAGGTGAATTAGCTCTTGTT 4080
EF058188  AGAATGACTGGTTGCCCTAACGGTTGTTCTCGTCCATGGCTAGGTGAATTAGCTCTTGTT 4080
PDM-1     AGAATGACTGGTTGCCCTAACGGTTGTTCTCGTCCATGGCTAGGTGAATTAGCTCTTGTT 4080
          *************************************** *******************

S288C     GGTAAAGCTCCACATACTTATAACTTGATGCTTGGTGGTGGTTACCTCGGCCAAAGGCTA 4140
PDM-2     GGTAAAGCTCCACATACTTATAACTTGATGCTTGGTGGTGGTTACCTCGGCCAAAGGCTA 4137
EF058187  GGTAAAGCTCCACATACTTATAACTTGATGCTTGGTGGTGGTTACCTCGGCCAAAGGCTA 4140
EF058185  GGTAAAGCTCCACATACTTATAACTTGATGCTTGGTGGTGGTTACCTCGGCCAAAGGCTA 4140
EF058186  GGTAAAGCTCCACATACTTATAACTTGATGCTTGGTGGTGGTTACCTCGGCCAAAGGCTA 4140
EF058188  GGTAAAGCTCCACATACTTATAACTTGATGCTTGGTGGTGGTTACCTCGGCCAAAGGCTA 4140
PDM-1     GGTAAAGCTCCACATACTTATAACTTGATGCTTGGTGGTGGTTACCTCGGCCAAAGGCTA 4140
          ************************************************************

S288C     AACAAATTGTATAAGGCCAATGTGAAGGATGAGGAAATTGTCGACTACATCAAACCATTG 4200
PDM-2     AACAAATTGTATAAGGCCAATGTGAAGGATGAGGAAATTGTCGACTACATCAAACCATTG 4197
EF058187  AACAAATTGTATAAGGCCAATGTGAAGGATGAGGAAATTGTCGACTACATCAAACCATTG 4200
EF058185  AACAAATTGTATAAGGCCAATGTGAAGGATGAGGAAATTGTCGACTACATCAAACCATTG 4200
EF058186  AACAAATTGTATAAGGCCAATGTGAAGGATGAGGAAATTGTCGACTACATCAAACCATTG 4200
EF058188  AACAAATTGTATAAGGCCAATGTGAAGGATGAGGAAATTGTCGACTACATCAAACCATTG 4200
PDM-1     AACAAATTGTATAAGGCCAATGTGAAGGATGAGGAAATTGTCGACTACATCAAACCATTG 4200
          ************************************************************
```

FIGURE 2 (continued)

```
S288C      TTTAAAAGGTATGCTTTAGAAAGAGAAGAAGGGGAACACTTTGGTGATTTCTGTATAAGA 4260
PDM-2      TTTAAAAGGTATGCTTTAGAAAGAGAAGAAGGGGAACACTTTGGTGATTTCTGTATAAGA 4257
EF058187   TTTAAAAGGTATGCTTTAGAAAGAGAAGAAGGGGAACACTTTGGTGATTTCTGTATAAGA 4260
EF058185   TTTAAAAGGTATGCTTTAGAAAGAGAAGAAGGGGAACACTTTGGTGATTTCTGTATAAGA 4260
EF058186   TTTAAAAGGTATGCTTTAGAAAGAGAAGAAGGGGAACACTTTGGTGATTTCTGTATAAGA 4260
EF058188   TTTAAAAGGTATGCTTTAGAAAGAGAAGAAGGGGAACACTTTGGTGATTTCTGTATAAGA 4260
PDM-1      TTTAAAAGGTATGCTTTAGAAAGAGAAGAAGGGGAACACTTTGGTGATTTCTGTATAAGA 4260
           ************************************************************

S288C      GTAGGTATCATTAAACCAACCACCGAGGGTAAATACTTCCATGAAGATGTGTCTGAAGAT 4320
PDM-2      GTAGGTATCATTAAACCAACCACCGAGGGTAAATACTTCCATGAAGATGTGTCTGAAGAT 4317
EF058187   GTAGGTATCATTAAACCAACCACCGAGGGTAAATACTTCCATGAAGATGTGTCTGAAGAT 4320
EF058185   GTAGGTATCATTAAACCAACCACCGAGGGTAAATACTTCCATGAAGATGTGTCTGAAGAT 4320
EF058186   GTAGGTATCATTAAACCAACCACCGAGGGTAAATACTTCCATGAAGATGTGTCTGAAGAT 4320
EF058188   GTAGGTATCATTAAACCAACCACCGAGGGTAAATACTTCCATGAAGATGTGTCTGAAGAT 4320
PDM-1      GTAGGTATCATTAAACCAACCACCGAGGGTAAATACTTCCATGAAGATGTGTCTGAAGAT 4320
           ************************************************************

S288C      GCCTATTAA 4329
PDM-2      GCCTATTAA 4326
EF058187   GCCTATTAA 4329
EF058185   GCCTATTAA 4329
EF058186   GCCTATTAA 4329
EF058188   GCCTATTAA 4329
PDM-1      GCCTATTAA 4329
           *********
```

FIGURE 2 (continued)

```
S288C      MTASDLLTLPQLLAQYSSSAPQNKVFYTTSTKNSHSSFKGLESVATDATHLLNNQDPLNT 60
PDM-2      MTASDLLTLPQLLAQYSSSAPQNKVFYTTSTKNSHSSFKGLESVATDATHLLNNQDPLNT 60
ABK59399   MTASDLLTLPQLLAQYSSSAPQNKVFYTTSTKNSHSSFKGLESVATDATHLLNNQDPLNT 60
ABK59398   MTASDLLTLPQLLAQYSSSAPQNKVFYTTSTKNSHSSFKGLESVATDATHLLNNQDPLNT 60
ABK59396   MTASDLLTLPQLLAQYSSSAPQNKVFYTTSTKNSHSSFKGLESVATDATHLLNNQDPLNT 60
ABK59397   MTASDLLTLPQLLAQYSSSAPQNKVFYTTSTKNSHSSFKGLESVATDATHLLNNQDPLNT 60
PDM-1      MTASDLLTLPQLLAQYSSSAPQNKVFYTTSTKNSHSSFKGLESVATDATHLLNNQDPLNT 60
           ************************************************************

S288C      IKDQLSKDILTTVFTDETTLVKSIHHLYSLPNKLPLVITVDLNLQDYSAIPALKDLSFPI 120
PDM-2      IKDQLSKDILTTVFTDETTLVKSIHHLYSLPNKLPLVITVDLNLQDYSAIPALKDLSFPI 120
ABK59399   IKDQLSKDILTTVFTDETTLVKSIHHLYSLPNKLPLVITVDLNLQDYSAIPALKDLSFPI 120
ABK59398   IKDQLSKDILTTVFTDETTLVKSIHHLYSLPNKLPLVITVDLNLQDYSAIPALKDLSFPI 120
ABK59396   IKDQLSKDILTTVFTDETTLVKSIHHLYSLPNKLPLVITVDLNLQDYSAIPALKDLSFPI 120
ABK59397   IKDQLSKDILTTVFTDETTLVKSIHHLYSLPNKLPLVITVDLNLQDYSAIPALKDLSFPI 120
PDM-1      IKDQLSKDILTTVFTDETTLVKSIHHLYSLPNKLPLVITVDLNLQDYSAIPALKDLSFPI 120
           ************************************************************

S288C      LISSDLQTAISNADSSYKIATSSLTPVFHFLNLEKIGTSTAIEQDIDFPTLEIANEETKV 180
PDM-2      LISSDLQTAISNADSSYKIATSSLTPVFHFLNLEKIGTSTAIEQDIDFPTLEIANEETKV 180
ABK59399   LISSDLQTAISNADSSYKIATSSLTPVFHFLNLEKIGTSTAIEQDIDFPTLEIANEETKV 180
ABK59398   LISSDLQTAISNADSSYKIATSSLTPVFHFLNLEKIGTSTAIEQDIDFPTLEIANEETKV 180
ABK59396   LISSDLQTAISNADSSYKIATSSLTPVFHFLNLEKIGTSTAIEQDIDFPTLEIANEETKV 180
ABK59397   LISSDLQTAISNADSSYKIATSSLTPVFHFLNLEKIGTSTAIEQDIDFPTLEIANEETKV 180
PDM-1      LISSDLQTAISNADSSYKIATSSLTPVFHFLNLEKIGTSTAIEQDIDFPTLEIANEETKV 180
           ************************************************************

S288C      ALSEATDSLTNFELVKGKESITTVIVNLSPYDAEFSSVLPSNVGLIKIRVYRPWNFSKFL 240
PDM-2      ALSEATDSLTNFELVKGKESITTVIVNLSPYDAEFSSVLPSNVGLIKIRVYRPWNFSKFL 240
ABK59399   ALSEATDSLTNFELVKGKESITTVIVNLSPYDAEFSSVLPSNVGLIKIRVYRPWNFSKFL 240
ABK59398   ALSEATDSLTNFELVKGKESITTVIVNLSPYDAEFSSVLPSNVGLIKIRVYRPWNFSKFL 240
ABK59396   ALSEATDSLTNFELVKGKESITTVIVNLSPYDAEFSSVLPSNVGLIKIRVYRPWNFSKFL 240
ABK59397   ALSEATDSLTNFELVKGKESITTVIVNLSPYDAEFSSVLPSNVGLIKIRVYRPWNFSKFL 240
PDM-1      ALSEATDSLTNFELVKGKESITTVIVNLSPYDAEFSSVLPSNVGLIKIRVYRPWNFSKFL 240
           ************************************************************

S288C      EILPSSVTKIAVLQGVSKKSQSNEFQPFLLDFFGNFNELVSRNIEQVVLTNIGNVNDYGN 300
PDM-2      EILPSSVTKIAVLQGVSKKSQSNEFQPFLLDFFGNFNELVSRNIEQ-VLTNIGNVNDYGN 299
ABK59399   EILPSSVTKIAVLQGVSKKSQSNEFQPFLLDFFGNFNELVSRNIEQVVLTNIGNVNDYGN 300
ABK59398   EILPSSVTKIAVLQGVSKKSQSNEFQPFLLDFFGNFNELVSRNIEQVVLTNIGNVNDYGN 300
ABK59396   EILPSSVTKIAVLQGVSKKSQSNEFQPFLLDFFGNFNELVSRNIEQVVLTNIGNVNDYGN 300
ABK59397   EILPSSVTKIAVLQGVSKKSQSNEFQPFLLDFFGNFNELVSRNIEQVVLTNIGNVNDYGN 300
PDM-1      EILPSSVTKIAVLQGVSKKSQSNEFQPFLLDFFGNFNELVSRNIEQVVLTNIGNVNDYGN 300
           ********************************************** *************

S288C      VINTVISNINKKEPDNNLFLGESNEKAEEQAEVTQLISSVKKVVNLEDAYIKVLKQLFSS 360
PDM-2      VINTVISNINKKEPDNNLFLGESNEKAEEQAEVTQLISSVKKVVNLEDAYIKVLKQLFSS 359
ABK59399   VINTVISNINKKEPDNNLFLGESNEKAEEQAEVTQLISSVKKVVNLEDAYIKVLKQLFSS 360
ABK59398   VINTVISNINKKEPDNNLFLGESNEKAEEQAEVTQLISSVKKVVNLEDAYIKVLKQLFSS 360
ABK59396   VINTVISNINKKEPDNNLFLGESNEKAEEQAEVTQLISSVKKVVNLEDAYIKVLKQLFSS 360
ABK59397   VINTVISNINKKEPDNNLFLGESNEKAEEQAEVTQLISSVKKVVNLEDAYIKVLKQLFSS 360
PDM-1      VINTVISNINKKEPDNNLFLGESNEKAEEQAEVTQLISSVKKVVNLEDAYIKVLKQLFSS 360
           ************************************************************

S288C      NLQILNQFSSETIEPSNPEFGFGRFLKQEAQREELISLAKTSLDPSLYLSEDANKIVQLL 420
PDM-2      NLQILNQFSSETIEPSNPEFGFGRFLKQEAQREELISLAKTSLDPSLYLSEDANKIVQLL 419
ABK59399   NLQILNQFSSETIEPSNPEFGFGRFLKQEAQREELISLAKTSLDPSLYLSEDANKIVQLL 420
ABK59398   NLQILNQFSSETIEPSNPEFGFGRFLKQEAQREELISLAKTSLDPSLYLSEDANKIVQLL 420
ABK59396   NLQILNQFSSETIEPSNPEFGFGRFLKQEAQREELISLAKTSLDPSLYLSEDANKIVQLL 420
ABK59397   NLQILNQFSSETIEPSNPEFGFGRFLKQEAQREELISLAKTSLDPSLYLSEDANKIVQLL 420
PDM-1      NLQILNQFSSETIEPSNPEFGFGRFLKQEAQREELISLAKTSLYPSLYLSEDANKIVQLL 420
           ******************************************* ****************
```

FIGURE 3

```
S288C      SKWLSFNGRDLDEAQLQEANATGLEIFQLLQSNQDSSTVLKFLKIAPTSDSFIFKSSWLI 480
PDM-2      SKWLSFNGRDLDEAQLQEANATGLEIFQLLQSNQDSSTVLKFLKIAPTSDSFIFKSSWLI 479
ABK59399   SKWLSFNGRDLDEAQLQEANATGLEIFQLLQSNQDSSTVLKFLKIAPTSDSFIFKSSWLI 480
ABK59398   SKWLSFNGRDLDEAQLQEANATGLEIFQLLQSNQDSSTVLKFLKIAPTSDSFIFKSSWLI 480
ABK59396   SKWLSFNGRDLDEAQLQEANATGLEIFQLLQSNQDSSTVLKFLXIAPTSDSFIFKSSWLI 480
ABK59397   SKWLSFNGRDLDEAQLQEANATGLEIFQLLQSNQDSSTVLKFLKIAPTSDSFIFKSSWLI 480
PDM-1      SKWLSFNGRDLDEAQLQEANATGLEIFQLLQSNQDSSTVLKFLKIAPTSDSFIFKSSWLI 480
           ******************************************  ***************

S288C      GSDAWSYDLGHSGIQQVLSSRKNINVLLIDSEPYDHRKQNQDRKKDVGLYAMNYYSAYVA 540
PDM-2      GSDAWSYDLGHSGIQQVLSSRKNINVLLIDSEPYDHRKQNQDRKKDVGLYAMNYYSAYVA 539
ABK59399   GSDAWSYDLGHSGIQQVLSSRKNINVLLIDSEPYDHRKQNQDRKKDVGLYAMNYYSAYVA 540
ABK59398   GSDAWSYDLGHSGIQQVLSSRKNINVLLIDSEPYDHRKQNQDRKKDVGLYAMNYYSAYVA 540
ABK59396   GSDAWSYDLGHSGIQQVLSSRKNINVLLIDSEPYDHRKQNQDRKKDVGLYAMNYYSAYVA 540
ABK59397   GSDAWSYDLGHSGIQQVLSSRKNINVLLIDSEPYDHRKQNQDRKKDVGLYAMNYYSAYVA 540
PDM-1      GSDAWSYDLGHSGIQQVLSSRKNINVLLIDSEPYDHRKQNQDRKKDVGLYAMNYYSAYVA 540
           ************************************************************

S288C      SVAVYASYTQLLTAIIEASKYNGPSIVLAYLPYNSENDTPLEVLKETKNAVESGYWPLYR 600
PDM-2      SVAVYASYTQLLTAIIEASKYNGPSIVLAYLPYNSENDTPLEVLKETKNAVESGYWPLYR 599
ABK59399   SVAVYASYTQLLTAIIEASKYNGPSIVLAYLPYNSENDTPLEVLKETKNAVESGYWPLYR 600
ABK59398   SVAVYASYTQLLTAIIEASKYNGPSIVLAYLPYNSENDTPLEVLKETKNAVESGYWPLYR ·600
ABK59396   SVAVYASYTQLLTAIIEASKYNGPSIVLAYLPYNSENDTPLEVLKETKNAVESGYWPLYR 600
ABK59397   SVAVYASYTQLLTAIIEASKYNGPSIVLAYLPYNSENDTPLEVLKETKNAVESGYWPLYR 600
PDM-1      SVAVYASYTQLLTAIIEASKYNGPSIVLAYLPYNSENDTPLEVLKETKNAVESGYWPLYR 600
           ************************************************************

S288C      FNPVYDDPSTDKEAFSLDSSVIRKQLQDFLDRENKLTLLTRKDPSLSRNLKQSAGDALTR 660
PDM-2      FNPVYDDPSTDKEAFSLDSSVIRKQLQDFLDRENKLTLLTRKDPSLSRNLKQSAGDALTR 659
ABK59399   FNPVYDDPSTDKEAFSLDSSVIRKQLQDFLDRENKLTLLTRKDPSLSRNLKQSAGDALTR 660
ABK59398   FNPVYDDPSTDKEAFSLDSSVIRKQLQDFLDRENKLTLLTRKDPSLSRNLKQSAGDALTR 660
ABK59396   FNPVYDDPSTDKEAFSLDSSVIRKQLQDFLDRENKLTLLTRKDPSLSRNLKQSAGDALTR 660
ABK59397   FNPVYDDPSTDKEAFSLDSSVIRKQLQDFLDRENKLTLLTRKDPSLSRNLKQSAGDALTR 660
PDM-1      FNPVYDDPSTDKEAFSLDSSVIRKQLQDFLDRENKLTLLTRKDPSLSRNLKQSAGDALTR 660
           ************************************************************

S288C      KQEKRSKAAFDQLLEGLSGPPLHVYYASDGGNAANLAKRLAARASARGLKATVLSMDDII 720
PDM-2      KQEKRSKAAFDQLLEGLSGPPLHVYYASDGGNAANLAKRLAARASARGLKATVLSMDDII 719
ABK59399   KQEKRSKAAFDQLLEGLSGPPLHVYYASDGGNAANLAKRLAARASARGLKATVLSMDDII 720
ABK59398   KQEKRSKAAFDQLLEGLSGPPLHVYYASDGGNAANLAKRLAARASARGLKATVLSMDDII 720
ABK59396   KQEKRSKAAFDQLLEGLSGPPLHVYYASDGGNAANLAKRLAARASARGLKATVLSMDDII 720
ABK59397   KQEKRSKAAFDQLLEGLSGPPLHVYYASDGGNAANLAKRLAARASARGLKATVLSMDDII 720
PDM-1      KQEKRSKAAFDQLLEGLSGPPLHVYYASDGGNAANLAKRLAARASARGLKATVLSMDDII 720
           ************************************************************

S288C      LEELPGEENVVFITSTAGQGEFPQDGKSFWEALKNDTDLDLASLNVAVFGLGDSEYWPRK 780
PDM-2      LEELPGEENVVFITSTAGQGEFPQDGKSFWEALKNDTDLDLASLNVAVFGLGDSEYWPRK 779
ABK59399   LEELPGEENVVFITSTAGQGEFPQDGKSFWEALKNDTDLDLASLNVAVFGLGDSEYWPRK 780
ABK59398   LEELPGEENVVFITSTAGQGEFPQDGKSFWEALKNDTDLDLASLNVAVFGLGDSEYWPRK 780
ABK59396   LEELPGEENVVFITSTAGQGEFPQDGKSFWEALKNDTDLDLASLNVAVFGLGDSEYWPRK 780
ABK59397   LEELPGEENVVFITSTAGQGEFPQDGKSFWEALKNDTDLDLASLNVAVFGLGDSEYWPRK 780
PDM-1      LEELPGEENVVFITSTAGQGEFPQDGKSFWEALKNDTDLDLASLNVAVFGLGDSEYWPRK 780
           ************************************************************

S288C      EDKHYFNKPSQDLFKRLELLSAKALIPLGLGDDQDADGFQTAYSEWEPKLWEALGVSGAA 840
PDM-2      EDKHYFNKPSQDLFKRLELLSAKALIPLGLGDDQDADGFQTAYSEWEPKLWEALGVSGAA 839
ABK59399   EDKHYFNKPSQDLFKRLELLSAKALIPLGLGDDQDADGFQTAYSEWEPKLWEALGVSGAA 840
ABK59398   EDKHYFNKPSQDLFKRLELLSAKALIPLGLGDDQDADGFQTAYSEWEPKLWEALGVSGAA 840
ABK59396   EDKHYFNKPSQDLFKRLELLSAKALIPLGLGDDQDADGFQTAYSEWEPKLWEALGVSGAA 840
ABK59397   EDKHYFNKPSQDLFKRLELLSAKALIPLGLGDDQDADGFQTAYSEWEPKLWEALGVSGAA 840
PDM-1      EDKHYFNKPSQDLFKRLELLSAKALIPLGLGDDQDADGFQTAYSEWEPKLWEALGVSGAA 840
           ************************************************************
```

FIGURE 3 (continued)

```
S288C       VDDEPKPVTNEDIKRESNFLRGTISENLKDTSSGGVTHANEQLMKFHGIYTQDDRDIREI 900
PDM-2       VDDEPKPVTNEDIKRESNFLRGTISENLKDTSSGGVTHANEQLMKFHGIYTQDDRDIREI 899
ABK59399    VDDEPKPVTNEDIKRESNFLRGTISENLKDTSSGGVTHANEQLMKFHGIYTQDDRDIREI 900
ABK59398    VDDEPKPVTNEDIKRESNFLRGTISENLKDTSSGGVTHANEQLMKFHGIYTQDDRDIREI 900
ABK59396    VDDEPKPVTNEDIKRESNFLRGTISENLKDTSSGGVTHANEQLMKFHGIYTQDDRDIREI 900
ABK59397    VDDEPKPVTNEDIKRESNFLRGTISENLKDTSSGGVTHANEQLMKFHGIYTQDDRDIREI 900
PDM-1       VDDEPKPVTNEDIKRESNFLRGTISENLKDTSSGGVTHANEQLMKFHGIYTQDDRDIREI 900
            ************************************************************

S288C       RKSQGLEPYYMFMARARLPGGKTTPQQWLALDHLSDTSGNGTLKLTTRATFQIHGVLKKN 960
PDM-2       RKSQGLEPYYMFMARARLPGGKTTPQQWLALDHLSDTSGNGTLKLTTRATFQIHGVLKKN 959
ABK59399    RKSQGLEPYYMFMARARLPGGKTTPQQWLALDHLSDTSGNGTLKLTTRATFQIHGVLKKN 960
ABK59398    RKSQGLEPYYMFMARARLPGGKTTPQQWLALDHLSDTSGNGTLKLTTRATFQIHGVLKKN 960
ABK59396    RKSQGLEPYYMFMARARLPGGKTTPQQWLALDHLSDTSGNGTLKLTTRATFQIHGVLKKN 960
ABK59397    RKSQGLEPYYMFMARARLPGGKTTPQQWLALDHLSDTSGNGTLKLTTRATFQIHGVLKKN 960
PDM-1       RKSQGLEPYYMFMARARLPGGKTTPQQWLALDHLSDTSGNGTLKLTTRATFQIHGVLKKN 960
            ************************************************************

S288C       LKHTLRGMNAVLMDTLAAAGDVNRNVMVSALPTNAKVHQQIADMGKLISDHFLPKTTAYH 1020
PDM-2       LKHTLRGMNAVLMDTLAAAGDVNRNVMVSALPTNAKVHQQIADMGKLISDHFLPKTTAYH 1019
ABK59399    LKHTLRGMNAVLMDTLAAAGDVNRNVMVSALPTNAKVHQQIADMGKLISDHFLPKTTAYH 1020
ABK59398    LKHTLRGMNAVLMDTLAAAGDVNRNVMVSALPTNAKVHQQIADMGKLISDHFLPKTTAYH 1020
ABK59396    LKHTLRGMNAVLMDTLAAAGDVNRNVMVSALPTNAKVHQQIADMGKLISDHFLPKTTAYH 1020
ABK59397    LKHTLRGMNAVLMDTLAAAGDVNRNVMVSALPTNAKVHQQIADMGKLISDHFLPKTTAYH 1020
PDM-1       LKHTLRGMNAVLMDTLAAAGDVNRNVMVSALPTNAKVHQQIADMGKLISDHFLPKTTAYH 1020
            ************************************************************

S288C       EVWLEGPEEQDDDPSWPSIFENRKDGPRKKKTLVSGNALVDIEPIYGPTYLPRKFKFNIA 1080
PDM-2       EVWLEGPEEQDDDPSWPSIFENRKDGPRKKKTLVSGNALVDIEPIYGPTYLPRKFKFNIA 1079
ABK59399    EVWLEGPEEQDDDPSWPSIFENRKDGPRKKKTLVSGNALVDIEPIYGPTYLPRKFKFNIA 1080
ABK59398    EVWLEGPEEQDDDPSWPSIFENRKDGPRKKKTLVSGNALVDIEPIYGPTYLPRKFKFNIA 1080
ABK59396    EVWLEGPEEQDDDPSWPSIFENRKDGPRKKKTLVSGNALVDIEPIYGPTYLPRKFKFNIA 1080
ABK59397    EVWLEGPEEQDDDPSWPSIFENRKDGPRKKKTLVSGNALVDIEPIYGPTYLPRKFKFNIA 1080
PDM-1       EVWLEGPEEQDDDPSWPSIFENRKDGPRKKKTLVSGNALVDIEPIYGPTYLPRKFKFNIA 1080
            ************************************************************

S288C       VPPYNDVDVLSIDVGLVAIVNPETQIVEGYNVFVGGGMGTTHNNKKTYPRLGSCLGFVKT 1140
PDM-2       VPPYNDVDVLSIDVGLVAIVNPETQIVEGYNVFVGGGMGTTHNNKKTYPRLGSCLGFVKT 1139
ABK59399    VPPYNDVDVLSIDVGLVAIVNPETQIVEGYNVFVGGGMGTTHNNKKTYPRLGSCLGFVKT 1140
ABK59398    VPPYNDVDVLSIDVGLVAIVNPETQIVEGYNVFVGGGMGTTHNNKKTYPRLGSCLGFVKT 1140
ABK59396    VPPYNDVDVLSIDVGLVAIVNPETQIVEGYNVFVGGGMGTTHNNKKTYPRLGSCLGFVKT 1140
ABK59397    VPPYNDVDVLSSDVGLVAIVNPETQIVEGYNVFVGGGMGTTHNNKKTYPRLGSCLGFVKT 1140
PDM-1       VPPYNDVDVLSIDVGLVAIVNPKTQIVEGYNVFVGGGMGTTHNNKKTYPRLGSCLGFVKT 1140
            ********** ********** :*************************************

S288C       EDIIPPLEGIVIVQRDHGDRKDRKHARLKYTVDDMGVEGFKQKVEEYWGKKFEPERPFEF 1200
PDM-2       EDIIPPLEGIVIVQRDHGDRKDRKHARLKYTVDDMGVEGFKQKVEEYWGKKFEPERPFEF 1199
ABK59399    EDIIPPLEGIVIVQRDHGDRKDRKHARLKYTVDDMGVEGFKQKVEEYWGKKFEPERPFEF 1200
ABK59398    EDIIPPLEGIVIVQRDHGDRKDRKHARLKYTVDDMGVEGFKQKVEEYWGKKFEPERPFEF 1200
ABK59396    EDIIPPLEGIVIVQRDHGDRKDRKHARLKYTVDDMGVEGFKQKVEEYWGKKFEPERPFEF 1200
ABK59397    EDIIPPLEGIVIVQRDHGDRKDRKHARLKYTVDDMGVEGFKQKVEEYWGKKFEPERPFEF 1200
PDM-1       EDIIPPLEGIVIVQRDHGDRKDRKHARLKYTVDDMGVEGFKQKVEEYWGKKFEPERPFEF 1200
            ************************************************************

S288C       KSNIDYFGWIKDETGLNHFTAFIENGRVEDTPDLPQKTGIRKVAEYMLKTNSGHFRLTGN 1260
PDM-2       KSNIDYFGWIKDETGLNHFTAFIENGRVEDTPDLPQKTGIRKVAEYMLKTNSGHFRLTGN 1259
ABK59399    KSNIDYFGWIKDETGLNHFTAFIENGXVEDTPDLPQKTGIRKVAEYMLKTNSGHFRLTGN 1260
ABK59398    KSNIDYFGWIKDETGLNHFTALIENGRVEDTPDLPQKTGIRKVAEYMLKTNSGHFRLTGN 1260
ABK59396    KSNIDYFGWIKDETGLNHFTAFIENGRVEDTPDLPQKTGIRKVAEYMLKTNSGHFRLTGN 1260
ABK59397    KSNIDYFGWIKDETGLNHFTAFIENGRVEDTPDLPQKTGIRKVAEYMLKTNSGHFRLTGN 1260
PDM-1       KSNIDYFGWIKDETGLNHFTAFIENGRVEDTPDLPQKTGIRKVAEYMLKTNSGHFRLTGN 1260
            ********************* :**** ********************************
```

FIGURE 3 (continued)

```
S288C     QHLVISNITDEHVAGIKSILKTYKLDNTDFSGLRLSSSSCVGLPTCGLAFAESERFLPDI  1320
PDM-2     QHLVISNITDEHVAGIKSILKTYKLDNTDFSGLRLSSSSCVGLPTCGLAFAESERFLPDI  1319
ABK59399  QHLVISNITDEHVAGIKSILKTYKLDNTDFSGLRLSSSSCVGLPTCGLAFAESERFLPDI  1320
ABK59398  QHLVISNITDEHVAGIKSILKTYKLDNTDFSGLRLSSSSCVGLPTCGLAFAESERFLPDI  1320
ABK59396  QHLVISNITDEHVAGIKSILKTYKLDNTDFSGLRLSSSSCVGLPTCGLAFAESERFLPDI  1320
ABK59397  QHLVISNITDEHVAGIKSILKTYKLDNTDFSGLRLSSSSCVGLPTCGLAFAESERFLPDI  1320
PDM-1     QHLVISNITDEHVAGIKSILKTYKLDNTDFSGLRLSSSSCVGLPTCGLAFAESERFLPDI  1320
          ************************************************************

S288C     ITQLEDCLEEYGLRHDSIIMRMTGCPNGCSRPWLGELALVGKAPHTYNLMLGGGYLGQRL  1380
PDM-2     ITQLEDCLEEYGLRHDSIIMRMTGCPNGCSRPWLGELALVGKAPHTYNLMLGGGYLGQRL  1379
ABK59399  ITQLEDCLEEYGLRHDSIIMRMTGCPNGCSRPWLGELALVGKAPHTYNLMLGGGYLGQRL  1380
ABK59398  ITQLEDCLEEYGLRHDSIIMRMTGCPNGCSRPWLGELALVGKAPHTYNLMLGGGYLGQRL  1380
ABK59396  ITQLEDCLEEYGLRHDSIIMRMTGCPNGCSRPWLGELALVGKAPHTYNLMLGGGYLGQRL  1380
ABK59397  ITQLEDCLEEYGLRHDSIIMRMTGCPNGCSRPWLGELALVGKAPHTYNLMLGGGYLGQRL  1380
PDM-1     ITQLEDCLEEYGLRHDSIIMRMTGCPNGCSRPWLGELALVGKAPHTYNLMLGGGYLGQRL  1380
          ************************************************************

S288C     NKLYKANVKDEEIVDYIKPLFKRYALEREEGEHFGDFCIRVGIIKPTTEGKYFHEDVSED  1440
PDM-2     NKLYKANVKDEEIVDYIKPLFKRYALEREEGEHFGDFCIRVGIIKPTTEGKYFHEDVSED  1439
ABK59399  NKLYKANVKDEEIVDYIKPLFKRYALEREEGEHFGDFCIRVGIIKPTTEGKYFHEDVSED  1440
ABK59398  NKLYKANVKDEEIVDYIKPLFKRYALEREEGEHFGDFCIRVGIIKPTTEGKYFHEDVSED  1440
ABK59396  NKLYKANVKDEEIVDYIKPLFKRYALEREEGEHFGDFCIRVGIIKPTTEGKYFHEDVSED  1440
ABK59397  NKLYKANVKDEEIVDYIKPLFKRYALEREEGEHFGDFCIRVGIIKPTTEGKYFHEDVSED  1440
PDM-1     NKLYKANVKDEEIVDYIKPLFKRYALEREEGEHFGDFCIRVGIIKPTTEGKYFHEDVSED  1440
          ************************************************************

S288C     AY  1442
PDM-2     AY  1441
ABK59399  AY  1442
ABK59398  AY  1442
ABK59396  AY  1442
ABK59397  AY  1442
PDM-1     AY  1442
          **
```

FIGURE 3 (continued)

```
D44610   AAGCTTTATATTCTCGACAGAAAGGGGACTTTCTTTGTGGAAGACTTTGCATATGGCTTG  60
S288C    ------------------------------------------------------------
PDM-1    ------------------------------------------------------------
PDM-2    ------------------------------------------------------------

D44610   CCCCAATCTCGCGAAATCACCAAATGTAAGCAAATATTCCACAAATAATGCATCTAAATA  120
S288C    ------------------------------------------------------------
PDM-1    ------------------------------------------------------------
PDM-2    ------------------------------------------------------------

D44610   TATACGTATGTTTAAGGTTCTGGTATACAGGTATTAAAAGAAAACACTATCAACATTCCG  180
S288C    ------------------------------------------------------------
PDM-1    ------------------------------------------------------------
PDM-2    ------------------------------------------------------------

D44610   AATAAGATATACCACACCACGTGAGCTTATAGAAGCACGTGACCACAATTCACCCCACAG  240
S288C    ------------------------------------------------------------
PDM-1    ------------------------------------------------------------
PDM-2    ------------------------------------------------------------

D44610   GTGTGGCTTTTTTGGTGCCGTAGAAAAGACTCATTCATGAATCGTCGGAAACCCATAGTC  300
S288C    ------------------------------------------------------------
PDM-1    ------------------------------------------------------------
PDM-2    ------------------------------------------------------------

D44610   ATCTTCGAGCAAAAGGTATATATAAGCAACAGAGGGCAGTAGTTCTCGAGACCACCATCT  360
S288C    ------------------------------------------------------------
PDM-1    ------------------------------------------------------------
PDM-2    ------------------------------------------------------------

D44610   TTTGATTGGAAATAGTTTCGTTTAGATGGGGTGCACATAGTTTTTTTCAACTGCTTTTCC  420
S288C    ------------------------------------------------------------
PDM-1    ------------------------------------------------------------
PDM-2    ------------------------------------------------------------

D44610   TCGAGGTCACCCAAATATACAACGAGATGCCAGTTGAGTTTGCTACCAATCCTTTTGGCG  480
S288C    ------------------------------ATGCCAGTTGAGTTTGCTACCAATCCTTTTGGCG  34
PDM-1    ------------------------------ATGCCAGTTGAGTTTGCTACCAATCCTTTTGGCG  34
PDM-2    ------------------------------ATGCCAGTTGAGTTTGCTACCAATCCTTTTGGCG  34
                                       **********************************

D44610   AGGCCAAAAATGCAACTTCACTGCCAAAATATGGTACACCCGTAACTGCCATTTCATCTG  540
S288C    AGGCCAAAAATGCAACTTCACTGCCAAAATATGGTACACCCGTAACTGCCATTTCATCTG  94
PDM-1    AGGCCAAAAATGCAACTTCACTGCCAAAATATGGTACACCCGTAACTGCCATTTCATCTG  94
PDM-2    AGGCCAAAAATGCAACTTCACTGCCAAAATATGGTACACCCGTAACTGCCATTTCATCTG  94
         ************************************************************

D44610   TGCTGTTCAATAACGTGGACTCCATTTTTGCTTACAAGTCCTTTTCTCAACCCGATTTGC  600
S288C    TGCTGTTCAATAACGTGGACTCCATTTTTGCTTACAAGTCCTTTTCTCAACCCGATTTGC  154
PDM-1    TGCTGTTCAATAACGTGGACTCCATTTTTGCTTACAAGTCCTTTTCTCAACCCGATTTGT  154
PDM-2    TGCTGTTCAATAACGTGGACTCCATTTTTGCTTACAAGTCCTTTTCTCAACCCGATTTGT  154
         ***********************************************************

D44610   TACACCAAGATCTAAAAAAATGGTCTGAAAAGCGTGGTAACGAATCACGTGGGAAGCCAT  660
S288C    TACACCAAGATCTAAAAAAATGGTCTGAAAAGCGTGGTAACGAATCACGTGGGAAGCCAT  214
PDM-1    TACACCAAGATCTAAAAAAATGGTCTGAAAAGCGTGGTAACGAATCACGTGGGAAGCCAT  214
PDM-2    TACACCAAGATCTAAAAAAATGGTCTGAAAAGCGTGGTAACGAATCACGTGGGAAGCCAT  214
         ************************************************************
```

FIGURE 4

```
D44610   TTTTCCAAGAGCTGGATATCAGATCTGGCGCTGGTTTGGCTCCTTTAGGGTTTTCTCATG  720
S288C    TTTTCCAAGAGCTGGATATCAGATCTGGCGCTGGTTTGGCTCCTTTAGGGTTTTCTCATG  274
PDM-1    TTTTCCAAGAGCTGGATATCAGATCTGGCGCTGGTTTGGCTCCTTTAGGGTTTTCTCATG  274
PDM-2    TTTTCCAAGAGCTGGATATCAGATCTGGCGCTGGTTTGGCTCCTTTAGGGTTTTCTCATG  274
         ************************************************************

D44610   GATTGAAGAACACTACAGCAATTGTTGCTCCAGGGTTTTCGCTGCCATACTTCATTAACT  780
S288C    GATTGAAGAACACTACAGCAATTGTTGCTCCAGGGTTTTCGCTGCCATACTTCATTAACT  334
PDM-1    GATTGAAGAACACTACAGCAATTGTTGCTCCAGGGTTTTCGCTGCCATACTTCATTAACT  334
PDM-2    GATTGAAGAACACTACAGCAATTGTTGCTCCAGGGTTTTCGCTGCCATACTTCATTAACT  334
         ************************************************************

D44610   CTTTGAAAACCGTCTCTCATGATGGTAAGTTTCTTTTGAATGTTGGTGCTTTAAACTACG  840
S288C    CTTTGAAAACCGTCTCTCATGATGGTAAGTTTCTTTTGAATGTTGGTGCTTTAAACTACG  394
PDM-1    CTTTGAAAACCGTCTCTCATGATGGTAAGTTTCTTTTGAATGTTGGTGCTTTAAACTACG  394
PDM-2    CTTTGAAAACCGTCTCTCATGATGGTAAGTTTCTTTTGAATGTTGGTGCTTTAAACTACG  394
         ************************************************************

D44610   ACAATGCTACCGGCTCTGTCACCAACGATTATGTAACCGCATTGGATGCTGCTTCCAAGC  900
S288C    ACAATGCTACCGGCTCTGTCACCAACGATTATGTAACCGCATTGGATGCTGCTTCCAAGC  454
PDM-1    ACAATGCTACCGGCTCTGTCACCAACGATTATGTAACCGCATTGGATGCTGCTTCCAAGC  454
PDM-2    ACAATGCTACCGGCTCTGTCACGAACGATTATGTAACCGCATTGGATGCTGCTTCCAAGC  454
         ********************** *************************************

D44610   TGAAGTATGGTGTCGTGACTCCGATTTCCGCTAACGAGGTACAAAGTGTCGCCTTACTGA  960
S288C    TGAAGTATGGTGTCGTGACTCCGATTTCCGCTAACGAGGTACAAAGTGTCGCCTTACTGG  514
PDM-1    TGAAGTATGGTGTCGTGACTCCGATTTCCGCTAACGAGGTACAAAGTGTCGCCTTACTGA  514
PDM-2    TGAAGTATGGTGTCGTGACTCCGATTTCCGCTAACGAGGTACAAAGTGTCGCCTTACTGG  514
         ***********************************************************

D44610   CATTGGCGATTGCCACTTTCAGTAATAACTCCGGAGCTATCAATTTATTTGACGGATTAA  1020
S288C    CATTGGCGATTGCCACTTTCAGTAATAACTCCGGAGCTATCAATTTATTTGACGGATTAA  574
PDM-1    CATTGGCGATTGCCACTTTCAGTAATAACTCCGGAGCTATCAATTTATTTGACGGATTAA  574
PDM-2    CATTGGCGATTGCCACTTTCAGTAATAACTCCGGAGCTATCAATTTATTTGACGGATTAA  574
         ************************************************************

D44610   ACTACTCGAAAACCGTCTTGCCGTTGGTCGAATCTGTTCCTGAGGCATCTATTTTGGCAA  1080
S288C    ACTACTCGAAAACCGTCTTGCCGTTGGTCGAATCTGTTCCTGAGGCATCTATTTTGGCAA  634
PDM-1    ACTACTCGAAAACCGTCTTGCCGTTGGTCGAATCTGTTCCTGAGGCATCTATTTTGGCAA  634
PDM-2    ACTACTCGAAAACCGTCTTGCCGTTGGTCGAATCTGTTCCTGAGGCATCTATTTTGGCAA  634
         ************************************************************

D44610   AACTATCCAAAGTTATTGCACCAGATGCTGCCTTTGATGATGTCTTGGATAAGTTTAATG  1140
S288C    AACTATCCAAAGTTATTGCACCAGATGCTGCCTTTGATGATGTCTTGGATAAGTTTAATG  694
PDM-1    AACTATCCAAAGTTATTGCACCAGATGCTGCCTTTGATGATGTCTTGGATAAGTTTAATG  694
PDM-2    AACTATCCAAAGTTATTGCACCAGATGCTGCCTTTGATGATGTCTTGGATAAGTTTAATG  694
         ************************************************************

D44610   AATTGACTGGATTGAGACTACATAATTTCCAATACTTTGGTGCTCAGGATGCTGAAACTG  1200
S288C    AATTGACTGGATTGAGACTACATAATTTCCAATACTTTGGTGCTCAGGATGCTGAAACTG  754
PDM-1    AATTGACTGGATTGAGACTACATAATTTCCAATACTTTGGTGCTCAGGATGCTGAAACTG  754
PDM-2    AATTGACTGGATTGAGACTACATAATTTCCAATACTTTGGTGCTCAGGATGCTGAAACTG  754
         ************************************************************

D44610   TGTTTATCACTTATGGGTCTTTAGAATCCGAATTGTTCAACTCTGCGATTAGTGGTAATA  1260
S288C    TGTTTATCACTTATGGGTCTTTAGAATCCGAATTGTTCAACTCTGCGATTAGTGGTAATA  814
PDM-1    TGTTTATCACTTATGGGTCTTTAGAATCCGAATTGTTCAACTCTGCGATTAGTGGTAATA  814
PDM-2    TGTTTATCACTTATGGGTCTTTAGAATCCGAATTGTTCAACTCTGCGATTAGTGGTAATA  814
         ************************************************************

D44610   ATTCCAAAATCGGGTTAATCAACGTCAGAGTACCATTACCTTTTAACGTTGCTAAGTTTG  1320
S288C    ATTCCAAAATCGGGTTAATCAACGTCAGAGTGCCATTACCTTTTAACGTTGCTAAGTTTG  874
PDM-1    ATTCCAAAATCGGGTTAATCAACGTCAGAGTACCATTACCTTTTAACGTTGCTAAGTTTG  874
PDM-2    ATTCCAAAATCGGGTTAATCAACGTCAGAGTACCATTACCTTTTAACGTTGCTAAGTTTG  874
         ******************************* ****************************
```

FIGURE 4 (continued)

```
D44610   TCACTCACGTTCCATCCACTACCAAACAAATTGTTGTTATAGGCCAAACTTTGGATGGTT 1380
S288C    TCACTCACGTTCCATCCACTACCAAACAAATTGTTGTTATAGGCCAAACTTTGGATGGTT 934
PDM-1    TCACTCACGTTCCATCCACTACCAAACAAATTGTTGTTATAGGCCAAACTTTGGATGGTT 934
PDM-2    TCACTCACGTTCCATCCACTACCAAACAAATTGTTGTTATAGGCCAAACTTTGGATGGTT 934
         ************************************************************

D44610   CTTCGCCTTCTTTCTTGAGATCTCAAGTTTCAGCCGCCTTATTTTACCACGGCCGCACCT 1440
S288C    CTTCGCCTTCTTTCTTGAGATCTCAAGTTTCAGCCGCCTTATTTTACCACGGCCGCACCT 994
PDM-1    CTTCGCCTTCTTTCTTGAGATCTCAAGTTTCAGCCGCCTTATTTTACCACGGCCGCACCT 994
PDM-2    CTTCGCCTTCTTTCTTGAGATCTCAAGTTTCAGCCGCCTTATTTTACCACGGCCGCACCT 994
         ************************************************************

D44610   CAATTAGCGTTTCTGAGTACATCTATCAACCAGATTTCATTTGGTCCCCAAAAGCTGTCA 1500
S288C    CAATTAGCGTTTCTGAGTACATCTATCAACCAGATTTCATTTGGTCCCCAAAAGCTGTCA 1054
PDM-1    CAATTAGCGTTTCTGAGTACATCTATCAACCAGATTTCATTTGGTCCCCAAAAGCTGTCA 1054
PDM-2    CAATTAGCGTTTCTGAGTACATCTATCAACCAGATTTCATTTGGTCCCCAAAAGCTGTCA 1054
         ************************************************************

D44610   AATCAATTGTATCGTCATTCATCCCTGAATTCACTTACAATGCCGATTCATCTTTCGGCG 1560
S288C    AATCAATTGTATCGTCATTCATCCCTGAATTCACTTACAATGCCGATTCATCTTTCGGCG 1114
PDM-1    AATCAATTGTATCGTCATTCATCCCTGAATTCACTTACAATGCCGATTCATCTTTCGGCG 1114
PDM-2    AATCAATTGTATCGTCATTCATCCCTGAATTCACTTACAATGCCGATTCATCTTTCGGCG 1114
         ************************************************************

D44610   AAGGATTCATTTATTGGGCCTCTGATAAGAGTATCAATATTGATGTTGCCTCCAAACTTG 1620
S288C    AAGGATTCATTTATTGGGCCTCTGATAAGAGTATCAATATTGATGTTGCCTCCAAACTTG 1174
PDM-1    AAGGATTCATTTATTGGGCCTCTGATAAGAGTATCAATATTGATGTTGCCTCCAAACTTG 1174
PDM-2    AAGGATTCATTTATTGGGCCTCTGATAAGAGTATCAATATTGATGTTGCCTCCAAACTTG 1174
         ************************************************************

D44610   TGAAAGCTCTGTCTTTGGAAGATGGGAAATTTGTGTCTTTGAGAACGAAATTTGATAACT 1680
S288C    TGAAAGCTCTGTCTTTGGAAGATGGGAAATTTGTGTCTTTGAGAACGAAATTTGATAACT 1234
PDM-1    TGAAAGCTCTGTCTTTGGAAGATGGGAAATTTGTGTCTTTGAGAACGAAATTTGATAACT 1234
PDM-2    TGAAAGCTCTGTCTTTGGAAGATGGGAAATTTGTGTCTTTGAGAACGAAATTTGATAACT 1234
         ************************************************************

D44610   TGGCTAATGCTGGTACCTTCCAAGCTCAATTTGTGACCTCGAAAGAACAGATACCTGTTT 1740
S288C    TGGCTAATGCTGGTACCTTCCAAGCTCAATTTGTGACCTCGAAAGAACAGATACCTGTTT 1294
PDM-1    TGGCTAATGCTGGTACCTTCCAAGCTCAATTTGTGACCTCGAAAGAACAGATACCTGTTT 1294
PDM-2    TGGCTAATGCTGGTACCTTCCAAGCTCAATTTGTGACCTCGAAGGAACAGATACCTGTTT 1294
         ******************************************* ****************

D44610   CAAACATCGATTCTACGAAATTATCAGTCGTTGAAGATGTCAGTTTATTGAAGCATTTAG 1800
S288C    CAAACATCGATTCTACGAAATTATCAGTCGTTGAAGATGTCAGTTTATTGAAGCATTTAG 1354
PDM-1    CAAACATCGATTCTACGAAATTATCAGTCGTTGAAGATGTCAGTTTATTGAAGCATTTAG 1354
PDM-2    CAAACATCGATTCTACGAAATTATCAGTCGTTGAAGATGTCAGTTTATTGAAGCATTTAG 1354
         ************************************************************

D44610   ACGTAGCTGCTACCGTCGCAGAACAAGGTTCAATTGCGTTGGTTTCCCAAAAGGCAGTTA 1860
S288C    ACGTAGCTGCTACCGTCGCAGAACAAGGTTCAATTGCGTTGGTTTCCCAAAAGGCAGTTA 1414
PDM-1    ACGTAGCTGCTACCGTCGCAGAACAAGGTTCAATTGCGTTGGTTTCCCAAAAGGCAGTTA 1414
PDM-2    ACGTAGCTGCTACCGTCACAGAACAAGGTTCAATTGCGTTGGTTTCCCAAAAGGCAGTTA 1414
         ***************** ******************************************

D44610   AAGATTTGGATTTAAATTCTGTAGAAAGTTACGTCAAGAATTTGGGAATTCCTGAATCAT 1920
S288C    AAGATTTGGATTTAAATTCTGTAGAAAGTTACGTCAAGAATTTGGGAATTCCTGAATCAT 1474
PDM-1    AAGATTTGGATTTAAATTCTGTAGAAAGTTACGTCAAGAATTTGGGAATTCCTGAATCAT 1474
PDM-2    AAGATTTGGATTTAAATTCTGTAGAAAGTTACGTCAAGAATTTGGGAATTCCTGAATCAT 1474
         ************************************************************

D44610   TCCTAATATCTATTGCGAAGAAAAACATCAAATTGTTTATCATCGATGGTGAGACCACTA 1980
S288C    TCCTAATATCTATTGCGAAGAAAAACATCAAATTGTTTATCATCGATGGTGAGACCACTA 1534
PDM-1    TCCTAATATCTATTGCGAAGAAAAACATCAAATTGTTTATCATCGATGGTGAGACCACTA 1534
PDM-2    TCCTAATATCTATTGCGAAGAAAAACATCAAATTGTTTATCATCGATGGTGAGACCATTA 1534
         ******************************************************** **
```

FIGURE 4 (continued)

```
D44610    ACGACGAGTCCAAATTGTCCTTGTTTATCCAAGCCGTTTTCTGGAAATTGGCCTTCGGTC 2040
S288C     ACGACGAGTCCAAATTGTCCTTGTTTATCCAAGCCGTTTTCTGGAAATTGGCCTTCGGTC 1594
PDM-1     ACGACGAGTCCAAATTGTCCTTGTTTATCCAAGCCGTTTTCTGGAAATTGGCCTTCGGTC 1594
PDM-2     ACGACGAGTCCAAATTGTCCTTGTTTATCCAAGCCGTTTTCTGGAAATTGGCCTTCGGTC 1594
          ************************************************************

D44610    TAGATGTCGCAGAATGTACCAACCGTATCTGGAAAAGCATTGATTCAGGTGCAGACATTT 2100
S288C     TAGATGTCGCAGAATGTACCAACCGTATCTGGAAAAGCATTGATTCAGGTGCAGACATTT 1654
PDM-1     TAGATGTCGCAGAATGTACCAACCGTATCTGGAAAAGCATTGATTCAGGTGCAGACATTT 1654
PDM-2     TAGATGTCGCAGAATGTACCAACCGTATCTGGAAAAGCATTGATTCAGGTGCAGACATTT 1654
          ************************************************************

D44610    CAGCAGCCTCGATTTCTGAATTTCTCACTGGTGCATTCAAAAACTTCCTCAGTGAGGTTC 2160
S288C     CAGCAGCCTCGATTTCTGAATTTCTCACTGGTGCATTCAAAAACTTCCTCAGTGAGGTTC 1714
PDM-1     CAGCAGCCTCGATTTCTGAATTTCTCACTGGTGCATTCAAAAACTTCCTCAGTGAGGTTC 1714
PDM-2     CAGCAGCCTCGATTTCTGAATTTCTCACTGGTGCATTCAAAAACTTCCTCAGTGAGGTTC 1714
          ************************************************************

D44610    CGCTAGCGCTGTACACTAAATTTTCTGAAATAAACATTGAAAAGAAAGAGGATGAGGAAG 2220
S288C     CGCTAGCGCTGTACACTAAATTTTCTGAAATAAACATTGAAAAGAAAGAGGATGAGGAAG 1774
PDM-1     CGCTAGCGCTGTACACTAAATTTTCTGAAATAAACATTGAAAAGAAAGAGGATGAGGAAG 1774
PDM-2     CGCTAGCGCTGTACACTAAATTTTCTGAAATAAACATTGAAAAGAAAGAGGATGAGGAAG 1774
          ************************************************************

D44610    AGCCTGCAGCTTTACCAATTTTCGTTAATGAAACATCTTTCCTCCCAAATAACAGTACCA 2280
S288C     AGCCTGCAGCTTTACCAATTTTCGTTAATGAAACATCTTTCCTCCCAAATAACAGTACCA 1834
PDM-1     AGCCTGCAGCTTTACCAATTTTCGTTAATGAAACATCTTTCCTCCCAAATAACAGTACCA 1834
PDM-2     AGCCTGCAGCTTTACCAATTTTCGTTAATGAAACATCTTTCCTCCCAAATAACAGTACCA 1834
          ************************************************************

D44610    TTGAAGAAATACCATTACCTGAGACCTCTGAGATCTCTGATATTGCCAAGAAGTTGTCCT 2340
S288C     TTGAAGAAATACCATTACCTGAGACCTCTGAGATCTCTGATATTGCCAAGAAGTTGTCCT 1894
PDM-1     TTGAAGAAATACCATTACCTGAGACCTCTGAGATCTCTGATATTGCCAAGAAGTTGTCCT 1894
PDM-2     TTGAAGAAATACCATTACCTGAGACCTCTGAGATCTCTGATATTGCCAAGAAGTTGTCCT 1894
          ************************************************************

D44610    TCAAAGAGGCATATGAAGTTGAGAATAAACTAAGACCCGATTTACCCGTCAAGAACTTCG 2400
S288C     TCAAAGAGGCATATGAAGTTGAGAATAAACTAAGACCCGATTTACCCGTCAAGAACTTCG 1954
PDM-1     TCAAAGAGGCATATGAAGTTGAGAATAAACTAAGACCCGATTTACCCGTCAAGAACTTCG 1954
PDM-2     TCAAAGAGGCATATGAAGTTGAGAATAAACTAAGACCCGATTTACCCGTCAAGAACTTCG 1954
          ************************************************************

D44610    TCGTGAAAGTTAAAGAAAATAGACGTGTTACGCCTGCTGATTATGATAGATATATTTTCC 2460
S288C     TCGTGAAAGTTAAAGAAAATAGACGTGTTACGCCTGCTGATTATGATAGATATATTTTCC 2014
PDM-1     TCGTGAAAGTTAAAGAAAATAGACGTGTTACGCCTGCTGATTATGATAGATATATTTTCC 2014
PDM-2     TCGTGAAAGTTAAAGAAAATAGACGTGTTACGCCTGCTGATTATGATAGATATATTTTCC 2014
          ************************************************************

D44610    ATATTGAATTCGATATTTCTGGTACTGGAATGACTTATGACATCGGTGAAGCCCTCGGTA 2520
S288C     ATATTGAATTCGATATTTCTGGTACTGGAATGACTTATGACATCGGTGAAGCCCTCGGTA 2074
PDM-1     ATATTGAATTCGATATTTCTGGTACTGGAATGACTTATGACATCGGTGAAGCCCTCGGTA 2074
PDM-2     ATATTGAATTCGATATTTCTGGTACTGGAATGACTTATGACATCGATGAAGCCCTCGGTA 2074
          ********************************************* **************

D44610    TTCATGCCAGAAACAATGAATCTTTGGTCAAAGAATTCTTAACCTTCTATGGTCTAAATG 2580
S288C     TTCATGCCAGAAACAATGAATCTTTGGTCAAAGAATTCTTAACCTTCTATGGTCTAAATG 2134
PDM-1     TTCATGCCAGAAACAATGAATCTTTGGTCAAAGAATTCTTAACCTTCTATGGTCTAAATG 2134
PDM-2     TTCATGCCAGAAACAATGAATCTTTGGTCAAAGAATTCTTAACCTTCTATGGTCTAAATG 2134
          ************************************************************

D44610    AATCCGATGTTGTCTTAGTCCCCAACAAGGACAACCACCATTTGTTAGAAACAAGAACCG 2640
S288C     AATCCGATGTTGTCTTAGTCCCCAACAAGGACAACCACCATTTGTTAGAAACAAGAACCG 2194
PDM-1     AATCCGATGTTGTCTTAGTCCCCAACAAGGACAACCACCATTTGTTAGAAACAAGAACCG 2194
PDM-2     AATCCGATGTTGTCTTAGTCCCCAACAAGGACAACCACCATTTGTTAGAAACAAGAACCG 2194
          ************************************************************
```

FIGURE 4 (continued)

```
D44610    TCTTACAAGCATTTGTGGAAAATTTGGATATTTTCGGTAAACCACCAAAAAGATTTTACG 2700
S288C     TCTTACAAGCATTTGTGGAAAATTTGGATATTTTCGGTAAACCACCAAAAAGATTTTACG 2254
PDM-1     TCTTACAAGCATTTGTGGAAAATTTGGATATTTTCGGTAAACCACCAAAAAGATTTTACG 2254
PDM-2     TCTTACAAGCATTTGTGGAAAATTTGGATATTTTCGGTAAACCACCAAAAAGATTTTACG 2254
          ************************************************************

D44610    AATCATTGATTCCATATGCCTCTAACGAAGAGGAGAAGAAAAAATTAGAGGATTTGGTTA 2760
S288C     AATCATTGATTCCATATGCCTCTAACGAAGAGGAGAAGAAAAAATTAGAGGATTTGGTTA 2314
PDM-1     AATCATTGATTCCATATGCCTCTAACGAAGAGGAGAAGAAAAAATTAGAGGATTTGGTTA 2314
PDM-2     AATCATTGATTCCATATGCCTCTAACGAAGAGGAGAAGAAAAAATTAGAGGATTTGGTTA 2314
          ************************************************************

D44610    CTCCTGCCGGTGCAGTAGATTTGAAGAGATTTCAAGATGTGGAGTATTATACATATGCTG 2820
S288C     CTCCTGCCGGTGCAGTAGATTTGAAGAGATTTCAAGATGTGGAGTATTATACATATGCTG 2374
PDM-1     CTCCTGCCGGTGCAGTAGATTTGAAGAGATTTCAAGATGTGGAGTATTATACATATGCTG 2374
PDM-2     CTCCTGCCGGTGCAGTAGATTTGAAGAGATTTCAAGATGTGGAGTATTATACATATGCTG 2374
          ************************************************************

D44610    ACATTTTTGAATTGTTCCCATCTGTTCGCCCATCTCTTGAGGAACTTGTTACTATCATTG 2880
S288C     ACATTTTTGAATTGTTCCCATCTGTTCGCCCATCTCTTGAGGAACTTGTTACTATCATTG 2434
PDM-1     ACATTTTTGAATTGTTCCCATCTGTTCGCCCATCTCTTGAGGAACTTGTTACTATCATTG 2434
PDM-2     ACATTTTTGAATTGTTCCCATCTGTTCGCCCATCTCTTAAGGAACTTGTTACTATCATTG 2434
          *************************************** *******************

D44610    AACCATTGAAGAGAAGAGAATACTCAATTGCCTCCTCTCAGAAAGTTCATCCAAATGAAG 2940
S288C     AACCATTGAAGAGAAGAGAATACTCAATTGCCTCCTCTCAGAAAGTTCATCCAAATGAAG 2494
PDM-1     AACCATTGAAGAGAAGAGAATACTCAATTGCCTCCTCTCAGAAAGTTCATCCAAATGAAG 2494
PDM-2     AACCATTGAAGAGAAGAGAATACTCAATTGCCTCCTCTCAGAAAGTTCATCCAAATGAAG 2494
          ************************************************************

D44610    TTCATTTATTGATCGTTGTTGTTGATTGGGTGGATAATAAAGGAAGAAAAAGGTACGGTC 3000
S288C     TTCATTTATTGATCGTTGTTGTTGATTGGGTGGATAATAAAGGAAGAAAAAGGTACGGTC 2554
PDM-1     TTCATTTATTGATCGTTGTTGTTGATTGGGTGGATAATAAAGGAAGAAAAAGGTACGGTC 2554
PDM-2     TTCATTTATTGATCGTTGTTGTTGATTGGGTGGATAATAAAGGAAGAAAAAGGTACGGTC 2554
          ************************************************************

D44610    AAGCTTCTAAGTATATCTCAGACCTTGCTGTCGGTTCAGAATTGGTCGTTAGCGTTAAAC 3060
S288C     AAGCTTCTAAGTATATCTCAGACCTTGCTGTCGGTTCAGAATTGGTCGTTAGCGTTAAAC 2614
PDM-1     AAGCTTCTAAGTATATCTCAGACCTTGCTGTCGGTTCAGAATTGGTCGTTAGCGTTAAAC 2614
PDM-2     AAGCTTCTAAGTATATCTCAGACCTTGCTGTCGGTTCAGAATTGGTCGTTAGCGTTAAAC 2614
          ************************************************************

D44610    CATCTGTTATGAAATTACCACCATCTCCAAAGCAACCAGTTATTATGAGTGGTTTAGGTA 3120
S288C     CATCTGTTATGAAATTACCACCATCTCCAAAGCAACCAGTTATTATGAGTGGTTTAGGTA 2674
PDM-1     CATCTGTTATGAAATTACCACCATCTCCAAAGCAACCAGTTATTATGAGTGGTTTAGGTA 2674
PDM-2     CATCTGTTATGAAATTACCACCATCTCCAAAGCAACCAGTTATTATGAGTGGTTTAGGTA 2674
          ************************************************************

D44610    CTGGTTTGGCACCATTCAAGGCCATTGTTGAAGAGAAATTATGGCAAAAGCAGCAAGGTT 3180
S288C     CTGGTTTGGCACCATTCAAGGCCATTGTTGAAGAGAAATTATGGCAAAAGCAGCAAGGTT 2734
PDM-1     CTGGTTTGGCACCATTCAAGGCCATTGTTGAAGAGAAATTATGGCAAAAGCAGCAAGGTT 2734
PDM-2     CTGGTTTGGCACCATTCAAGGCCATTGTTGAAGAGAAATTATGGCAAAAGCAGCAAGGTT 2734
          ************************************************************

D44610    ATGAGATTGGTGAAGTCTTCCTATATCTAGGTTCAAGACACAAAAGAGAAGAATATTTAT 3240
S288C     ATGAGATTGGTGAAGTCTTCCTATATCTAGGTTCAAGACACAAAAGAGAAGAATATTTAT 2794
PDM-1     ATGAGATTGGTGAAGTCTTCCTATATCTAGGTTCAAGACACAAAAGAGAAGAATATTTAT 2794
PDM-2     ATGAGATTGGTGAAGTCTTCCTATATCTAGGTTCAAGACACAAAAGAGAAGAATATTTAT 2794
          ************************************************************

D44610    ATGGTGAGTTATGGGAGGCTTACAAAGATGCAGGTATTATCACACACATCGGCGCTGCTT 3300
S288C     ATGGTGAGTTATGGGAGGCTTACAAAGATGCAGGTATTATCACACACATCGGCGCTGCTT 2854
PDM-1     ATGGTGAGTTATGGGAGGCTTACAAAGATGCAGGTATTATCACACACATCGGCGCTGCTT 2854
PDM-2     ATGGTGAGTTATGGGAGGCTTACAAAGATGCAGGTATTATCACATACATCGGCGCTGCTT 2854
          ******************************************** **************
```

FIGURE 4 (continued)

```
D44610    TCTCAAGAGACCAACCTCAAAAAATTTACATTCAAGATCGTATCAAAGAGAATTTGGATG 3360
S288C     TCTCAAGAGACCAACCTCAAAAAATTTACATTCAAGATCGTATCAAAGAGAATTTGGATG 2914
PDM-1     TCTCAAGAGACCAACCTCAAAAAATTTACATTCAAGATCGTATCAAAGAGAATTTGGATG 2914
PDM-2     TCTCAAGAGACCAACCTCAAAAAATTTACATTCAAGATCGTATCAAAGAGAATTTGGATG 2914
          ************************************************************

D44610    AATTAAAAACTGCAATGATTGATAATAAAGGTTCATTTTACTTGTGTGGCCCTACTTGGC 3420
S288C     AATTAAAAACTGCAATGATTGATAATAAAGGTTCATTTTACTTGTGTGGCCCTACTTGGC 2974
PDM-1     AATTAAAAACTGCAATGATTGATAATAAAGGTTCATTTTACTTGTGTGGCCCTACTTGGC 2974
PDM-2     AATTAAAAACTGCAATGATTGATAATAAAGGTTCATTTTACTTGTGTGGCCCTACTTGGC 2974
          ************************************************************

D44610    CAGTTCCAGATATTACTCAAGCTTTGCAAGACATTCTGGCTAAAGACGCCGAGGAAAGAG 3480
S288C     CAGTTCCAGATATTACTCAAGCTTTGCAAGACATTCTGGCTAAAGACGCCGAGGAAAGAG 3034
PDM-1     CAGTTCCAGATATTACTCAAGCTTTGCAAGACATTCTGGCTAAAGACGCCGAGGAAAGAG 3034
PDM-2     CAGTTCCAGATATTACTCAAGCTTTGCAAGACATTCTGGCTAAAGACGCCGAGGAAAGAG 3034
          ************************************************************

D44610    GCATCAAAGTCGACTTGGATGCCGCAATTGAAGAATTAAAGGAAGCATCAAGATACATTT 3540
S288C     GCATCAAAGTCGACTTGGATGCCGCAATTGAAGAATTAAAGGAAGCATCAAGATACATTT 3094
PDM-1     GCATCAAAGTCGACTTGGATGCCGCAATTGAAGAATTAAAGGAAGCATCAAGATACATTT 3094
PDM-2     GCATCAAAGTCGACTTGGATGCCGCAATTGAAGAATTAAAGGAAGCATCAAGATACATTT 3094
          ************************************************************

D44610    TAGAAGTCTACTAAATTAATATAGTAATAAAAACTAAATATCTATTTATTGAACCTGTCT 3600
S288C     TAGAAGTCTACTAA---------------------------------------------- 3108
PDM-1     TAGAAGTCTACTAA---------------------------------------------- 3108
PDM-2     TAGAAGTCTACTAA---------------------------------------------- 3108
          **************

D44610    TGAACATTTCTATTTTTTTTTTACTTTTAGTTTTCTTCTATGCGCAAGCTTTTCTATTGG 3660
S288C     ------------------------------------------------------------
PDM-1     ------------------------------------------------------------
PDM-2     ------------------------------------------------------------

D44610    CTGCCAAATAGAAAATTATTGAAATATGATTACATTACAATATTTATTTGTCTTATGAAA 3720
S288C     ------------------------------------------------------------
PDM-1     ------------------------------------------------------------
PDM-2     ------------------------------------------------------------

D44610    ACTAACCATCACATTATACTAACTACGGAGGTACC 3755
S288C     -----------------------------------
PDM-1     -----------------------------------
PDM-2     -----------------------------------
```

FIGURE 4 (continued)

```
BAA08076    MPVEFATNPFGEAKNATSLPKYGTPVTAISSVLFNNVDSIFAYKSFSQPDLLHQDLKKWS  60
PDM-1       MPVEFATNPFGEAKNATSLPKYGTPVTAISSVLFNNVDSIFAYKSFSQPDLLHQDLKKWS  60
S288C       MPVEFATNPFGEAKNATSLPKYGTPVTAISSVLFNNVDSIFAYKSFSQPDLLHQDLKKWS  60
PDM-2       MPVEFATNPFGEAKNATSLPKYGTPVTAISSVLFNNVDSIFAYKSFSQPDLLHQDLKKWS  60
            ************************************************************

BAA08076    EKRGNESRGKPFFQELDIRSGAGLAPLGFSHGLKNTTAIVAPGFSLPYFINSLKTVSHDG  120
PDM-1       EKRGNESRGKPFFQELDIRSGAGLAPLGFSHGLKNTTAIVAPGFSLPYFINSLKTVSHDG  120
S288C       EKRGNESRGKPFFQELDIRSGAGLAPLGFSHGLKNTTAIVAPGFSLPYFINSLKTVSHDG  120
PDM-2       EKRGNESRGKPFFQELDIRSGAGLAPLGFSHGLKNTTAIVAPGFSLPYFINSLKTVSHDG  120
            ************************************************************

BAA08076    KFLLNVGALNYDNATGSVTNDYVTALDAASKLKYGVVTPISANEVQSVALLTLAIATFSN  180
PDM-1       KFLLNVGALNYDNATGSVTNDYVTALDAASKLKYGVVTPISANEVQSVALLTLAIATFSN  180
S288C       KFLLNVGALNYDNATGSVTNDYVTALDAASKLKYGVVTPISANEVQSVALLALAIATFSN  180
PDM-2       KFLLNVGALNYDNATGSVTNDYVTALDAASKLKYGVVTPISANEVQSVALLALAIATFSN  180
            *********************************************** ***********

BAA08076    NSGAINLFDGLNYSKTVLPLVESVPEASILAKLSKVIAPDAAFDDVLDKFNELTGLRLHN  240
PDM-1       NSGAINLFDGLNYSKTVLPLVESVPEASILAKLSKVIAPDAAFDDVLDKFNELTGLRLHN  240
S288C       NSGAINLFDGLNYSKTVLPLVESVPEASILAKLSKVIAPDAAFDDVLDKFNELTGLRLHN  240
PDM-2       NSGAINLFDGLNYSKTVLPLVESVPEASILAKLSKVIAPDAAFDDVLDKFNELTGLRLHN  240
            ************************************************************

BAA08076    FQYFGAQDAETVFITYGSLESELFNSAISGNNSKIGLINVRVPLPFNVAKFVTHVPSTTK  300
PDM-1       FQYFGAQDAETVFITYGSLESELFNSAISGNNSKIGLINVRVPLPFNVAKFVTHVPSTTK  300
S288C       FQYFGAQDAETVFITYGSLESELFNSAISGNNSKIGLINVRVPLPFNVAKFVTHVPSTTK  300
PDM-2       FQYFGAQDAETVFITYGSLESELFNSAISGNNSKIGLINVRVPLPFNVAKFVTHVPSTTK  300
            ************************************************************

BAA08076    QIVVIGQTLDGSSPSFLRSQVSAALFYHGRTSISVSEYIYQPDFIWSPKAVKSIVSSFIP  360
PDM-1       QIVVIGQTLDGSSPSFLRSQVSAALFYHGRTSISVSEYIYQPDFIWSPKAVKSIVSSFIP  360
S288C       QIVVIGQTLDGSSPSFLRSQVSAALFYHGRTSISVSEYIYQPDFIWSPKAVKSIVSSFIP  360
PDM-2       QIVVIGQTLDGSSPSFLRSQVSAALFYHGRTSISVSEYIYQPDFIWSPKAVKSIVSSFIP  360
            ************************************************************

BAA08076    EFTYNADSSFGEGFIYWASDKSINIDVASKLVKALSLEDGKFVSLRTKFDNLANAGTFQA  420
PDM-1       EFTYNADSSFGEGFIYWASDKSINIDVASKLVKALSLEDGKFVSLRTKFDNLANAGTFQA  420
S288C       EFTYNADSSFGEGFIYWASDKSINIDVASKLVKALSLEDGKFVSLRTKFDNLANAGTFQA  420
PDM-2       EFTYNADSSFGEGFIYWASDKSINIDVASKLVKALSLEDGKFVSLRTKFDNLANAGTFQA  420
            ************************************************************

BAA08076    QFVTSKEQIPVSNIDSTKLSVVEDVSLLKHLDVAATVAEQGSIALVSQKAVKDLDLNSVE  480
PDM-1       QFVTSKEQIPVSNIDSTKLSVVEDVSLLKHLDVAATVAEQGSIALVSQKAVKDLDLNSVE  480
S288C       QFVTSKEQIPVSNIDSTKLSVVEDVSLLKHLDVAATVAEQGSIALVSQKAVKDLDLNSVE  480
PDM-2       QFVTSKEQIPVSNIDSTKLSVVEDVSLLKHLDVAATVTEQGSIALVSQKAVKDLDLNSVE  480
            ************************************* **********************

BAA08076    SYVKNLGIPESFLISIAKKNIKLFIIDGETTNDESKLSLFIQAVFWKLAFGLDVAECTNR  540
PDM-1       SYVKNLGIPESFLISIAKKNIKLFIIDGETTNDESKLSLFIQAVFWKLAFGLDVAECTNR  540
S288C       SYVKNLGIPESFLISIAKKNIKLFIIDGETTNDESKLSLFIQAVFWKLAFGLDVAECTNR  540
PDM-2       SYVKNLGIPESFLISIAKKNIKLFIIDGETINDESKLSLFIQAVFWKLAFGLDVAECTNR  540
            ****************************** *****************************

BAA08076    IWKSIDSGADISAASISEFLTGAFKNFLSEVPLALYTKFSEINIEKKEDEEEPAALPIFV  600
PDM-1       IWKSIDSGADISAASISEFLTGAFKNFLSEVPLALYTKFSEINIEKKEDEEEPAALPIFV  600
S288C       IWKSIDSGADISAASISEFLTGAFKNFLSEVPLALYTKFSEINIEKKEDEEEPAALPIFV  600
PDM-2       IWKSIDSGADISAASISEFLTGAFKNFLSEVPLALYTKFSEINIEKKEDEEEPAALPIFV  600
            ************************************************************

BAA08076    NETSFLPNNSTIEEIPLPETSEISDIAKKLSFKEAYEVENKLRPDLPVKNFVVKVKENRR  660
PDM-1       NETSFLPNNSTIEEIPLPETSEISDIAKKLSFKEAYEVENKLRPDLPVKNFVVKVKENRR  660
S288C       NETSFLPNNSTIEEIPLPETSEISDIAKKLSFKEAYEVENKLRPDLPVKNFVVKVKENRR  660
PDM-2       NETSFLPNNSTIEEIPLPETSEISDIAKKLSFKEAYEVENKLRPDLPVKNFVVKVKENRR  660
            ************************************************************
```

FIGURE 5

```
BAA08076    VTPADYDRYIFHIEFDISGTGMTYDIGEALGIHARNNESLVKEFLTFYGLNESDVVLVPN  720
PDM-1       VTPADYDRYIFHIEFDISGTGMTYDIGEALGIHARNNESLVKEFLTFYGLNESDVVLVPN  720
S288C       VTPADYDRYIFHIEFDISGTGMTYDIGEALGIHARNNESLVKEFLTFYGLNESDVVLVPN  720
PDM-2       VTPADYDRYIFHIEFDISGTGMTYDIDEALGIHARNNESLVKEFLTFYGLNESDVVLVPN  720
            **************************:*********************************

BAA08076    KDNHHLLETRTVLQAFVENLDIFGKPPKRFYESLIPYASNEEEKKKLEDLVTPAGAVDLK  780
PDM-1       KDNHHLLETRTVLQAFVENLDIFGKPPKRFYESLIPYASNEEEKKKLEDLVTPAGAVDLK  780
S288C       KDNHHLLETRTVLQAFVENLDIFGKPPKRFYESLIPYASNEEEKKKLEDLVTPAGAVDLK  780
PDM-2       KDNHHLLETRTVLQAFVENLDIFGKPPKRFYESLIPYASNEEEKKKLEDLVTPAGAVDLK  780
            ************************************************************

BAA08076    RFQDVEYYTYADIFELFPSVRPSLEELVTIIEPLKRREYSIASSQKVHPNEVHLLIVVVD  840
PDM-1       RFQDVEYYTYADIFELFPSVRPSLEELVTIIEPLKRREYSIASSQKVHPNEVHLLIVVVD  840
S288C       RFQDVEYYTYADIFELFPSVRPSLEELVTIIEPLKRREYSIASSQKVHPNEVHLLIVVVD  840
PDM-2       RFQDVEYYTYADIFELFPSVRPSLKELVTIIEPLKRREYSIASSQKVHPNEVHLLIVVVD  840
            ***********************:************************************

BAA08076    WVDNKGRKRYGQASKYISDLAVGSELVVSVKPSVMKLPPSPKQPVIMSGLGTGLAPFKAI  900
PDM-1       WVDNKGRKRYGQASKYISDLAVGSELVVSVKPSVMKLPPSPKQPVIMSGLGTGLAPFKAI  900
S288C       WVDNKGRKRYGQASKYISDLAVGSELVVSVKPSVMKLPPSPKQPVIMSGLGTGLAPFKAI  900
PDM-2       WVDNKGRKRYGQASKYISDLAVGSELVVSVKPSVMKLPPSPKQPVIMSGLGTGLAPFKAI  900
            ************************************************************

BAA08076    VEEKLWQKQQGYEIGEVFLYLGSRHKREEYLYGELWEAYKDAGIITHIGAAFSRDQPQKI  960
PDM-1       VEEKLWQKQQGYEIGEVFLYLGSRHKREEYLYGELWEAYKDAGIITYIGAAFSRDQPQKI  960
S288C       VEEKLWQKQQGYEIGEVFLYLGSRHKREEYLYGELWEAYKDAGIITHIGAAFSRDQPQKI  960
PDM-2       VEEKLWQKQQGYEIGEVFLYLGSRHKREEYLYGELWEAYKDAGIITHIGAAFSRDQPQKI  960
            **********************************************:************

BAA08076    YIQDRIKENLDELKTAMIDNKGSFYLCGPTWPVPDITQALQDILAKDAEERGIKVDLDAA 1020
PDM-1       YIQDRIKENLDELKTAMIDNKGSFYLCGPTWPVPDITQALQDILAKDAEERGIKVDLDAA 1020
S288C       YIQDRIKENLDELKTAMIDNKGSFYLCGPTWPVPDITQALQDILAKDAEERGIKVDLDAA 1020
PDM-2       YIQDRIKENLDELKTAMIDNKGSFYLCGPTWPVPDITQALQDILAKDAEERGIKVDLDAA 1020
            ************************************************************

BAA08076    IEELKEASRYILEVY 1035
PDM-1       IEELKEASRYILEVY 1035
S288C       IEELKEASRYILEVY 1035
PDM-2       IEELKEASRYILEVY 1035
            ***************
```

FIGURE 5 (continued)

A
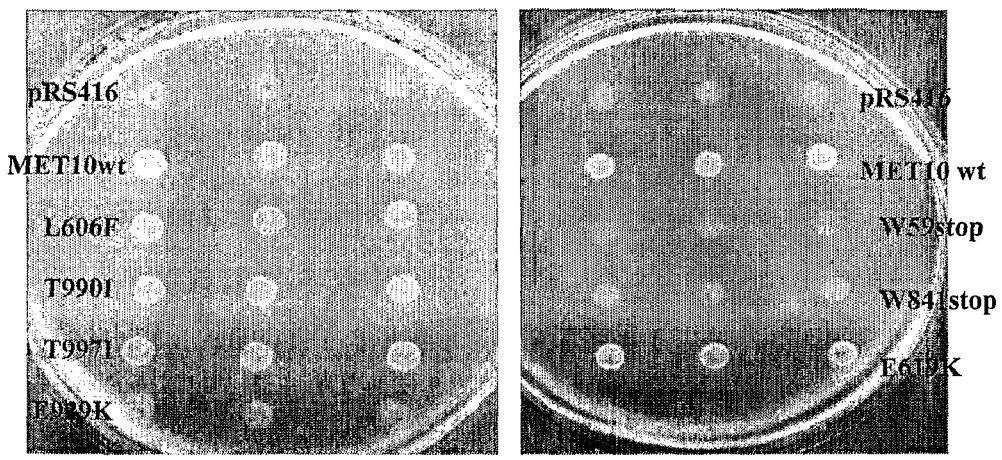
B
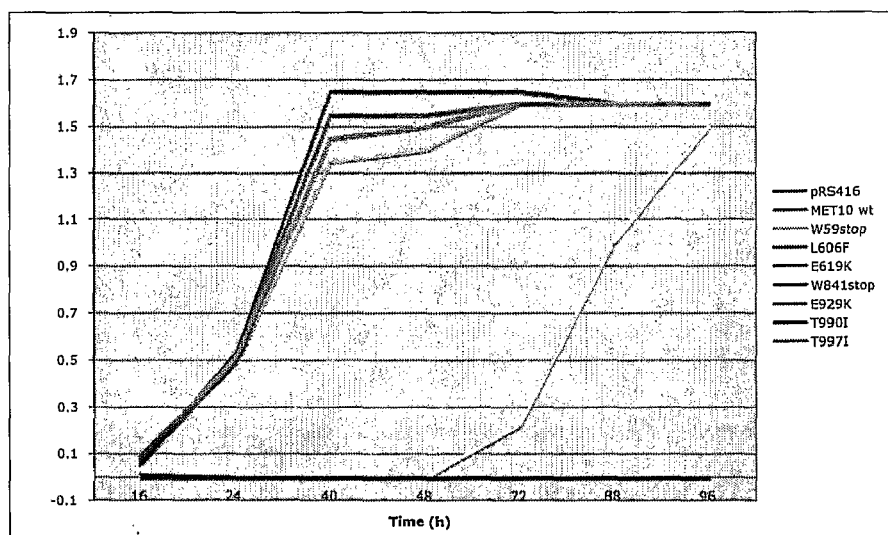
C
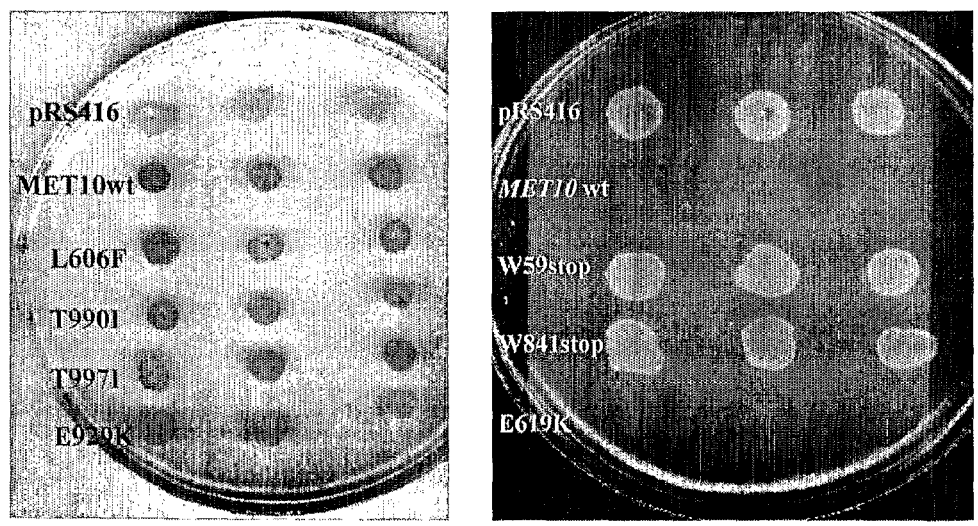
FIGURE 13

MODIFIED INDUSTRIAL YEAST STRAINS

RELATED APPLICATIONS

This application is a national stage application, filed under 35 U.S.C. §371, of International Application No. PCT/AU2008/001485, filed Oct. 6, 2008, which claims the benefit of 2007905528AU, filed Oct. 9, 2007, the contents of which are incorporated by reference in their entireties.

FIELD OF THE INVENTION

The present invention relates to modified industrial yeast strains that show reduced hydrogen sulfide production. The present invention also relates to methods of manufacturing these modified industrial yeast strains and their use in the production of fermented products.

BACKGROUND OF THE INVENTION

The production of hydrogen sulfide by *Saccharomyces cerevisiae* during wine fermentation has long been a problem for wine makers as it has a low odour threshold.

Hydrogen sulfide can be formed metabolically by yeast from either inorganic sulfur compounds, sulfate and sulfite, or organic sulfur compounds, cysteine and glutathione. Cell growth creates a metabolic requirement for organic sulfur compounds, including cysteine, methionine, S-adenosyl methionine and glutathione. When these organic compounds are absent, the cell must synthesise them from inorganic sulfur compounds accumulated from the must. Under certain conditions, hydrogen sulfide is liberated during the reduction of inorganic sulfur to become detectable by the winemaker. The concentration of hydrogen sulfide produced varies with the availability of sulfur compounds, yeast strain and fermentation conditions, and the nutritional status of the environment. However, some strains appear to form unregulated amounts of hydrogen sulfide and presumably represent metabolic defects, at least in the wine environment (Mendes-Ferreira et al. 2002).

In *Saccharomyces cerevisiae*, hydrogen sulfide is the product of the Sulfate Reduction Sequence (SRS) pathway and acts as an intermediate in the biosynthesis of sulfur-containing amino acids. The ability of a strain to produce hydrogen sulfide is, at least, partly genetic, since hydrogen sulfide production by different wine strains varies under the same conditions (Henschke and Jiranek 1991, Jiranek et al. 1995a, Jiranek et al. 1995b, Jiranek et al. 1996). Mendes-Ferreira et al. (2002) recently screened a large selection of commercial wine yeast, in addition to non-Saccharomyces yeasts, which, when tested under identical physiological conditions, all had the same growth characteristics but varied in sulfite reductase (the enzyme producing hydrogen sulfide) activity. After fermentation in grape musts, yeast strains could be classified as nonproducers of hydrogen sulfide, must composition-dependent producers and invariable producers (Mendes-Ferreira et al. 2002).

The first step of the SRS metabolic pathway involves the transport of sulfate from the medium into the yeast cell via sulfate permease (FIG. 1). Sulfate is then reduced to sulfide through a series of steps using the enzymes ATP-sulfurylase (using two ATP molecules) and sulfite reductase. Sulfite reductase is a heterotetramer, consisting of two α- and two β-subunits, which are encoded by MET10 and MET5 genes, respectively. The enzyme, a hemoflavoprotein, binds the cofactors flavin adenine dinucleotide, flavin mononucleotide and siroheme. The next step leads to the sequestering of the sulfide: O-acetylserine (from the amino acid serine) combines with sulfide to form cysteine, and O-acetylhomoserine (from the amino acid aspartate) to form homocysteine, which can then be converted to methionine.

The problem of hydrogen sulfide production during wine making can be dealt with through the use of copper (which results in the formation of copper sulfide) or aeration (resulting in oxidation of the sulfide). Nevertheless, elimination of the use of copper salts by wineries is a desirable food processing goal and the presence of oxidised sulfur compounds in young wine could be related to the reductive character in bottled wine. Recent studies have therefore turned to investigating genetic methods for reducing hydrogen sulfide production.

One particular study (Spiropoulos and Bisson 2000) has investigated the role of the bifunctional O-acetylserine/O-acetylhomoserine sulfhydrylase as means to modulate hydrogen sulfide production by industrial yeast. Overexpression of the MET17 gene, which encodes O-acetylserine/O-acetylhomoserine sulfhydrylase, in a strain of *Saccharomyces cerevisiae* resulted in greatly reduced hydrogen sulfide formation. However, this was not the case with another strain, indicating that O-acetylserine/O-acetylhomoserine sulfhydrylase activity is not directly related to hydrogen sulfide formation.

Linderholm and Bisson (2005) have also evaluated the role of the sequence and level of expression of genes immediately downstream of sulfite reductase encoded by MET17, MET6 and CYS4. The genes were overexpressed in laboratory and brewing strains, but there was no universal reduction in hydrogen sulfide production. These genes were also sequenced in 12 wine isolates of this yeast. The MET17 alleles were identical in sequence to each other and to the sequence of the standard laboratory strain, S288C. For one additional commercial strain, a disruption of one of the MET17 alleles was found, but the other allele was identical to the consensus sequence. All 12 strains showed the identical five neutral base pair changes in CYS4 sequence when compared to the sequence reported for S288C. One strain contained an additional base pair change that led to an amino acid change. Two neutral base pair changes were observed in the sequences of MET6 for one wine yeast strain and three other strains had changes in sequence that were not neutral and altered the amino acid sequence. Genes encoding different alleles were used to transform a corresponding null mutation of S288C and enzyme activity and hydrogen sulfide production evaluated. The $CYS4^{UCD932}$ allele resulted in faster fermentation rates and reduced hydrogen sulfide production when compared with the same strain transformed with $CYS4^{S288C}$. The MET6 alleles showed no effects on sulfide formation in a null background.

Overexpression of the two genes MET14 and SSU1 have been shown to increase the formation of sulfite (Donalies and Stahl 2002). It has therefore been postulated that the deletion of the MET14 adenosylphosphosulphate kinase gene or the MRX1 methionine sulfoxide reductase gene might be the most effective way to prevent wine yeast from producing hydrogen sulfide (Pretorius and Bauer 2002, Pretorius 2003, 2004).

Modification of industrial yeast strains, particularly brewing and wine yeast strains, to reduce hydrogen sulfide production is still a highly desirable goal and the subject of ongoing investigations.

SUMMARY OF THE INVENTION

The present inventors have now produced modified industrial yeast strains that show reduced production of hydrogen sulfide when compared to the original unmodified strain. These modified strains have one or more point mutations in a MET5 gene and/or MET10 genes.

Accordingly, the present invention provides an industrial yeast strain comprising a modification in gene sequence which results in the production of reduced levels of sulfur compounds during fermentation when compared to the corresponding industrial yeast strain without the modification.

The present invention also provides an industrial yeast strain comprising a modification in gene sequence which results in reduced hydrogen sulfide ($H_2S$) production during fermentation when compared to the corresponding industrial yeast strain without the modification.

The present invention also provides an industrial yeast strain comprising one or more point mutations in a MET5 gene and/or a MET10 gene which results in reduced hydrogen sulfide production when compared to the corresponding industrial yeast strain without the modification.

In a preferred example of the present invention the industrial yeast strain is a *Saccharomyces cerevisiae* yeast strain.

The industrial yeast strain may be, for example, a baker's yeast strain, or any yeast strain involved in production of an alcoholic beverage, including a brewer's yeast strain, a wine yeast strain or a sake yeast strain. Preferably, the industrial yeast strain is a wine yeast strain.

The original or unmodified wine yeast strain may be any yeast strain suitable for wine making. For example, the original wine yeast strain may be selected from the group consisting of Maurivin Altesse, Maurivin AWRI 350, Maurivin AWRI 796, Maurivin AWRI Fusion, Maurivin AWRI 1503, Maurivin AWRI Cerebay, Maurivin AWRI R2, Maurivin BP 725, Maurivin Cm Blanc, Maurivin Elegance, Maurivin EP2, Maurivin B, Maurivin HX, Maurivin PDM, Maurivin SW, Maurivin Primeur, Maurivin Sauvignon L3 and Maurivin UCD 522.

In a preferred embodiment of the present invention the unmodified wine yeast strain is Maurivin PDM (also referred to herein as "PDM").

In one embodiment of the present invention the modification which results in reduced hydrogen sulfide production is one or more point mutations in a MET5 gene.

The one or more point mutations in the MET5 gene may result, for example, in the following amino acid substitutions in the polypeptide encoded by MET5:
  (i) P210L;
  (ii) A979T;
  (iii) G980D;
  (iv) G1115D;
  (v) E1356K
  (vi) any combination of the amino acid substitutions in (i) to (v).

In another embodiment of the present invention the modification which results in reduced hydrogen sulfide production is one or more point mutations in a MET10 gene.

The one or more point mutations in the MET10 gene may result, for example, in the following amino acid substitutions in the polypeptide encoded by MET10:
  (i) W59stop;
  (ii) L606F;
  (iii) E619K;
  (iv) W841 stop;
  (v) G911S;
  (vi) E929K;
  (vii) T990I;
  (viii) T997I; or
  (ix) any combination of the amino acid substitutions in (i) to (viii).

In one embodiment of the present invention, an endogenous MET5 gene and/or MET10 gene of an industrial yeast strain is modified to achieve reduced hydrogen sulfide production. One or more or all alleles of the MET5 gene and/or MET10 genes in the industrial yeast strain may be modified in this manner.

For example, modification of an endogenous MET5 gene and/or MET10 gene may be achieved by random mutagenesis. As will be appreciated by those skilled in the art, random mutagenesis can be achieved by exposing the original yeast strain to a mutagen. Examples of suitable mutagens include nitrosoguanidine (NTG), hydroxylamine $NH_3OH$, base analogs (e.g. BrdU), simple chemicals (e.g. acids), alkylating agents (e.g. N-ethyl-N-nitrosourea (ENU)), methylating agents (e.g. ethyl methanesulfonate (EMS)), polycyclic hydrocarbons (e.g. benzopyrenes found in internal combustion engine exhaust), DNA intercalating agents (e.g. ethidium bromide), DNA crosslinkers (e.g. platinum), and radiation such as ultraviolet radiation (nonionizing radiation) or ionizing radiation.

In yet a further embodiment of the present invention, modification of an endogenous MET5 gene and/or MET10 gene may be achieved by targeted mutagenesis. The targeted mutagenesis may be achieved by any suitable technique, such as site directed mutagenesis, which will be known to those skilled in the art. Methods of site directed mutagenesis are disclosed, for example, in: Rothstein, 1991; Simon and Moore, 1987; Winzeler et al., 1999; and, Negritto et al., 1997.

In another embodiment, the industrial yeast strain is modified by introducing an exogenous nucleic acid molecule encoding a Met5p or Met10p polypeptide comprising one or more amino acid changes due to point mutations in the nucleic acid sequence, when compared with the Met5p or Met10p polypeptide sequence of the original industrial yeast strain, which results in reduced hydrogen sulfide production. The exogenous nucleic acid molecule may be in the form of a recombinant expression cassette or vector. The recombinant expression cassette or vector may be self-replicating or it may be designed for integration into the host genome.

In a further embodiment of the invention, the modified yeast strain shows more than 10%, more preferably more than 20%, more preferably more than 50% and more preferably more than 60% reduction in hydrogen sulfide production when compared to the corresponding unmodified industrial yeast strain under the same culturing conditions.

In one embodiment the modified yeast strain shows 100% reduction in hydrogen sulfide production when compared to the corresponding unmodified industrial yeast strain under the same culturing conditions.

In a further embodiment of the invention, the modified yeast strain also has one or more of the following properties:
  (i) efficient fermentation rate to sugar dryness (preferably to less that 2 g/L total sugar, and preferably at a rate no more than 10% slower than the corresponding unmodified industrial yeast strain);
  (ii) low volatile acidity production (preferably no more than 0.2 g/L higher than the corresponding unmodified industrial yeast strain); and/or
  (iii) high ethanol tolerance (preferably no more than 0.5% less tolerance to ethanol than the corresponding unmodified industrial yeast strain).

The present invention also provides a modified yeast strain deposited with The National Measurement Institute (NMI), Australia, under accession number V07/022167, V07/022168, V07/022169, V07/022170, V07/022171 or V07/022172.

The present invention also provides a method for producing a modified industrial yeast strain which produces reduced levels of sulfur compounds during fermentation when compared to the corresponding industrial yeast strain without the modification, comprising:

subjecting an industrial yeast strain to mutagenesis; and selecting one or more mutant strains for reduced production of sulfur compounds on a medium that evaluates relative production of sulfide.

In the context of this method of the invention, any suitable form of mutagenesis may be employed. For example, the method may involve random mutagenesis by a chemical mutagen (such as EMS), ultraviolet (UV), adaptive evolution or any other mutagen described herein. Alternatively, the method may involve targeted mutagenesis of a gene involved in production of sulfur compounds.

In one embodiment of this method, the medium that evaluates relative production of sulfide is BiGGY agar. In one embodiment, the BiGGY agar comprises sulfite as the sulfur source. In another embodiment, the BiGGY agar comprises sulfate as the sulfur source.

The present invention also provides a method of manufacturing an industrial yeast strain which comprises culturing a modified industrial yeast strain according to the present invention under conditions which allows large scale production of the modified yeast strain.

In a preferred embodiment of the invention the manufacturing process results in the production of active dried yeast.

The present invention also provides use of a modified industrial yeast strain of the present invention in the production of a fermented product. The fermented product may be, for example, bread, beer, wine, brandy or sake. The fermented product may also be a spirit, for example, vodka, gin, whiskey or rum or a ready-to-drink spirit-soda blend. The fermented product may also include products made from the production of a modified industrial yeast strain blended with other fermentation ingredients such as, but not limited to, vitamins, trace elements and nitrogen.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF THE FIGURES

FIG. 2: Sequence alignment of MET5 genes from strains of *Saccharomyces cerevisiae*: S288C MET5 gene (SEQ ID NO:5), PDM-2 MET5 gene (SEQ ID NO:7), EF058187 (SEQ ID NO:2), EF058185 (SEQ ID NO:4), EF058186 (SEQ ID NO:3), EF058188 (SEQ ID NO:1), and PDM-1 MET5 gene (SEQ ID NO:6).

FIG. 3: Sequence alignment of Met5p polypeptides from strains of *Saccharomyces cerevisiae*: S288C Met5 protein (SEQ ID NO:12), PDM-2 Met5 protein (SEQ ID NO:14), ABK59399 (SEQ ID NO:8), ABK59398 (SEQ ID NO:9), ABK59396 (SEQ ID NO:11), ABK59397 (SEQ ID NO:10), and PDM-1 Met5 protein (SEQ ID NO:13).

FIG. 4: Sequence alignment of MET10 genes from strains of *Saccharomyces cerevisiae*: D44610 (SEQ ID NO:15), S288C-MET10 gene (SEQ ID NO:16), PDM-1 MET10 gene (SEQ ID NO:17), PDM-2 MET10 gene (SEQ ID NO:18).

FIG. 5: Sequence alignment of Met10p polypeptides from strains of *Saccharomyces cerevisiae*: BAA08076 (SEQ ID NO:19), PDM-1 Met10 protein (SEQ ID NO:21), S288C Met10 protein (SEQ ID NO:20), and PDM-2 Met10 protein (SEQ ID NO:22).

FIG. 13: Growth of the MET10 mutants in minimal media lacking methionine: (a) on plate; (b) on liquid; and (c) phenotype of MET10 mutants in BiGGY agar plates

SEQUENCE LISTINGS

Figure 1:
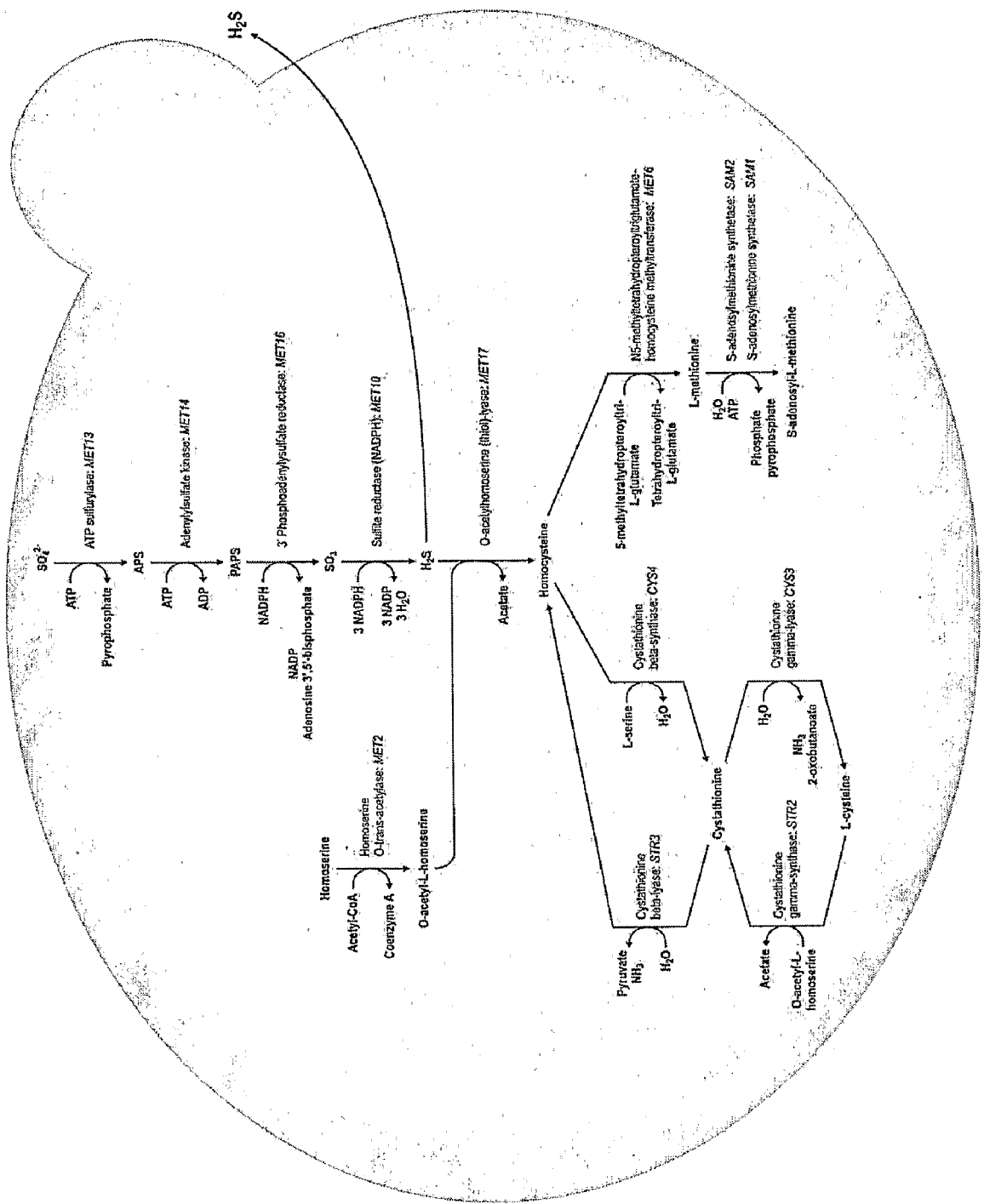
FIG. 1: The pathway for production of $H_2S$ in wine yeast.

SEQ ID NO: 1-MET5 gene (ACCESSION NO: EF058188)

SEQ ID NO: 2-MET5 gene (ACCESSION NO: EF058187)

SEQ ID NO: 3-MET5 gene (ACCESSION NO: EF058186)

SEQ ID NO: 4-MET5 gene (ACCESSION NO: EF058185)

SEQ ID NO: 5-S288C MET5 gene

SEQ ID NO: 6-PDM MET5 gene allele 1

SEQ ID NO: 7-PDM MET5 gene allele 2

SEQ ID NO: 8-Met5 protein (ACCESSION NO: ABK59399)

SEQ ID NO: 9-Met5 protein (ACCESSION NO: ABK59398)

SEQ ID NO: 10-Met5 protein (ACCESSION NO: ABK59397)

SEQ ID NO: 11-Met5 protein (ACCESSION NO: ABK59396)

SEQ ID NO: 12-S288C Met5 protein

SEQ ID NO 13-PDM Met 5 protein allele 1

SEQ ID NO 14-PDM Met 5 protein allele 2

SEQ ID NO: 15-MET10 gene (ACCESSION NO: D44610)

SEQ ID NO: 16-S288C MET10 gene

SEQ ID NO: 17-PDM MET10 gene allele 1

SEQ ID NO: 18-PDM MET 10 gene allele 2

-continued

SEQ ID NO: 19-Met10 protein
(ACCESSION NO: BAA08076)

SEQ ID NO: 20-S288C Met 10 protein

SEQ ID NO: 21-PDM Met 10 protein allele 1

SEQ ID NO: 22-PDM Met 10 protein allele 2

Micro-Organism Deposit Details

The following strains of *Saccharomyces cerevisiae* have been deposited with The National Measurement Institute (NMI), Australia under the accession number indicated:

| AWRI strain | AWRI mutant number | NMI accession number |
|---|---|---|
| AWRI 1637 | 45.2 | V07/022167 |
| AWRI 1638 | 2.1 | V07/022168 |
| AWRI 1639 | 22.1 | V07/022169 |
| AWRI 1640 | 23.2 | V07/022170 |
| AWRI 1641 | 51.1 | V07/022171 |
| AWRI 1642 | 4.2 | V07/022172 |

These deposits were made under the provisions of the Budapest Treaty on the International Recognition of the Deposit of Microorganisms for the Purpose of Patent Procedure and the Regulations thereunder.

DETAILED DESCRIPTION OF THE PREFERRED EMBODIMENTS OF THE INVENTION

General Techniques

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), E. Harlow and D. Lane (editors), Antibodies: A Laboratory Manual, Cold Spring Harbour Laboratory, (1988), and J. E. Coligan et al. (editors), Current Protocols in Immunology, John Wiley & Sons (including all updates until present).

Met5 and Met10 Polypeptides and Polynucleotides

The yeast sulfite reductase, catalyzing the six electron reduction of sulfite to sulfide, is a key enzyme in the biosynthesis of methionine. It is an NADPH-dependent enzyme with multiple catalytic activities. The enzyme, with a molecular mass of 604 kDa is considered to consist of two α subunits (116 kDa) and two β subunits (167 kDa) and contains two flavin adenine dinucleotides, two flavin mononucleotides and two siroheme chromophores. The α and β subunits are encoded by MET10 and MET5 genes, respectively.

In one embodiment, the present invention involves introducing point mutations into a MET10 and/or MET5 gene of an industrial yeast strain.

The MET5 gene and encoded polypeptide has been sequenced in a number of different yeast strains, including the Maurivin PDM strain. An alignment of the polynucleotide sequences is shown in FIG. 2 and an alignment of the encoded polypeptides is shown in FIG. 3.

The MET10 gene and encoded polypeptide has also been sequenced in a number of different yeast strains, including the Maurivin PDM strain. An alignment of the polynucleotide sequences from a representative strain and the Maurivin PDM strain is shown in FIG. 4 and an alignment of the encoded polypeptide sequences is shown in FIG. 5.

In a preferred embodiment of the invention, the parental strain used to introduce the one or more modifications has a MET5 gene sequence which has at least 70%, more preferably at least 80%, more preferably at least 90%, more preferably at least 95% and more preferably at least 98% identity with one of the sequences shown in FIG. 2. Preferably, the MET5 gene of the parental strain encodes a polypeptide that has at least 70%, more preferably at least 80%, more preferably at least 90%, more preferably at least 95% and more preferably at least 98% identity with one of the sequences shown in FIG. 3.

In a preferred embodiment of the invention, the parental strain used to introduce the one or more modifications has a MET10 gene sequence which has at least 70%, more preferably at least 80%, more preferably at least 90%, more preferably at least 95% and more preferably at least 98% identity with one of the sequences shown in FIG. 4. Preferably, the MET10 gene of the parental strain encodes a polypeptide that has at least 70%, more preferably at least 80%, more preferably at least 90%, more preferably at least 95% and more preferably at least 98% identity with one of the sequences shown in FIG. 5.

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

Amino acid sequence mutants of the polypeptides of the present invention can be prepared by introducing appropriate nucleotide changes into a nucleic acid of the present invention.

Substitution mutants have at least one amino acid residue in the polypeptide molecule removed and a different residue inserted in its place. The sites of greatest interest for substitutional mutagenesis include sites identified as important for $H_2S$ production as identified herein. Other sites of interest are those in which particular residues obtained from various strains or species are identical. These positions may be important for biological activity.

Measurement of $H_2S$ Production

Any suitable method can be used to measure $H_2S$ production in the modified yeast strains of the present invention.

Since hydrogen sulfide forms a dark-colored precipitate with heavy metal ions, colony color analyses have been developed that correlate the amount of dark pigment produced with the level of hydrogen sulfide being formed under the given growth conditions.

One such medium is called "BiGGY" agar. BiGGY (bismuth glucose glycine yeast agar), is a differential medium that evaluates relative production of hydrogen. Hydrogen sulfide generated by the yeast colony forms a black precipitate and the intensity of color is dependent on the amount of sulfide produced. Studies have confirmed that that the use of BiGGY media is a valid means for predicting $H_2S$ producing potential of wine yeast strains (Jiranek et al., 1995). Copper-based media can also be used in a similar way.

Alternatively, the hydrogen sulfide formed during growth in liquid media can be quantified in the gaseous phase released during fermentation. Since $H_2S$ is volatile, it is driven off in the carbon dioxide stream produced during fermentation of sugar. The $H_2S$ in this stream can be trapped and quantified. This can be done using a liquid trap-based method (Jiranek et al., 1995) or by allowing the gas stream to pass over a paper strip containing lead that will bind to the $H_2S$ (Giudici and Kunkee, 1994).

Hydrogen sulfide in fermentation media can be also determined using the $H_2S$-Spectroquant test kit (Merck) (Nowak et al., 2004). This kit is based on the reaction of $H_2S$ with dimethyl-p-phenylenediamine and iron (III) ions to form methylene blue which can be determined spectrophotometrically.

Hydrogen sulfide from the headspace can also be analyzed using gas chromatography mass spectrometry (GC-MS).

Manufacturing Yeast Strains

The present invention encompasses modified industrial yeasts strains that are produced for commercial use. For example, the invention extends to modified yeast strains produced in the form of liquid cultures, compressed (cream) yeast and dried yeast, particularly active dried yeast.

Figure 6:
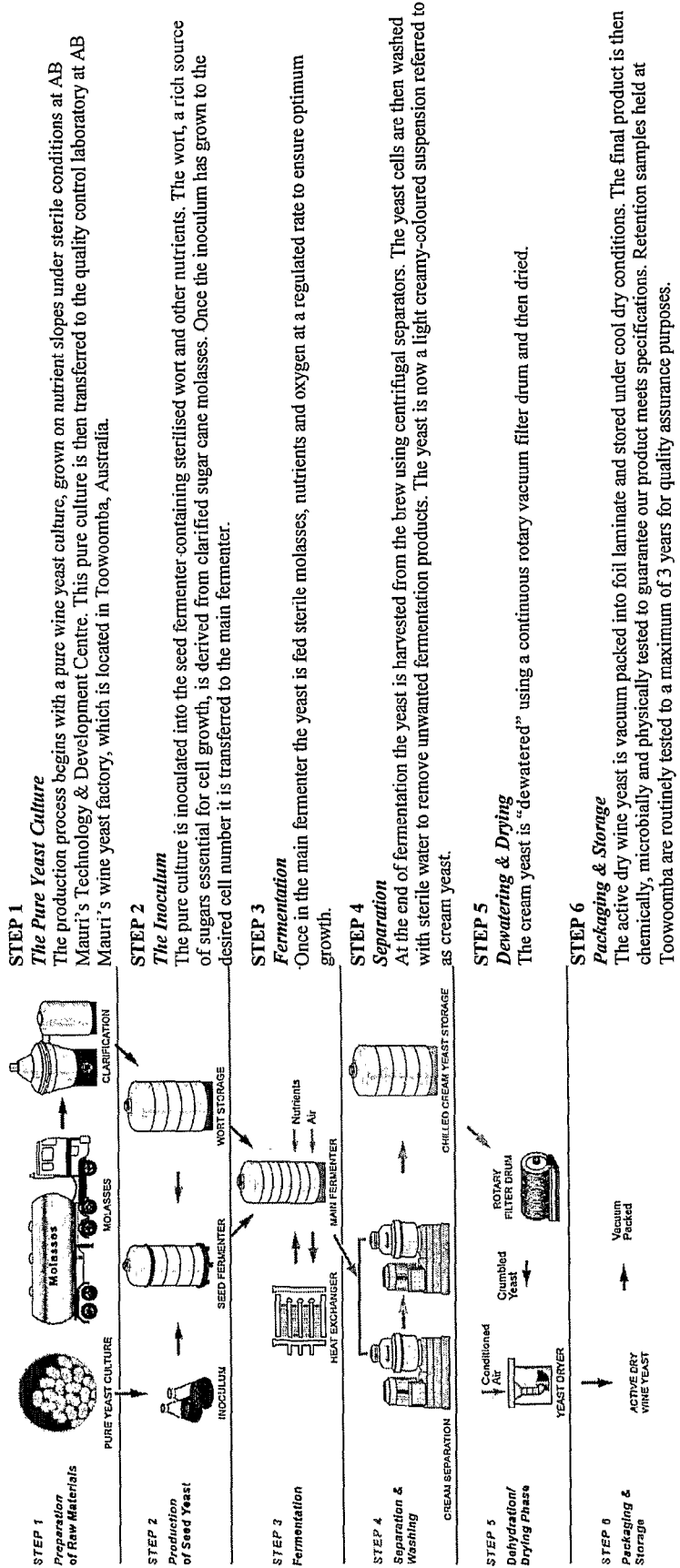
FIG. 6: Method of production of active dried yeast

Methods for producing compressed and dried yeast strains will be well known to those skilled in the art. A general outline of a suitable but non-limiting process for the production of active dried yeast strains is shown in FIG. 6.

EXAMPLES

Example 1

Random Mutagenesis of Wine Yeast Strain

The Maurivin PDM strain was inoculated in YPD media (1% yeast extract, 2% peptone, 2% glucose) overnight, washed with 50 mM potassium phosphate buffer, pH 7.0, and resuspended in 10 ml of this buffer.

A number of optimisation experiments were conducted where EMS (ethyl methane sulfonate) was added in different concentrations and the cells incubated for 30 min at 30° C. in order to obtain a survival rate of 50%. Mutagenised cells were spread on YPD plates (~200 colonies per plate) and allowed to grow for 2 days at 30° C. A total of 16,000 mutants were isolated.

Yeast colonies were replica plated on commercial BiGGY agar and onto a modified BiGGY Agar containing sulfate instead of sulfite. Commercial BiGGY agar contains sulfite as a substrate which is converted by sulfite reductase to $H_2S$. Yeast mutants screened on commercial BiGGY agar that show a white phenotype are likely to contain a mutation in MET10 or MET5. Screening on modified BiGGY agar containing sulfate allows identification of mutations in other genes upstream such as MET3, MET14 and MET16.

A total of 32,000 mutants were replica plated for screening. Replica plated yeast colonies were allowed to grow for 2 days at 30° C.

A number of $H_2S$ mutant yeast strains were selected for further analysis based on the colour of the colonies.

Example 2

Small Scale Fermentation Screening (1)

A synthetic grape juice medium approximating the composition of typical grape juice has been previously described (Henschke and Jiranek, 1991). This medium was modified such that the nitrogen concentration was reduced from 350 to 100 mg/L, and the initial sugar concentration was 237 g/L. Of the 100 mg/L of yeast assimilable nitrogen (YAN), 70 mg/L corresponded to amino acids and 30 mg/L to ammonia.

A total of 17 mutant strains were selected and inoculated for fermentation into 150 ml of the synthetic grape medium. Maurivin PDM (unmodified strain) was used as a control. The initial concentration of cells was $1 \times 10^6$ cells/mL.

The fermentations were conducted at 15° C. in 250 ml conical flasks fitted with an air lock and side arm septa for sampling. A lead acetate strip was placed inside the flask and was used as a semi-quantitative measure of $H_2S$ production (the strips are sensitive and colour changes from white to black indicate the slightest presence of $H_2S$).

All the fermentations were performed in duplicate, and sugar concentration and yeast growth (optical density or "OD") were measured every 3-4 days.

The ferment inoculated with the PDM strain was dry after 38 days. The 4.2 mutant strain showed a faster fermentation rate than that of the PDM strain as the ferment was dry after 34 days. A number of the other mutants (1.1, 2.1, 51.1, 114.1, 72.2, 75.1, 4.4) fermented at a similar rate as the PDM strain.

Of the 17 mutants, a total of 9 strains (1.1, 45.2, 2.1, 22.1, 23.2, 51.1, 72.2, 114.1, and 4.2) were selected for the next screening trial. The selection was based on the fermentation rates and the colour of the colonies on BiGGY agar.

The production of $H_2S$ was very low in these ferments since the lead acetate strips did not show any colour change in any of the ferments. This could be due to the high concentration of sulfur amino acids in the must (22 mg/L methionine, 8.5 mg/L cysteine) which may prevent the formation of $H_2S$.

In addition, we performed an HPLC analysis of the following fermentation properties: ethanol yield, acetic acid production, glycerol production, and production of organic acids such as malic, lactic, citric, tartaric and succinic acid (Table 1). None of the mutant strains tested showed significantly different properties than those of the PDM strain.

Example 3

Small Scale Fermentation Screening (2)

A synthetic grape juice medium similar to that described in Example 2 above was used for a second small scale fermentation screening. Again, the total YAN concentration was 100 mg/L, however, unlike the medium used in Example 2, the highest contribution to the total YAN was in the form of inorganic ammonium ion (80 mg/L), with only 20 mg/L contributed by amino acids. The concentrations of the sulfur amino acids cysteine and methionine were reduced to 1 mg/L in order to encourage production of $H_2S$ by the mutant strains.

The initial sugar concentration was 244 g/L, and the fermentations were conducted at 18° C. in 250 mL conical flasks fitted with an air lock and side arm septa for sampling. A lead acetate strip was placed inside the flask to follow $H_2S$ production.

A total of 9 mutant strains (1.1, 45.2, 2.1, 22.1, 23.2, 51.1, 72.2, 114.1, and 4.2) were selected from the screening described in Example 2 and inoculated for fermentation into 150 mL of the synthetic grape must. The initial cell concentration was about $1\times10^6$ cells/mL. The PDM strain was used as a control.

The fermentations were performed in triplicate, and sugar concentration and optical density were measured every 3-4 days.

Figure 7:
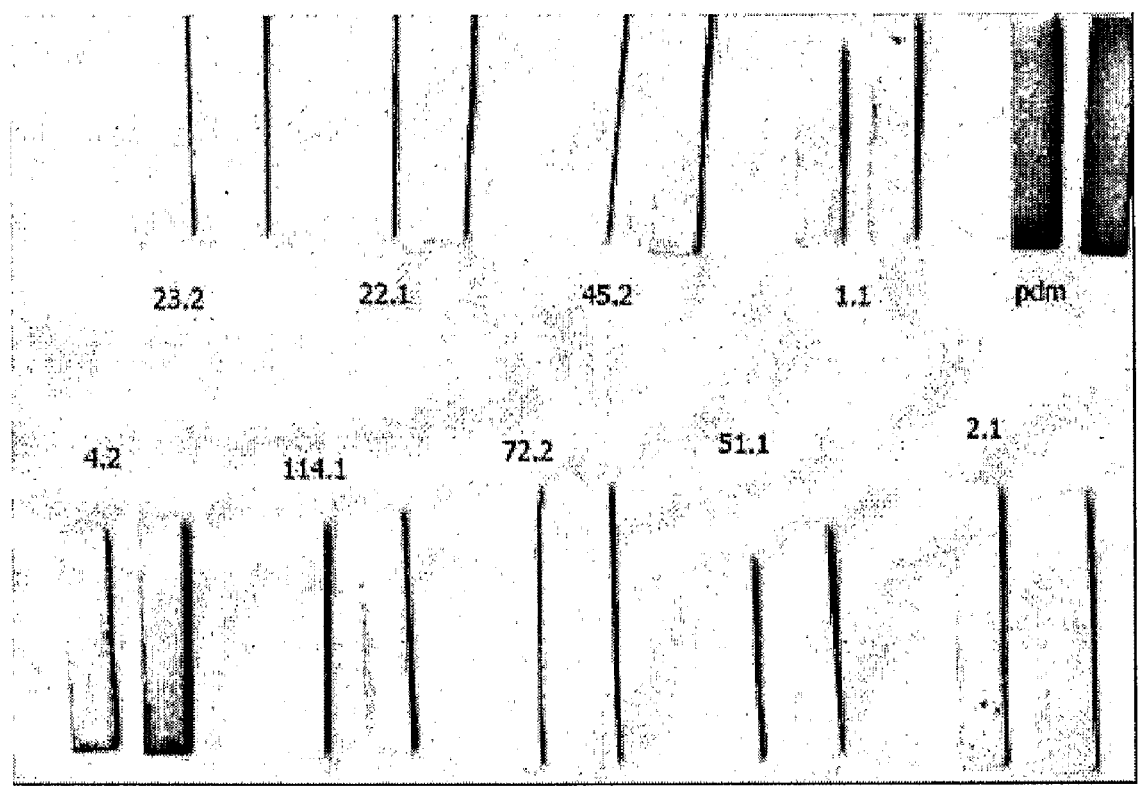
FIG. 7: Lead acetate ($H_2S$ indicator) strips taken from the end of ferments conducted using mutant (1.1, 45.2, 2.1, 22.1, 23.2, 51.1, 72.2, 114.1, and 4.2) and control (PDM) for a small scale synthetic grape juice fermentation screening 2.

The PDM strain produced a considerable amount of $H_2S$; the 1.1, 2.1 and 4.2 mutant strains produced some $H_2S$ during the fermentation, although to a lesser extent than the PDM strain; with the remaining mutant strains producing very small amounts of $H_2S$ (see FIG. 7).

Figure 8:
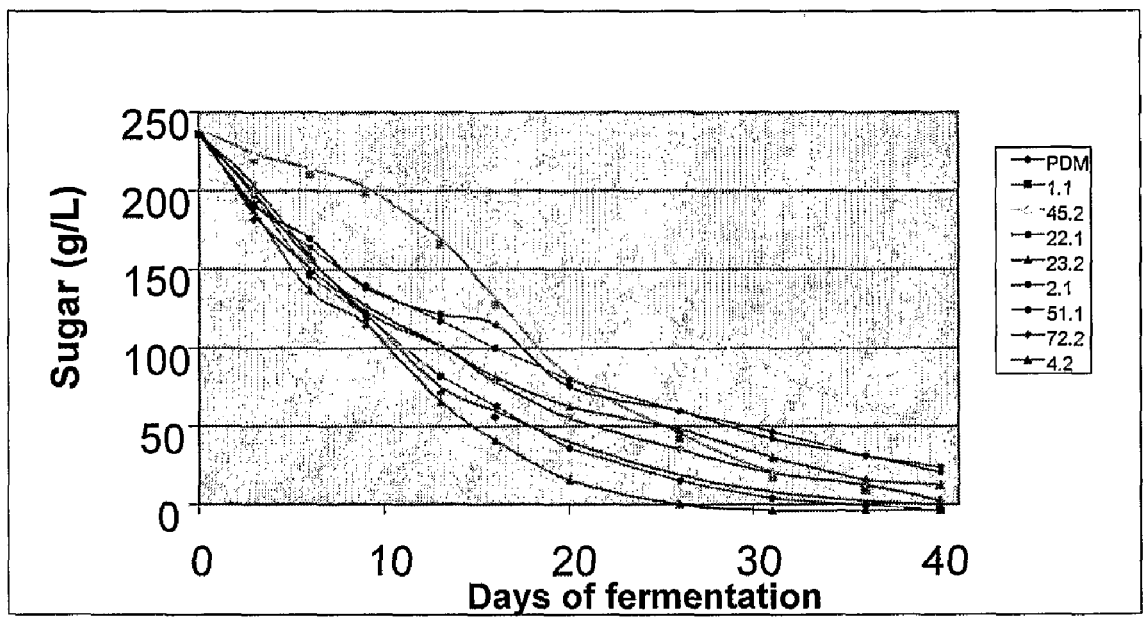
FIG. 8: Graph showing sugar consumption during ferments conducted using mutant (1.1, 45.2, 2.1, 22.1, 23.2, 51.1, 72.2, 114.1, and 4.2) and control (PDM) strains during a small scale synthetic grape juice fermentation screening 2.

The fermentation rates (or rates of sugar consumption) of the strains are shown in FIG. 8. The ferment inoculated with the PDM strain was dry after 36 days. Again, the 4.2 strain showed a faster fermentation rate than the PDM strain as the ferment was dry after 31 days. The mutants 51.1 and 114.1 fermented at a similar rate as the PDM strain, and mutants 1.1, 23.2, and 72.2 fermented at a slightly slower rate than the PDM strain. Finally, the 2.1, 45.2, and 22.1 strains fermented at a significantly slower rate than the PDM strain; in the case of the 2.1 and 45.2 strains this could be due to the fact that they are methionine auxotrophs and therefore struggle to grow in a media with only 1 mg/L of methionine.

In addition, we performed an HPLC analysis of the following fermentation properties: ethanol yield, acetic acid production, glycerol production, and production of organic acids such as malic, lactic, citric, tartaric and succinic. None of the mutant strains tested showed significantly different properties than those of the PDM strain. The $SO_2$ levels (free and bound $SO_2$) were also measured at the end of the fermentation. The PDM strain did not accumulate any $SO_2$ and this was also the case of the 2.1 and 4.2 mutants. The remaining mutants accumulate considerably amounts of $SO_2$ as shown in Table 2.

Mutant strains were plated on BiGGY agar plates, at the beginning and at the end of the fermentation, to check whether there was any change in the colour (phenotype) of the mutant strains after the fermentation. Mutants 1.1 and 45.2 produced white colonies at the start of the fermentation but showed a partial reversion at the end of fermentation since half all the colonies were brown at that stage.

Example 4

Fermentation Screening Using Chardonnay Grape Juice

Fermentation screening of the mutant strains was carried out in 2006 non-sterile Chardonnay juice. Two white mutant strains (1.1 and 45.2), two light tan mutant strains (22.1 and 23.2) and the control PDM strain were inoculated in 200 ml sterile Chardonnay juice for propagation. The yeast were then inoculated, from the juice propagated samples, in 3 L Chardonnay ferments at $1\times10^6$ cell/mL and incubated at 15° C. No duplicates were included. Strains 1.1 and 45.2 (methionine auxotrophs) showed a lower optical density than PDM throughout the fermentation. Commercial lead acetate strips were attached inside the fermenters in order to assess $H_2S$ production.

With regard to fermentation of the control PDM strain, the $H_2S$ indicator strip turned light brown after 1 day and was black thereafter. The $H_2S$ indicator stayed white in the ferments with the white strains (1.1 and 45.2) until halfway through the fermentation and then turned black. There was no apparent contamination of wild yeast in these ferments as assessed by transposon PCR.

The indicator strips stayed white in the ferments with the light-tan strains (22.1 and 23.2). Also, there was no change in the colour of the colonies in BiGGY agar during the fermentation and no apparent contamination of wild yeast was observed.

Figure 9:
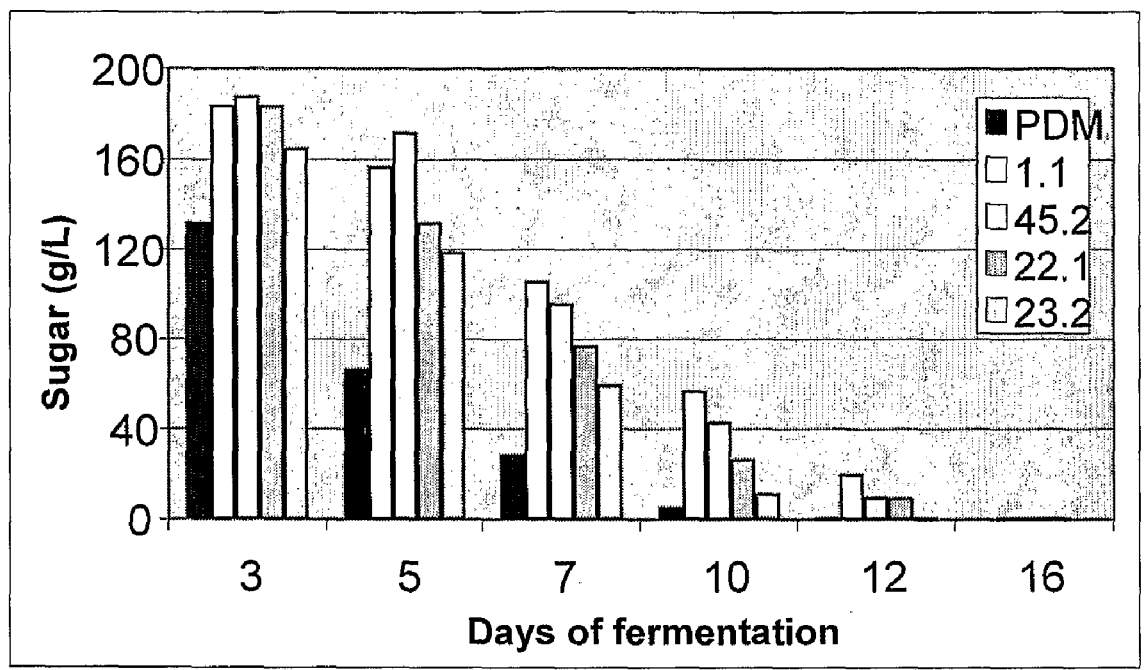
FIG. 9: Graph showing sugar consumption during ferments conducted using mutant (1.1, 45.2, 22.1 and 23.2) and control (PDM) strains during a fermentation screening in Chardonnay grape juice.

In general, all the strains were fermenting slower than PDM with the exception of one light-tan mutant (23.2) that finished almost at the same time as the PDM strain (12 days) (See FIG. 9).

We attempted to stabilise the reverting phenotypes of mutants 1.1 and 45.2 by growing the cells in YND, selecting the white colonies on BiGGY agar, reinoculating in YND and repeating this process 4 times until only white mutants could be observed on BiGGY agar. Only mutant 45.2 could be stabilised.

Example 5

Fermentation Screening Using Sauvignon Blanc Grape Juice

Fermentation screening of the mutant strains was carried out in 2007 non-sterile Sauvignon Blanc juice. One white strain (45.2-stabilised), two light tan strains (2.1 and 51.1), one tan strain (4.2) and the control PDM strain were inoculated in YPD for propagation. Yeast were then inoculated, from the YPD propagated samples, in 3 L Sauvignon blanc ferments at $1\times10^6$ cell/mL and incubated at 18° C. The fermentation experiments were performed in duplicate. Commercial lead acetate strips were attached inside the fermenters to assay $H_2S$ production.

The following grape juice properties were analysed (prior to fermentation):

| Analyte | Units |
| --- | --- |
| pH | 3.3 |
| TA | 5.1 |
| Sugar | 190 g/L |
| YAN | 247 mg/L |
| Ammonia | 83 mg/L |

-continued

| Analyte | Units |
|---|---|
| Alpha amino nitrogen | 179 mg/L |
| L-cysteine | Not detected |
| L-methionine | 6.6 mg/L |

Figure 10:
FIG. 10: Lead acetate ($H_2S$ indicator) strips taken from the end of ferments conducted using mutant (45.2, 2.1, 51.1 and 4.2) and control (PDM) for a fermentation screening using Sauvignon blanc grape juice.

Strains 45.2 and 4.2 (to a lesser extent) were slow to grow in the grape juice as indicated by their OD readings which were lower than those of the PDM strain throughout the fermentation. The $H_2S$ indicator strip in the PDM strain ferment turned gradually darker and after 8 days was completely black. The strip stayed white in the ferments with the 45.2 and 51.1 strains; it turned slightly brown in the 2.1 ferment, and brown in the 4.2 ferment (see FIG. 10).

Figure 11:
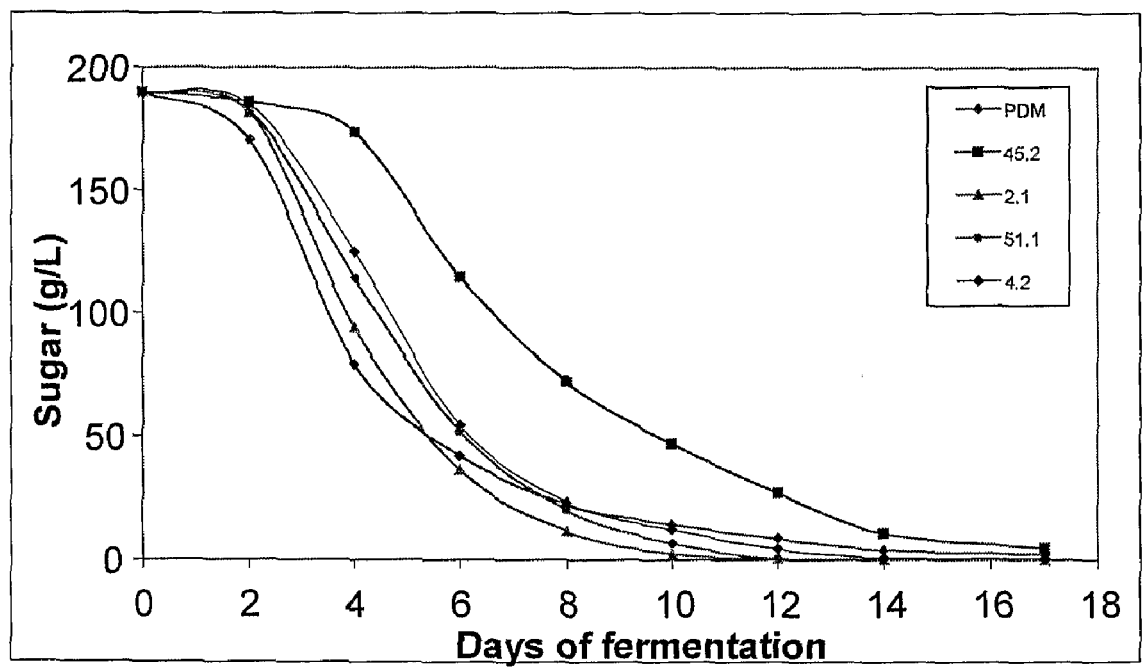
FIG. 11: Graph showing sugar consumption during ferments conducted using mutant (45.2, 2.1, 51.1 and 4.2) and control (PDM) strains during a fermentation screening in Sauvignon blanc grape juice.

The fermentation rates (or rates of sugar consumption) of the strains are shown in FIG. 11. All of the mutant strains, except the 45.2 strain, fermented at the same rate as the PDM strain. The mutant 2.1 strain fermented at a slightly faster rate than the PDM strain. Although the fermentation rate of the 45.2 strain was slower, it finished more or less at the same time as the PDM strain. In addition, an HPLC analysis of some of the fermentation properties was performed: ethanol yield, acetic acid production, glycerol production, and production of organic acids. The mutant 2.1 showed a decreased production of acetic acid when compared with the PDM strain (0.06 and 0.28 g/L, respectively). $SO_2$ levels were also measured for these mutants. As seen in the small ferments, the 2.1 and 4.2 mutants accumulated only small amounts of $SO_2$ (as the PDM control strain), whereas mutants 45.2 and 51.1 showed high levels of $SO_2$ production (Table 3).

Example 6

Sequence Analysis of the MET5 and MET10 Genes in Mutant Strains

The MET10 and MET5 genes were fully sequenced in seven of the most interesting mutant strains (1.1, 45.2, 2.1, 22.1, 23.2, 51.1 and 4.2). Mutations were observed in both the MET10 and MET5 genes. The mutations (in the amino acid sequence) are shown in Table 4.

For MET10, the fact that in two of the mutants (22.1 and 23.2) the observed mutation creates a stop codon means that one of the two copies of the gene produces a truncated (and possibly inactive) protein. Two of the mutations (G911S and E929K) are present in conserved amino acids within the yeast sulfite reductase family, suggesting that these amino acids are important for enzyme function.

Five mutations were identified in MET5. Two of the mutated amino acids are highly conserved within the sulfite reductase family (G1115D and E1356K).

Example 7

Expression of the MET5/MET10 Mutations

To determine whether the mutations in MET5/MET10 (see Table 4) were responsible for the observed phenotype in the PDM mutant strains, several MET5 and MET10 mutant genes were cloned in a centromeric plasmid (pRS416) with their respective promoters and expressed in BY4742 cells.
MET5
Four of the most interesting mutations (P210L, A979T, G1115D, and E1356K) were individually introduced in the plasmid expressing MET5, which was then transformed in BY4742 ΔMET5 cells.

Figure 12:
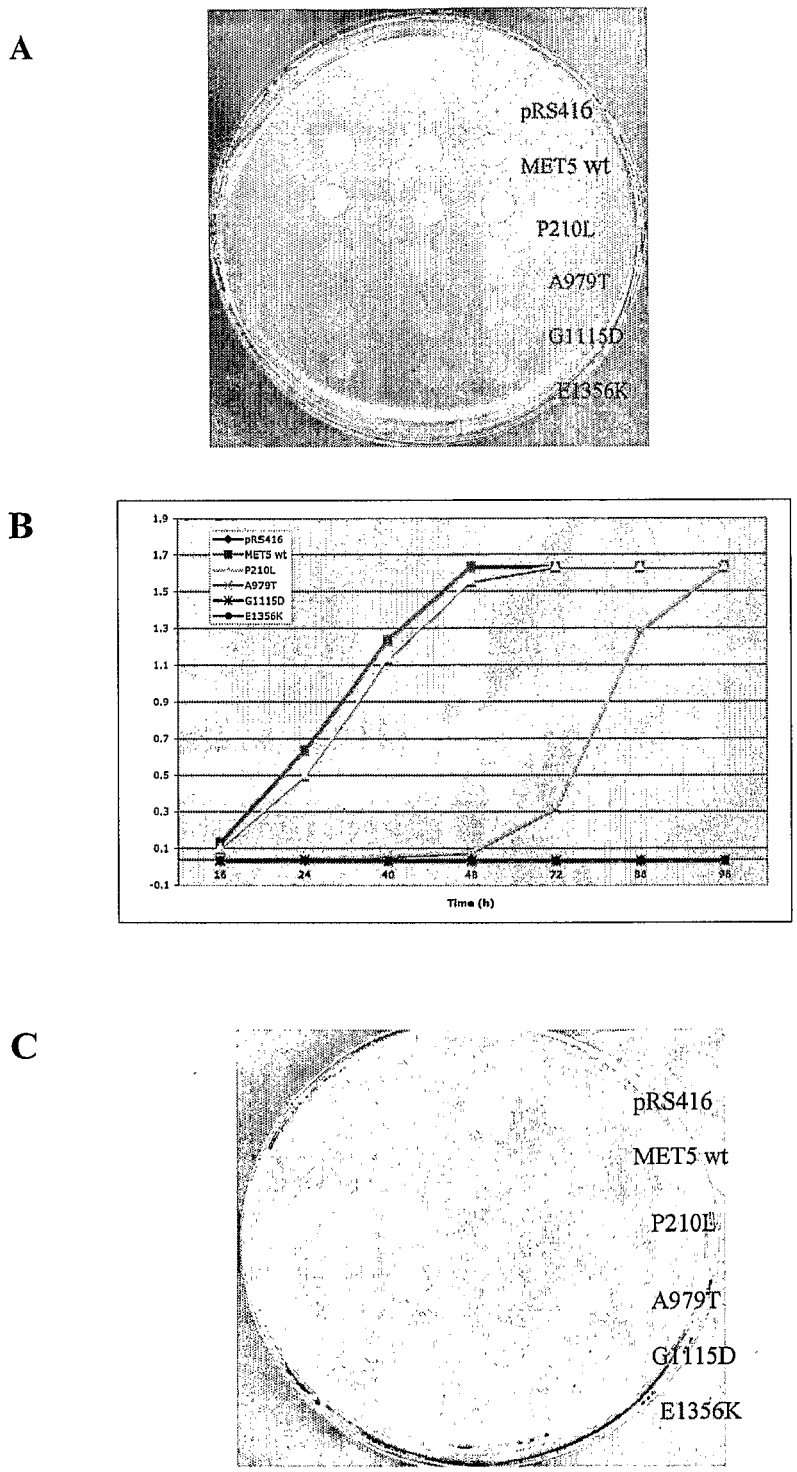
FIG. 12: Growth of the MET10 mutants in minimal media lacking methionine: (a) on plate; (b) on liquid; and (c) phenotype of MET5 mutants in BiGGY agar plates

Growth in the absence of methionine was tested. On plate, three of the mutants failed to grow (A979T, G1115D and E1356K), whereas the P210L mutant grew in those conditions (FIG. 12a). On a liquid culture, the MET5 mutants G1115D and E1356K failed to grow, but mutant A979T started to grow after 48 hours of incubation (FIG. 12b). The growth of this particular mutant therefore explains the leaky phenotype observed in the mutant 1.1.

Cells were also spotted in BiGGY agar plates (FIG. 12c). Mutant P210L showed the same phenotype as MET5 wt, whereas the other 3 mutants showed a white phenotype. The same mutants that were unable to grow in the absence of methionine displayed a white phenotype in BiGGY. These results indicate that the mutations observed in the 1.1 mutant (A979T and G115D) and in the 45.2 mutant (E1356K) are responsible for the white phenotype and methionine auxotrophy of both mutant strains. In contrast, the mutation found in the 2.1 mutant (MET5 P210L) would not appear to contribute to the phenotype of this strain. Another mutation is present in this strain (MET10 E619K), and is discussed below.

To confirm that MET5 was being expressed in the mutants, a reverse transcriptase-PCR experiment was performed and confirmed that MET5 was being transcribed in all four MET5 mutants, but not in cells expressing the empty plasmid, as expected (data not shown).
MET10
Seven of the most interesting mutations (W59stop, L606F, E619K, W841stop, E929K, T990I and T997I) were individually introduced in the plasmid expressing MET10, and plasmids were transformed in BY4742 ΔMET10 cells.

Growth in the absence of methionine was tested. On plate, mutants W59stop, W841stop and E929K failed to grow (FIG. 13a). This result was expected since both W59stop and W841stop mutations create a stop codon, and E929 is a conserved amino acid. On liquid media, mutant W59stop began to grow after 48 hours of incubation (FIG. 13b).

MET10 mutants were then spotted in BiGGY agar plates (FIG. 13c). All 3 mutants (W59stop, W841stop, and E929K) that failed to grow in the media lacking methionine showed no sulfite reductase activity. These results indicate that both mutations which create a stop codon in the protein (W59stop and W841stop) are responsible for the phenotype of their respective mutant strains (23.2 and 22.1). The E929K mutation also explains the phenotype of the 51.1 strain. In contrast, the E619K mutation (2.1 strain) has no effect on sulfite reductase activity.

Both plasmids carrying the MET10 E610K and MET5 P210L mutations were expressed together in the same yeast to assess the effect when both mutated proteins interact. The results showed that the double mutant behaves as the wt strain since it displays a brown phenotype in BiGGY and grows in the absence of methionine (data not shown). Therefore, it can be concluded that both mutations observed in the 2.1 strain are not responsible for their phenotype.

To confirm that MET10 was being expressed in the mutants, a reverse transcriptase-PCR experiment was performed and confirmed that MET10 was being transcribed in all seven mutants, but not in the cells expressing the empty plasmid, as expected (data not shown).

Example 8

Hydrogen Sulfide Production by the MET5/MET10 Mutants

A small-scale fermentation experiment was carried out using filter sterilised low YAN Riesling juice to study the fermentation performance of the six mutant strains, 2.1, 4.2, 22.1, 23.2, 45.2 and 51.1, in real grape juice, and more importantly, to obtain a quantitative measurement of the $H_2S$ productivity in these conditions.

Mutants 2.1 and 51.1 fermented at a similar rate as the control PDM strain, and 4.2 fermented even faster. Mutants 22.1 and 23.2 fermented slightly slower than PDM, and 45.2 mutant showed a very slow fermentation rate.

Figure 14:
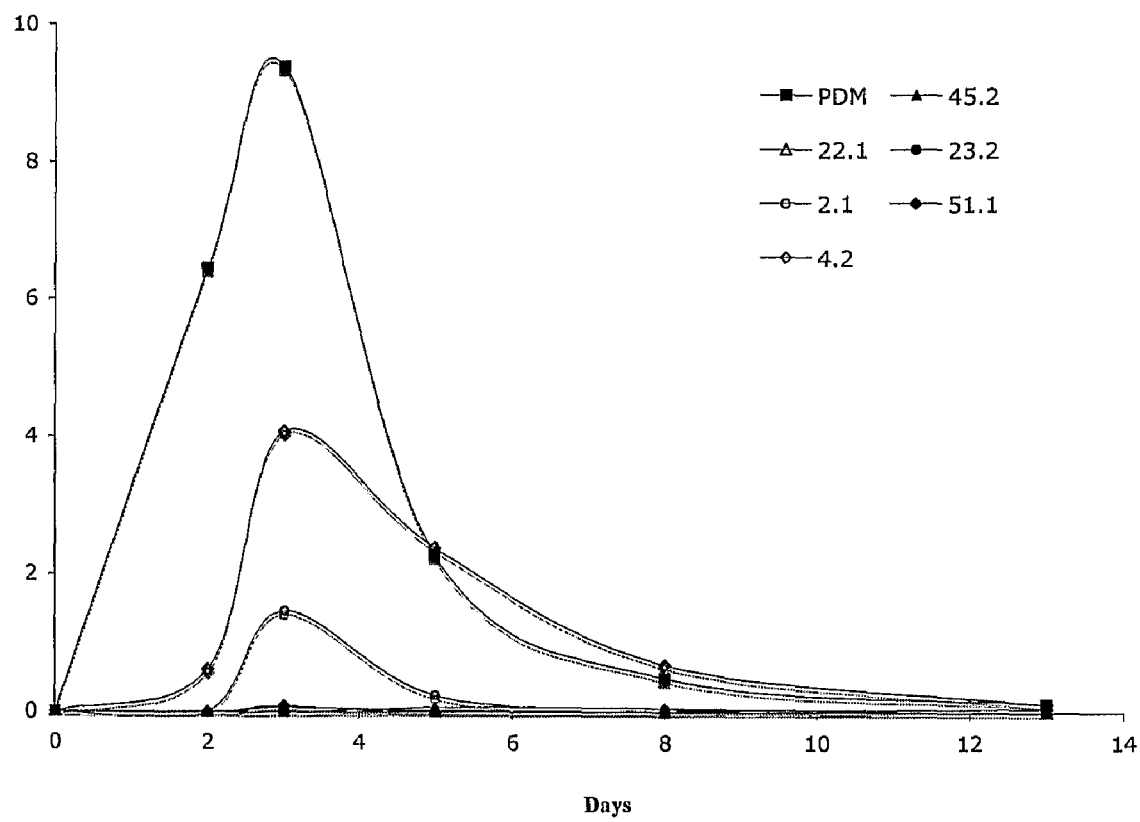
FIG. 14: $H_2S$ productivity by PDM and 6 of the mutant strains.

The control PDM strain produced considerable amounts of $H_2S$ throughout fermentation, and maximum levels were observed after 3 days of fermentation. After this point, the rate of $H_2S$ productivity diminished dramatically with time (FIG. 14). Mutants 4.2 and 2.1 also produced significant amounts of $H_2S$ throughout the fermentation, and again maximum $H_2S$ productivity was observed after 3 days. The total $H_2S$ production during fermentation by the 4.2 strain was about half that of the control PDM, and this figure was only 11% for the 2.1 mutant (Table 5). Low rates of $H_2S$ liberation were observed for the remaining mutant strains (45.2, 22.1, 23.2, and 51.1). In all cases, the total $H_2S$ production during fermentation was only about 1% of that of the control strain.

The fermentation properties and $SO_2$ production at the end of fermentation were also analysed (Table 6). As expected, the PDM strain accumulated small amounts of $SO_2$ (32 mg/L), and this was also the case for the 2.1 and 4.2 mutants. The remaining mutants accumulated considerable amounts of bound $SO_2$ (between 143 and 179 mg/L). There is an inverse correlation between $H_2S$ and $SO_2$ production for these strains. It has been shown that strains with an inactive sulfite reductase cannot reduce sulfite to sulfide, therefore sulfite accumulates and diffuses from the cell to the media (Hansen & Kielland-Brandt, 1996).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Documents referred to above are incorporated herein in their entirety by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Donalies U. E. and Stahl U. "Increasing sulphite formation in *Saccharomyces cerevisiae* by overexpression of MET14 and SSU1" Yeast. 19(6):475-84 (2002)

Giudici, P. and R. E. Kunkee. "The effect of nitrogen deficiency and sulfur-containing amino acids on the reduction of sulfate to hydrogen sulfide by wine yeasts." Am. J. Enol. & Vitic. 45: 107-112 (1994).

Hansen, J. and Kielland-Brandt, M. C. Inactivation of MET10 in brewer's yeast specifically increases SO2 formation during beer production. Nat. Biotechnol. 11:1587-91 (1996).

Henschke, P., and V. Jiranek. "Hydrogen sulfide formation during fermentation: effect of nitrogen composition in model grape musts", p. 172-184. In Proceedings of the International Nitrogen Symposium, Seattle, Wash. American Society of Enology and Viticulture, Davis, Calif. (1991)

Jiranek, V., P. Langridge, and P. Henschke. "Validation of bismuth-containing indicator media for predicting $H_2S$-producing potential of *Saccharomyces cerevisiae* wine yeasts under enological conditions." Am. J. Enol. Vitic. 46:269-273 (1995a)

Jiranek, V., P. Langridge, and P. A. Henschke. "Regulation of hydrogen sulfide liberation in wine-producing *Saccharomyces cerevisiae* strains by assimillable nitrogen." Appl. & Environ. Micro. 61: 461-467 (1995b).

Jiranek, V., P. Langridge, and P. A. Henschke. "Determination of sulphite reductase activity and its response to assimilable nitrogen status in a commercial *Saccharomyces cerevisiae* wine yeast." J. Appl. Bacteriol. 81:329-336 (1996).

Linderholm, A. and Bisson, L. F. "Eliminating formation of hydrogen sulphide by *Saccharomyces*" Practical winery and vineyard magazine, November/December 2005.

Mendes-Ferreira A. et al., "Survey of hydrogen sulphide production by wine yeasts" J. Food Prot. 65(6):1033-7 (2002).

Negritto, M T, Wu, X, Kuo, T, Chu, S, Bailis, A M: "Influence of DNA sequence identity on efficiency of targeted gene replacement." Mol Cell Biol 17: 278-286 (1997).

Nowak, A., Kusewicz, D., Kalinowska, H., Turkiewicz, M., and Patelski, P. "Production of $H_2S$ and properties of sulfite reductase from selected strains of wine-producing yeasts." *Eur Food Res Technol* 219: 84-89 (2004).

Pretorius, I. S. & F. F. Bauer. "Meeting the consumer challenge through genetically customised wine yeast strains." *Trends in Biotechnology* 20:426-432 (2002)

Pretorius, I. S. "The genetic analysis and tailoring of wine yeasts." In: S. Hohmann (ser. ed.), *Topics in Current Genetics*, Vol 2; J. H. de Winde (ed.), *Functional Genetics of Industrial Yeasts* (pp. 99-142). Springer Verlag, Heidelberg, Germany (2003)

Pretorius, I. S. "The genetic improvement of wine yeasts." In: D. Arora, P. D. Bridge & D. Bhatnagar (eds.), *Handbook of Fungal Biotechnology* (2nd edn.). Marcel Dekker, Inc., New York, USA. pp. 209-232 (2004)

Rothstein, R: Targeting, disruption, replacement, and allele rescue: integrative DNA transformation in yeast." Methods Enzymol. 194: 281-301 (1991).

Simon, J R, Moore, P D. "Homologous recombination between single-stranded DNA and chromosomal genes in *Saccharomyces cerevisiae*." Mol Cell Biochem 7, pp. 2329-2334.1987.

Spiropoulos, A. and L. F. Bisson. "MET17 and hydrogen sulfide formation in *Saccharomyces cerevisiae*." Appl. & Environ. Micro. 66: 4421-4426 (2000).

Winzeler, et al.: "Functional characterization of the *S. cerevisiae* genome by gene deletion and parallel analysis." Science 285: 901-906 (1999).

TABLE 1

Small scale fermentation screening (1).

|  |  | PDM | 1.1 | 45.2 | 2.1 | 22.1 | 23.2 | 51.1 | 72.2 | 4.2 |
|---|---|---|---|---|---|---|---|---|---|---|
| Residual sugar | g/L | 0 | 0 | 1.3 | 0 | 2.6 | 0 | 0 | 0 | 0 |
| Glycerol | g/L | 6.5 | 6.6 | 6.0 | 6.8 | 6.3 | 6.8 | 6.4 | 6.4 | 7.4 |
| Acetic acid | g/L | 0.83 | 0.68 | 0.81 | 0.76 | 0.88 | 0.83 | 0.81 | 0.79 | 0.92 |
| Ethanol | % | 14.4 | 14.3 | 14.2 | 14.3 | 14.2 | 14.5 | 14.3 | 14.5 | 14.4 |
| Days to dryness (<2 g/L) |  | 35 | 37 | 42 | 34 | 45 | 39 | 34 | 36 | 30 |

After 45 days

TABLE 2

Small scale fermentation screening (2).

|  |  | PDM | 1.1 | 45.2 | 2.1 | 22.1 | 23.2 | 51.1 | 72.2 | 4.2 |
|---|---|---|---|---|---|---|---|---|---|---|
| Sulfite (free/total) | mg/L | 0/0 | 5/198 | 2/241 | 0/0 | 0/63 | 4/173 | 0/178 | 2/150 | 0/5 |
| Residual sugar | g/L | 0 | 2.0 | 57 | 25 | 29 | 17 | 0.5 | 6.1 | 0 |
| Glycerol | g/L | 7.0 | 6.8 | 6.5 | 7.6 | 6.3 | 6.6 | 6.6 | 6.8 | 7.7 |
| Acetic acid | g/L | 0.75 | 0.58 | 0.60 | 0.74 | 0.73 | 0.71 | 0.72 | 0.75 | 0.79 |
| Ethanol | % | 14.8 | 14.7 | 11.1 | 13.0 | 12.9 | 13.7 | 14.9 | 14.6 | 14.9 |
| Days to dryness (<2 g/L) |  | 36 | 40 | >40 | >40 | >40 | >40 | 40 | >40 | 30 |

After 40 days

TABLE 3

Sauvignon blanc fermentation screening.

|  |  | PDM | 45.2 | 2.1 | 51.1 | 4.2 |
|---|---|---|---|---|---|---|
| Sulfite (free/total) | mg/L | 0/80 | 0/174 | 0/95 | 0/177 | 0/89 |
| Residual sugar (Fructose) | g/L | 1.7 | 1.2 | 0.2 | 0 | 0.7 |
| Glycerol | g/L | 4.8 | 5.8 | 5.2 | 5.3 | 5.7 |
| Acetic acid | g/L | 0.28 | 0.35 | 0.06 | 0.2 | 0.36 |
| Ethanol | % | 11.4 | 11.3 | 11.3 | 11.5 | 11.5 |
| Days to dryness (<2 g/L) |  | 17 | 19 | 12 | 12 | 14 |

After 19 days

TABLE 4

Mutations in the MET5 and MET10 genes. Amino acids conserved in the eukaryotic sulfite reductase family are shown in bold. In red are amino acids conserved in the sulfite reductase family. In the case that more than one mutation was found in the same gene, it is indicated whether the mutations are in the same allele or in different alleles.

| Mutant | MET5 | MET10 | PHENOTYPE |
|---|---|---|---|
| 1.1 | A979T/G1115D (different alleles) |  | White/Met aux. |
| 45.2 | E1356K |  | White/Met aux. |
| 2.1 | P210L | E619K | Light tan/Met aux. |
| 22.1 |  | W841stop/G911S (same allele) | Light tan |
| 23.2 | G980D | W59stop | Light tan |
| 51.1 |  | E929K/T990I (different alleles) | Light tan |
| 4.2 |  | L606F/T997I (different alleles) | Tan |

TABLE 5

Total $H_2S$ production by PDM and the mutant strains throughout the fermentation.

|  | μg $H_2S$/g dry yeast | μg $H_2S$/L |
|---|---|---|
| PDM | 22.5 | 71.6 |
| 45.2 | 0.31 (1%) | 0.4 |
| 2.1 | 2.39 (11%) | 8.1 |
| 22.1 | 0.19 (1%) | 0.7 |
| 23.2 | 0.03 (0.1%) | 0.2 |
| 51.1 | 0.25 (1%) | 0.9 |
| 4.2 | 12.2 (54%) | 43.5 |

TABLE 6

Fermentation properties and $SO_2$ production at the end of fermentation.

|  |  | PDM | 45.2 | 2.1 | 22.1 | 23.2 | 51.1 | 4.2 |
|---|---|---|---|---|---|---|---|---|
| Sulfite (free/total) | mg/L | 0/32 | 0/164 | 0/30 | 0/143 | 0/179 | 4/173 | 0/39 |
| Residual sugar | g/L | 0 | 32.5 | 0 | 0.6 | 3.8 | 0 | 0 |
| Glycerol | g/L | 6.5 | 7.4 | 7.2 | 7.0 | 8.4 | 6.8 | 6.5 |
| Acetic acid | g/L | 0.28 | 0.46 | 0.22 | 0.39 | 0.11 | 0.21 | 0.33 |
| Ethanol | % | 14.5 | 11.3 | 14.5 | 14.5 | 14.1 | 14.6 | 14.6 |
| $H_2S$ | μg/L | 71.6 | 0.4 | 8.1 | 0.7 | 0.2 | 0.9 | 43.5 |
| Days to dryness |  | 12 | >17 | 11 | 15 | 17 | 12 | 10 |

The invention claimed is:

1. An isolated industrial *Saccharomyces cerevisiae* yeast strain comprising one or more point mutations in the MET5 gene or the MET10 gene which results in reduced hydrogen sulfide production when compared to the corresponding industrial yeast strain without the modification, wherein the unmodified yeast strain is *Saccharomyces cerevisiae*,
   wherein the one or more point mutations in the MET5 gene result in the following amino acid substitutions in the polypeptide encoded by the MET5 gene:
   (i) P210L;
   (ii) A979T;
   (iii) G980D;
   (iv) G1115D;
   (v) E1356K; or
   (vi) a combination of A979T and G1115D; and
   wherein the one or more point mutations in the MET10 gene result in the following amino acid substitutions in the polypeptide encoded by the MET10 gene:
   (i) W59stop;
   (ii) L606F;
   (iii) E619K;
   (iv) W841 stop;
   (v) G911S;
   (vi) E929K;
   (vii) T990I
   (viii) T997I; or
   (ix) a combination of W841stop/G911S, E929K, T990I or L606F and T997I.

2. The industrial yeast strain according to claim 1 which is a wine yeast strain.

3. The industrial yeast strain according to claim 1, wherein the unmodified yeast strain is Maurivin PDM.

4. The industrial yeast strain according to claim 1, wherein the modification is one or more point mutations in the MET10 gene.

5. The industrial yeast strain according to claim 1 wherein the modified yeast strain produces less than 80% hydrogen sulfide when compared to the corresponding unmodified industrial yeast strain under the same culturing conditions.

6. The industrial yeast strain according to claim 1 wherein the modified yeast strain produces less than 50% hydrogen sulfide when compared to the corresponding unmodified industrial yeast strain under the same culturing conditions.

7. The industrial yeast strain according to claim 1 which is capable of fermenting grape juice to a wine product having less than 2 g/L total sugar.

8. The industrial yeast strain according to claim 1 wherein the volatile acidity production is no more than 0.2 g/L higher than the corresponding unmodified industrial yeast strain.

9. The industrial yeast strain according to claim 1 which has no more than 0.5% less tolerance to ethanol than the corresponding unmodified industrial yeast strain.

10. A modified yeast strain deposited with The National Measurement Institute (NMI) Australia under the accession numbers V07/022167, V07/022168, V07/022169, V07/022170, V07/022171 or V07/022172.

11. A method of manufacturing an industrial yeast strain which comprises culturing the modified industrial yeast strain according to claim 1 under conditions which allows large scale production of the modified yeast strain.

12. A method of producing a fermentated product comprising contacting a product with the modified industrial yeast strain according to claim 1 to produce a fermented product, wherein the fermented product is bread, beer, wine, spirits, or sake.

13. The industrial yeast strain according to claim 1 comprising said one or more point mutations in the MET5 gene and the MET10 gene.

14. The industrial yeast strain according to claim 1, wherein the modification is one or more point mutations in the MET5 gene.

* * * * *

SEQUENCE LISTING

<160> NUMBER OF SEQ ID NOS: 22

<210> SEQ ID NO 1
<211> LENGTH: 4329
<212> TYPE: DNA
<213> ORGANISM: Saccharomyces cerevisiae

<400> SEQUENCE: 1

| | | | | | | |
|---|---|---|---|---|---|---|
| atgactgctt | ctgacctctt | gacgctccca | caattgttgg | cgcaatattc | ctctagtgct | 60 |
| ccccaaaata | aagtgttcta | cactactagc | acaaaaaata | gtcattcatc | cttcaaaggg | 120 |
| ctagaatctg | ttgccacaga | tgctactcat | ctattgaaca | atcaagatcc | attgaatacc | 180 |
| atcaaagatc | aactctctaa | ggacatttta | actaccgttt | ttacagatga | aactactttg | 240 |
| gtcaaatcca | tccaccatct | atattctctt | cctaataaac | ttccattggt | gattacagtg | 300 |
| gatttgaatt | tgcaagatta | ttccgcaatt | cctgcgttaa | aggatctttc | tttccccatc | 360 |
| ttaatatctt | ctgatttgca | aactgcaatt | tcaaacgcgg | actcttctta | taagattgct | 420 |
| acaagttctc | tgaccccagt | tttccatttt | cttaacttgg | agaaaattgg | cacgagtaca | 480 |
| gctattgaac | aagacatcga | ctttcctacc | ttggagattg | ctaacgaaga | gactaaagta | 540 |
| gcattatcag | aagctactga | ttcattgaca | aattttgaac | tggttaaagg | taaagagtca | 600 |
| attaccactg | tcattgttaa | cctgtcacca | tatgacgcgg | aattcagtag | cgtattgcct | 660 |
| tcaaacgtag | gattgatcaa | gattagagta | tacagaccat | ggaattttc | caagttcttg | 720 |
| gaaatactgc | catcttctgt | taccaaaatc | gccgttttac | agggtgtctc | taagaaatcg | 780 |
| caatcaaacg | aatttcaacc | atttcttttg | gacttctttg | gcaattttaa | tgaattagtt | 840 |
| tctaggaaca | tcgagcaggt | agtgttgact | aatattggta | atgtgaatga | ttatggcaac | 900 |
| gttatcaaca | ccgtcatatc | gaatattaac | aagaaggaac | cagataataa | cttattttta | 960 |
| ggtgaatcca | tgaaaaggc | tgaggaacaa | gctgaagtta | ctcaacttat | ttcttctgtc | 1020 |
| aaaaaagttg | tgaacttaga | gacgccctat | atcaaagtgc | taaaacagtt | attttcatca | 1080 |
| aatctacaaa | ttttgaatca | attttccagt | gagacaattg | aaccaagtaa | tccagaattt | 1140 |
| ggttttggac | gcttttaaa | acaagaagcc | cagcgtgaag | aattgatcag | cttagcaaaa | 1200 |
| acctctcttg | atccaagtct | ttacttgtcc | gaggatgcaa | ataaaattgt | tcaactatta | 1260 |
| tctaaatggt | tgtcattcaa | tggacgcgat | cttgacgaag | ctcaattaca | agaggccaat | 1320 |
| gcgacaggtt | tggaaatatt | tcagttatta | caatctaatc | aagattcctc | tactgtctta | 1380 |
| aaattcttaa | agatagctcc | aacaagcgat | tcttttattt | tcaaatcaag | ctggctaatt | 1440 |
| ggctccgatg | cctggtctta | tgatttgggt | cactcaggta | ttcaacaggt | tttatcctcc | 1500 |
| cgtaaaaaca | ttaatgtttt | attgattgat | tcagagccat | atgaccatag | aaagcaaaac | 1560 |
| caggatagaa | agaaagatgt | tggtttgtac | gccatgaatt | attacagtgc | ctatgttgcc | 1620 |
| tctgtagcag | tatatgcttc | ttacacccaa | ctattgactg | caataataga | ggcatctaaa | 1680 |
| tacaatggtc | cttctattgt | cttggcttat | ttgccgtata | attccgaaaa | tgatactcca | 1740 |
| ttagaagtct | taaggaaac | caaaaacgcc | gttgaatctg | ttactggcc | attgtatagg | 1800 |
| tttaatcctg | tttatgacga | tccatcaaca | gataaggagg | catttagctt | ggattcttcg | 1860 |
| gttatcagaa | aacaattaca | ggacttctta | gaccgtgaga | ataagcttac | cctattaacc | 1920 |
| agaaaagatc | catctttgtc | aagaaatcta | aagcaatctg | ctggtgatgc | gttgacaagg | 1980 |
| aaacaagaaa | aaagaagcaa | ggctgccttc | gatcagttat | tggagggttt | gtccggccca | 2040 |

```
ccgctacacg tctattatgc ttctgacggt ggtaatgctg caaacttggc aaagagacta    2100
gcagcaaggg catctgcaag aggtttaaag gctactgttc tgtccatgga tgacattatt    2160
ttggaagaat tacctggtga agagaatgta gttttcatta cttccacggc tgggcaaggt    2220
gaattccccc aagacggtaa gtctttctgg gaagctctga aaaatgacac cgacttggat    2280
ttagctagtt tgaatgttgc tgttttggt ctcggtgatt ctgagtattg gccacgtaaa    2340
gaagataaac attatttaa caagccttca caggatttat ttaagcgctt ggaattattg    2400
agtgccaaag ccctaattcc cttgggactg ggtgatgatc aagatgctga tggtttccaa    2460
actgcttatt ctgagtggga acctaaaatta tgggaagctc ttggtgtttc cggcgctgct    2520
gttgatgatg agccaaaacc tgttacaaac gaggatatta agagagaatc taatttcttg    2580
agaggtacta tcagtgagaa cttaaaggat acttcttcag gtggtgttac tcacgctaat    2640
gaacaattaa tgaaatttca cggtatttac acccaagacg atcgtgacat tagagaaata    2700
cgtaagtcac aaggcttaga gccatactat atgtttatgg caagagctcg tttaccaggt    2760
ggtaagacca ctccacaaca atggcttgct ctggatcact tatctgatac ttcaggcaat    2820 ggtacctga aattaacaac aagggcaacc ttccagattc atggtgtgct aaagaagaac    2880
ttgaaacaca cattgagagg aatgaatgca gttcttatgg atacattagc tgctgcaggt    2940
gacgtgaaca gaaatgtcat ggtttctgct ctaccaacca atgccaaggt tcaccaacaa    3000
atcgctgata tgggaaaatt gatttctgat catttcttac caaagactac ggcctaccac    3060
gaagtttggc tggagggccc agaagaacag gacgatgatc catcctggcc atctattttt    3120
gaaaacagaa aagatggtcc aagaaaaaag aagactctag ttagcggtaa cgctttggtc    3180
gatattgaac caatttacgg tccaacttat ctgccaagaa agtttaaatt caacatcgcc    3240
gttcctccat ataacgatgt ggatgtatta tctatcgatg tcggtttagt tgctatagtt    3300
aacccagaaa ctcaaatcgt ggagggttat aatgttttg ttggtggtgg tatgggtacc    3360
actcataaca acaagaaaac ttacccaaga ttagggtcat gcttaggttt tgttaaaact    3420
gaagacatta ttccaccact tgaaggtatc gttattgtcc aaagagatca cggtgaccgt    3480
aaagaccgta agcatgctcg tttaaagtat actgtagatg atatgggtgt cgaaggcttc    3540
aagcaaaaag tggaggaata ctggggtaag aaattcgagc ctgagagacc atttgagttt    3600
aaatctaata ttgattactt tggatggatt aaagatgaaa ctgggttaaa ccactttacc    3660
gcatttattg aaaatggtar ggttgaagat acaccagatt tgcctcaaaa gacaggtatt    3720
agaaaggttc tgaatacat gcttaagact aattctggtc atttcagatt gactggtaat    3780
caacatttgg ttatctctaa tattacagat gaacatgttg ctggaataaa atctatttta    3840
aagacctata aattggataa caccgatttc agcggtttga gattatcttc atcttcctgt    3900
gttggtttgc caacatgtgg tttagcgttt gccgaatctg aacgtttcct acctgacatt    3960
attactcagt tggaagattg tttagaagag tatggtttac gccatgattc cattattatg    4020
agaatgactg gttgccctaa cggttgttct cgtccatggc taggtgaatt agctcttgtt    4080
ggtaaagctc cacatactta taacttgatg cttggtggtg gttacctcgg ccaaaggcta    4140
aacaaattgt ataaggccaa tgtgaaggat gaggaaattg tcgactacat caaaccattg    4200
tttaaaaggt atgctttaga aagagaagaa ggggaacact ttggtgattt ctgtataaga    4260
gtaggtatca ttaaaccaac caccgagggt aaatacttcc atgaagatgt gtctgaagat    4320
gcctattaa                                                           4329
```

<210> SEQ ID NO 2

<211> LENGTH: 4329
<212> TYPE: DNA
<213> ORGANISM: Saccharomyces cerevisiae

<400> SEQUENCE: 2

```
atgactgctt ctgacctctt gacgctccca caattgttgg cgcaatattc ctctagtgct      60
ccccaaaata aagtgttcta cactactagc acaaaaaata gtcattcatc cttcaaaggg     120
ctagaatctg ttgccacaga tgctactcat ctattgaaca atcaagatcc attgaatacc     180
atcaaagatc aactctctaa ggacatttta actaccgttt ttacagatga aactactttg     240
gtcaaatcca tccaccatct atattctctt cctaataaac ttccattggt gattacagtg     300
gatttgaatt tgcaagatta ttccgcaatt cctgcgttaa aggatctttc tttccccatc     360
ttaatatctt ctgatttgca aactgcaatt caaacgcgg actcttctta taagattgct      420
acaagttctc tgaccccagt tttccatttt cttaacttgg agaaaattgg cacgagtaca     480
gctattgaac aagacatcga ctttcctacc ttggagattg ctaacgaaga gactaaagta     540
gcattatcag aagctactga ttcattgaca aattttgaac tggttaaagg taaagagtca     600
attaccactg tcattgttaa cctgtccacca tatgacgcgg aattcagtag cgtattgcct     660
tcaaacgtag gattgatcaa gattagagta tacagaccat ggaatttttc caagttcttg     720
gaaatactgc catcttctgt taccaaaatc gccgttttac agggtgtctc taagaaatcg     780
caatcaaacg aatttcaacc atttcttttg gacttctttg gcaattttaa tgaattagtt     840
tctaggaaca tcgagcaggt agtgttgact aatattggta atgtgaatga ttatggcaac     900
gttatcaaca ccgtcatatc gaatattaac aagaaggaac cagataataa cttatttta      960
ggtgaatcca tgaaaaggc tgaggaacaa gctgaagtta ctcaacttat tcttctgtc     1020
aaaaaagttg tgaacttaga gacgcctat atcaaagtgc taaaacagtt atttttcatca    1080
aatctacaaa ttttgaatca atttccagt gagacaattg aaccaagtaa tccagaattt    1140
ggttttggac gcttttaaa acaagaagcc cagcgtgaag aattgatcag cttagcaaaa    1200
acctctcttg atccaagtct ttacttgtcc gaggatgcaa ataaaattgt tcaactatta   1260
tctaaatggt tgtcattcaa tggacgcgat cttgacgaag ctcaattaca agaggccaat   1320
gcgacaggtt tggaaatatt tcagttatta caatctaatc aagattcctc tactgtctta   1380
aaattcttaa agatagctcc aacaagcgat tcttttattt tcaaatcaag ctggctaatt   1440
ggctccgatg cctggtctta tgatttgggt cactcaggta ttcaacaggt tttatcctcc   1500
cgtaaaaaca ttaatgtttt attgattgat tcagagccat atgaccatag aaagcaaaac   1560
caggatagaa agaaagatgt tggtttgtac gccatgaatt attacagtgc ctatgttgcc   1620
tctgtagcag tatatgcttc ttacacccaa ctattgactg caataataga ggcatctaaa   1680
tacaatggtc cttctattgt cttggcttat ttgccgtata ttccgaaaa tgatactcca    1740
ttagaagtct taaggaaac caaaaacgcc gttgaatctg ttactggcc attgtatagg    1800
tttaatcctg tttatgacga tccatcaaca gataaggagg catttagctt ggattcttcg   1860
gttatcagaa acaattaca ggacttctta gaccgtgaga ataagcttac cctattaacc    1920
agaaaagatc catctttgtc aagaaatcta aagcaatctg ctggtgatgc gttgacaagg   1980
aaacaagaaa aagaagcaa ggctgccttc gatcagttat tggagggttt gtccggccca    2040
ccgctacacg tctattatgc ttctgacggt ggtaatgctg caaacttggc aaagagacta   2100
gcagcaaggg catctgcaag aggtttaaag gctactgttc tgtccatgga tgacattatt   2160
ttggaagaat tacctggtga agagaatgta gttttcatta cttccacggc tgggcaaggt   2220
```

```
gaattccccc aagacggtaa gtctttctgg gaagctctga aaaatgacac cgacttggat    2280
ttagctagtt tgaatgttgc tgttttggt ctcggtgatt ctgagtattg gccacgtaaa    2340
gaagataaac attattttaa caagccttca caggatttat ttaagcgctt ggaattattg    2400
agtgccaaag ccctaattcc cttgggactg ggtgatgatc aagatgctga tggtttccaa    2460
actgcttatt ctgagtggga acctaaatta tgggaagctc ttggtgtttc cggcgctgct    2520
gttgatgatg agccaaaacc tgttacaaac gaggatatta agagagaatc taatttcttg    2580
agaggtacta tcagtgagaa cttaaaggat acttcttcag gtggtgttac tcacgctaat    2640
gaacaattaa tgaaatttca cggtatttac acccaagacg atcgtgacat tagagaaata    2700
cgtaagtcac aaggcttaga gccatactat atgtttatgg caagagctcg tttaccaggt    2760
ggtaagacca ctccacaaca atggcttgct ctggatcact tatctgatac ttcaggcaat    2820
ggtaccctga aattaacaac aagggcaacc ttccagattc atggtgtgct aaagaagaac    2880
ttgaaacaca cattgagagg aatgaatgca gttcttatgg atacattagc tgctgcaggt    2940
gacgtgaaca gaaatgtcat ggtttctgct ctaccaacca atgccaaggt tcaccaacaa    3000
atcgctgata tgggaaaatt gatttctgat catttcttac caagactac ggcctaccac     3060
gaagtttggc tggagggccc agaagaacag gacgatgatc catcctggcc atctattttt    3120
gaaaacagaa aagatggtcc aagaaaaaag aagactctag ttagcggtaa cgctttggtc    3180
gatattgaac caatttacgg tccaacttat ctgccaagaa gtttaaatt caacatcgcc     3240
gttcctccat ataacgatgt ggatgtatta tctatcgatg tcggtttagt tgctatagtt    3300
aacccagaaa ctcaaatcgt ggagggttat aatgttttg ttggtggtgg tatgggtacc     3360
actcataaca acaagaaaac ttacccaaga ttagggtcat gcttaggttt tgttaaaact    3420
gaagacatta ttccaccact tgaaggtatc gttattgtcc aaagagatca cggtgaccgt    3480
aaagaccgta agcatgctcg tttaaagtat actgtagatg atatgggtgt cgaaggcttc    3540
aagcaaaaag tggaggaata ctggggtaag aaattcgagc tgagagacc atttgagttt     3600
aaatctaata ttgattactt tggatggatt aaagatgaaa ctgggttaaa ccactttacc    3660
gcacttattg aaaatggtag ggttgaagat acaccagatt tgcctcaaaa gacaggtatt    3720
agaaaggttg ctgaatacat gcttaagact aattctggtc atttcagatt gactggtaat    3780
caacatttgg ttatctctaa tattacagat gaacatgttg ctggaataaa atctattta     3840
aagacctata aattggataa caccgatttc agcggtttga gattatcttc atcttcctgt    3900
gttggtttgc caacatgtgg tttagcgttt gccgaatctg aacgtttcct acctgacatt    3960
attactcagt tggaagattg tttagaagag tatggtttac gccatgattc cattattatg    4020
agaatgactg gttgccctaa cggttgttct cgtccatggc taggtgaatt agctcttgtt    4080
ggtaaagctc acatactta aacttgatgc ttggtggtg gttacctcgg ccaaaggcta     4140
aacaaattgt ataaggccaa tgtgaaggat gaggaaattg tcgactacat caaaccattg    4200
tttaaaaggt atgctttaga aagagaagaa ggggaacact ttggtgattt ctgtataaga    4260
gtaggtatca ttaaaccaac caccgagggt aaatacttcc atgaagatgt gtctgaagat    4320
gcctattaa                                                            4329
```

<210> SEQ ID NO 3
<211> LENGTH: 4329
<212> TYPE: DNA
<213> ORGANISM: Saccharomyces cerevisiae

<400> SEQUENCE: 3

```
atgactgctt ctgacctctt gacgctccca caattgttgg cgcaatattc ctctagtgct    60 cccaaaata  aagtgttcta cactactagc acaaaaaata gtcattcatc cttcaaaggg   120
ctagaatctg ttgccacaga tgctactcat ctattgaaca atcaagatcc attgaatacc   180
atcaaagatc aactctctaa ggacatttta actaccgttt ttacagatga aactactttg   240
gtcaaatcca tccaccatct atattctctt cctaataaac ttccattggt gattacagtg   300
gatttgaatt tgcaagatta ttccgcaatt cctgcgttaa aggatctttc tttccccatc   360
ttaatatctt ctgatttgca aactgcaatt tcaaacgcgg actcttctta taagattgct   420
acaagttctc tgaccccagt tttccatttt cttaacttgg agaaaattgg cacgagtaca   480
gctattgaac aagacatcga cttcctacc  ttggagattg ctaacgaaga gactaaagta   540
gcattatcag aagctactga ttcattgaca aatttgaac  tggttaaagg taagagtca    600 attaccactg tcattgttaa cctgtcacca tatgacgcgg aattcagtag cgtattgcct   660
tcaaacgtag gattgatcaa gattagagta tacagaccat ggattttttc caagttcttg   720
gaaatactgc catcttctgt taccaaaatc gccgttttac agggtgtctc taagaaatcg   780
caatcaaacg aatttcaacc atttcttttg gacttcttg  gcaattttaa tgaattagtt   840
tctaggaaca tcgagcaggt agtgttgact aatattggta atgtgaatga ttatggcaac   900
gttatcaaca ccgtcatatc gaatattaac aagaaggaac cagataataa cttatttta   960 ggtgaatcca atgaaaaggc tgaggaacaa gctgaagtta ctcaacttat ttcttctgtc   1020 aaaaagttg  tgaacttaga agacgcctat atcaaagtgc taaaacagtt atttcatca    1080 aatctacaaa ttttgaatca atttccagt  gagacaattg aaccaagtaa tccagaattt   1140
ggttttggac gcttttaaaa acaagaagcc cagcgtgaag aattgatcag cttagcaaaa   1200
acctctcttg atccaagtct ttacttgtcc gaggatgcaa ataaaattgt tcaactatta   1260
tctaaatggt tgtcattcaa tggacgcgat cttgacgaag ctcaattaca agaggccaat   1320
gcgacaggtt tggaaatatt tcagttatta caatctaatc aagattcctc tactgtctta   1380
aaattcttaa agatagctcc aacaagcgat tctttatttt tcaaatcaag ctggctaatt   1440
ggctccgatg cctggtctta tgatttgggt cactcaggta ttcaacaggt tttatcctcc   1500
cgtaaaaaca ttaatgtttt attgattgat tcagagccat atgaccatag aaagcaaaac   1560
caggatagaa agaaagatgt tggtttgtac gccatgaatt attacagtgc ctatgttgcc   1620
tctgtagcag tatatgcttc ttacacccaa ctattgactg caataataga ggcatctaaa   1680
tacaatggtc cttctattgt cttggcttat ttgccgtata attccgaaaa tgatactcca   1740
ttagaagtct taaaggaaac caaaaacgcc gttgaatctg ttactggcc  attgtatagg   1800 tttaatcctg tttatgacga tccatcaaca gataaggagg catttagctt ggattcttcg   1860
gttatcagaa acaattaca  ggacttctta gaccgtgaga ataagcttac cctattaacc   1920 agaaagatc  catctttgtc aagaaatcta agcaatctg  ctggtgatgc gttgacaagg   1980
aaacaagaaa aagaagcaa  ggctgccttc gatcagttat ggagggttt  gtccggccca   2040 ccgctacacg tctattatgc ttctgacggt ggtaatgctg caaacttggc aaagagacta   2100
gcagcaaggg catctgcaag aggttaaag  gctactgttc tgtccatgga tgacattatt   2160
ttggaagaat tacctggtga agagaatgta gtcttcatta cttccacggc tgggcaaggt   2220
gaattccccc aagacggtaa gtctttctgg gaagctctga aaaatgacac cgacttggat   2280
ttagctagtt tgaatgttgc tgttttggt  ctcggtgatt ctgagtattg gccacgtaaa   2340
gaagataaac attatttaa  caagccttca caggatttat ttaagcgctt ggaattattg   2400
```

```
agtgccaaag ccctaattcc cttgggactg ggtgatgatc aagatgctga tggtttccaa   2460
actgcttatt ctgagtggga acctaaatta tgggaagctc ttggtgtttc cggcgctgct   2520
gttgatgatg agccaaaacc tgttacaaac gaggatatta agagagaatc taatttcttg   2580
agaggtacta tcagtgagaa cttaaaggat acttcttcag gtggtgttac tcacgctaat   2640
gaacaattaa tgaaatttca cggtatttac acccaagacg atcgtgacat tagagaaata   2700
cgtaagtcac aaggcttaga gccatactat atgtttatgg caagagctcg tttaccaggt   2760
ggtaagacca ctccacaaca atggcttgct ctggatcact tatctgatac ttcaggcaat   2820
ggtaccctga aattaacaac aagggcaacc ttccagattc atggtgtgct aaagaagaac   2880
ttgaaacaca cattgagagg aatgaatgca gttcttatgg atacattagc tgctgcaggt   2940
gacgtgaaca gaaatgtcat ggtttctgct ctaccaacca atgccaaggt tcaccaacaa   3000
atcgctgata tgggaaaatt gatttctgat catttcttac caaagactac ggcctaccac   3060
gaagtttggc tggagggccc agaagaacag gacgatgatc catcctggcc atctattttt   3120
gaaaacagaa aagatggtcc aagaaaaaag aagactctag ttagcggtaa cgctttggtc   3180
gatattgaac caatttacgg tccaacttat ctgccaagaa agtttaaatt caacatcgcc   3240
gttcctccat ataacgatgt ggatgtatta tctagcgatg tcggtttagt tgctatagtt   3300
aacccagaaa ctcaaatcgt ggagggttat aatgtttttg ttggtggtgg tatgggtacc   3360
actcataaca acaagaaaac ttacccaaga ttagggtcat gcttaggttt tgttaaaact   3420
gaagacatta ttccaccact tgaaggtatc gttattgtcc aaagagatca cggtgaccgt   3480
aaagaccgta agcatgctcg tttaaagtat actgtagatg atatgggtgt cgaaggcttc   3540
aagcaaaaag tggaggaata ctggggtaag aaattcgagc ctgagagacc atttgagttt   3600
aaatctaata ttgattactt tggatggatt aaagatgaaa ctgggttaaa ccactttacc   3660
gcatttattg aaaatggtag ggttgaagat acaccagatt tgcctcaaaa gacaggtatt   3720
agaaaggttg ctgaatacat gcttaagact aattctggtc atttcagatt gactggtaat   3780
caacatttgg ttatctctaa tattacagat gaacatgttg ctggaataaa atctattta   3840 aagacctata aattggataa caccgatttc agcggtttga gattatcttc atcttcctgt   3900
gttggtttgc caacatgtgg tttagcgttt gccgaatctg aacgtttcct acctgacatt   3960
attactcagt tggaagattg tttagaagag tatggtttac gccatgattc cattattatg   4020
agaatgactg gttgccctaa cggttgttct cgtccatggc taggtgaatt agctcttgtt   4080
ggtaaagctc cacatactta taacttgatg cttggtggtg gttacctcgg ccaaaggcta   4140
aacaaattgt ataaggccaa tgtgaaggat gaggaaattg tcgactacat caaaccattg   4200
tttaaaaggt atgctttaga aagagaagaa ggggaacact tggtgatttt ctgtataaga   4260
gtaggtatca ttaaaccaac caccgagggt aaatacttcc atgaagatgt gtctgaagat   4320
gcctattaa                                                            4329
```

<210> SEQ ID NO 4
<211> LENGTH: 4329
<212> TYPE: DNA
<213> ORGANISM: Saccharomyces cerevisiae

<400> SEQUENCE: 4

```
atgactgctt ctgacctctt gacgctccca caattgttgg cgcaatattc ctctagtgct     60
ccccaaaata aagtgttcta cactactagc acaaaaaata gtcattcatc cttcaaaggg    120
ctagaatctg ttgccacaga tgctactcat ctattgaaca atcaagatcc attgaatacc    180
```

```
atcaaagatc aactctctaa ggacatttta actaccgttt ttacagatga aactactttg    240
gtcaaatcca tccaccatct atattctctt cctaataaac ttccattggt gattacagtg    300
gatttgaatt tgcaagatta ttccgcaatt cctgcgttaa aggatctttc tttccccatc    360
ttaatatctt ctgatttgca aactgcaatt tcaaacgcgg actcttctta taagattgct    420
acaagttctc tgaccccagt tttccatttt cttaacttgg agaaaattgg cacgagtaca    480
gctattgaac aagacatcga ctttcctacc ttggagattg ctaacgaaga gactaaagta    540
gcattatcag aagctactga ttcattgaca aattttgaac tggttaaagg taaagagtca    600
attaccactg tcattgttaa cctgtcacca tatgacgcgg aattcagtag cgtattgcct    660
tcaaacgtag gattgatcaa gattagagta tacagaccat ggaattttc caagttcttg     720 gaaatactgc catcttctgt taccaaaatc gccgttttac agggtgtctc taagaaatcg    780
caatcaaacg aatttcaacc atttcttttg gacttctttg gcaattttaa tgaattagtt    840
tctaggaaca tcgagcaggt agtgttgact aatattggta atgtgaatga ttatggcaac    900
gttatcaaca ccgtcatatc gaatattaac aagaaggaac cagataataa cttatttta    960 ggtgaatcca tgaaaaggc tgaggaacaa gctgaagtta ctcaacttat ttcttctgtc    1020
aaaaaagttg tgaacttaga agacgcctat atcaaagtgc taaaacagtt attttcatca    1080
aatctacaaa ttttgaatca attttccagt gagacaattg aaccaagtaa tccagaattt    1140
ggttttggac gcttttaaa acaagaagcc agcgtgaag aattgatcag cttagcaaaa    1200
acctctcttg atccaagtct ttacttgtcc gaggatgcaa ataaaattgt tcaactatta    1260
tctaaatggt tgtcattcaa tggacgcgat cttgacgaag ctcaattaca agaggccaat    1320
gcgacaggtt tggaaatatt tcagttatta caatctaatc aagattcctc tactgtctta    1380
aaattcttaa mgatagctcc aacaagcgat tctttattt tcaaatcaag ctggctaatt    1440
ggctccgatg cctggtctta tgatttgggt cactcaggta ttcaacaggt tttatcctcc    1500
cgtaaaaaca ttaatgtttt attgattgat tcagagccat atgaccatag aaagcaaaac    1560
caggatagaa agaaagatgt tggtttgtac gccatgaatt attacagtgc ctatgttgcc    1620
tctgtagcag tatatgcttc ttacacccaa ctattgactg caataataga ggcatctaaa    1680
tacaatggtc cttctattgt cttggcttat ttgccgtata attccgaaaa tgatactcca    1740
ttagaagtct taaggaaac caaaaacgcc gttgaatctg gttactggcc attgtatagg    1800
tttaatcctg tttatgacga tccatcaaca gataaggagg catttagctt ggattcttcg    1860
gttatcagaa aacaattaca ggacttctta gaccgtgaga ataagcttac cctattaacc    1920
agaaaagatc catctttgtc aagaaatcta aagcaatctg ctggtgatgc gttgacaagg    1980
aaacaagaaa aagaagcaa ggctgccttc gatcagttat ggagggtttt gtccggccca    2040
ccgctacacg tctattatgc ttctgacggt ggtaatgctg caaacttggc aaagagacta    2100
gcagcaaggg catctgcaag aggtttaaag gctactgttc tgtccatgga tgacattatt    2160
ttggaagaat tacctggtga agagaatgta gttttcatta cttccacggc tgggcaaggt    2220
gaattccccc aagacggtaa gtctttctgg aagctctga aaatgacac cgacttggat     2280 ttagctagtt tgaatgttgc tgttttttggt ctcggtgatt ctgagtattg gccacgtaaa    2340
gaagataaac attattttaa caagccttca caggattta ttaagcgctt ggaattattg     2400
agtgccaaag ccctaattcc cttgggactg ggtgatgatc aagatgctga tggtttccaa    2460
actgcttatt ctgagtggga acctaaatta tgggaagctc ttggtgtttc cggcgctgct    2520
gttgatgatg agccaaaacc tgttacaaac gaggatatta agagagaatc taatttcttg    2580
```

```
agaggtacta tcagtgagaa cttaaaggat acttcttcag gtggtgttac tcacgctaat    2640
gaacaattaa tgaaatttca cggtatttac acccaagacg atcgtgacat tagagaaata    2700
cgtaagtcac aaggcttaga gccatactat atgtttatgg caagagctcg tttaccaggt    2760
ggtaagacca ctccacaaca atggcttgct ctggatcact tatctgatac ttcaggcaat    2820
ggtaccctga aattaacaac aagggcaacc ttccagattc atggtgtgct aaagaagaac    2880
ttgaaacaca cattgagagg aatgaatgca gttcttatgg atacattagc tgctgcaggt    2940
gacgtgaaca gaaatgtcat ggtttctgct ctaccaacca atgccaaggt tcaccaacaa    3000
atcgctgata tgggaaaatt gatttctgat catttcttac caaagactac ggcctaccac    3060
gaagtttggc tggagggccc agaagaacag gacgatgatc catcctggcc atctattttt    3120
gaaaacagaa aagatggtcc aagaaaaaag aagactctag ttagcggtaa cgctttggtc    3180
gatattgaac caatttacgg tccaacttat ctgccaagaa agtttaaatt caacatcgcc    3240
gttcctccat ataacgatgt ggatgtatta tctatcgatg tcggtttagt tgctatagtt    3300
aacccagaaa ctcaaatcgt ggagggttat aatgttttg ttggtggtgg tatgggtacc    3360
actcataaca acaagaaaac ttacccaaga ttagggtcat gcttaggttt tgttaaaact    3420
gaagacatta ttccaccact tgaaggtatc gttattgtcc aaagagatca cggtgaccgt    3480
aaagaccgta agcatgctcg tttaaagtat actgtagatg atatgggtgt cgaaggcttc    3540
aagcaaaaag tggaggaata ctgggggtaag aaattcgagc ctgagagacc atttgagttt    3600
aaatctaata ttgattactt tggatggatt aaagatgaaa ctgggttaaa ccactttacc    3660
gcatttattg aaaatggtag ggttgaagat acaccagatt tgcctcaaaa gacaggtatt    3720
agaaaggttg ctgaatacat gcttaagact aattctggtc atttcagatt gactggtaat    3780
caacatttgg ttatctctaa tattacagat gaacatgttg ctggaataaa atctattta    3840 aagacctata aattggataa caccgatttc agcggtttga gattatcttc atcttcctgt    3900
gttggtttgc aacatgtgg tttagcgttt gccgaatctg aacgtttcct acctgacatt    3960
attactcagt tggaagattg tttagaagag tatggtttac gccatgattc cattattatg    4020
agaatgactg gttgccctaa cggttgttct cgtccatggc taggtgaatt agctcttgtt    4080
ggtaaagctc cacatactta taacttgatg cttggtggtg gttacctcgg ccaaaggcta    4140
aacaaattgt ataaggccaa tgtgaaggat gaggaaattg tcgactacat caaaccattg    4200
tttaaaaggt atgctttaga aagagaagaa ggggaacact ttggtgattt ctgtataaga    4260
gtaggtatca ttaaaccaac caccgagggt aaatacttcc atgaagatgt gtctgaagat    4320
gcctattaa                                                           4329
```

<210> SEQ ID NO 5
<211> LENGTH: 4329
<212> TYPE: DNA
<213> ORGANISM: Saccharomyces cerevisiae

<400> SEQUENCE: 5

```
atgactgctt ctgacctctt gacgctccca caattgttgg cgcaatattc ctctagtgct      60
ccccaaaata aagtgttcta cactactagc acaaaaaata gtcattcatc cttcaaaggg     120
ctagaatctg ttgccacaga tgctactcat ctattgaaca atcaagatcc attgaatacc     180
atcaaagatc aactctctaa ggacatttta actaccgttt ttacagatga aactactttg     240
gtcaaatcca tccaccatct atattctctt cctaataaac ttccattggt gattacagtg     300
gatttgaatt tgcaagatta ttccgcaatt cctgcgttaa aggatctttc tttccccatc     360
```

```
ttaatatctt ctgatttgca aactgcaatt tcaaacgcgg actcttctta taagattgct    420
acaagttctc tgaccccagt tttccatttt cttaacttgg agaaaattgg cacgagtaca    480
gctattgaac aagacatcga cttttcctacc ttggagattg ctaacgaaga gactaaagta    540
gcattatcag aagctactga ttcattgaca aattttgaac tggttaaagg taagagtca     600 attaccactg tcattgttaa cctgtcacca tatgacgcgg aattcagtag cgtattgcct    660
tcaaacgtag gattgatcaa gattagagta tacagaccat ggaattttc caagttcttg     720 gaaatactgc catcttctgt taccaaaatc gccgttttac agggtgtctc taagaaatcg    780
caatcaaacg aatttcaacc atttcttttg gacttctttg gcaattttaa tgaattagtt    840
tctaggaaca tcgagcaggt agtgttgact aatattggta atgtgaatga ttatggcaac    900
gttatcaaca ccgtcatatc gaatattaac aagaaggaac cagataataa cttattttta    960
ggtgaatcca atgaaaaggc tgaggaacaa gctgaagtta ctcaacttat ttcttctgtc   1020
aaaaaagttg tgaacttaga agacgcctat atcaaagtgc taaaacagtt attttcatca   1080
aatctacaaa ttttgaatca attttccagt gagacaattg aaccaagtaa tccagaattt   1140
ggttttggac gcttttttaaa acaagaagcc cagcgtgaag aattgatcag cttagcaaaa   1200
acctctcttg atccaagtct ttacttgtcc gaggatgcaa ataaaattgt tcaactatta   1260
tctaaatggt tgtcattcaa tggacgcgat cttgacgaag ctcaattaca agaggccaat   1320
gcgacaggtt tggaaatatt tcagttatta caatctaatc aagattcctc tactgtctta   1380
aaattcttaa agatagctcc aacaagcgat tcttttattt tcaaatcaag ctggctaatt   1440
ggctccgatg cctggtctta tgatttgggt cactcaggta ttcaacaggt tttatcctcc   1500
cgtaaaaaca ttaatgtttt attgattgat tcagagccat atgaccatag aaagcaaaac   1560
caggatagaa agaaagatgt tggtttgtac gccatgaatt attacagtgc ctatgttgcc   1620
tctgtagcag tatatgcttc ttacacccaa ctattgactg caataataga ggcatctaaa   1680
tacaatggtc cttctattgt cttggcttat ttgccgtata attccgaaaa tgatactcca   1740
ttagaagtct taaaggaaac caaaaacgcc gttgaatctg ttactggcc attgtatagg     1800 tttaatcctg tttatgacga tccatcaaca gataaggagg catttagctt ggattcttcg   1860
gttatcagaa acaattaca ggacttctta gaccgtgaga ataagcttac cctattaacc    1920
agaaaagatc catctttgtc aagaaatcta agcaatctg ctggtgatgc gttgacaagg    1980
aaacaagaaa aagaagcaa ggctgccttc gatcagttat ggagggttt gtccggccca    2040 ccgctacacg tctattatgc ttctgacggt ggtaatgctg caaacttggc aaagagacta   2100
gcagcaaggg catctgcaag aggtttaaag gctactgttc tgtccatgga tgacattatt   2160
ttggaagaat tacctggtga agagaatgta gttttcatta cttccacggc tgggcaaggt   2220
gaattccccc aagacggtaa gtctttctgg gaagctctga aaaatgacac cgacttggat   2280
ttagctagtt tgaatgttgc tgttttttggt ctcggtgatt ctgagtattg ccacgtaaa    2340 gaagataaac attattttaa caagccttca caggatttat ttaagcgctt ggaattattg   2400
agtgccaaag ccctaattcc cttgggactg ggtgatgatc aagatgctga tggtttccaa   2460
actgcttatt ctgagtggga acctaaatta tgggaagctc ttggtgtttc cggcgctgct   2520
gttgatgatg agccaaaacc tgttacaaac gaggatatta agagagaatc taatttcttg   2580
agaggtacta tcagtgagaa cttaaaggat acttcttcag gtggtgttac tcacgctaat   2640
gaacaattaa tgaaatttca cggtatttac acccaagacg atcgtgacat tagagaaata   2700
cgtaagtcac aaggcttaga gccatactat atgtttatgg caagagctcg tttaccaggt   2760
```

-continued

```
ggtaagacca ctccacaaca atggcttgct ctggatcact tatctgatac ttcaggcaat    2820
ggtaccctga aattaacaac aagggcaacc ttccagattc atggtgtgct aaagaagaac    2880
ttgaaacaca cattgagagg aatgaatgca gttcttatgg atacattagc tgctgcaggt    2940
gacgtgaaca gaaatgtcat ggtttctgct ctaccaacca atgccaaggt tcaccaacaa    3000
atcgctgata tgggaaaatt gatttctgat catttcttac caaagactac ggcctaccac    3060
gaagtttggc tggagggccc agaagaacag gacgatgatc catcctggcc atctattttt    3120
gaaaacagaa aagatggtcc aagaaaaaag aagactctag ttagcggtaa cgctttggtc    3180
gatattgaac caatttacgg tccaacttat ctgccaagaa agtttaaatt caacatcgcc    3240
gttcctccat ataacgatgt ggatgtatta tctatcgatg tcggtttagt tgctatagtt    3300
aacccagaaa ctcaaatcgt ggagggttat aatgtttttg ttggtggtgg tatgggtacc    3360
actcataaca acaagaaaac ttacccaaga ttagggtcat gcttaggttt tgttaaaact    3420
gaagacatta ttccaccact tgaaggtatc gttattgtcc aaagagatca cggtgaccgt    3480
aaagaccgta agcatgctcg tttaaagtat actgtagatg atatgggtgt cgaaggcttc    3540
aagcaaaaag tggaggaata ctggggtaag aaattcgagc ctgagagacc atttgagttt    3600
aaatctaata ttgattactt tggatggatt aaagatgaaa ctgggttaaa ccactttacc    3660
gcatttattg aaaatggtag ggttgaagat acaccagatt tgcctcaaaa gacaggtatt    3720
agaaaggttg ctgaatacat gcttaagact aattctggtc atttcagatt gactggtaat    3780
caacatttgg ttatctctaa tattacagat gaacatgttg ctggaataaa atctatttta    3840
aagacctata aattggataa caccgatttc agcggtttga gattatcttc atcttcctgt    3900
gttggtttgc caacatgtgg tttagcgttt gccgaatctg aacgttttcct acctgacatt    3960 attactcagt tggaagattg tttagaagag tatggtttac gccatgattc cattattatg    4020
agaatgactg gttgccctaa cggttgttct cgtccatggc taggtgaatt agctcttgtt    4080
ggtaaagctc acatacttaa acttgatgtc cttggtggtg gttacctcgg ccaaaggcta    4140
aacaaattgt ataaggccaa tgtgaaggat gaggaaattg tcgactacat caaaccattg    4200
tttaaaaggt atgctttaga aagagaagaa ggggaacact ttggtgattt ctgtataaga    4260
gtaggtatca ttaaaccaac caccgagggt aaatacttcc atgaagatgt gtctgaagat    4320
gcctattaa                                                           4329
```

<210> SEQ ID NO 6
<211> LENGTH: 4329
<212> TYPE: DNA
<213> ORGANISM: Saccharomyces cerevisiae

<400> SEQUENCE: 6

```
atgactgctt ctgacctctt gacgctccca caattgttgg cgcaatattc ctctagtgct     60
ccccaaaata aagtgttcta cactactagc acaaaaaata gtcattcatc cttcaaaggg    120
ctagaatctg ttgccacaga tgctactcat ctattgaaca atcaagatcc attgaatacc    180
atcaaagatc aactctctaa ggacatttta actaccgttt ttacagatga aactactttg    240
gtcaaatcca tccaccatct atattctctt cctaataaac ttccattggt gattacagtg    300
gatttgaatt tgcaagatta ttccgcaatt cctgcgttaa aggatctttc tttcccatc     360 ttaatatctt ctgatttgca aactgcaatt tcaaacgcgg actcttctta taagattgct    420
acaagttctc tgaccccagt ttttcatttt cttaacttgg agaaaattgg cacaagtaca    480
gctattgaac aagacatcga ctttcctacc ttggagattg ctaacgaaga gactaaagta    540
```

```
gcattatcag aagctactga ttcattgaca aattttgaac tggttaaagg taaagagtca    600
attaccactg tcattgttaa cctgtcacca tatgacgcgg aattcagtag cgtattgcct    660
tcaaacgtag gattgatcaa gattagagta tacagaccat ggaattttc  caagttcttg    720 gaaatactgc catcttctgt taccaaaatc gccgttttac agggtgtctc taagaaatcg    780
caatcaaacg aatttcaacc atttcttttg gacttctttg gcaattttaa tgaattagtt    840
tctaggaaca tcgagcaggt agtgttgact aatattggta atgtgaatga ttatggcaac    900
gttatcaaca ccgtcatatc gaatattaac aagaaggaac cagataataa cttatttta   960 ggtgaatcca atgaaaaggc tgaggaacaa gctgaagtta ctcaacttat ttcttctgtc   1020
aaaaaagttg tgaacttaga agacgcctat atcaaagtgc taaaacagtt attttcatca   1080
aatctacaaa ttttgaatca attttccagt gagacaattg aaccaagtaa tccagaattt   1140
ggttttggac gctttttaaa acaagaagcc cagcgtgaag aattgatcag cttagcaaaa   1200
acctctcttt atccaagtct ttacttgtcc gaggatgcaa ataaaattgt tcaactatta   1260
tctaaatggt tgtcattcaa tggacgcgat cttgacgaag ctcaattaca agaggccaat   1320
gcgacaggtt tggaaatatt tcagttatta caatctaatc aagattcctc tactgtctta   1380
aaattcttaa agatagctcc aacaagcgat tcttttattt tcaaatcaag ctggctaatt   1440
ggctccgatg cctggtctta tgatttgggt cactcaggta ttcaacaggt tttatcctcc   1500
cgtaaaaaca ttaatgtttt attgattgat tcagagccat atgaccatag aaagcaaaac   1560
caggatagaa agaaagatgt tggtttgtac gccatgaatt attacagtgc ctatgttgcc   1620
tctgtagcag tatatgcttc ttcacacccaa ctattgactg caataataga ggcatctaaa   1680
tacaatggtc cttctattgt cttggcttat ttgccgtata attccgaaaa tgatactcca   1740
ttagaagtct taaggaaac  caaaaacgcc gttgaatctg gttactggcc attgtatagg   1800
tttaatcctg tttatgacga tccatcaaca gataaggagg catttagctt ggattcttcg   1860
gttatcagaa aacaattaca ggacttctta gaccgtgaga ataagcttac cctattaacc   1920
agaaaagatc catctttgtc aagaaatcta aagcaatctg ctggtgatgc gttgacaagg   1980
aaacaagaaa aaagaagcaa ggctgccttc gatcagttat tggagggttt gtccggccca   2040 ccgctcacg  tctattatgc ttctgacggt ggtaatgctg caaacttggc aaagagacta   2100
gcagcaaggg catctgcaag aggtttaaag gctactgttc tgtccatgga tgacattatt   2160
ttggaagaat tacctggtga agagaatgta gttttcatta cttccacggc tgggcaaggt   2220
gaattccccc aagacggtaa gtctttctgg gaagctctga aaaatgacac cgacttggat   2280
ttagctagtt tgaatgttgc tgttttttggt ctcggtgatt ctgagtattg gccacgtaaa   2340
gaagataaac attattttaa caagccttca caggatttat ttaagcgctt ggaattattg   2400
agtgccaaag ccctaattcc cttgggactg ggtgatgatc aagatgctga tggtttccaa   2460
actgcttatt ctgagtggga acctaaatta tgggaagctc ttggtgtttc cggcgctgct   2520
gttgatgatg agccaaaacc tgttacaaac gaggatatta agagagaatc taatttcttg   2580
agaggtacta tcagtgagaa cttaaaggat acttcttcag gtggtgttac tcacgctaat   2640
gaacaattaa tgaaatttca cggtatttac acccaagacg atcgtgacat tagagaaata   2700
cgtaagtcac aaggcttaga gccatactat atgtttatgg caagagctcg tttaccaggt   2760
ggtaagacca ctccacaaca atggcttgct ctggatcact tatctgatac ttcaggcaat   2820
ggtaccctga aattaacaac aagggcaacc ttccagattc atggtgtgct aaagaagaac   2880
ttgaaacaca cattgagagg aatgaatgca gttcttatgg atacattagc tgctgcaggt   2940
```

| | |
|---|---|
| gacgtgaaca gaaatgtcat ggtttctgct ctaccaacca atgccaaggt tcaccaacaa | 3000 |
| atcgctgata tgggaaaatt gatttctgat catttcttac caaagactac ggcctaccac | 3060 |
| gaagtttggc tggagggccc agaagaacag gacgatgatc catcctggcc atctattttt | 3120 |
| gaaaacagaa aagatggtcc aagaaaaaag aagactctag ttagcggtaa cgctttggtc | 3180 |
| gatattgaac caatttacgg tccaacttat ctgccaagaa agtttaaatt caacatcgcc | 3240 |
| gttcctccat ataacgatgt ggatgtatta tctatcgatg tcggtttagt tgctatagtt | 3300 |
| aacccaaaaa ctcaaatcgt ggagggttat aatgttttg ttggtggtgg tatgggtacc | 3360 |
| actcataaca caagaaaac ttacccaaga ttagggtcat gcttaggttt tgttaaaact | 3420 |
| gaagacatta ttccaccact tgaaggtatc gttattgtcc aaagagatca cggtgaccgt | 3480 |
| aaagaccgta agcatgctcg tttaaagtat actgtagatg atatgggtgt cgaaggcttc | 3540 |
| aagcaaaaag tggaggaata ctggggtaag aaattcgagc ctgagagacc atttgagttt | 3600 |
| aaatctaata ttgattactt tggatggatt aaagatgaaa ctgggttaaa ccactttacc | 3660 |
| gcatttattg aaaatggtag ggttgaagat acaccagatt tgcctcaaaa gacaggtatt | 3720 |
| agaaaggttg ctgaatacat gcttaagact aattctggtc atttcagatt gactggtaat | 3780 |
| caacatttgg ttatctctaa tattacagat gaacatgttg ctggaataaa atctatttta | 3840 |
| aagacctata aattggataa caccgatttc agcggtttga gattatcttc atcttcctgt | 3900 |
| gttggtttgc caacatgtgg tttagcgttt gccgaatctg aacgtttcct acctgacatt | 3960 |
| attactcagt tggaagattg tttagaagag tatggtttac gccatgattc cattattatg | 4020 |
| agaatgactg gttgccctaa cggttgttct cgtccatggc taggtgaatt agctcttgtt | 4080 |
| ggtaaagctc cacatactta taacttgatg cttggtggtg gttacctcgg ccaaaggcta | 4140 |
| aacaaattgt ataaggccaa tgtgaaggat gaggaaattg tcgactacat caaaccattg | 4200 |
| tttaaaaggt atgctttaga aagagaagaa ggggaacact ttggtgattt ctgtataaga | 4260 |
| gtaggtatca ttaaaccaac caccgagggt aaatacttcc atgaagatgt gtctgaagat | 4320 |
| gcctattaa | 4329 |

<210> SEQ ID NO 7
<211> LENGTH: 4326
<212> TYPE: DNA
<213> ORGANISM: Saccharomyces cerevisiae

<400> SEQUENCE: 7

| | |
|---|---|
| atgactgctt ctgacctctt gacgctccca caattgttgg cgcaatattc ctctagtgct | 60 |
| ccccaaaata aagtgttcta cactactagc acaaaaaata gtcattcatc cttcaaaggg | 120 |
| ctagaatctg ttgccacaga tgctactcat ctattgaaca atcaagatcc attgaatacc | 180 |
| atcaaagatc aactctctaa ggacatttta actaccgttt ttacagatga aactactttg | 240 |
| gtcaaatcca tccaccatct atattctctt cctaataaac ttccattggt gattacagtg | 300 |
| gatttgaatt tgcaagatta ttccgcaatt cctgcgttaa aggatctttc tttccccatc | 360 |
| ttaatatctt ctgatttgca aactgcaatt tcaaacgcgg actcttctta taagattgct | 420 |
| acaagttctc tgaccccagt tttccatttt cttaacttgg agaaaattgg cacgagtaca | 480 |
| gctattgaac aagacatcga ctttcctacc ttggagattg ctaacgaaga gactaaagta | 540 |
| gcattatcag aagctactga ttcattgaca aattttgaac tggttaaagg taagagtca | 600 |
| attaccactg tcattgttaa cctgtcacca tatgacgcgg aattcagtag cgtattgcct | 660 |
| tcaaacgtag gattgatcaa gattagagta tacagaccat ggaattttc caagttcttg | 720 |

```
gaaatactgc catcttctgt taccaaaatc gccgttttac agggtgtctc taagaaatcg    780
caatcaaacg aatttcaacc atttcttttg gacttctttg gcaattttaa tgaattagtt    840
tctaggaaca tcgagcaggt gttgactaat attggtaatg tgaatgatta tggcaacgtt    900
atcaacaccg tcatatcgaa tattaacaag aaggaaccag ataataactt attttaggt     960 gaatccaatg aaaaggctga ggaacaagct gaagttactc aacttatttc ttctgtcaaa   1020
aaagttgtga acttagaaga cgcctatatc aaagtgctaa acagttatt ttcatcaaat    1080 ctacaaattt tgaatcaatt ttccagtgag acaattgaac caagtaatcc agaatttggt   1140
tttggacgct ttttaaaaca agaagcccag cgtgaagaat tgatcagctt agcaaaaacc   1200
tctcttgatc caagtcttta cttgtccgag gatgcaaata aaattgttca actattatct   1260
aaatggttgt cattcaatgg acgcgatctt gacgaagctc aattacaaga ggccaatgcg   1320
acaggtttgg aaatatttca gttattacaa tctaatcaag attcctctac tgtcttaaaa   1380
ttcttaaaga tagctccaac aagcgattct tttatttca aatcaagctg gctaattggc    1440
tccgatgcct ggtcttatga tttgggtcac tcaggtattc aacaggtttt atcctcccgt   1500
aaaaacatta atgttttatt gattgattca gagccatatg accatagaaa gcaaaaccag   1560
gatagaaaga aagatgttgg tttgtacgcc atgaattatt acagtgccta tgttgcctct   1620
gtagcagtat atgcttctta cacccaacta ttgactgcaa taatagaggc atctaaatac   1680
aatggtcctt ctattgtctt ggcttatttg ccgtataatt ccgaaaatga tactccatta   1740
gaagtcttaa aggaaaccaa aaacgccgtt gaatctggtt actggccatt gtataggttt   1800
aatcctgttt atgacgatcc atcaacagat aaggaggcat ttagcttgga ttcttcggtt   1860
atcagaaaac aattcaggga cttcttagac cgtgagaata agcttaccct attaaccaga   1920
aaagatccat cttttgtcaag aaatctaaag caatctgctg gtgatgcgtt gacaaggaaa   1980
caagaaaaaa gaagcaaggc tgccttcgat cagttattgg agggttttgtc cggcccaccg   2040 ctacacgtct attatgcttc tgacggtggt aatgctgcaa acttggcaaa gagactagca   2100
gcaagggcat ctgcaagagg tttaaaggct actgttctgt ccatggatga cattattttg   2160
gaagaattac ctggtgaaga gaatgtagtt ttcattactt ccacggctgg gcaaggtgaa   2220
ttcccccaag acggtaagtc ttttctgggaa gctctgaaaa atgacaccga cttggattta   2280
gctagtttga atgttgctgt ttttggtctc ggtgattctg agtattggcc acgtaaagaa   2340
gataaacatt attttaacaa gccttcacag gatttattta agcgcttgga attattgagt   2400
gccaaagccc taattccctt gggactgggt gatgatcaag atgctgatgg tttccaaact   2460
gcttattctg agtgggaacc taaattatgg gaagctcttg gtgtttccgg cgctgctgtt   2520
gatgatgagc aaaacctgt tacaaacgag gatattaaga gagaatctaa tttcttgaga   2580
ggtactatca gtgagaactt aaaggatact tcttcaggtg gtgttactca cgctaatgaa   2640
caattaatga aatttcacgg tatttacacc caagacgatc gtgacattag agaaatacgt   2700
aagtcacaag gcttagagcc atactatatg tttatggcaa gagctcgttt accaggtggt   2760
aagaccactc cacaacaatg gcttgctctg atcacttat ctgatacttc aggcaatggt    2820
accctgaaat taacaacaag ggcaaccttc cagattcatg gtgtgctaaa gaagaacttg   2880
aaacacacat tgagaggaat gaatgcagtt cttatggata cattagctgc tgcaggtgac   2940
gtgaacagaa atgtcatggt ttctgctcta ccaaccaatg ccaaggttca ccaacaaatc   3000
gctgatatgg gaaaattgat ttctgatcat ttcttaccaa agactacggc ctaccacgaa   3060
gtttggctgg agggcccaga agaacaggac gatgatccat cctggccatc tatttttgaa   3120
```

```
aacagaaaag atggtccaag aaaaaagaag actctagtta gcggtaacgc tttggtcgat    3180
attgaaccaa tttacggtcc aacttatctg ccaagaaagt ttaaattcaa catcgccgtt    3240
cctccatata acgatgtgga tgtattatct atcgatgtcg gtttagttgc tatagttaac    3300
ccagaaactc aaatcgtgga gggttataat gttttttgttg gtggtggtat gggtaccact   3360
cataacaaca agaaaactta cccaagatta gggtcatgct taggttttgt taaaactgaa    3420
gacattattc caccacttga aggtatcgtt attgtccaaa gagatcacgg tgaccgtaaa    3480
gaccgtaagc atgctcgttt aaagtatact gtagatgata tgggtgtcga aggcttcaag    3540
caaaaagtgg aggaatactg gggtaagaaa ttcgagcctg agagaccatt tgagtttaaa    3600
tctaatattg attactttgg atggattaaa gatgaaactg ggttaaacca ctttaccgca    3660
tttattgaaa atggtagggt tgaagataca ccagatttgc ctcaaaagac aggtattaga    3720
aaggttgctg aatacatgct taagactaat tctggtcatt tcagattgac tggtaatcaa    3780
catttggtta tctctaatat tacagatgaa catgttgctg gaataaaatc tattttaaag    3840
acctataaat tggataacac cgatttcagc ggtttgagat tatcttcatc ttcctgtgtt    3900
ggtttgccaa catgtggttt agcgtttgcc gaatctgaac gtttcctacc tgacattatt    3960
actcagttgg aagattgttt agaagagtat ggtttacgcc atgattccat tattatgaga    4020
atgactggtt gccctaacgg ttgttctcgt ccatggttag gtgaattagc tcttgttggt    4080
aaagctccac atacttataa cttgatgctt ggtggtggtt acctcggcca aaggctaaac    4140
aaattgtata aggccaatgt gaaggatgag gaaattgtcg actacatcaa accattgttt    4200
aaaaggtatg ctttagaaag agaagaaggg gaacactttg gtgatttctg tataagagta    4260
ggtatcatta aaccaaccac cgagggtaaa tacttccatg aagatgtgtc tgaagatgcc    4320
tattaa                                                               4326
```

<210> SEQ ID NO 8
<211> LENGTH: 1442
<212> TYPE: PRT
<213> ORGANISM: Saccharomyces cerevisiae
<220> FEATURE:
<221> NAME/KEY: MISC_FEATURE
<222> LOCATION: (1227)..(1227)
<223> OTHER INFORMATION: Wherein Xaa can be any naturally occurring
      amino acid.

<400> SEQUENCE: 8

```
Met Thr Ala Ser Asp Leu Leu Thr Leu Pro Gln Leu Leu Ala Gln Tyr
 1               5                  10                  15

Ser Ser Ser Ala Pro Gln Asn Lys Val Phe Tyr Thr Ser Thr Lys
            20                  25                  30

Asn Ser His Ser Ser Phe Lys Gly Leu Glu Ser Val Ala Thr Asp Ala
        35                  40                  45

Thr His Leu Leu Asn Asn Gln Asp Pro Leu Asn Thr Ile Lys Asp Gln
    50                  55                  60

Leu Ser Lys Asp Ile Leu Thr Thr Val Phe Thr Asp Glu Thr Thr Leu
65                  70                  75                  80

Val Lys Ser Ile His His Leu Tyr Ser Leu Pro Asn Lys Leu Pro Leu
                85                  90                  95

Val Ile Thr Val Asp Leu Asn Leu Gln Asp Tyr Ser Ala Ile Pro Ala
            100                 105                 110

Leu Lys Asp Leu Ser Phe Pro Ile Leu Ile Ser Ser Asp Leu Gln Thr
        115                 120                 125

Ala Ile Ser Asn Ala Asp Ser Ser Tyr Lys Ile Ala Thr Ser Ser Leu
```

```
               130                 135                 140
Thr Pro Val Phe His Phe Leu Asn Leu Glu Lys Ile Gly Thr Ser Thr
145                 150                 155                 160

Ala Ile Glu Gln Asp Ile Asp Phe Pro Thr Leu Glu Ile Ala Asn Glu
                165                 170                 175

Glu Thr Lys Val Ala Leu Ser Glu Ala Thr Asp Ser Leu Thr Asn Phe
                180                 185                 190

Glu Leu Val Lys Gly Lys Glu Ser Ile Thr Thr Val Ile Val Asn Leu
                195                 200                 205

Ser Pro Tyr Asp Ala Glu Phe Ser Ser Val Leu Pro Ser Asn Val Gly
210                 215                 220

Leu Ile Lys Ile Arg Val Tyr Arg Pro Trp Asn Phe Ser Lys Phe Leu
225                 230                 235                 240

Glu Ile Leu Pro Ser Ser Val Thr Lys Ile Ala Val Leu Gln Gly Val
                245                 250                 255

Ser Lys Lys Ser Gln Ser Asn Glu Phe Gln Pro Phe Leu Leu Asp Phe
                260                 265                 270

Phe Gly Asn Phe Asn Glu Leu Val Ser Arg Asn Ile Glu Gln Val Val
                275                 280                 285

Leu Thr Asn Ile Gly Asn Val Asn Asp Tyr Gly Asn Val Ile Asn Thr
290                 295                 300

Val Ile Ser Asn Ile Asn Lys Lys Glu Pro Asp Asn Asn Leu Phe Leu
305                 310                 315                 320

Gly Glu Ser Asn Glu Lys Ala Glu Gln Ala Glu Val Thr Gln Leu
                325                 330                 335

Ile Ser Ser Val Lys Lys Val Val Asn Leu Glu Asp Ala Tyr Ile Lys
                340                 345                 350

Val Leu Lys Gln Leu Phe Ser Ser Asn Leu Gln Ile Leu Asn Gln Phe
                355                 360                 365

Ser Ser Glu Thr Ile Glu Pro Ser Asn Pro Glu Phe Gly Phe Gly Arg
                370                 375                 380

Phe Leu Lys Gln Glu Ala Gln Arg Glu Glu Leu Ile Ser Leu Ala Lys
385                 390                 395                 400

Thr Ser Leu Asp Pro Ser Leu Tyr Leu Ser Glu Asp Ala Asn Lys Ile
                405                 410                 415

Val Gln Leu Leu Ser Lys Trp Leu Ser Phe Asn Gly Arg Asp Leu Asp
                420                 425                 430

Glu Ala Gln Leu Gln Glu Ala Asn Ala Thr Gly Leu Gly Ile Phe Gln
                435                 440                 445

Leu Leu Gln Ser Asn Gln Asp Ser Ser Thr Val Leu Lys Phe Leu Lys
                450                 455                 460

Ile Ala Pro Thr Ser Asp Ser Phe Ile Phe Lys Ser Ser Trp Leu Ile
465                 470                 475                 480

Gly Ser Asp Ala Trp Ser Tyr Asp Leu Gly His Ser Gly Ile Gln Gln
                485                 490                 495

Val Leu Ser Ser Arg Lys Asn Ile Asn Val Leu Leu Ile Asp Ser Glu
                500                 505                 510

Pro Tyr Asp His Arg Lys Gln Asn Gln Asp Arg Lys Lys Asp Val Gly
                515                 520                 525

Leu Tyr Ala Met Asn Tyr Tyr Ser Ala Tyr Val Ala Ser Val Ala Val
                530                 535                 540

Tyr Ala Ser Tyr Thr Gln Leu Leu Thr Ala Ile Ile Glu Ala Ser Lys
545                 550                 555                 560
```

-continued

Tyr Asn Gly Pro Ser Ile Val Leu Ala Tyr Leu Pro Tyr Asn Ser Glu
              565                 570                 575

Asn Asp Thr Pro Leu Glu Val Leu Lys Glu Thr Lys Asn Ala Val Glu
              580                 585                 590

Ser Gly Tyr Trp Pro Leu Tyr Arg Phe Asn Pro Val Tyr Asp Asp Pro
              595                 600                 605

Ser Thr Asp Lys Glu Ala Phe Ser Leu Asp Ser Ser Val Ile Arg Lys
              610                 615                 620

Gln Leu Gln Asp Phe Leu Asp Arg Glu Asn Lys Leu Thr Leu Leu Thr
625                 630                 635                 640

Arg Lys Asp Pro Ser Leu Ser Arg Asn Leu Lys Gln Ser Ala Gly Asp
              645                 650                 655

Ala Leu Thr Arg Lys Gln Glu Lys Arg Ser Lys Ala Ala Phe Asp Gln
              660                 665                 670

Leu Leu Glu Gly Leu Ser Gly Pro Pro Leu His Val Tyr Tyr Ala Ser
              675                 680                 685

Asp Gly Gly Asn Ala Ala Asn Leu Ala Lys Arg Leu Ala Ala Arg Ala
              690                 695                 700

Ser Ala Arg Gly Leu Lys Ala Thr Val Leu Ser Met Asp Asp Ile Ile
705                 710                 715                 720

Leu Glu Glu Leu Pro Gly Glu Glu Asn Val Val Phe Ile Thr Ser Thr
              725                 730                 735

Ala Gly Gln Gly Glu Phe Pro Gln Asp Gly Lys Ser Phe Trp Glu Ala
              740                 745                 750

Leu Lys Asn Asp Thr Asp Leu Asp Leu Ala Ser Leu Asn Val Ala Val
              755                 760                 765

Phe Gly Leu Gly Asp Ser Glu Tyr Trp Pro Arg Lys Glu Asp Lys His
770                 775                 780

Tyr Phe Asn Lys Pro Ser Gln Asp Leu Phe Lys Arg Leu Glu Leu Leu
785                 790                 795                 800

Ser Ala Lys Ala Leu Ile Pro Leu Gly Leu Gly Asp Asp Gln Asp Ala
              805                 810                 815

Asp Gly Phe Gln Thr Ala Tyr Ser Glu Trp Glu Pro Lys Leu Trp Glu
              820                 825                 830

Ala Leu Gly Val Ser Gly Ala Ala Val Asp Asp Glu Pro Lys Pro Val
              835                 840                 845

Thr Asn Glu Asp Ile Lys Arg Glu Ser Asn Phe Leu Arg Gly Thr Ile
850                 855                 860

Ser Glu Asn Leu Lys Asp Thr Ser Ser Gly Val Thr His Ala Asn
865                 870                 875                 880

Glu Gln Leu Met Lys Phe His Gly Ile Tyr Thr Gln Asp Asp Arg Asp
              885                 890                 895

Ile Arg Glu Ile Arg Lys Ser Gln Gly Leu Glu Pro Tyr Tyr Met Phe
              900                 905                 910

Met Ala Arg Ala Arg Leu Pro Gly Gly Lys Thr Thr Pro Gln Gln Trp
              915                 920                 925

Leu Ala Leu Asp His Leu Ser Asp Thr Ser Gly Asn Gly Thr Leu Lys
              930                 935                 940

Leu Thr Thr Arg Ala Thr Phe Gln Ile His Gly Val Leu Lys Lys Asn
945                 950                 955                 960

Leu Lys His Thr Leu Arg Gly Met Asn Ala Val Leu Met Asp Thr Leu
              965                 970                 975

Ala Ala Ala Gly Asp Val Asn Arg Asn Val Met Val Ser Ala Leu Pro
              980                 985                 990

-continued

Thr Asn Ala Lys Val His Gln Gln Ile Ala Asp Met Gly Lys Leu Ile
       995                 1000                1005

Ser Asp His Phe Leu Pro Lys Thr Thr Ala Tyr His Glu Val Trp
    1010                1015                1020

Leu Glu Gly Pro Glu Glu Gln Asp Asp Pro Ser Trp Pro Ser
    1025                1030                1035

Ile Phe Glu Asn Arg Lys Asp Gly Pro Arg Lys Lys Thr Leu
    1040                1045                1050

Val Ser Gly Asn Ala Leu Val Asp Ile Glu Pro Ile Tyr Gly Pro
    1055                1060                1065

Thr Tyr Leu Pro Arg Lys Phe Lys Phe Asn Ile Ala Val Pro Pro
    1070                1075                1080

Tyr Asn Asp Val Asp Val Leu Ser Ile Asp Val Gly Leu Val Ala
    1085                1090                1095

Ile Val Asn Pro Glu Thr Gln Ile Val Glu Gly Tyr Asn Val Phe
    1100                1105                1110

Val Gly Gly Gly Met Gly Thr Thr His Asn Asn Lys Lys Thr Tyr
    1115                1120                1125

Pro Arg Leu Gly Ser Cys Leu Gly Phe Val Lys Thr Glu Asp Ile
    1130                1135                1140

Ile Pro Pro Leu Glu Gly Ile Val Ile Val Gln Arg Asp His Gly
    1145                1150                1155

Asp Arg Lys Asp Arg Lys His Ala Arg Leu Lys Tyr Thr Val Asp
    1160                1165                1170

Asp Met Gly Val Glu Gly Phe Lys Gln Lys Val Glu Glu Tyr Trp
    1175                1180                1185

Gly Lys Lys Phe Glu Pro Glu Arg Pro Phe Glu Phe Lys Ser Asn
    1190                1195                1200

Ile Asp Tyr Phe Gly Trp Ile Lys Asp Glu Thr Gly Leu Asn His
    1205                1210                1215

Phe Thr Ala Phe Ile Glu Asn Gly Xaa Val Glu Asp Thr Pro Asp
    1220                1225                1230

Leu Pro Gln Lys Thr Gly Ile Arg Lys Val Ala Glu Tyr Met Leu
    1235                1240                1245

Lys Thr Asn Ser Gly His Phe Arg Leu Thr Gly Asn Gln His Leu
    1250                1255                1260

Val Ile Ser Asn Ile Thr Asp Glu His Val Ala Gly Ile Lys Ser
    1265                1270                1275

Ile Leu Lys Thr Tyr Lys Leu Asp Asn Thr Asp Phe Ser Gly Leu
    1280                1285                1290

Arg Leu Ser Ser Ser Ser Cys Val Gly Leu Pro Thr Cys Gly Leu
    1295                1300                1305

Ala Phe Ala Glu Ser Glu Arg Phe Leu Pro Asp Ile Ile Thr Gln
    1310                1315                1320

Leu Glu Asp Cys Leu Glu Glu Tyr Gly Leu Arg His Asp Ser Ile
    1325                1330                1335

Ile Met Arg Met Thr Gly Cys Pro Asn Gly Cys Ser Arg Pro Trp
    1340                1345                1350

Leu Gly Glu Leu Ala Leu Val Gly Lys Ala Pro His Thr Tyr Asn
    1355                1360                1365

Leu Met Leu Gly Gly Gly Tyr Leu Gly Gln Arg Leu Asn Lys Leu
    1370                1375                1380

Tyr Lys Ala Asn Val Lys Asp Glu Glu Ile Val Asp Tyr Ile Lys

```
              1385              1390              1395

Pro Leu Phe Lys Arg Tyr Ala Leu Glu Arg Glu Gly Glu His
    1400              1405              1410

Phe Gly Asp Phe Cys Ile Arg Val Gly Ile Ile Lys Pro Thr Thr
    1415              1420              1425

Glu Gly Lys Tyr Phe His Glu Asp Val Ser Glu Asp Ala Tyr
    1430              1435              1440

<210> SEQ ID NO 9
<211> LENGTH: 1442
<212> TYPE: PRT
<213> ORGANISM: Saccharomyces cerevisiae

<400> SEQUENCE: 9

Met Thr Ala Ser Asp Leu Leu Thr Leu Pro Gln Leu Leu Ala Gln Tyr
1               5                   10                  15

Ser Ser Ser Ala Pro Gln Asn Lys Val Phe Tyr Thr Thr Ser Thr Lys
                20                  25                  30

Asn Ser His Ser Ser Phe Lys Gly Leu Glu Ser Val Ala Thr Asp Ala
            35                  40                  45

Thr His Leu Leu Asn Asn Gln Asp Pro Leu Asn Thr Ile Lys Asp Gln
    50                  55                  60

Leu Ser Lys Asp Ile Leu Thr Thr Val Phe Thr Asp Glu Thr Thr Leu
65                  70                  75                  80

Val Lys Ser Ile His His Leu Tyr Ser Leu Pro Asn Lys Leu Pro Leu
                85                  90                  95

Val Ile Thr Val Asp Leu Asn Leu Gln Asp Tyr Ser Ala Ile Pro Ala
            100                 105                 110

Leu Lys Asp Leu Ser Phe Pro Ile Leu Ile Ser Ser Asp Leu Gln Thr
    115                 120                 125

Ala Ile Ser Asn Ala Asp Ser Ser Tyr Lys Ile Ala Thr Ser Ser Leu
130                 135                 140

Thr Pro Val Phe His Phe Leu Asn Leu Glu Lys Ile Gly Thr Ser Thr
145                 150                 155                 160

Ala Ile Glu Gln Asp Ile Asp Phe Pro Thr Leu Glu Ile Ala Asn Glu
                165                 170                 175

Glu Thr Lys Val Ala Leu Ser Glu Ala Thr Asp Ser Leu Thr Asn Phe
            180                 185                 190

Glu Leu Val Lys Gly Lys Glu Ser Ile Thr Thr Val Ile Val Asn Leu
    195                 200                 205

Ser Pro Tyr Asp Ala Glu Phe Ser Ser Val Leu Pro Ser Asn Val Gly
210                 215                 220

Leu Ile Lys Ile Arg Val Tyr Arg Pro Trp Asn Phe Ser Lys Phe Leu
225                 230                 235                 240

Glu Ile Leu Pro Ser Ser Val Thr Lys Ile Ala Val Leu Gln Gly Val
                245                 250                 255

Ser Lys Lys Ser Gln Ser Asn Glu Phe Gln Pro Phe Leu Leu Asp Phe
            260                 265                 270

Phe Gly Asn Phe Asn Glu Leu Val Ser Arg Asn Ile Glu Gln Val Val
    275                 280                 285

Leu Thr Asn Ile Gly Asn Val Asn Asp Tyr Gly Asn Val Ile Asn Thr
    290                 295                 300

Val Ile Ser Asn Ile Asn Lys Lys Glu Pro Asp Asn Leu Phe Leu
305                 310                 315                 320

Gly Glu Ser Asn Glu Lys Ala Glu Glu Gln Ala Glu Val Thr Gln Leu
```

-continued

```
                325                 330                 335
Ile Ser Ser Val Lys Lys Val Asn Leu Glu Asp Ala Tyr Ile Lys
                340                 345                 350

Val Leu Lys Gln Leu Phe Ser Ser Asn Leu Gln Ile Leu Asn Gln Phe
                355                 360                 365

Ser Ser Glu Thr Ile Glu Pro Ser Asn Pro Glu Phe Gly Phe Gly Arg
                370                 375                 380

Phe Leu Lys Gln Glu Ala Gln Arg Glu Leu Ile Ser Leu Ala Lys
385                 390                 395                 400

Thr Ser Leu Asp Pro Ser Leu Tyr Leu Ser Glu Asp Ala Asn Lys Ile
                405                 410                 415

Val Gln Leu Leu Ser Lys Trp Leu Ser Phe Asn Gly Arg Asp Leu Asp
                420                 425                 430

Glu Ala Gln Leu Gln Glu Ala Asn Ala Thr Gly Leu Glu Ile Phe Gln
                435                 440                 445

Leu Leu Gln Ser Asn Gln Asp Ser Ser Thr Val Leu Lys Phe Leu Lys
                450                 455                 460

Ile Ala Pro Thr Ser Asp Ser Phe Ile Phe Lys Ser Ser Trp Leu Ile
465                 470                 475                 480

Gly Ser Asp Ala Trp Ser Tyr Asp Leu Gly His Ser Gly Ile Gln Gln
                485                 490                 495

Val Leu Ser Ser Arg Lys Asn Ile Asn Val Leu Leu Ile Asp Ser Glu
                500                 505                 510

Pro Tyr Asp His Arg Lys Gln Asn Gln Asp Arg Lys Lys Asp Val Gly
                515                 520                 525

Leu Tyr Ala Met Asn Tyr Tyr Ser Ala Tyr Val Ala Ser Val Ala Val
                530                 535                 540

Tyr Ala Ser Tyr Thr Gln Leu Leu Thr Ala Ile Ile Glu Ala Ser Lys
545                 550                 555                 560

Tyr Asn Gly Pro Ser Ile Val Leu Ala Tyr Leu Pro Tyr Asn Ser Glu
                565                 570                 575

Asn Asp Thr Pro Leu Glu Val Leu Lys Glu Thr Lys Asn Ala Val Glu
                580                 585                 590

Ser Gly Tyr Trp Pro Leu Tyr Arg Phe Asn Pro Val Tyr Asp Asp Pro
                595                 600                 605

Ser Thr Asp Lys Glu Ala Phe Ser Leu Asp Ser Ser Val Ile Arg Lys
                610                 615                 620

Gln Leu Gln Asp Phe Leu Asp Arg Glu Asn Lys Leu Thr Leu Leu Thr
625                 630                 635                 640

Arg Lys Asp Pro Ser Leu Ser Arg Asn Leu Lys Gln Ser Ala Gly Asp
                645                 650                 655

Ala Leu Thr Arg Lys Gln Glu Lys Arg Ser Lys Ala Ala Phe Asp Gln
                660                 665                 670

Leu Leu Glu Gly Leu Ser Gly Pro Pro Leu His Val Tyr Tyr Ala Ser
                675                 680                 685

Asp Gly Gly Asn Ala Ala Asn Leu Ala Lys Arg Leu Ala Ala Arg Ala
                690                 695                 700

Ser Ala Arg Gly Leu Lys Ala Thr Val Leu Ser Met Asp Asp Ile Ile
705                 710                 715                 720

Leu Glu Glu Leu Pro Gly Glu Glu Asn Val Val Phe Ile Thr Ser Thr
                725                 730                 735

Ala Gly Gln Gly Glu Phe Pro Gln Asp Gly Lys Ser Phe Trp Glu Ala
                740                 745                 750
```

-continued

Leu Lys Asn Asp Thr Asp Leu Asp Leu Ala Ser Leu Asn Val Ala Val
        755                 760                 765

Phe Gly Leu Gly Asp Ser Glu Tyr Trp Pro Arg Lys Glu Asp Lys His
770                 775                 780

Tyr Phe Asn Lys Pro Ser Gln Asp Leu Phe Lys Arg Leu Glu Leu Leu
785                 790                 795                 800

Ser Ala Lys Ala Leu Ile Pro Leu Gly Leu Gly Asp Asp Gln Asp Ala
        805                 810                 815

Asp Gly Phe Gln Thr Ala Tyr Ser Glu Trp Glu Pro Lys Leu Trp Glu
        820                 825                 830

Ala Leu Gly Val Ser Gly Ala Val Asp Asp Glu Pro Lys Pro Val
        835                 840                 845

Thr Asn Glu Asp Ile Lys Arg Glu Ser Asn Phe Leu Arg Gly Thr Ile
        850                 855                 860

Ser Glu Asn Leu Lys Asp Thr Ser Ser Gly Gly Val Thr His Ala Asn
865                 870                 875                 880

Glu Gln Leu Met Lys Phe His Gly Ile Tyr Thr Gln Asp Arg Asp
                885                 890                 895

Ile Arg Glu Ile Arg Lys Ser Gln Gly Leu Glu Pro Tyr Tyr Met Phe
        900                 905                 910

Met Ala Arg Ala Arg Leu Pro Gly Gly Lys Thr Thr Pro Gln Gln Trp
        915                 920                 925

Leu Ala Leu Asp His Leu Ser Asp Thr Ser Gly Asn Gly Thr Leu Lys
        930                 935                 940

Leu Thr Thr Arg Ala Thr Phe Gln Ile His Gly Val Leu Lys Lys Asn
945                 950                 955                 960

Leu Lys His Thr Leu Arg Gly Met Asn Ala Val Leu Met Asp Thr Leu
                965                 970                 975

Ala Ala Ala Gly Asp Val Asn Arg Asn Val Met Val Ser Ala Leu Pro
        980                 985                 990

Thr Asn Ala Lys Val His Gln Gln Ile Ala Asp Met Gly Lys Leu Ile
        995                 1000                1005

Ser Asp His Phe Leu Pro Lys Thr Thr Ala Tyr His Glu Val Trp
    1010                1015                1020

Leu Glu Gly Pro Glu Glu Gln Asp Asp Asp Pro Ser Trp Pro Ser
    1025                1030                1035

Ile Phe Glu Asn Arg Lys Asp Gly Pro Arg Lys Lys Lys Thr Leu
    1040                1045                1050

Val Ser Gly Asn Ala Leu Val Asp Ile Glu Pro Ile Tyr Gly Pro
    1055                1060                1065

Thr Tyr Leu Pro Arg Lys Phe Lys Phe Asn Ile Ala Val Pro Pro
    1070                1075                1080

Tyr Asn Asp Val Asp Val Leu Ser Ile Asp Val Gly Leu Val Ala
    1085                1090                1095

Ile Val Asn Pro Glu Thr Gln Ile Val Glu Gly Tyr Asn Val Phe
    1100                1105                1110

Val Gly Gly Gly Met Gly Thr Thr His Asn Asn Lys Lys Thr Tyr
    1115                1120                1125

Pro Arg Leu Gly Ser Cys Leu Gly Phe Val Lys Thr Glu Asp Ile
    1130                1135                1140

Ile Pro Pro Leu Glu Gly Ile Val Ile Gln Arg Asp His Gly
    1145                1150                1155

Asp Arg Lys Asp Arg Lys His Ala Arg Leu Lys Tyr Thr Val Asp
    1160                1165                1170

```
Asp Met Gly Val Glu Gly Phe Lys Gln Lys Val Glu Glu Tyr Trp
    1175                1180                1185
Gly Lys Lys Phe Glu Pro Glu Arg Pro Phe Glu Phe Lys Ser Asn
    1190                1195                1200
Ile Asp Tyr Phe Gly Trp Ile Lys Asp Glu Thr Gly Leu Asn His
    1205                1210                1215
Phe Thr Ala Leu Ile Glu Asn Gly Arg Val Glu Asp Thr Pro Asp
    1220                1225                1230
Leu Pro Gln Lys Thr Gly Ile Arg Lys Val Ala Glu Tyr Met Leu
    1235                1240                1245
Lys Thr Asn Ser Gly His Phe Arg Leu Thr Gly Asn Gln His Leu
    1250                1255                1260
Val Ile Ser Asn Ile Thr Asp Glu His Val Ala Gly Ile Lys Ser
    1265                1270                1275
Ile Leu Lys Thr Tyr Lys Leu Asp Asn Thr Asp Phe Ser Gly Leu
    1280                1285                1290
Arg Leu Ser Ser Ser Ser Cys Val Gly Leu Pro Thr Cys Gly Leu
    1295                1300                1305
Ala Phe Ala Glu Ser Glu Arg Phe Leu Pro Asp Ile Ile Thr Gln
    1310                1315                1320
Leu Glu Asp Cys Leu Glu Glu Tyr Gly Leu Arg His Asp Ser Ile
    1325                1330                1335
Ile Met Arg Met Thr Gly Cys Pro Asn Gly Cys Ser Arg Pro Trp
    1340                1345                1350
Leu Gly Glu Leu Ala Leu Val Gly Lys Ala Pro His Thr Tyr Asn
    1355                1360                1365
Leu Met Leu Gly Gly Gly Tyr Leu Gly Gln Arg Leu Asn Lys Leu
    1370                1375                1380
Tyr Lys Ala Asn Val Lys Asp Glu Glu Ile Val Asp Tyr Ile Lys
    1385                1390                1395
Pro Leu Phe Lys Arg Tyr Ala Leu Glu Arg Glu Glu Gly Glu His
    1400                1405                1410
Phe Gly Asp Phe Cys Ile Arg Val Gly Ile Ile Lys Pro Thr Thr
    1415                1420                1425
Glu Gly Lys Tyr Phe His Glu Asp Val Ser Glu Asp Ala Tyr
    1430                1435                1440

<210> SEQ ID NO 10
<211> LENGTH: 1442
<212> TYPE: PRT
<213> ORGANISM: Saccharomyces cerevisiae

<400> SEQUENCE: 10

Met Thr Ala Ser Asp Leu Leu Thr Leu Pro Gln Leu Leu Ala Gln Tyr
1               5                   10                  15
Ser Ser Ser Ala Pro Gln Asn Lys Val Phe Tyr Thr Ser Thr Lys
                20                  25                  30
Asn Ser His Ser Ser Phe Lys Gly Leu Glu Ser Val Ala Thr Asp Ala
            35                  40                  45
Thr His Leu Leu Asn Asn Gln Asp Pro Leu Asn Thr Ile Lys Asp Gln
        50                  55                  60
Leu Ser Lys Asp Ile Leu Thr Thr Val Phe Asp Glu Thr Thr Leu
65                  70                  75                  80
Val Lys Ser Ile His His Leu Tyr Ser Leu Pro Asn Lys Leu Pro Leu
                85                  90                  95
```

```
Val Ile Thr Val Asp Leu Asn Leu Gln Asp Tyr Ser Ala Ile Pro Ala
             100                 105                 110

Leu Lys Asp Leu Ser Phe Pro Ile Leu Ile Ser Ser Asp Leu Gln Thr
         115                 120                 125

Ala Ile Ser Asn Ala Asp Ser Ser Tyr Lys Ile Ala Thr Ser Ser Leu
    130                 135                 140

Thr Pro Val Phe His Phe Leu Asn Leu Glu Lys Ile Gly Thr Ser Thr
145                 150                 155                 160

Ala Ile Glu Gln Asp Ile Asp Phe Pro Thr Leu Glu Ile Ala Asn Glu
                165                 170                 175

Glu Thr Lys Val Ala Leu Ser Glu Ala Thr Asp Ser Leu Thr Asn Phe
                180                 185                 190

Glu Leu Val Lys Gly Lys Glu Ser Ile Thr Thr Val Ile Val Asn Leu
            195                 200                 205

Ser Pro Tyr Asp Ala Glu Phe Ser Ser Val Leu Pro Ser Asn Val Gly
    210                 215                 220

Leu Ile Lys Ile Arg Val Tyr Arg Pro Trp Asn Phe Ser Lys Phe Leu
225                 230                 235                 240

Glu Ile Leu Pro Ser Ser Val Thr Lys Ile Ala Val Leu Gln Gly Val
                245                 250                 255

Ser Lys Lys Ser Gln Ser Asn Glu Phe Gln Pro Phe Leu Leu Asp Phe
                260                 265                 270

Phe Gly Asn Phe Asn Glu Leu Val Ser Arg Asn Ile Glu Gln Val Val
            275                 280                 285

Leu Thr Asn Ile Gly Asn Val Asn Asp Tyr Gly Asn Val Ile Asn Thr
    290                 295                 300

Val Ile Ser Asn Ile Asn Lys Lys Glu Pro Asp Asn Asn Leu Phe Leu
305                 310                 315                 320

Gly Glu Ser Asn Glu Lys Ala Glu Glu Gln Ala Glu Val Thr Gln Leu
                325                 330                 335

Ile Ser Ser Val Lys Lys Val Val Asn Leu Glu Asp Ala Tyr Ile Lys
                340                 345                 350

Val Leu Lys Gln Leu Phe Ser Ser Asn Leu Gln Ile Leu Asn Gln Phe
            355                 360                 365

Ser Ser Glu Thr Ile Glu Pro Ser Asn Pro Glu Phe Gly Phe Gly Arg
    370                 375                 380

Phe Leu Lys Gln Glu Ala Gln Arg Glu Glu Leu Ile Ser Leu Ala Lys
385                 390                 395                 400

Thr Ser Leu Asp Pro Ser Leu Tyr Leu Ser Glu Asp Ala Asn Lys Ile
                405                 410                 415

Val Gln Leu Leu Ser Lys Trp Leu Ser Phe Asn Gly Arg Asp Leu Asp
            420                 425                 430

Glu Ala Gln Leu Gln Glu Ala Asn Ala Thr Gly Leu Glu Ile Phe Gln
    435                 440                 445

Leu Leu Gln Ser Asn Gln Asp Ser Ser Thr Val Leu Lys Phe Leu Lys
    450                 455                 460

Ile Ala Pro Thr Ser Asp Ser Phe Ile Phe Lys Ser Ser Trp Leu Ile
465                 470                 475                 480

Gly Ser Asp Ala Trp Ser Tyr Asp Leu Gly His Ser Gly Ile Gln Gln
                485                 490                 495

Val Leu Ser Ser Arg Lys Asn Ile Asn Val Leu Leu Ile Asp Ser Glu
                500                 505                 510

Pro Tyr Asp His Arg Lys Gln Asn Gln Asp Arg Lys Lys Asp Val Gly
```

-continued

```
            515                 520                 525
Leu Tyr Ala Met Asn Tyr Tyr Ser Ala Tyr Val Ala Ser Val Ala Val
530                 535                 540

Tyr Ala Ser Tyr Thr Gln Leu Leu Thr Ala Ile Ile Glu Ala Ser Lys
545                 550                 555                 560

Tyr Asn Gly Pro Ser Ile Val Leu Ala Tyr Leu Pro Tyr Asn Ser Glu
                    565                 570                 575

Asn Asp Thr Pro Leu Glu Val Leu Lys Glu Thr Lys Asn Ala Val Glu
                580                 585                 590

Ser Gly Tyr Trp Pro Leu Tyr Arg Phe Asn Pro Val Tyr Asp Asp Pro
            595                 600                 605

Ser Thr Asp Lys Glu Ala Phe Ser Leu Asp Ser Ser Val Ile Arg Lys
610                 615                 620

Gln Leu Gln Asp Phe Leu Asp Arg Glu Asn Lys Leu Thr Leu Leu Thr
625                 630                 635                 640

Arg Lys Asp Pro Ser Leu Ser Arg Asn Leu Lys Gln Ser Ala Gly Asp
                    645                 650                 655

Ala Leu Thr Arg Lys Gln Glu Lys Arg Ser Lys Ala Ala Phe Asp Gln
                660                 665                 670

Leu Leu Glu Gly Leu Ser Gly Pro Leu His Val Tyr Tyr Ala Ser
            675                 680                 685

Asp Gly Gly Asn Ala Ala Asn Leu Ala Lys Arg Leu Ala Ala Arg Ala
690                 695                 700

Ser Ala Arg Gly Leu Lys Ala Thr Val Leu Ser Met Asp Asp Ile Ile
705                 710                 715                 720

Leu Glu Glu Leu Pro Gly Glu Asn Val Val Phe Ile Thr Ser Thr
                    725                 730                 735

Ala Gly Gln Gly Glu Phe Pro Gln Asp Gly Lys Ser Phe Trp Glu Ala
                740                 745                 750

Leu Lys Asn Asp Thr Asp Leu Asp Leu Ala Ser Leu Asn Val Ala Val
            755                 760                 765

Phe Gly Leu Gly Asp Ser Glu Tyr Trp Pro Arg Lys Glu Asp Lys His
770                 775                 780

Tyr Phe Asn Lys Pro Ser Gln Asp Leu Phe Lys Arg Leu Glu Leu Leu
785                 790                 795                 800

Ser Ala Lys Ala Leu Ile Pro Leu Gly Leu Gly Asp Asp Gln Asp Ala
                    805                 810                 815

Asp Gly Phe Gln Thr Ala Tyr Ser Glu Trp Glu Pro Lys Leu Trp Glu
                820                 825                 830

Ala Leu Gly Val Ser Gly Ala Ala Val Asp Asp Glu Pro Lys Pro Val
            835                 840                 845

Thr Asn Glu Asp Ile Lys Arg Glu Ser Asn Phe Leu Arg Gly Thr Ile
850                 855                 860

Ser Glu Asn Leu Lys Asp Thr Ser Ser Gly Val Thr His Ala Asn
865                 870                 875                 880

Glu Gln Leu Met Lys Phe His Gly Ile Tyr Thr Gln Asp Asp Arg Asp
                    885                 890                 895

Ile Arg Glu Ile Arg Lys Ser Gln Gly Leu Glu Pro Tyr Tyr Met Phe
                900                 905                 910

Met Ala Arg Ala Arg Leu Pro Gly Gly Lys Thr Thr Pro Gln Gln Trp
            915                 920                 925

Leu Ala Leu Asp His Leu Ser Asp Thr Ser Gly Asn Gly Thr Leu Lys
930                 935                 940
```

-continued

Leu Thr Thr Arg Ala Thr Phe Gln Ile His Gly Val Leu Lys Lys Asn
945                 950                 955                 960

Leu Lys His Thr Leu Arg Gly Met Asn Ala Val Leu Met Asp Thr Leu
            965                 970                 975

Ala Ala Ala Gly Asp Val Asn Arg Asn Val Met Val Ser Ala Leu Pro
            980                 985                 990

Thr Asn Ala Lys Val His Gln Gln Ile Ala Asp Met Gly Lys Leu Ile
        995                 1000                1005

Ser Asp His Phe Leu Pro Lys Thr Thr Ala Tyr His Glu Val Trp
    1010                1015                1020

Leu Glu Gly Pro Glu Glu Gln Asp Asp Pro Ser Trp Pro Ser
    1025                1030                1035

Ile Phe Glu Asn Arg Lys Asp Gly Pro Arg Lys Lys Thr Leu
    1040                1045                1050

Val Ser Gly Asn Ala Leu Val Asp Ile Glu Pro Ile Tyr Gly Pro
    1055                1060                1065

Thr Tyr Leu Pro Arg Lys Phe Lys Phe Asn Ile Ala Val Pro Pro
    1070                1075                1080

Tyr Asn Asp Val Asp Val Leu Ser Ser Asp Val Gly Leu Val Ala
    1085                1090                1095

Ile Val Asn Pro Glu Thr Gln Ile Val Glu Gly Tyr Asn Val Phe
    1100                1105                1110

Val Gly Gly Gly Met Gly Thr Thr His Asn Asn Lys Lys Thr Tyr
    1115                1120                1125

Pro Arg Leu Gly Ser Cys Leu Gly Phe Val Lys Thr Glu Asp Ile
    1130                1135                1140

Ile Pro Pro Leu Glu Gly Ile Val Ile Val Gln Arg Asp His Gly
    1145                1150                1155

Asp Arg Lys Asp Arg Lys His Ala Arg Leu Lys Tyr Thr Val Asp
    1160                1165                1170

Asp Met Gly Val Glu Gly Phe Lys Gln Lys Val Glu Glu Tyr Trp
    1175                1180                1185

Gly Lys Lys Phe Glu Pro Glu Arg Pro Phe Glu Phe Lys Ser Asn
    1190                1195                1200

Ile Asp Tyr Phe Gly Trp Ile Lys Asp Glu Thr Gly Leu Asn His
    1205                1210                1215

Phe Thr Ala Phe Ile Glu Asn Gly Arg Val Glu Asp Thr Pro Asp
    1220                1225                1230

Leu Pro Gln Lys Thr Gly Ile Arg Lys Val Ala Glu Tyr Met Leu
    1235                1240                1245

Lys Thr Asn Ser Gly His Phe Arg Leu Thr Gly Asn Gln His Leu
    1250                1255                1260

Val Ile Ser Asn Ile Thr Asp Glu His Val Ala Gly Ile Lys Ser
    1265                1270                1275

Ile Leu Lys Thr Tyr Lys Leu Asp Asn Thr Asp Phe Ser Gly Leu
    1280                1285                1290

Arg Leu Ser Ser Ser Ser Cys Val Gly Leu Pro Thr Cys Gly Leu
    1295                1300                1305

Ala Phe Ala Glu Ser Glu Arg Phe Leu Pro Asp Ile Ile Thr Gln
    1310                1315                1320

Leu Glu Asp Cys Leu Glu Glu Tyr Gly Leu Arg His Asp Ser Ile
    1325                1330                1335

Ile Met Arg Met Thr Gly Cys Pro Asn Gly Cys Ser Arg Pro Trp
    1340                1345                1350

```
Leu Gly Glu Leu Ala Leu Val Gly Lys Ala Pro His Thr Tyr Asn
    1355                1360                1365

Leu Met Leu Gly Gly Gly Tyr Leu Gly Gln Arg Leu Asn Lys Leu
    1370                1375                1380

Tyr Lys Ala Asn Val Lys Asp Glu Glu Ile Val Asp Tyr Ile Lys
    1385                1390                1395

Pro Leu Phe Lys Arg Tyr Ala Leu Glu Arg Glu Gly Glu His
    1400                1405                1410

Phe Gly Asp Phe Cys Ile Arg Val Gly Ile Ile Lys Pro Thr Thr
    1415                1420                1425

Glu Gly Lys Tyr Phe His Glu Asp Val Ser Glu Asp Ala Tyr
    1430                1435                1440

<210> SEQ ID NO 11
<211> LENGTH: 1442
<212> TYPE: PRT
<213> ORGANISM: Saccharomyces cerevisiae
<220> FEATURE:
<221> NAME/KEY: MISC_FEATURE
<222> LOCATION: (464)..(464)
<223> OTHER INFORMATION: Wherein Xaa can be any naturally occurring
      amino acid.

<400> SEQUENCE: 11

Met Thr Ala Ser Asp Leu Leu Thr Leu Pro Gln Leu Leu Ala Gln Tyr
1               5                   10                  15

Ser Ser Ser Ala Pro Gln Asn Lys Val Phe Tyr Thr Thr Ser Thr Lys
            20                  25                  30

Asn Ser His Ser Ser Phe Lys Gly Leu Glu Ser Val Ala Thr Asp Ala
        35                  40                  45

Thr His Leu Leu Asn Asn Gln Asp Pro Leu Asn Thr Ile Lys Asp Gln
    50                  55                  60

Leu Ser Lys Asp Ile Leu Thr Val Phe Thr Asp Glu Thr Thr Leu
65                  70                  75                  80

Val Lys Ser Ile His His Leu Tyr Ser Leu Pro Asn Lys Leu Pro Leu
                85                  90                  95

Val Ile Thr Val Asp Leu Asn Leu Gln Asp Tyr Ser Ala Ile Pro Ala
            100                 105                 110

Leu Lys Asp Leu Ser Phe Pro Ile Leu Ile Ser Ser Asp Leu Gln Thr
        115                 120                 125

Ala Ile Ser Asn Ala Asp Ser Ser Tyr Lys Ile Ala Thr Ser Ser Leu
    130                 135                 140

Thr Pro Val Phe His Phe Leu Asn Leu Glu Lys Ile Gly Thr Ser Thr
145                 150                 155                 160

Ala Ile Glu Gln Asp Ile Asp Phe Pro Thr Leu Glu Ile Ala Asn Glu
                165                 170                 175

Glu Thr Lys Val Ala Leu Ser Glu Ala Thr Asp Ser Leu Thr Asn Phe
            180                 185                 190

Glu Leu Val Lys Gly Lys Glu Ser Ile Thr Thr Val Ile Val Asn Leu
        195                 200                 205

Ser Pro Tyr Asp Ala Glu Phe Ser Ser Val Leu Pro Ser Asn Val Gly
    210                 215                 220

Leu Ile Lys Ile Arg Val Tyr Arg Pro Trp Asn Phe Ser Lys Phe Leu
225                 230                 235                 240

Glu Ile Leu Pro Ser Ser Val Thr Lys Ile Ala Val Leu Gln Gly Val
                245                 250                 255
```

```
Ser Lys Lys Ser Gln Ser Asn Glu Phe Gln Pro Phe Leu Leu Asp Phe
            260                 265                 270

Phe Gly Asn Phe Asn Glu Leu Val Ser Arg Asn Ile Glu Gln Val Val
        275                 280                 285

Leu Thr Asn Ile Gly Asn Val Asn Asp Tyr Gly Asn Val Ile Asn Thr
290                 295                 300

Val Ile Ser Asn Ile Asn Lys Lys Glu Pro Asp Asn Asn Leu Phe Leu
305                 310                 315                 320

Gly Glu Ser Asn Glu Lys Ala Glu Glu Gln Ala Glu Val Thr Gln Leu
                325                 330                 335

Ile Ser Ser Val Lys Lys Val Val Asn Leu Glu Asp Ala Tyr Ile Lys
            340                 345                 350

Val Leu Lys Gln Leu Phe Ser Ser Asn Leu Gln Ile Leu Asn Gln Phe
        355                 360                 365

Ser Ser Glu Thr Ile Glu Pro Ser Asn Pro Glu Phe Gly Phe Gly Arg
370                 375                 380

Phe Leu Lys Gln Glu Ala Gln Arg Glu Glu Leu Ile Ser Leu Ala Lys
385                 390                 395                 400

Thr Ser Leu Asp Pro Ser Leu Tyr Leu Ser Glu Asp Ala Asn Lys Ile
                405                 410                 415

Val Gln Leu Leu Ser Lys Trp Leu Ser Phe Asn Gly Arg Asp Leu Asp
            420                 425                 430

Glu Ala Gln Leu Gln Glu Ala Asn Ala Thr Gly Leu Glu Ile Phe Gln
        435                 440                 445

Leu Leu Gln Ser Asn Gln Asp Ser Ser Thr Val Leu Lys Phe Leu Xaa
450                 455                 460

Ile Ala Pro Thr Ser Asp Ser Phe Ile Phe Lys Ser Ser Trp Leu Ile
465                 470                 475                 480

Gly Ser Asp Ala Trp Ser Tyr Asp Leu Gly His Ser Gly Ile Gln Gln
                485                 490                 495

Val Leu Ser Ser Arg Lys Asn Ile Asn Val Leu Leu Ile Asp Ser Glu
            500                 505                 510

Pro Tyr Asp His Arg Lys Gln Asn Gln Asp Arg Lys Lys Asp Val Gly
        515                 520                 525

Leu Tyr Ala Met Asn Tyr Tyr Ser Ala Tyr Val Ala Ser Val Ala Val
530                 535                 540

Tyr Ala Ser Tyr Thr Gln Leu Leu Thr Ala Ile Ile Glu Ala Ser Lys
545                 550                 555                 560

Tyr Asn Gly Pro Ser Ile Val Leu Ala Tyr Leu Pro Tyr Asn Ser Glu
                565                 570                 575

Asn Asp Thr Pro Leu Glu Val Leu Lys Glu Thr Lys Asn Ala Val Glu
            580                 585                 590

Ser Gly Tyr Trp Pro Leu Tyr Arg Phe Asn Pro Val Tyr Asp Asp Pro
        595                 600                 605

Ser Thr Asp Lys Glu Ala Phe Ser Leu Asp Ser Ser Val Ile Arg Lys
610                 615                 620

Gln Leu Gln Asp Phe Leu Asp Arg Glu Asn Lys Leu Thr Leu Leu Thr
625                 630                 635                 640

Arg Lys Asp Pro Ser Leu Ser Arg Asn Leu Lys Gln Ser Ala Gly Asp
                645                 650                 655

Ala Leu Thr Arg Lys Gln Glu Lys Arg Ser Lys Ala Ala Phe Asp Gln
            660                 665                 670

Leu Leu Glu Gly Leu Ser Gly Pro Pro Leu His Val Tyr Tyr Ala Ser
        675                 680                 685
```

-continued

Asp Gly Gly Asn Ala Ala Asn Leu Ala Lys Arg Leu Ala Ala Arg Ala
    690                 695                 700

Ser Ala Arg Gly Leu Lys Ala Thr Val Leu Ser Met Asp Ile Ile
705                 710                 715                 720

Leu Glu Glu Leu Pro Gly Glu Glu Asn Val Val Phe Ile Thr Ser Thr
                725                 730                 735

Ala Gly Gln Gly Glu Phe Pro Gln Asp Gly Lys Ser Phe Trp Glu Ala
            740                 745                 750

Leu Lys Asn Asp Thr Asp Leu Asp Leu Ala Ser Leu Asn Val Ala Val
        755                 760                 765

Phe Gly Leu Gly Asp Ser Glu Tyr Trp Pro Arg Lys Glu Asp Lys His
    770                 775                 780

Tyr Phe Asn Lys Pro Ser Gln Asp Leu Phe Lys Arg Leu Glu Leu Leu
785                 790                 795                 800

Ser Ala Lys Ala Leu Ile Pro Leu Gly Leu Gly Asp Asp Gln Asp Ala
                805                 810                 815

Asp Gly Phe Gln Thr Ala Tyr Ser Glu Trp Glu Pro Lys Leu Trp Glu
            820                 825                 830

Ala Leu Gly Val Ser Gly Ala Val Asp Asp Glu Pro Lys Pro Val
        835                 840                 845

Thr Asn Glu Asp Ile Lys Arg Glu Ser Asn Phe Leu Arg Gly Thr Ile
    850                 855                 860

Ser Glu Asn Leu Lys Asp Thr Ser Ser Gly Gly Val Thr His Ala Asn
865                 870                 875                 880

Glu Gln Leu Met Lys Phe His Gly Ile Tyr Thr Gln Asp Arg Asp
                885                 890                 895

Ile Arg Glu Ile Arg Lys Ser Gln Gly Leu Glu Pro Tyr Tyr Met Phe
            900                 905                 910

Met Ala Arg Ala Arg Leu Pro Gly Gly Lys Thr Thr Pro Gln Gln Trp
        915                 920                 925

Leu Ala Leu Asp His Leu Ser Asp Thr Ser Gly Asn Gly Thr Leu Lys
    930                 935                 940

Leu Thr Thr Arg Ala Thr Phe Gln Ile His Gly Val Leu Lys Lys Asn
945                 950                 955                 960

Leu Lys His Thr Leu Arg Gly Met Asn Ala Val Leu Met Asp Thr Leu
                965                 970                 975

Ala Ala Ala Gly Asp Val Asn Arg Asn Val Met Val Ser Ala Leu Pro
            980                 985                 990

Thr Asn Ala Lys Val His Gln Gln Ile Ala Asp Met Gly Lys Leu Ile
        995                 1000                1005

Ser Asp His Phe Leu Pro Lys Thr Thr Ala Tyr His Glu Val Trp
    1010                1015                1020

Leu Glu Gly Pro Glu Glu Gln Asp Asp Asp Pro Ser Trp Pro Ser
    1025                1030                1035

Ile Phe Glu Asn Arg Lys Asp Gly Pro Arg Lys Lys Lys Thr Leu
    1040                1045                1050

Val Ser Gly Asn Ala Leu Val Asp Ile Glu Pro Ile Tyr Gly Pro
    1055                1060                1065

Thr Tyr Leu Pro Arg Lys Phe Lys Phe Asn Ile Ala Val Pro Pro
    1070                1075                1080

Tyr Asn Asp Val Asp Val Leu Ser Ile Asp Val Gly Leu Val Ala
    1085                1090                1095

Ile Val Asn Pro Glu Thr Gln Ile Val Glu Gly Tyr Asn Val Phe

-continued

```
              1100                1105                1110

Val Gly Gly Gly Met Gly Thr Thr His Asn Asn Lys Lys Thr Tyr
    1115                1120                1125

Pro Arg Leu Gly Ser Cys Leu Gly Phe Val Lys Thr Glu Asp Ile
    1130                1135                1140

Ile Pro Pro Leu Glu Gly Ile Val Ile Val Gln Arg Asp His Gly
    1145                1150                1155

Asp Arg Lys Asp Arg Lys His Ala Arg Leu Lys Tyr Thr Val Asp
    1160                1165                1170

Asp Met Gly Val Glu Gly Phe Lys Gln Lys Val Glu Glu Tyr Trp
    1175                1180                1185

Gly Lys Lys Phe Glu Pro Glu Arg Pro Phe Glu Phe Lys Ser Asn
    1190                1195                1200

Ile Asp Tyr Phe Gly Trp Ile Lys Asp Glu Thr Gly Leu Asn His
    1205                1210                1215

Phe Thr Ala Phe Ile Glu Asn Gly Arg Val Glu Asp Thr Pro Asp
    1220                1225                1230

Leu Pro Gln Lys Thr Gly Ile Arg Lys Val Ala Glu Tyr Met Leu
    1235                1240                1245

Lys Thr Asn Ser Gly His Phe Arg Leu Thr Gly Asn Gln His Leu
    1250                1255                1260

Val Ile Ser Asn Ile Thr Asp Glu His Val Ala Gly Ile Lys Ser
    1265                1270                1275

Ile Leu Lys Thr Tyr Lys Leu Asp Asn Thr Asp Phe Ser Gly Leu
    1280                1285                1290

Arg Leu Ser Ser Ser Cys Val Gly Leu Pro Thr Cys Gly Leu
    1295                1300                1305

Ala Phe Ala Glu Ser Glu Arg Phe Leu Pro Asp Ile Ile Thr Gln
    1310                1315                1320

Leu Glu Asp Cys Leu Glu Glu Tyr Gly Leu Arg His Asp Ser Ile
    1325                1330                1335

Ile Met Arg Met Thr Gly Cys Pro Asn Gly Cys Ser Arg Pro Trp
    1340                1345                1350

Leu Gly Glu Leu Ala Leu Val Gly Lys Ala Pro His Thr Tyr Asn
    1355                1360                1365

Leu Met Leu Gly Gly Gly Tyr Leu Gly Gln Arg Leu Asn Lys Leu
    1370                1375                1380

Tyr Lys Ala Asn Val Lys Asp Glu Glu Ile Val Asp Tyr Ile Lys
    1385                1390                1395

Pro Leu Phe Lys Arg Tyr Ala Leu Glu Arg Glu Glu Gly Glu His
    1400                1405                1410

Phe Gly Asp Phe Cys Ile Arg Val Gly Ile Ile Lys Pro Thr Thr
    1415                1420                1425

Glu Gly Lys Tyr Phe His Glu Asp Val Ser Glu Asp Ala Tyr
    1430                1435                1440

<210> SEQ ID NO 12
<211> LENGTH: 1442
<212> TYPE: PRT
<213> ORGANISM: Saccharomyces cerevisiae

<400> SEQUENCE: 12

Met Thr Ala Ser Asp Leu Leu Thr Leu Pro Gln Leu Leu Ala Gln Tyr
1               5                   10                  15

Ser Ser Ser Ala Pro Gln Asn Lys Val Phe Tyr Thr Thr Ser Thr Lys
```

```
                20                  25                  30
Asn Ser His Ser Ser Phe Lys Gly Leu Glu Ser Val Ala Thr Asp Ala
         35                  40                  45
Thr His Leu Leu Asn Asn Gln Asp Pro Leu Asn Thr Ile Lys Asp Gln
         50                  55                  60
Leu Ser Lys Asp Ile Leu Thr Thr Val Phe Thr Asp Glu Thr Thr Leu
65                  70                  75                  80
Val Lys Ser Ile His His Leu Tyr Ser Leu Pro Asn Lys Leu Pro Leu
                 85                  90                  95
Val Ile Thr Val Asp Leu Asn Leu Gln Asp Tyr Ser Ala Ile Pro Ala
                100                 105                 110
Leu Lys Asp Leu Ser Phe Pro Ile Leu Ile Ser Ser Asp Leu Gln Thr
            115                 120                 125
Ala Ile Ser Asn Ala Asp Ser Ser Tyr Lys Ile Ala Thr Ser Ser Leu
            130                 135                 140
Thr Pro Val Phe His Phe Leu Asn Leu Glu Lys Ile Gly Thr Ser Thr
145                 150                 155                 160
Ala Ile Glu Gln Asp Ile Asp Phe Pro Thr Leu Glu Ile Ala Asn Glu
                165                 170                 175
Glu Thr Lys Val Ala Leu Ser Glu Ala Thr Asp Ser Leu Thr Asn Phe
            180                 185                 190
Glu Leu Val Lys Gly Lys Glu Ser Ile Thr Thr Val Ile Val Asn Leu
            195                 200                 205
Ser Pro Tyr Asp Ala Glu Phe Ser Ser Val Leu Pro Ser Asn Val Gly
            210                 215                 220
Leu Ile Lys Ile Arg Val Tyr Arg Pro Trp Asn Phe Ser Lys Phe Leu
225                 230                 235                 240
Glu Ile Leu Pro Ser Ser Val Thr Lys Ile Ala Val Leu Gln Gly Val
                245                 250                 255
Ser Lys Lys Ser Gln Ser Asn Glu Phe Gln Pro Phe Leu Leu Asp Phe
            260                 265                 270
Phe Gly Asn Phe Asn Glu Leu Val Ser Arg Asn Ile Glu Gln Val Val
            275                 280                 285
Leu Thr Asn Ile Gly Asn Val Asn Asp Tyr Gly Asn Val Ile Asn Thr
            290                 295                 300
Val Ile Ser Asn Ile Asn Lys Lys Glu Pro Asp Asn Asn Leu Phe Leu
305                 310                 315                 320
Gly Glu Ser Asn Glu Lys Ala Glu Gly Gln Ala Glu Val Thr Gln Leu
                325                 330                 335
Ile Ser Ser Val Lys Lys Val Val Asn Leu Glu Asp Ala Tyr Ile Lys
            340                 345                 350
Val Leu Lys Gln Leu Phe Ser Ser Asn Leu Gln Ile Leu Asn Gln Phe
            355                 360                 365
Ser Ser Glu Thr Ile Glu Pro Ser Asn Pro Glu Phe Gly Phe Gly Arg
            370                 375                 380
Phe Leu Lys Gln Glu Ala Gln Arg Glu Glu Leu Ile Ser Leu Ala Lys
385                 390                 395                 400
Thr Ser Leu Asp Pro Ser Leu Tyr Leu Ser Glu Asp Ala Asn Lys Ile
                405                 410                 415
Val Gln Leu Leu Ser Lys Trp Leu Ser Phe Asn Gly Arg Asp Leu Asp
            420                 425                 430
Glu Ala Gln Leu Gln Glu Ala Asn Ala Thr Gly Leu Glu Ile Phe Gln
            435                 440                 445
```

-continued

Leu Leu Gln Ser Asn Gln Asp Ser Ser Thr Val Leu Lys Phe Leu Lys
450                 455                 460

Ile Ala Pro Thr Ser Asp Ser Phe Ile Phe Lys Ser Ser Trp Leu Ile
465                 470                 475                 480

Gly Ser Asp Ala Trp Ser Tyr Asp Leu Gly His Ser Gly Ile Gln Gln
                485                 490                 495

Val Leu Ser Ser Arg Lys Asn Ile Asn Val Leu Leu Ile Asp Ser Glu
                500                 505                 510

Pro Tyr Asp His Arg Lys Gln Asn Gln Asp Arg Lys Lys Asp Val Gly
                515                 520                 525

Leu Tyr Ala Met Asn Tyr Ser Ala Tyr Val Ala Ser Val Ala Val
530                 535                 540

Tyr Ala Ser Tyr Thr Gln Leu Leu Thr Ala Ile Ile Glu Ala Ser Lys
545                 550                 555                 560

Tyr Asn Gly Pro Ser Ile Val Leu Ala Tyr Leu Pro Tyr Asn Ser Glu
                565                 570                 575

Asn Asp Thr Pro Leu Glu Val Leu Lys Glu Thr Lys Asn Ala Val Glu
                580                 585                 590

Ser Gly Tyr Trp Pro Leu Tyr Arg Phe Asn Pro Val Tyr Asp Asp Pro
                595                 600                 605

Ser Thr Asp Lys Glu Ala Phe Ser Leu Asp Ser Ser Val Ile Arg Lys
610                 615                 620

Gln Leu Gln Asp Phe Leu Asp Arg Glu Asn Lys Leu Thr Leu Leu Thr
625                 630                 635                 640

Arg Lys Asp Pro Ser Leu Ser Arg Asn Leu Lys Gln Ser Ala Gly Asp
                645                 650                 655

Ala Leu Thr Arg Lys Gln Glu Lys Arg Ser Lys Ala Ala Phe Asp Gln
                660                 665                 670

Leu Leu Glu Gly Leu Ser Gly Pro Leu His Val Tyr Tyr Ala Ser
                675                 680                 685

Asp Gly Gly Asn Ala Ala Asn Leu Ala Lys Arg Leu Ala Ala Arg Ala
690                 695                 700

Ser Ala Arg Gly Leu Lys Ala Thr Val Leu Ser Met Asp Asp Ile Ile
705                 710                 715                 720

Leu Glu Glu Leu Pro Gly Glu Asn Val Val Phe Ile Thr Ser Thr
                725                 730                 735

Ala Gly Gln Gly Glu Phe Pro Gln Asp Gly Lys Ser Phe Trp Glu Ala
                740                 745                 750

Leu Lys Asn Asp Thr Asp Leu Asp Leu Ala Ser Leu Asn Val Ala Val
                755                 760                 765

Phe Gly Leu Gly Asp Ser Glu Tyr Trp Pro Arg Lys Glu Asp Lys His
770                 775                 780

Tyr Phe Asn Lys Pro Ser Gln Asp Leu Phe Lys Arg Leu Glu Leu Leu
785                 790                 795                 800

Ser Ala Lys Ala Leu Ile Pro Leu Gly Leu Gly Asp Gln Asp Ala
                805                 810                 815

Asp Gly Phe Gln Thr Ala Tyr Ser Glu Trp Glu Pro Lys Leu Trp Glu
                820                 825                 830

Ala Leu Gly Val Ser Gly Ala Ala Val Asp Asp Glu Pro Lys Pro Val
835                 840                 845

Thr Asn Glu Asp Ile Lys Arg Glu Ser Asn Phe Leu Arg Gly Thr Ile
850                 855                 860

Ser Glu Asn Leu Lys Asp Thr Ser Ser Gly Gly Val Thr His Ala Asn
865                 870                 875                 880

-continued

Glu Gln Leu Met Lys Phe His Gly Ile Tyr Thr Gln Asp Arg Asp
            885                 890                 895

Ile Arg Glu Ile Arg Lys Ser Gln Gly Leu Glu Pro Tyr Tyr Met Phe
            900                 905                 910

Met Ala Arg Ala Arg Leu Pro Gly Gly Lys Thr Thr Pro Gln Gln Trp
            915                 920                 925

Leu Ala Leu Asp His Leu Ser Asp Thr Ser Gly Asn Gly Thr Leu Lys
            930                 935                 940

Leu Thr Thr Arg Ala Thr Phe Gln Ile His Gly Val Leu Lys Lys Asn
945                 950                 955                 960

Leu Lys His Thr Leu Arg Gly Met Asn Ala Val Leu Met Asp Thr Leu
                965                 970                 975

Ala Ala Ala Gly Asp Val Asn Arg Asn Val Met Val Ser Ala Leu Pro
            980                 985                 990

Thr Asn Ala Lys Val His Gln Gln Ile Ala Asp Met Gly Lys Leu Ile
            995                 1000                1005

Ser Asp His Phe Leu Pro Lys Thr Thr Ala Tyr His Glu Val Trp
        1010                1015                1020

Leu Glu Gly Pro Glu Glu Gln Asp Asp Pro Ser Trp Pro Ser
        1025                1030                1035

Ile Phe Glu Asn Arg Lys Asp Gly Pro Arg Lys Lys Lys Thr Leu
        1040                1045                1050

Val Ser Gly Asn Ala Leu Val Asp Ile Glu Pro Ile Tyr Gly Pro
        1055                1060                1065

Thr Tyr Leu Pro Arg Lys Phe Lys Phe Asn Ile Ala Val Pro Pro
        1070                1075                1080

Tyr Asn Asp Val Asp Val Leu Ser Ile Asp Val Gly Leu Val Ala
        1085                1090                1095

Ile Val Asn Pro Glu Thr Gln Ile Val Glu Gly Tyr Asn Val Phe
        1100                1105                1110

Val Gly Gly Gly Met Gly Thr Thr His Asn Asn Lys Lys Thr Tyr
        1115                1120                1125

Pro Arg Leu Gly Ser Cys Leu Gly Phe Val Lys Thr Glu Asp Ile
        1130                1135                1140

Ile Pro Pro Leu Glu Gly Ile Val Ile Val Gln Arg Asp His Gly
        1145                1150                1155

Asp Arg Lys Asp Arg Lys His Ala Arg Leu Lys Tyr Thr Val Asp
        1160                1165                1170

Asp Met Gly Val Glu Gly Phe Lys Gln Lys Val Glu Glu Tyr Trp
        1175                1180                1185

Gly Lys Lys Phe Glu Pro Glu Arg Pro Phe Glu Phe Lys Ser Asn
        1190                1195                1200

Ile Asp Tyr Phe Gly Trp Ile Lys Asp Glu Thr Gly Leu Asn His
        1205                1210                1215

Phe Thr Ala Phe Ile Glu Asn Gly Arg Val Glu Asp Thr Pro Asp
        1220                1225                1230

Leu Pro Gln Lys Thr Gly Ile Arg Lys Val Ala Glu Tyr Met Leu
        1235                1240                1245

Lys Thr Asn Ser Gly His Phe Arg Leu Thr Gly Asn Gln His Leu
        1250                1255                1260

Val Ile Ser Asn Ile Thr Asp Glu His Val Ala Gly Ile Lys Ser
        1265                1270                1275

Ile Leu Lys Thr Tyr Lys Leu Asp Asn Thr Asp Phe Ser Gly Leu

```
                1280                1285                1290

Arg Leu Ser Ser Ser Ser Cys Val Gly Leu Pro Thr Cys Gly Leu
    1295                1300                1305

Ala Phe Ala Glu Ser Glu Arg Phe Leu Pro Asp Ile Ile Thr Gln
    1310                1315                1320

Leu Glu Asp Cys Leu Glu Glu Tyr Gly Leu Arg His Asp Ser Ile
    1325                1330                1335

Ile Met Arg Met Thr Gly Cys Pro Asn Gly Cys Ser Arg Pro Trp
    1340                1345                1350

Leu Gly Glu Leu Ala Leu Val Gly Lys Ala Pro His Thr Tyr Asn
    1355                1360                1365

Leu Met Leu Gly Gly Gly Tyr Leu Gly Gln Arg Leu Asn Lys Leu
    1370                1375                1380

Tyr Lys Ala Asn Val Lys Asp Glu Glu Ile Val Asp Tyr Ile Lys
    1385                1390                1395

Pro Leu Phe Lys Arg Tyr Ala Leu Glu Arg Glu Glu Gly Glu His
    1400                1405                1410

Phe Gly Asp Phe Cys Ile Arg Val Gly Ile Ile Lys Pro Thr Thr
    1415                1420                1425

Glu Gly Lys Tyr Phe His Glu Asp Val Ser Glu Asp Ala Tyr
    1430                1435                1440

<210> SEQ ID NO 13
<211> LENGTH: 1442
<212> TYPE: PRT
<213> ORGANISM: Saccharomyces cerevisiae

<400> SEQUENCE: 13

Met Thr Ala Ser Asp Leu Leu Thr Leu Pro Gln Leu Leu Ala Gln Tyr
1               5                   10                  15

Ser Ser Ser Ala Pro Gln Asn Lys Val Phe Tyr Thr Thr Ser Thr Lys
                20                  25                  30

Asn Ser His Ser Ser Phe Lys Gly Leu Glu Ser Val Ala Thr Asp Ala
            35                  40                  45

Thr His Leu Leu Asn Asn Gln Asp Pro Leu Asn Thr Ile Lys Asp Gln
        50                  55                  60

Leu Ser Lys Asp Ile Leu Thr Val Phe Thr Asp Glu Thr Thr Leu
65                  70                  75                  80

Val Lys Ser Ile His His Leu Tyr Ser Leu Pro Asn Lys Leu Pro Leu
                    85                  90                  95

Val Ile Thr Val Asp Leu Asn Leu Gln Asp Tyr Ser Ala Ile Pro Ala
                100                 105                 110

Leu Lys Asp Leu Ser Phe Pro Ile Leu Ile Ser Ser Asp Leu Gln Thr
            115                 120                 125

Ala Ile Ser Asn Ala Asp Ser Ser Tyr Lys Ile Ala Thr Ser Ser Leu
        130                 135                 140

Thr Pro Val Phe His Phe Leu Asn Leu Glu Lys Ile Gly Thr Ser Thr
145                 150                 155                 160

Ala Ile Glu Gln Asp Ile Asp Phe Pro Thr Leu Glu Ile Ala Asn Glu
                165                 170                 175

Glu Thr Lys Val Ala Leu Ser Glu Ala Thr Asp Ser Leu Thr Asn Phe
                180                 185                 190

Glu Leu Val Lys Gly Lys Glu Ser Ile Thr Thr Val Ile Val Asn Leu
            195                 200                 205

Ser Pro Tyr Asp Ala Glu Phe Ser Ser Val Leu Pro Ser Asn Val Gly
```

```
            210                 215                 220
Leu Ile Lys Ile Arg Val Tyr Arg Pro Trp Asn Phe Ser Lys Phe Leu
225                 230                                 240

Glu Ile Leu Pro Ser Ser Val Thr Lys Ile Ala Val Leu Gln Gly Val
                    245                 250                 255

Ser Lys Lys Ser Gln Ser Asn Glu Phe Gln Pro Phe Leu Leu Asp Phe
                260                 265                 270

Phe Gly Asn Phe Asn Glu Leu Val Ser Arg Asn Ile Glu Gln Val Val
                275                 280                 285

Leu Thr Asn Ile Gly Asn Val Asn Asp Tyr Gly Asn Val Ile Asn Thr
290                 295                 300

Val Ile Ser Asn Ile Asn Lys Lys Glu Pro Asp Asn Leu Phe Leu
305                 310                 315                 320

Gly Glu Ser Asn Glu Lys Ala Glu Gln Ala Glu Val Thr Gln Leu
                325                 330                 335

Ile Ser Ser Val Lys Lys Val Val Asn Leu Glu Asp Ala Tyr Ile Lys
                340                 345                 350

Val Leu Lys Gln Leu Phe Ser Ser Asn Leu Gln Ile Leu Asn Gln Phe
                355                 360                 365

Ser Ser Glu Thr Ile Glu Pro Ser Asn Pro Glu Phe Gly Phe Gly Arg
370                 375                 380

Phe Leu Lys Gln Glu Ala Gln Arg Glu Leu Ile Ser Leu Ala Lys
385                 390                 395                 400

Thr Ser Leu Tyr Pro Ser Leu Tyr Leu Ser Glu Asp Ala Asn Lys Ile
                405                 410                 415

Val Gln Leu Leu Ser Lys Trp Leu Ser Phe Asn Gly Arg Asp Leu Asp
                420                 425                 430

Glu Ala Gln Leu Gln Glu Ala Asn Ala Thr Gly Leu Glu Ile Phe Gln
                435                 440                 445

Leu Leu Gln Ser Asn Gln Asp Ser Ser Thr Val Leu Lys Phe Leu Lys
                450                 455                 460

Ile Ala Pro Thr Ser Asp Ser Phe Ile Phe Lys Ser Ser Trp Leu Ile
465                 470                 475                 480

Gly Ser Asp Ala Trp Ser Tyr Asp Leu Gly His Ser Gly Ile Gln Gln
                    485                 490                 495

Val Leu Ser Ser Arg Lys Asn Ile Asn Val Leu Leu Ile Asp Ser Glu
                500                 505                 510

Pro Tyr Asp His Arg Lys Gln Asn Gln Asp Arg Lys Lys Asp Val Gly
                515                 520                 525

Leu Tyr Ala Met Asn Tyr Tyr Ser Ala Tyr Val Ala Ser Val Ala Val
                530                 535                 540

Tyr Ala Ser Tyr Thr Gln Leu Leu Thr Ala Ile Ile Glu Ala Ser Lys
545                 550                 555                 560

Tyr Asn Gly Pro Ser Ile Val Leu Ala Tyr Leu Pro Tyr Asn Ser Glu
                565                 570                 575

Asn Asp Thr Pro Leu Glu Val Leu Lys Glu Thr Lys Asn Ala Val Glu
                580                 585                 590

Ser Gly Tyr Trp Pro Leu Tyr Arg Phe Asn Pro Val Tyr Asp Asp Pro
                595                 600                 605

Ser Thr Asp Lys Glu Ala Phe Ser Leu Asp Ser Ser Val Ile Arg Lys
                610                 615                 620

Gln Leu Gln Asp Phe Leu Asp Arg Glu Asn Lys Leu Thr Leu Leu Thr
625                 630                 635                 640
```

-continued

Arg Lys Asp Pro Ser Leu Ser Arg Asn Leu Lys Gln Ser Ala Gly Asp
            645                 650                 655

Ala Leu Thr Arg Lys Gln Glu Lys Arg Ser Lys Ala Ala Phe Asp Gln
            660                 665                 670

Leu Leu Glu Gly Leu Ser Gly Pro Pro Leu His Val Tyr Tyr Ala Ser
            675                 680                 685

Asp Gly Gly Asn Ala Ala Asn Leu Ala Lys Arg Leu Ala Ala Arg Ala
            690                 695                 700

Ser Ala Arg Gly Leu Lys Ala Thr Val Leu Ser Met Asp Asp Ile Ile
705                 710                 715                 720

Leu Glu Glu Leu Pro Gly Glu Glu Asn Val Val Phe Ile Thr Ser Thr
            725                 730                 735

Ala Gly Gln Gly Glu Phe Pro Gln Asp Gly Lys Ser Phe Trp Glu Ala
            740                 745                 750

Leu Lys Asn Asp Thr Asp Leu Asp Leu Ala Ser Leu Asn Val Ala Val
            755                 760                 765

Phe Gly Leu Gly Asp Ser Glu Tyr Trp Pro Arg Lys Glu Asp Lys His
            770                 775                 780

Tyr Phe Asn Lys Pro Ser Gln Asp Leu Phe Lys Arg Leu Glu Leu Leu
785                 790                 795                 800

Ser Ala Lys Ala Leu Ile Pro Leu Gly Leu Gly Asp Asp Gln Asp Ala
            805                 810                 815

Asp Gly Phe Gln Thr Ala Tyr Ser Glu Trp Glu Pro Lys Leu Trp Glu
            820                 825                 830

Ala Leu Gly Val Ser Gly Ala Ala Val Asp Asp Glu Pro Lys Pro Val
            835                 840                 845

Thr Asn Glu Asp Ile Lys Arg Glu Ser Asn Phe Leu Arg Gly Thr Ile
            850                 855                 860

Ser Glu Asn Leu Lys Asp Thr Ser Ser Gly Val Thr His Ala Asn
865                 870                 875                 880

Glu Gln Leu Met Lys Phe His Gly Ile Tyr Thr Gln Asp Asp Arg Asp
            885                 890                 895

Ile Arg Glu Ile Arg Lys Ser Gln Gly Leu Glu Pro Tyr Tyr Met Phe
            900                 905                 910

Met Ala Arg Ala Arg Leu Pro Gly Gly Lys Thr Thr Pro Gln Gln Trp
            915                 920                 925

Leu Ala Leu Asp His Leu Ser Asp Thr Ser Gly Asn Gly Thr Leu Lys
            930                 935                 940

Leu Thr Thr Arg Ala Thr Phe Gln Ile His Gly Val Leu Lys Lys Asn
945                 950                 955                 960

Leu Lys His Thr Leu Arg Gly Met Asn Ala Val Leu Met Asp Thr Leu
            965                 970                 975

Ala Ala Ala Gly Asp Val Asn Arg Asn Val Met Val Ser Ala Leu Pro
            980                 985                 990

Thr Asn Ala Lys Val His Gln Gln Ile Ala Asp Met Gly Lys Leu Ile
            995                 1000                1005

Ser Asp His Phe Leu Pro Lys Thr Thr Ala Tyr His Glu Val Trp
            1010                1015                1020

Leu Glu Gly Pro Glu Glu Gln Asp Asp Asp Pro Ser Trp Pro Ser
            1025                1030                1035

Ile Phe Glu Asn Arg Lys Asp Gly Pro Arg Lys Lys Lys Thr Leu
            1040                1045                1050

Val Ser Gly Asn Ala Leu Val Asp Ile Glu Pro Ile Tyr Gly Pro
            1055                1060                1065

Thr Tyr Leu Pro Arg Lys Phe Lys Phe Asn Ile Ala Val Pro Pro
    1070            1075            1080

Tyr Asn Asp Val Asp Val Leu Ser Ile Asp Val Gly Leu Val Ala
    1085            1090            1095

Ile Val Asn Pro Lys Thr Gln Ile Val Glu Gly Tyr Asn Val Phe
    1100            1105            1110

Val Gly Gly Gly Met Gly Thr Thr His Asn Asn Lys Lys Thr Tyr
    1115            1120            1125

Pro Arg Leu Gly Ser Cys Leu Gly Phe Val Lys Thr Glu Asp Ile
    1130            1135            1140

Ile Pro Pro Leu Glu Gly Ile Val Ile Val Gln Arg Asp His Gly
    1145            1150            1155

Asp Arg Lys Asp Arg Lys His Ala Arg Leu Lys Tyr Thr Val Asp
    1160            1165            1170

Asp Met Gly Val Glu Gly Phe Lys Gln Lys Val Glu Glu Tyr Trp
    1175            1180            1185

Gly Lys Lys Phe Glu Pro Glu Arg Pro Phe Glu Phe Lys Ser Asn
    1190            1195            1200

Ile Asp Tyr Phe Gly Trp Ile Lys Asp Glu Thr Gly Leu Asn His
    1205            1210            1215

Phe Thr Ala Phe Ile Glu Asn Gly Arg Val Glu Asp Thr Pro Asp
    1220            1225            1230

Leu Pro Gln Lys Thr Gly Ile Arg Lys Val Ala Glu Tyr Met Leu
    1235            1240            1245

Lys Thr Asn Ser Gly His Phe Arg Leu Thr Gly Asn Gln His Leu
    1250            1255            1260

Val Ile Ser Asn Ile Thr Asp Glu His Val Ala Gly Ile Lys Ser
    1265            1270            1275

Ile Leu Lys Thr Tyr Lys Leu Asp Asn Thr Asp Phe Ser Gly Leu
    1280            1285            1290

Arg Leu Ser Ser Ser Ser Cys Val Gly Leu Pro Thr Cys Gly Leu
    1295            1300            1305

Ala Phe Ala Glu Ser Glu Arg Phe Leu Pro Asp Ile Ile Thr Gln
    1310            1315            1320

Leu Glu Asp Cys Leu Glu Glu Tyr Gly Leu Arg His Asp Ser Ile
    1325            1330            1335

Ile Met Arg Met Thr Gly Cys Pro Asn Gly Cys Ser Arg Pro Trp
    1340            1345            1350

Leu Gly Glu Leu Ala Leu Val Gly Lys Ala Pro His Thr Tyr Asn
    1355            1360            1365

Leu Met Leu Gly Gly Gly Tyr Leu Gly Gln Arg Leu Asn Lys Leu
    1370            1375            1380

Tyr Lys Ala Asn Val Lys Asp Glu Glu Ile Val Asp Tyr Ile Lys
    1385            1390            1395

Pro Leu Phe Lys Arg Tyr Ala Leu Glu Arg Glu Glu Gly Glu His
    1400            1405            1410

Phe Gly Asp Phe Cys Ile Arg Val Gly Ile Ile Lys Pro Thr Thr
    1415            1420            1425

Glu Gly Lys Tyr Phe His Glu Asp Val Ser Glu Asp Ala Tyr
    1430            1435            1440

<210> SEQ ID NO 14
<211> LENGTH: 1441
<212> TYPE: PRT

<213> ORGANISM: Saccharomyces cerevisiae

<400> SEQUENCE: 14

| | | | | | | | | | | | | | | |
|---|---|---|---|---|---|---|---|---|---|---|---|---|---|---|
| Met | Thr | Ala | Ser | Asp | Leu | Leu | Thr | Leu | Pro | Gln | Leu | Leu | Ala | Gln | Tyr |
| 1 | | | | 5 | | | | | 10 | | | | | 15 | |
| Ser | Ser | Ser | Ala | Pro | Gln | Asn | Lys | Val | Phe | Tyr | Thr | Thr | Ser | Thr | Lys |
| | | | 20 | | | | | 25 | | | | | 30 | | |
| Asn | Ser | His | Ser | Ser | Phe | Lys | Gly | Leu | Glu | Ser | Val | Ala | Thr | Asp | Ala |
| | | 35 | | | | | 40 | | | | | 45 | | | |
| Thr | His | Leu | Leu | Asn | Asn | Gln | Asp | Pro | Leu | Asn | Thr | Ile | Lys | Asp | Gln |
| | 50 | | | | | 55 | | | | | 60 | | | | |
| Leu | Ser | Lys | Asp | Ile | Leu | Thr | Thr | Val | Phe | Thr | Asp | Glu | Thr | Thr | Leu |
| 65 | | | | | 70 | | | | | 75 | | | | | 80 |
| Val | Lys | Ser | Ile | His | His | Leu | Tyr | Ser | Leu | Pro | Asn | Lys | Leu | Pro | Leu |
| | | | | 85 | | | | | 90 | | | | | 95 | |
| Val | Ile | Thr | Val | Asp | Leu | Asn | Leu | Gln | Asp | Tyr | Ser | Ala | Ile | Pro | Ala |
| | | | 100 | | | | | 105 | | | | | 110 | | |
| Leu | Lys | Asp | Leu | Ser | Phe | Pro | Ile | Leu | Ile | Ser | Ser | Asp | Leu | Gln | Thr |
| | | 115 | | | | | 120 | | | | | 125 | | | |
| Ala | Ile | Ser | Asn | Ala | Asp | Ser | Ser | Tyr | Lys | Ile | Ala | Thr | Ser | Ser | Leu |
| | 130 | | | | | 135 | | | | | 140 | | | | |
| Thr | Pro | Val | Phe | His | Phe | Leu | Asn | Leu | Glu | Lys | Ile | Gly | Thr | Ser | Thr |
| 145 | | | | | 150 | | | | | 155 | | | | | 160 |
| Ala | Ile | Glu | Gln | Asp | Ile | Asp | Phe | Pro | Thr | Leu | Glu | Ile | Ala | Asn | Glu |
| | | | | 165 | | | | | 170 | | | | | 175 | |
| Glu | Thr | Lys | Val | Ala | Leu | Ser | Glu | Ala | Thr | Asp | Ser | Leu | Thr | Asn | Phe |
| | | | 180 | | | | | 185 | | | | | 190 | | |
| Glu | Leu | Val | Lys | Gly | Lys | Glu | Ser | Ile | Thr | Thr | Val | Ile | Val | Asn | Leu |
| | | 195 | | | | | 200 | | | | | 205 | | | |
| Ser | Pro | Tyr | Asp | Ala | Glu | Phe | Ser | Ser | Val | Leu | Pro | Ser | Asn | Val | Gly |
| | 210 | | | | | 215 | | | | | 220 | | | | |
| Leu | Ile | Lys | Ile | Arg | Val | Tyr | Arg | Pro | Trp | Asn | Phe | Ser | Lys | Phe | Leu |
| 225 | | | | | 230 | | | | | 235 | | | | | 240 |
| Glu | Ile | Leu | Pro | Ser | Ser | Val | Thr | Lys | Ile | Ala | Val | Leu | Gln | Gly | Val |
| | | | | 245 | | | | | 250 | | | | | 255 | |
| Ser | Lys | Lys | Ser | Gln | Ser | Asn | Glu | Phe | Gln | Pro | Phe | Leu | Leu | Asp | Phe |
| | | | 260 | | | | | 265 | | | | | 270 | | |
| Phe | Gly | Asn | Phe | Asn | Glu | Leu | Val | Ser | Arg | Asn | Ile | Glu | Gln | Val | Leu |
| | | 275 | | | | | 280 | | | | | 285 | | | |
| Thr | Asn | Ile | Gly | Asn | Val | Asn | Asp | Tyr | Gly | Asn | Val | Ile | Asn | Thr | Val |
| | 290 | | | | | 295 | | | | | 300 | | | | |
| Ile | Ser | Asn | Ile | Asn | Lys | Lys | Glu | Pro | Asp | Asn | Asn | Leu | Phe | Leu | Gly |
| 305 | | | | | 310 | | | | | 315 | | | | | 320 |
| Glu | Ser | Asn | Glu | Lys | Ala | Glu | Glu | Gln | Ala | Glu | Val | Thr | Gln | Leu | Ile |
| | | | | 325 | | | | | 330 | | | | | 335 | |
| Ser | Ser | Val | Lys | Lys | Val | Val | Asn | Leu | Glu | Asp | Ala | Tyr | Ile | Lys | Val |
| | | | 340 | | | | | 345 | | | | | 350 | | |
| Leu | Lys | Gln | Leu | Phe | Ser | Ser | Asn | Leu | Gln | Ile | Leu | Asn | Gln | Phe | Ser |
| | | 355 | | | | | 360 | | | | | 365 | | | |
| Ser | Glu | Thr | Ile | Glu | Pro | Ser | Asn | Pro | Glu | Phe | Gly | Phe | Gly | Arg | Phe |
| | 370 | | | | | 375 | | | | | 380 | | | | |
| Leu | Lys | Gln | Glu | Ala | Gln | Arg | Glu | Glu | Leu | Ile | Ser | Leu | Ala | Lys | Thr |
| 385 | | | | | 390 | | | | | 395 | | | | | 400 |
| Ser | Leu | Asp | Pro | Ser | Leu | Tyr | Leu | Ser | Glu | Asp | Ala | Asn | Lys | Ile | Val |

-continued

```
                405                 410                 415
Gln Leu Leu Ser Lys Trp Leu Ser Phe Asn Gly Arg Asp Leu Asp Glu
            420                 425                 430

Ala Gln Leu Gln Glu Ala Asn Ala Thr Gly Leu Glu Ile Phe Gln Leu
            435                 440                 445

Leu Gln Ser Asn Gln Asp Ser Ser Thr Val Leu Lys Phe Leu Lys Ile
        450                 455                 460

Ala Pro Thr Ser Asp Ser Phe Ile Phe Lys Ser Ser Trp Leu Ile Gly
465                 470                 475                 480

Ser Asp Ala Trp Ser Tyr Asp Leu Gly His Ser Gly Ile Gln Gln Val
                485                 490                 495

Leu Ser Ser Arg Lys Asn Ile Asn Val Leu Leu Ile Asp Ser Glu Pro
            500                 505                 510

Tyr Asp His Arg Lys Gln Asn Gln Asp Arg Lys Lys Asp Val Gly Leu
        515                 520                 525

Tyr Ala Met Asn Tyr Tyr Ser Ala Tyr Val Ala Ser Val Ala Val Tyr
530                 535                 540

Ala Ser Tyr Thr Gln Leu Leu Thr Ala Ile Ile Glu Ala Ser Lys Tyr
545                 550                 555                 560

Asn Gly Pro Ser Ile Val Leu Ala Tyr Leu Pro Tyr Asn Ser Glu Asn
                565                 570                 575

Asp Thr Pro Leu Glu Val Leu Lys Glu Thr Lys Asn Ala Val Glu Ser
            580                 585                 590

Gly Tyr Trp Pro Leu Tyr Arg Phe Asn Pro Val Tyr Asp Asp Pro Ser
        595                 600                 605

Thr Asp Lys Glu Ala Phe Ser Leu Asp Ser Ser Val Ile Arg Lys Gln
610                 615                 620

Leu Gln Asp Phe Leu Asp Arg Glu Asn Lys Leu Thr Leu Leu Thr Arg
625                 630                 635                 640

Lys Asp Pro Ser Leu Ser Arg Asn Leu Lys Gln Ser Ala Gly Asp Ala
                645                 650                 655

Leu Thr Arg Lys Gln Glu Lys Arg Ser Lys Ala Ala Phe Asp Gln Leu
            660                 665                 670

Leu Glu Gly Leu Ser Gly Pro Pro Leu His Val Tyr Tyr Ala Ser Asp
        675                 680                 685

Gly Gly Asn Ala Ala Asn Leu Ala Lys Arg Leu Ala Ala Arg Ala Ser
690                 695                 700

Ala Arg Gly Leu Lys Ala Thr Val Leu Ser Met Asp Asp Ile Ile Leu
705                 710                 715                 720

Glu Glu Leu Pro Gly Glu Glu Asn Val Val Phe Ile Thr Ser Thr Ala
                725                 730                 735

Gly Gln Gly Glu Phe Pro Gln Asp Gly Lys Ser Phe Trp Glu Ala Leu
            740                 745                 750

Lys Asn Asp Thr Asp Leu Asp Leu Ala Ser Leu Asn Val Ala Val Phe
        755                 760                 765

Gly Leu Gly Asp Ser Glu Tyr Trp Pro Arg Lys Glu Asp Lys His Tyr
770                 775                 780

Phe Asn Lys Pro Ser Gln Asp Leu Phe Lys Arg Leu Glu Leu Leu Ser
785                 790                 795                 800

Ala Lys Ala Leu Ile Pro Leu Gly Leu Gly Asp Asp Gln Asp Ala Asp
                805                 810                 815

Gly Phe Gln Thr Ala Tyr Ser Glu Trp Glu Pro Lys Leu Trp Glu Ala
            820                 825                 830
```

-continued

Leu Gly Val Ser Gly Ala Ala Val Asp Asp Glu Pro Lys Pro Val Thr
    835                 840                 845

Asn Glu Asp Ile Lys Arg Glu Ser Asn Phe Leu Arg Gly Thr Ile Ser
850                 855                 860

Glu Asn Leu Lys Asp Thr Ser Ser Gly Gly Val Thr His Ala Asn Glu
865                 870                 875                 880

Gln Leu Met Lys Phe His Gly Ile Tyr Thr Gln Asp Asp Arg Asp Ile
                885                 890                 895

Arg Glu Ile Arg Lys Ser Gln Gly Leu Glu Pro Tyr Tyr Met Phe Met
            900                 905                 910

Ala Arg Ala Arg Leu Pro Gly Gly Lys Thr Thr Pro Gln Gln Trp Leu
        915                 920                 925

Ala Leu Asp His Leu Ser Asp Thr Ser Gly Asn Gly Thr Leu Lys Leu
    930                 935                 940

Thr Thr Arg Ala Thr Phe Gln Ile His Gly Val Leu Lys Lys Asn Leu
945                 950                 955                 960

Lys His Thr Leu Arg Gly Met Asn Ala Val Leu Met Asp Thr Leu Ala
                965                 970                 975

Ala Ala Gly Asp Val Asn Arg Asn Val Met Val Ser Ala Leu Pro Thr
            980                 985                 990

Asn Ala Lys Val His Gln Gln Ile Ala Asp Met Gly Lys Leu Ile Ser
        995                 1000                1005

Asp His Phe Leu Pro Lys Thr Thr Ala Tyr His Glu Val Trp Leu
    1010                1015                1020

Glu Gly Pro Glu Glu Gln Asp Asp Asp Pro Ser Trp Pro Ser Ile
    1025                1030                1035

Phe Glu Asn Arg Lys Asp Gly Pro Arg Lys Lys Lys Thr Leu Val
    1040                1045                1050

Ser Gly Asn Ala Leu Val Asp Ile Glu Pro Ile Tyr Gly Pro Thr
    1055                1060                1065

Tyr Leu Pro Arg Lys Phe Lys Phe Asn Ile Ala Val Pro Pro Tyr
    1070                1075                1080

Asn Asp Val Asp Val Leu Ser Ile Asp Val Gly Leu Val Ala Ile
    1085                1090                1095

Val Asn Pro Glu Thr Gln Ile Val Glu Gly Tyr Asn Val Phe Val
    1100                1105                1110

Gly Gly Gly Met Gly Thr Thr His Asn Asn Lys Lys Thr Tyr Pro
    1115                1120                1125

Arg Leu Gly Ser Cys Leu Gly Phe Val Lys Thr Glu Asp Ile Ile
    1130                1135                1140

Pro Pro Leu Glu Gly Ile Val Ile Val Gln Arg Asp His Gly Asp
    1145                1150                1155

Arg Lys Asp Arg Lys His Ala Arg Leu Lys Tyr Thr Val Asp Asp
    1160                1165                1170

Met Gly Val Glu Gly Phe Lys Gln Lys Val Glu Glu Tyr Trp Gly
    1175                1180                1185

Lys Lys Phe Glu Pro Glu Arg Pro Phe Glu Phe Lys Ser Asn Ile
    1190                1195                1200

Asp Tyr Phe Gly Trp Ile Lys Asp Glu Thr Gly Leu Asn His Phe
    1205                1210                1215

Thr Ala Phe Ile Glu Asn Gly Arg Val Glu Asp Thr Pro Asp Leu
    1220                1225                1230

Pro Gln Lys Thr Gly Ile Arg Lys Val Ala Glu Tyr Met Leu Lys
    1235                1240                1245

```
Thr Asn Ser Gly His Phe Arg Leu Thr Gly Asn Gln His Leu Val
    1250            1255                1260

Ile Ser Asn Ile Thr Asp Glu His Val Ala Gly Ile Lys Ser Ile
    1265            1270                1275

Leu Lys Thr Tyr Lys Leu Asp Asn Thr Asp Phe Ser Gly Leu Arg
    1280            1285                1290

Leu Ser Ser Ser Ser Cys Val Gly Leu Pro Thr Cys Gly Leu Ala
    1295            1300                1305

Phe Ala Glu Ser Glu Arg Phe Leu Pro Asp Ile Ile Thr Gln Leu
    1310            1315                1320

Glu Asp Cys Leu Glu Glu Tyr Gly Leu Arg His Asp Ser Ile Ile
    1325            1330                1335

Met Arg Met Thr Gly Cys Pro Asn Gly Cys Ser Arg Pro Trp Leu
    1340            1345                1350

Gly Glu Leu Ala Leu Val Gly Lys Ala Pro His Thr Tyr Asn Leu
    1355            1360                1365

Met Leu Gly Gly Gly Tyr Leu Gly Gln Arg Leu Asn Lys Leu Tyr
    1370            1375                1380

Lys Ala Asn Val Lys Asp Glu Glu Ile Val Asp Tyr Ile Lys Pro
    1385            1390                1395

Leu Phe Lys Arg Tyr Ala Leu Glu Arg Glu Glu Gly Glu His Phe
    1400            1405                1410

Gly Asp Phe Cys Ile Arg Val Gly Ile Ile Lys Pro Thr Thr Glu
    1415            1420                1425

Gly Lys Tyr Phe His Glu Asp Val Ser Glu Asp Ala Tyr
    1430            1435                1440

<210> SEQ ID NO 15
<211> LENGTH: 3755
<212> TYPE: DNA
<213> ORGANISM: Saccharomyces cerevisiae

<400> SEQUENCE: 15
aagctttata ttctcgacag aaaggggact ttctttgtgg aagactttgc atatggcttg      60
ccccaatctc gcgaaatcac caaatgtaag caaatattcc acaataatg catctaaata     120 tatacgtatg tttaaggttc tggtatacag gtattaaaag aaaacactat caacattccc     180
aataagatat accacaccac gtgagcttat agaagcacgt gaccacaatt caccccacag     240
gtgtggcttt tttggtgccg tagaaaagac tcattcatga atcgtcggaa acccatagtc     300
atcttcgagc aaaaggtata taagcaac agagggcagt agttctcgag accaccatct     360
tttgattgga aatagtttcg tttagatggg gtgcacatag tttttttcaa ctgcttttcc     420
tcgaggtcac ccaaatatac aacgagatgc cagttgagtt tgctaccaat ccttttggcg     480
aggccaaaaa tgcaacttca ctgccaaaat atggtacacc cgtaactgcc atttcatctg     540
tgctgttcaa taacgtggac tccattttg cttacaagtc ctttctcaa cccgatttgc     600 tacaccaaga tctaaaaaaa tggtctgaaa agcgtggtaa cgaatcacgt gggaagccat     660
ttttccaaga gctggatatc agatctggcg ctggtttggc tcctttaggg ttttctcatg     720
gattgaagaa cactacagca attgttgctc cagggttttc gctgccatac ttcattaact     780
ctttgaaaac cgtctctcat gatggtaagt ttcttttgaa tgttggtgct ttaaactacg     840
acaatgctac cggctctgtc accaacgatt atgtaaccgc attggatgct gcttccaagc     900
tgaagtatgg tgtcgtgact ccgatttccg ctaacgaggt acaaagtgtc gccttactga     960
```

```
cattggcgat tgccactttc agtaataact ccggagctat caatttattt gacggattaa      1020
actactcgaa aaccgtcttg ccgttggtcg aatctgttcc tgaggcatct attttggcaa      1080
aactatccaa agttattgca ccagatgctg cctttgatga tgtcttggat aagtttaatg      1140
aattgactgg attgagacta cataatttcc aatactttgg tgctcaggat gctgaaactg      1200
tgtttatcac ttatgggtct ttagaatccg aattgttcaa ctctgcgatt agtggtaata      1260
attccaaaat cgggttaatc aacgtcagag taccattacc ttttaacgtt gctaagtttg      1320
tcactcacgt tccatccact accaaacaaa ttgttgttat aggccaaact ttggatggtt      1380
cttcgccttc tttcttgaga tctcaagttt cagccgcctt attttaccac ggccgcacct      1440
caattagcgt ttctgagtac atctatcaac cagatttcat ttggtcccca aaagctgtca      1500
aatcaattgt atcgtcattc atccctgaat tcacttacaa tgccgattca tctttcggcg      1560
aaggattcat ttattgggcc tctgataaga gtatcaatat tgatgttgcc tccaaacttg      1620
tgaaagctct gtctttggaa gatgggaaat ttgtgtcttt gagaacgaaa tttgataact      1680
tggctaatgc tggtaccttc caagctcaat ttgtgacctc gaaagaacag atacctgttt      1740
caaacatcga ttctacgaaa ttatcagtcg ttgaagatgt cagtttattg aagcatttag      1800
acgtagctgc taccgtcgca gaacaaggtt caattgcgtt ggtttcccaa aaggcagtta      1860
aagatttgga tttaaattct gtagaaagtt acgtcaagaa tttgggaatt cctgaatcat      1920
tcctaatatc tattgcgaag aaaaacatca aattgtttat catcgatggt gagaccacta      1980
acgacgagtc caaattgtcc ttgtttatcc aagccgtttt ctggaaattg gccttcggtc      2040
tagatgtcgc agaatgtacc aaccgtatct ggaaaagcat tgattcaggt gcagacattt      2100
cagcagcctc gatttctgaa tttctcactg gtgcattcaa aaacttcctc agtgaggttc      2160
cgctagcgct gtacactaaa ttttctgaaa taaacattga aaagaaagag gatgaggaag      2220
agcctgcagc tttaccaatt ttcgttaatg aaacatcttt cctcccaaat aacagtacca      2280
ttgaagaaat accattacct gagacctctg agatctctga tattgccaag aagttgtcct      2340
tcaaagaggc atatgaagtt gagaataaac taagacccga tttacccgtc aagaacttcg      2400
tcgtgaaagt taaagaaaat agacgtgtta cgcctgctga ttatgataga tatattttcc      2460
atattgaatt cgatatttct ggtactggaa tgacttatga catcggtgaa gccctcggta      2520
ttcatgccag aaaacaatgaa tctttggtca aagaattctt aaccttctat ggtctaaatg      2580
aatccgatgt tgtcttagtc cccaacaagg acaaccacca tttgttagaa acaagaaccg      2640
tcttacaagc atttgtggaa aatttggata ttttcggtaa accaccaaaa agattttacg      2700
aatcattgat tccatatgcc tctaacgaag aggagaagaa aaaattagag gatttggtta      2760
ctcctgccgg tgcagtagat ttgaagagat tcaagatgt ggagtattat acatatgctg      2820 acattttga attgttccca tctgttcgcc catctcttga ggaacttgtt actatcattg      2880
aaccattgaa gagaagagaa tactcaattg cctcctctca gaaagttcat ccaaatgaag      2940
ttcatttatt gatcgttgtt gttgattggg tgataataa aggaagaaaa aggtacggtc      3000
aagcttctaa gtatatctca gaccttgctg tcggttcaga attggtcgtt agcgttaaac      3060
catctgttat gaaattacca ccatctccaa agcaaccagt tattatgagt ggtttaggta      3120
ctggtttggc accattcaag gccattgttg aagagaaatt atggcaaaag cagcaaggtt      3180
atgagattgg tgaagtcttc ctatatctag gttcaagaca caaaagagaa gaatatttat      3240
atggtgagtt atgggaggct tacaaagatg caggtattat cacacacatc ggcgctgctt      3300
tctcaagaga ccaacctcaa aaaatttaca ttcaagatcg tatcaaagag aatttggatg      3360
```

| | |
|---|---:|
| aattaaaaac tgcaatgatt gataataaag gttcatttta cttgtgtggc cctacttggc | 3420 |
| cagttccaga tattactcaa gctttgcaag acattctggc taaagacgcc gaggaaagag | 3480 |
| gcatcaaagt cgacttggat gccgcaattg aagaattaaa ggaagcatca agatacattt | 3540 |
| tagaagtcta ctaaattaat atagtaataa aaactaaata tctatttatt gaacctgtct | 3600 |
| tgaacatttc tattttttt ttacttttag ttttcttcta tgcgcaagct tttctattgg | 3660 |
| ctgccaaata gaaaattatt gaaatatgat tacattacaa tatttatttg tcttatgaaa | 3720 |
| actaaccatc acattatact aactacggag gtacc | 3755 |

<210> SEQ ID NO 16
<211> LENGTH: 3108
<212> TYPE: DNA
<213> ORGANISM: Saccharomyces cerevisiae

<400> SEQUENCE: 16

| | |
|---|---:|
| atgccagttg agtttgctac caatcctttt ggcgaggcca aaaatgcaac ttcactgcca | 60 |
| aaatatggta cacccgtaac tgccatttca tctgtgctgt tcaataacgt ggactccatt | 120 |
| tttgcttaca agtccttttc tcaacccgat ttgctacacc aagatctaaa aaaatggtct | 180 |
| gaaaagcgtg gtaacgaatc acgtgggaag ccattttttcc aagagctgga tatcagatct | 240 |
| ggcgctggtt tggctccttt agggttttct catggattga agaacactac agcaattgtt | 300 |
| gctccagggt tttcgctgcc atacttcatt aactctttga aaaccgtctc tcatgatggt | 360 |
| aagtttcttt tgaatgttgg tgcttaaac tacgacaatg ctaccggctc tgtcaccaac | 420 |
| gattatgtaa ccgcattgga tgctgcttcc aagctgaagt atggtgtcgt gactccgatt | 480 |
| tccgctaacg aggtacaaag tgtcgcctta ctggcattgg cgattgccac tttcagtaat | 540 |
| aactccggag ctatcaattt atttgacgga ttaaactact cgaaaaccgt cttgccgttg | 600 |
| gtcgaatctg ttcctgaggc atctattttg gcaaaactat ccaaagttat tgcaccagat | 660 |
| gctgcctttg atgatgtctt ggataagttt aatgaattga ctggattgag actacataat | 720 |
| ttccaatact tggtgctca ggatgctgaa actgtgttta tcacttatgg gtctttagaa | 780 |
| tccgaattgt tcaactctgc gattagtggt aataattcca aaatcgggtt aatcaacgtc | 840 |
| agagtgccat taccttttaa cgttgctaag tttgtcactc acgttccatc cactaccaaa | 900 |
| caaattgttt tataggcca aactttggat ggttcttcgc cttctttctt gagatctcaa | 960 |
| gtttcagccg ccttatttta ccacggccgc acctcaatta gcgtttctga gtacatctat | 1020 |
| caaccagatt tcatttggtc cccaaaagct gtcaaatcaa ttgtatcgtc attcatccct | 1080 |
| gaattcactt acaatgccga ttcatctttc ggcgaaggat tcatttattg ggcctctgat | 1140 |
| aagagtatca atattgatgt tgcctccaaa cttgtgaaag ctctgtcttt ggaagatggg | 1200 |
| aaatttgtgt ctttgagaac gaaatttgat aacttggcta atgctggtac cttccaagct | 1260 |
| caatttgtga cctcgaaaga acagataccct gtttcaaaca tcgattctac gaaattatca | 1320 |
| gtcgttgaag atgtcagttt attgaagcat ttagacgtag ctgctaccgt cgcagaacaa | 1380 |
| ggttcaattg cgttggtttc ccaaaaggca gttaaagatt tggatttaaa ttctgtagaa | 1440 |
| agttacgtca agaatttggg aattcctgaa tcattcctaa tatctattgc gaagaaaaac | 1500 |
| atcaaattgt ttatcatcga tggtgagacc actaacgacg agtccaaatt gtccttgttt | 1560 |
| atccaagccg ttttctggaa attggccttc ggtctagatg tcgcagaatg taccaaccgt | 1620 |
| atctggaaaa gcattgattc aggtgcagac atttcagcag cctcgatttc tgaatttctc | 1680 |
| actggtgcat tcaaaaactt cctcagtgag gttccgctag cgctgtacac taaattttct | 1740 |

```
gaaataaaca ttgaaaagaa agaggatgag gaagagcctg cagctttacc aatttttcgtt    1800 aatgaaacat ctttcctccc aaataacagt accattgaag aaataccatt acctgagacc    1860
tctgagatct ctgatattgc caagaagttg tccttcaaag aggcatatga agttgagaat    1920
aaactaagac ccgatttacc cgtcaagaac ttcgtcgtga agttaaaga aaatagacgt     1980 gttacgcctg ctgattatga tagatatatt ttccatattg aattcgatat ttctggtact    2040
ggaatgactt atgacatcgg tgaagccctc ggtattcatg ccagaaacaa tgaatctttg    2100
gtcaaagaat tcttaacctt ctatggtcta atgaatccg atgttgtctt agtccccaac     2160
aaggacaacc accatttgtt agaaacaaga accgtcttac aagcatttgt ggaaaatttg    2220
gatattttcg gtaaaccacc aaaaagattt tacgaatcat tgattccata tgcctctaac    2280
gaagaggaga agaaaaaatt agaggatttg gttactcctg ccggtgcagt agatttgaag    2340
agatttcaag atgtggagta ttatacatat gctgacattt ttgaattgtt cccatctgtt    2400
cgcccatctc ttgaggaact tgttactatc attgaaccat tgaagagaag agaatactca    2460
attgcctcct ctcagaaagt tcatccaaat gaagttcatt tattgatcgt tgttgttgat    2520
tgggtggata taaaggaag aaaaaggtac ggtcaagctt ctaagtatat ctcagacctt     2580
gctgtcggtt cagaattggt cgttagcgtt aaaccatctg ttatgaaatt accaccatct    2640
ccaaagcaac cagttattat gagtggttta ggtactggtt tggcaccatt caaggccatt    2700
gttgaagaga aattatggca aaagcagcaa ggttatgaga ttggtgaagt cttcctatat    2760
ctaggttcaa gacacaaaag agaagaatat ttatatggtg agttatggga ggcttacaaa    2820
gatgcaggta ttatcacaca catcggcgct gctttctcaa gagaccaacc tcaaaaaatt    2880
tacattcaag atcgtatcaa agagaatttg gatgaattaa aaactgcaat gattgataat    2940
aaaggttcat tttacttgtg tggccctact tggccagttc cagatattac tcaagctttg    3000
caagacattc tggctaaaga cgccgaggaa agaggcatca agtcgactt ggatgccgca     3060 attgaagaat taaggaagc atcaagatac attttagaag tctactaa                 3108
```

<210> SEQ ID NO 17
<211> LENGTH: 3108
<212> TYPE: DNA
<213> ORGANISM: Saccharomyces cerevisiae

<400> SEQUENCE: 17

```
atgccagttg agtttgctac caatcctttt ggcgaggcca aaaatgcaac ttcactgcca      60
aaatatggta cacccgtaac tgccatttca tctgtgctgt tcaataacgt ggactccatt    120
tttgcttaca gtcctttttc tcaacccgat ttgttacacc aagatctaaa aaaatggtct    180
gaaaagcgtg gtaacgaatc acgtgggaag ccatttttcc aagagctgga tatcagatct    240
ggcgctggtt tggctccttt agggttttct catggattga agaacactac agcaattgtt    300
gctccagggt tttcgctgcc atacttcatt aactctttga aaaccgtctc tcatgatggt    360
aagtttcttt tgaatgttgg tgcttttaaac tacgacaatg ctaccggctc tgtcaccaac    420
gattatgtaa ccgcattgga tgctgcttcc aagctgaagt atggtgtcgt gactccgatt    480
tccgctaacg aggtacaaag tgtcgcctta ctgacattgg cgattgccac tttcagtaat    540
aactccggag ctatcaattt atttgacgga ttaaactact cgaaaaccgt cttgccgttg    600
gtcgaatctg ttcctgaggc atctatttg gcaaaactat ccaaagttat tgcaccagat     660
gctgcctttg atgatgtctt ggataagttt aatgaattga ctggattgag actacataat    720
ttccaatact ttggtgctca ggatgctgaa actgtgttta tcacttatgg gtctcttagaa  780
```

```
tccgaattgt tcaactctgc gattagtggt aataattcca aaatcgggtt aatcaacgtc    840
agagtaccat tacctttttaa cgttgctaag tttgtcactc acgttccatc cactaccaaa    900
caaattgttg ttataggcca aactttggat ggttcttcgc cttctttctt gagatctcaa    960
gtttcagccg ccttatttta ccacggccgc acctcaatta gcgtttctga gtacatctat   1020
caaccagatt tcatttggtc cccaaaagct gtcaaatcaa ttgtatcgtc attcatccct   1080
gaattcactt acaatgccga ttcatctttc ggcgaaggat tcatttattg ggcctctgat   1140
aagagtatca atattgatgt tgcctccaaa cttgtgaaag ctctgtcttt ggaagatggg   1200
aaatttgtgt ctttgagaac gaaatttgat aacttggcta atgctggtac cttccaagct   1260
caatttgtga cctcgaaaga acagataccct gtttcaaaca tcgattctac gaaattatca   1320
gtcgttgaag atgtcagttt attgaagcat ttagacgtag ctgctaccgt cgcagaacaa   1380
ggttcaattg cgttggtttc ccaaaaggca gttaaagatt tggatttaaa ttctgtagaa   1440
agttacgtca agaatttggg aattcctgaa tcattcctaa tatctattgc gaagaaaaac   1500
atcaaattgt ttatcatcga tggtgagacc actaacgacg agtccaaatt gtccttgttt   1560
atccaagccg ttttctggaa attggccttc ggtctagatg tcgcagaatg taccaaccgt   1620
atctggaaaa gcattgattc aggtgcagac atttcagcag cctcgatttc tgaatttctc   1680
actggtgcat tcaaaaactt cctcagtgag gttccgctag cgctgtacac taaatttttct   1740
gaaataaaca ttgaaaagaa agaggatgag gaagagcctg cagctttacc aattttcgtt   1800
aatgaaacat ctttcctccc aaataacagt accattgaag aaataccatt acctgagacc   1860
tctgagatct ctgatattgc caagaagttg tccttcaaag aggcatatga agttgagaat   1920
aaactaagac ccgatttacc cgtcaagaac ttcgtcgtga agttaaagaa aaatagacgt   1980
gttacgcctg ctgattatga tagatatatt ttccatattg aattcgatat ttctggtact   2040
ggaatgactt atgacatcgg tgaagccctc ggtattcatg ccagaaacaa tgaatctttg   2100
gtcaaagaat tcttaacctt ctatggtcta aatgaatccg atgttgtctt agtccccaac   2160
aaggacaacc accatttgtt agaaacaaga accgtcttac aagcatttgt ggaaaatttg   2220
gatatttttcg gtaaaccacc aaaaagattt tacgaatcat tgattccata tgcctctaac   2280
gaagaggaga agaaaaaatt agaggatttg gttactcctg ccggtgcagt agatttgaag   2340
agatttcaag atgtgagta ttatacatat gctgacattt ttgaattgtt cccatctgtt   2400
cgcccatctc ttgaggaact tgttactatc attgaaccat tgaagagaag agaatactca   2460
attgcctcct ctcagaaagt tcatccaaat gaagttcatt tattgatcgt tgttgttgat   2520
tgggtggata taaaggaag aaaaaggtac ggtcaagctt ctaagtatat ctcagaccct   2580
gctgtcggtt cagaattggt cgttagcgtt aaaccatctg ttatgaaatt accaccatct   2640
ccaaagcaac cagttattat gagtggttta ggtactggtt tggcaccatt caaggccatt   2700
gttgaagaga aattatggca aaagcagcaa ggttatgaga ttggtgaagt cttcctatat   2760
ctaggttcaa gacacaaaag agaagaatat ttatatggtg agttatggga ggcttacaaa   2820
gatgcaggta ttatcacata catcggcgct gctttctcaa gagaccaacc tcaaaaaatt   2880
tacattcaag atcgtatcaa agagaatttg gatgaattaa aaactgcaat gattgataat   2940
aaaggttcat tttacttgtg tggccctact tggccagttc cagatattac tcaagctttg   3000
caagacattc tggctaaaga cgccgaggaa agaggcatca aagtcgactt ggatgccgca   3060
attgaagaat taaggaagc atcaagatac attttagaag tctactaa             3108

<210> SEQ ID NO 18
```

<211> LENGTH: 3108
<212> TYPE: DNA
<213> ORGANISM: Saccharomyces cerevisiae

<400> SEQUENCE: 18

| | | | | | |
|---|---|---|---|---|---|
| atgccagttg | agtttgctac | caatccttt | ggcgaggcca | aaaatgcaac | ttcactgcca | 60 |
| aaatatggta | cacccgtaac | tgccatttca | tctgtgctgt | tcaataacgt | ggactccatt | 120 |
| tttgcttaca | agtcctttc | tcaacccgat | ttgttacacc | aagatctaaa | aaaatggtct | 180 |
| gaaaagcgtg | gtaacgaatc | acgtgggaag | ccattttcc | aagagctgga | tatcagatct | 240 |
| ggcgctggtt | tggctccttt | agggttttct | catggattga | agaacactac | agcaattgtt | 300 |
| gctccagggt | tttcgctgcc | atacttcatt | aactctttga | aaaccgtctc | tcatgatggt | 360 |
| aagtttcttt | tgaatgttgg | tgctttaaac | tacgacaatg | ctaccggctc | tgtcacgaac | 420 |
| gattatgtaa | ccgcattgga | tgctgcttcc | aagctgaagt | atggtgtcgt | gactccgatt | 480 |
| tccgctaacg | aggtacaaag | tgtcgcctta | ctggcattgg | cgattgccac | tttcagtaat | 540 |
| aactccggag | ctatcaattt | atttgacgga | ttaaactact | cgaaaccgt | cttgccgttg | 600 |
| gtcgaatctg | ttcctgaggc | atctattttg | gcaaaactat | ccaaagttat | tgcaccagat | 660 |
| gctgcctttg | atgatgtctt | ggataagttt | aatgaattga | ctggattgag | actacataat | 720 |
| ttccaatact | tggtgctca | ggatgctgaa | actgtgttta | tcacttatgg | gtctttagaa | 780 |
| tccgaattgt | tcaactctgc | gattagtggt | aataattcca | aaatcgggtt | aatcaacgtc | 840 |
| agagtaccat | accttttaa | cgttgctaag | tttgtcactc | acgttccatc | cactaccaaa | 900 |
| caaattgttg | ttataggcca | aactttggat | ggttcttcgc | cttctttctt | gagatctcaa | 960 |
| gtttcagccg | cctattttta | ccacggccgc | acctcaatta | gcgtttctga | gtacatctat | 1020 |
| caaccagatt | tcatttggtc | cccaaaagct | gtcaaatcaa | ttgtatcgtc | attcatccct | 1080 |
| gaattcactt | acaatgccga | ttcatctttc | ggcgaaggat | tcatttattg | ggcctctgat | 1140 |
| aagagtatca | atattgatgt | tgcctccaaa | cttgtgaaag | ctctgtcttt | ggaagatggg | 1200 |
| aaatttgtgt | ctttgagaac | gaaatttgat | aacttggcta | atgctggtac | cttccaagct | 1260 |
| caatttgtga | cctcgaagga | acagatacct | gtttcaaaca | tcgattctac | gaaattatca | 1320 |
| gtcgttgaag | atgtcagttt | attgaagcat | ttagacgtag | ctgctaccgt | cacagaacaa | 1380 |
| ggttcaattg | cgttggtttc | ccaaaaggca | gttaaagatt | tggattaaa | ttctgtagaa | 1440 |
| agttacgtca | agaatttggg | aattcctgaa | tcattcctaa | tatctattgc | gaagaaaaac | 1500 |
| atcaaattgt | ttatcatcga | tggtgagacc | attaacgacg | agtccaaatt | gtccttgttt | 1560 |
| atccaagccg | ttttctggaa | attggccttc | ggtctagatg | tcgcagaatg | taccaaccgt | 1620 |
| atctggaaaa | gcattgattc | aggtgcagac | atttcagcag | cctcgatttc | tgaatttctc | 1680 |
| actggtgcat | tcaaaaactt | cctcagtgag | gttccgctag | cgctgtacac | taaattttct | 1740 |
| gaaataaaca | ttgaaaagaa | agaggatgag | gaagagcctg | cagctttacc | aattttcgtt | 1800 |
| aatgaaacat | ctttcctccc | aaataacagt | accattgaag | aaataccatt | acctgagacc | 1860 |
| tctgagatct | ctgatattgc | caagaagttg | tccttcaaag | aggcatatga | agttgagaat | 1920 |
| aaactaagac | ccgatttacc | cgtcaagaac | ttcgtcgtga | agttaaaga | aaatagacgt | 1980 |
| gttacgcctg | ctgattatga | tagatatatt | ttccatattg | aattcgatat | ttctggtact | 2040 |
| ggaatgactt | atgacatcga | tgaagccctc | ggtattcatg | ccagaaacaa | tgaatctttg | 2100 |
| gtcaaagaat | tcttaacctt | ctatggtcta | aatgaatccg | atgttgtctt | agtccccaac | 2160 |
| aaggacaacc | accatttgtt | agaaacaaga | accgtcttac | aagcatttgt | ggaaaatttg | 2220 |

```
gatattttcg gtaaaccacc aaaaagattt tacgaatcat tgattccata tgcctctaac    2280
gaagaggaga agaaaaaatt agaggatttg gttactcctg ccggtgcagt agatttgaag    2340
agatttcaag atgtggagta ttatacatat gctgacattt ttgaattgtt cccatctgtt    2400
cgcccatctc ttaaggaact tgttactatc attgaaccat tgaagagaag agaatactca    2460
attgcctcct ctcagaaagt tcatccaaat gaagttcatt tattgatcgt tgttgttgat    2520
tgggtggata ataaaggaag aaaaaggtac ggtcaagctt ctaagtatat ctcagacctt    2580
gctgtcggtt cagaattggt cgttagcgtt aaaccatctg ttatgaaatt accaccatct    2640
ccaaagcaac cagttattat gagtggttta ggtactggtt tggcaccatt caaggccatt    2700
gttgaagaga aattatggca aaagcagcaa ggttatgaga ttggtgaagt cttcctatat    2760
ctaggttcaa gacacaaaag agaagaatat ttatatggtg agttatggga ggcttacaaa    2820
gatgcaggta ttatcacaca catcggcgct gctttctcaa gagaccaacc tcaaaaaatt    2880
tacattcaag atcgtatcaa agagaatttg atgaattaa aaactgcaat gattgataat    2940
aaaggttcat tttacttgtg tggccctact tggccagttc agatattac tcaagctttg    3000 caagacattc tggctaaaga cgccgaggaa agaggcatca agtcgactt ggatgccgca    3060 attgaagaat taaggaagc atcaagatac attttagaag tctactaa                 3108
```

<210> SEQ ID NO 19
<211> LENGTH: 1035
<212> TYPE: PRT
<213> ORGANISM: Saccharomyces cerevisiae

<400> SEQUENCE: 19

```
Met Pro Val Glu Phe Ala Thr Asn Pro Phe Gly Glu Ala Lys Asn Ala
1               5                   10                  15

Thr Ser Leu Pro Lys Tyr Gly Thr Pro Val Thr Ala Ile Ser Ser Val
            20                  25                  30

Leu Phe Asn Asn Val Asp Ser Ile Phe Ala Tyr Lys Ser Phe Ser Gln
        35                  40                  45

Pro Asp Leu Leu His Gln Asp Leu Lys Lys Trp Ser Glu Lys Arg Gly
    50                  55                  60

Asn Glu Ser Arg Gly Lys Pro Phe Gln Glu Leu Asp Ile Arg Ser
65                  70                  75                  80

Gly Ala Gly Leu Ala Pro Leu Gly Phe Ser His Gly Leu Lys Asn Thr
                85                  90                  95

Thr Ala Ile Val Ala Pro Gly Phe Ser Leu Pro Tyr Phe Ile Asn Ser
            100                 105                 110

Leu Lys Thr Val Ser His Asp Gly Lys Phe Leu Leu Asn Val Gly Ala
        115                 120                 125

Leu Asn Tyr Asp Asn Ala Thr Gly Ser Val Thr Asn Asp Tyr Val Thr
    130                 135                 140

Ala Leu Asp Ala Ala Ser Lys Leu Lys Tyr Gly Val Val Thr Pro Ile
145                 150                 155                 160

Ser Ala Asn Glu Val Gln Ser Val Ala Leu Leu Thr Leu Ala Ile Ala
                165                 170                 175

Thr Phe Ser Asn Asn Ser Gly Ala Ile Asn Leu Phe Asp Gly Leu Asn
            180                 185                 190

Tyr Ser Lys Thr Val Leu Pro Leu Val Glu Ser Val Pro Glu Ala Ser
        195                 200                 205

Ile Leu Ala Lys Leu Ser Lys Val Ile Ala Pro Asp Ala Ala Phe Asp
    210                 215                 220
```

```
Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
            245                 250                 255

Gly Ser Leu Glu Ser Glu Leu Phe Asn Ser Ala Ile Ser Gly Asn Asn
                260                 265                 270

Ser Lys Ile Gly Leu Ile Asn Val Arg Val Pro Leu Pro Phe Asn Val
        275                 280                 285

Ala Lys Phe Val Thr His Val Pro Ser Thr Thr Lys Gln Ile Val Val
    290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                325                 330                 335

Glu Tyr Ile Tyr Gln Pro Asp Phe Ile Trp Ser Pro Lys Ala Val Lys
                340                 345                 350

Ser Ile Val Ser Ser Phe Ile Pro Glu Phe Thr Tyr Asn Ala Asp Ser
        355                 360                 365

Ser Phe Gly Glu Gly Phe Ile Tyr Trp Ala Ser Asp Lys Ser Ile Asn
    370                 375                 380

Ile Asp Val Ala Ser Lys Leu Val Lys Ala Leu Ser Leu Glu Asp Gly
385                 390                 395                 400

Lys Phe Val Ser Leu Arg Thr Lys Phe Asp Asn Leu Ala Asn Ala Gly
                405                 410                 415

Thr Phe Gln Ala Gln Phe Val Thr Ser Lys Glu Gln Ile Pro Val Ser
                420                 425                 430

Asn Ile Asp Ser Thr Lys Leu Ser Val Val Glu Asp Val Ser Leu Leu
        435                 440                 445

Lys His Leu Asp Val Ala Ala Thr Val Ala Glu Gln Gly Ser Ile Ala
    450                 455                 460

Leu Val Ser Gln Lys Ala Val Lys Asp Leu Asp Leu Asn Ser Val Glu
465                 470                 475                 480

Ser Tyr Val Lys Asn Leu Gly Ile Pro Glu Ser Phe Leu Ile Ser Ile
                485                 490                 495

Ala Lys Lys Asn Ile Lys Leu Phe Ile Ile Asp Gly Glu Thr Thr Asn
                500                 505                 510

Asp Glu Ser Lys Leu Ser Leu Phe Ile Gln Ala Val Phe Trp Lys Leu
        515                 520                 525

Ala Phe Gly Leu Asp Val Ala Glu Cys Thr Asn Arg Ile Trp Lys Ser
    530                 535                 540

Ile Asp Ser Gly Ala Asp Ile Ser Ala Ala Ser Ile Ser Glu Phe Leu
545                 550                 555                 560

Thr Gly Ala Phe Lys Asn Phe Leu Ser Glu Val Pro Leu Ala Leu Tyr
                565                 570                 575

Thr Lys Phe Ser Glu Ile Asn Ile Glu Lys Lys Glu Asp Glu Glu Glu
                580                 585                 590

Pro Ala Ala Leu Pro Ile Phe Val Asn Glu Thr Ser Phe Leu Pro Asn
        595                 600                 605

Asn Ser Thr Ile Glu Glu Ile Pro Leu Pro Glu Thr Ser Glu Ile Ser
    610                 615                 620

Asp Ile Ala Lys Lys Leu Ser Phe Lys Glu Ala Tyr Glu Val Glu Asn
625                 630                 635                 640

Lys Leu Arg Pro Asp Leu Pro Val Lys Asn Phe Val Val Lys Val Lys
                645                 650                 655
```

Glu Asn Arg Arg Val Thr Pro Ala Asp Tyr Asp Arg Tyr Ile Phe His
            660                 665                 670

Ile Glu Phe Asp Ile Ser Gly Thr Gly Met Thr Tyr Asp Ile Gly Glu
675                 680                 685

Ala Leu Gly Ile His Ala Arg Asn Asn Glu Ser Leu Val Lys Glu Phe
690                 695                 700

Leu Thr Phe Tyr Gly Leu Asn Glu Ser Asp Val Val Leu Val Pro Asn
705                 710                 715                 720

Lys Asp Asn His His Leu Leu Glu Thr Arg Thr Val Leu Gln Ala Phe
            725                 730                 735

Val Glu Asn Leu Asp Ile Phe Gly Lys Pro Pro Lys Arg Phe Tyr Glu
            740                 745                 750

Ser Leu Ile Pro Tyr Ala Ser Asn Glu Glu Lys Lys Lys Leu Glu
            755                 760                 765

Asp Leu Val Thr Pro Ala Gly Ala Val Asp Leu Lys Arg Phe Gln Asp
770                 775                 780

Val Glu Tyr Tyr Thr Tyr Ala Asp Ile Phe Glu Leu Phe Pro Ser Val
785                 790                 795                 800

Arg Pro Ser Leu Glu Glu Leu Val Thr Ile Ile Glu Pro Leu Lys Arg
            805                 810                 815

Arg Glu Tyr Ser Ile Ala Ser Ser Gln Lys Val His Pro Asn Glu Val
            820                 825                 830

His Leu Leu Ile Val Val Val Asp Trp Val Asp Asn Lys Gly Arg Lys
            835                 840                 845

Arg Tyr Gly Gln Ala Ser Lys Tyr Ile Ser Asp Leu Ala Val Gly Ser
850                 855                 860

Glu Leu Val Val Ser Val Lys Pro Ser Val Met Lys Leu Pro Pro Ser
865                 870                 875                 880

Pro Lys Gln Pro Val Ile Met Ser Gly Leu Gly Thr Gly Leu Ala Pro
            885                 890                 895

Phe Lys Ala Ile Val Glu Glu Lys Leu Trp Gln Lys Gln Gly Tyr
            900                 905                 910

Glu Ile Gly Glu Val Phe Leu Tyr Leu Gly Ser Arg His Lys Arg Glu
            915                 920                 925

Glu Tyr Leu Tyr Gly Glu Leu Trp Glu Ala Tyr Lys Asp Ala Gly Ile
930                 935                 940

Ile Thr His Ile Gly Ala Ala Phe Ser Arg Asp Gln Pro Gln Lys Ile
945                 950                 955                 960

Tyr Ile Gln Asp Arg Ile Lys Glu Asn Leu Asp Glu Leu Lys Thr Ala
            965                 970                 975

Met Ile Asp Asn Lys Gly Ser Phe Tyr Leu Cys Gly Pro Thr Trp Pro
            980                 985                 990

Val Pro Asp Ile Thr Gln Ala Leu Gln Asp Ile Leu Ala Lys Asp Ala
            995                 1000                1005

Glu Glu Arg Gly Ile Lys Val Asp Leu Asp Ala Ala Ile Glu Glu
        1010                1015                1020

Leu Lys Glu Ala Ser Arg Tyr Ile Leu Glu Val Tyr
        1025                1030                1035

<210> SEQ ID NO 20
<211> LENGTH: 1035
<212> TYPE: PRT
<213> ORGANISM: Saccharomyces cerevisiae

<400> SEQUENCE: 20

Met Pro Val Glu Phe Ala Thr Asn Pro Phe Gly Glu Ala Lys Asn Ala
1               5                   10                  15

Thr Ser Leu Pro Lys Tyr Gly Thr Pro Val Thr Ala Ile Ser Ser Val
            20                  25                  30

Leu Phe Asn Val Asp Ser Ile Phe Ala Tyr Lys Ser Phe Ser Gln
        35                  40                  45

Pro Asp Leu Leu His Gln Asp Leu Lys Lys Trp Ser Glu Lys Arg Gly
    50                  55                  60

Asn Glu Ser Arg Gly Lys Pro Phe Phe Gln Glu Leu Asp Ile Arg Ser
65                  70                  75                  80

Gly Ala Gly Leu Ala Pro Leu Gly Phe Ser His Gly Leu Lys Asn Thr
                85                  90                  95

Thr Ala Ile Val Ala Pro Gly Phe Ser Leu Pro Tyr Phe Ile Asn Ser
                100                 105                 110

Leu Lys Thr Val Ser His Asp Gly Lys Phe Leu Leu Asn Val Gly Ala
            115                 120                 125

Leu Asn Tyr Asp Asn Ala Thr Gly Ser Val Thr Asn Asp Tyr Val Thr
    130                 135                 140

Ala Leu Asp Ala Ala Ser Lys Leu Lys Tyr Gly Val Val Thr Pro Ile
145                 150                 155                 160

Ser Ala Asn Glu Val Gln Ser Val Ala Leu Leu Ala Leu Ala Ile Ala
                165                 170                 175

Thr Phe Ser Asn Asn Ser Gly Ala Ile Asn Leu Phe Asp Gly Leu Asn
            180                 185                 190

Tyr Ser Lys Thr Val Leu Pro Leu Val Glu Ser Val Pro Glu Ala Ser
        195                 200                 205

Ile Leu Ala Lys Leu Ser Lys Val Ile Ala Pro Asp Ala Ala Phe Asp
    210                 215                 220

Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
                245                 250                 255

Gly Ser Leu Glu Ser Glu Leu Phe Asn Ser Ala Ile Ser Gly Asn Asn
            260                 265                 270

Ser Lys Ile Gly Leu Ile Asn Val Arg Val Pro Leu Pro Phe Asn Val
        275                 280                 285

Ala Lys Phe Val Thr His Val Pro Ser Thr Thr Lys Gln Ile Val Val
    290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                325                 330                 335

Glu Tyr Ile Tyr Gln Pro Asp Phe Ile Trp Ser Pro Lys Ala Val Lys
            340                 345                 350

Ser Ile Val Ser Ser Phe Ile Pro Glu Phe Thr Tyr Asn Ala Asp Ser
        355                 360                 365

Ser Phe Gly Glu Gly Phe Ile Tyr Trp Ala Ser Asp Lys Ser Ile Asn
    370                 375                 380

Ile Asp Val Ala Ser Lys Leu Val Lys Ala Leu Ser Leu Glu Asp Gly
385                 390                 395                 400

Lys Phe Val Ser Leu Arg Thr Lys Phe Asp Asn Leu Ala Asn Ala Gly
                405                 410                 415

Thr Phe Gln Ala Gln Phe Val Thr Ser Lys Glu Gln Ile Pro Val Ser

```
                    420                 425                 430
Asn Ile Asp Ser Thr Lys Leu Ser Val Val Glu Asp Val Ser Leu Leu
                435                 440                 445

Lys His Leu Asp Val Ala Ala Thr Val Ala Glu Gln Gly Ser Ile Ala
            450                 455                 460

Leu Val Ser Gln Lys Ala Val Lys Asp Leu Asp Leu Asn Ser Val Glu
465                 470                 475                 480

Ser Tyr Val Lys Asn Leu Gly Ile Pro Glu Ser Phe Leu Ile Ser Ile
                485                 490                 495

Ala Lys Lys Asn Ile Lys Leu Phe Ile Ile Asp Gly Glu Thr Thr Asn
                500                 505                 510

Asp Glu Ser Lys Leu Ser Leu Phe Ile Gln Ala Val Phe Trp Lys Leu
            515                 520                 525

Ala Phe Gly Leu Asp Val Ala Glu Cys Thr Asn Arg Ile Trp Lys Ser
        530                 535                 540

Ile Asp Ser Gly Ala Asp Ile Ser Ala Ala Ser Ile Ser Glu Phe Leu
545                 550                 555                 560

Thr Gly Ala Phe Lys Asn Phe Leu Ser Glu Val Pro Leu Ala Leu Tyr
                565                 570                 575

Thr Lys Phe Ser Glu Ile Asn Ile Glu Lys Lys Glu Asp Glu Glu Glu
                580                 585                 590

Pro Ala Ala Leu Pro Ile Phe Val Asn Glu Thr Ser Phe Leu Pro Asn
            595                 600                 605

Asn Ser Thr Ile Glu Glu Ile Pro Leu Pro Gly Thr Ser Glu Ile Ser
        610                 615                 620

Asp Ile Ala Lys Lys Leu Ser Phe Lys Glu Ala Tyr Glu Val Glu Asn
625                 630                 635                 640

Lys Leu Arg Pro Asp Leu Pro Val Lys Asn Phe Val Lys Val Lys
                645                 650                 655

Glu Asn Arg Arg Val Thr Pro Ala Asp Tyr Arg Tyr Ile Phe His
                660                 665                 670

Ile Glu Phe Asp Ile Ser Gly Thr Gly Met Thr Tyr Asp Ile Gly Glu
            675                 680                 685

Ala Leu Gly Ile His Ala Arg Asn Asn Glu Ser Leu Val Lys Glu Phe
        690                 695                 700

Leu Thr Phe Tyr Gly Leu Asn Glu Ser Asp Val Val Leu Val Pro Asn
705                 710                 715                 720

Lys Asp Asn His His Leu Leu Glu Thr Arg Thr Val Leu Gln Ala Phe
                725                 730                 735

Val Glu Asn Leu Asp Ile Phe Gly Lys Pro Pro Lys Arg Phe Tyr Glu
            740                 745                 750

Ser Leu Ile Pro Tyr Ala Ser Asn Glu Glu Glu Lys Lys Lys Leu Glu
        755                 760                 765

Asp Leu Val Thr Pro Ala Gly Ala Val Asp Leu Lys Arg Phe Gln Asp
            770                 775                 780

Val Glu Tyr Tyr Thr Tyr Ala Asp Ile Phe Glu Leu Phe Pro Ser Val
785                 790                 795                 800

Arg Pro Ser Leu Glu Glu Leu Val Thr Ile Ile Glu Pro Leu Lys Arg
                805                 810                 815

Arg Glu Tyr Ser Ile Ala Ser Ser Gln Lys Val His Pro Asn Glu Val
            820                 825                 830

His Leu Leu Ile Val Val Asp Trp Val Asp Asn Lys Gly Arg Lys
        835                 840                 845
```

```
Arg Tyr Gly Gln Ala Ser Lys Tyr Ile Ser Asp Leu Ala Val Gly Ser
            850                 855                 860

Glu Leu Val Val Ser Val Lys Pro Ser Val Met Lys Leu Pro Pro Ser
865                 870                 875                 880

Pro Lys Gln Pro Val Ile Met Ser Gly Leu Gly Thr Gly Leu Ala Pro
                885                 890                 895

Phe Lys Ala Ile Val Glu Glu Lys Leu Trp Gln Lys Gln Gln Gly Tyr
            900                 905                 910

Glu Ile Gly Glu Val Phe Leu Tyr Leu Gly Ser Arg His Lys Arg Glu
            915                 920                 925

Glu Tyr Leu Tyr Gly Glu Leu Trp Glu Ala Tyr Lys Asp Ala Gly Ile
            930                 935                 940

Ile Thr His Ile Gly Ala Ala Phe Ser Arg Asp Gln Pro Gln Lys Ile
945                 950                 955                 960

Tyr Ile Gln Asp Arg Ile Lys Glu Asn Leu Asp Glu Leu Lys Thr Ala
                965                 970                 975

Met Ile Asp Asn Lys Gly Ser Phe Tyr Leu Cys Gly Pro Thr Trp Pro
            980                 985                 990

Val Pro Asp Ile Thr Gln Ala Leu  Gln Asp Ile Leu Ala  Lys Asp Ala
            995                 1000                1005

Glu Glu  Arg Gly Ile Lys Val  Asp Leu Asp Ala Ala  Ile Glu Glu
1010                1015                1020

Leu Lys  Glu Ala Ser Arg Tyr  Ile Leu Glu Val Tyr
            1025                1030                1035

<210> SEQ ID NO 21
<211> LENGTH: 1035
<212> TYPE: PRT
<213> ORGANISM: Saccharomyces cerevisiae

<400> SEQUENCE: 21

Met Pro Val Glu Phe Ala Thr Asn Pro Phe Gly Glu Ala Lys Asn Ala
1               5                   10                  15

Thr Ser Leu Pro Lys Tyr Gly Thr Pro Val Thr Ala Ile Ser Ser Val
            20                  25                  30

Leu Phe Asn Asn Val Asp Ser Ile Phe Ala Tyr Lys Ser Phe Ser Gln
        35                  40                  45

Pro Asp Leu Leu His Gln Asp Leu Lys Lys Trp Ser Glu Lys Arg Gly
50                  55                  60

Asn Glu Ser Arg Gly Lys Pro Phe Phe Gln Glu Leu Asp Ile Arg Ser
65                  70                  75                  80

Gly Ala Gly Leu Ala Pro Leu Gly Phe Ser His Gly Leu Lys Asn Thr
                85                  90                  95

Thr Ala Ile Val Ala Pro Gly Phe Ser Leu Pro Tyr Phe Ile Asn Ser
            100                 105                 110

Leu Lys Thr Val Ser His Asp Gly Lys Phe Leu Leu Asn Val Gly Ala
        115                 120                 125

Leu Asn Tyr Asp Asn Ala Thr Gly Ser Val Thr Asn Asp Tyr Val Thr
130                 135                 140

Ala Leu Asp Ala Ala Ser Lys Leu Lys Tyr Gly Val Val Thr Pro Ile
145                 150                 155                 160

Ser Ala Asn Glu Val Gln Ser Val Ala Leu Leu Thr Leu Ala Ile Ala
                165                 170                 175

Thr Phe Ser Asn Asn Ser Gly Ala Ile Asn Leu Phe Asp Gly Leu Asn
            180                 185                 190
```

-continued

```
Tyr Ser Lys Thr Val Leu Pro Leu Val Glu Ser Val Pro Glu Ala Ser
        195                 200                 205

Ile Leu Ala Lys Leu Ser Lys Val Ile Ala Pro Asp Ala Ala Phe Asp
210                 215                 220

Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
                245                 250                 255

Gly Ser Leu Glu Ser Glu Leu Phe Asn Ser Ala Ile Ser Gly Asn Asn
            260                 265                 270

Ser Lys Ile Gly Leu Ile Asn Val Arg Val Pro Leu Pro Phe Asn Val
        275                 280                 285

Ala Lys Phe Val Thr His Val Pro Ser Thr Thr Lys Gln Ile Val Val
290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                325                 330                 335

Glu Tyr Ile Tyr Gln Pro Asp Phe Ile Trp Ser Pro Lys Ala Val Lys
            340                 345                 350

Ser Ile Val Ser Ser Phe Ile Pro Glu Phe Thr Tyr Asn Ala Asp Ser
        355                 360                 365

Ser Phe Gly Glu Gly Phe Ile Tyr Trp Ala Ser Asp Lys Ser Ile Asn
370                 375                 380

Ile Asp Val Ala Ser Lys Leu Val Lys Ala Leu Ser Leu Glu Asp Gly
385                 390                 395                 400

Lys Phe Val Ser Leu Arg Thr Lys Phe Asp Asn Leu Ala Asn Ala Gly
                405                 410                 415

Thr Phe Gln Ala Gln Phe Val Thr Ser Lys Glu Gln Ile Pro Val Ser
            420                 425                 430

Asn Ile Asp Ser Thr Lys Leu Ser Val Val Glu Asp Val Ser Leu Leu
        435                 440                 445

Lys His Leu Asp Val Ala Ala Thr Val Ala Glu Gln Gly Ser Ile Ala
450                 455                 460

Leu Val Ser Gln Lys Ala Val Lys Asp Leu Asp Leu Asn Ser Val Glu
465                 470                 475                 480

Ser Tyr Val Lys Asn Leu Gly Ile Pro Glu Ser Phe Leu Ile Ser Ile
                485                 490                 495

Ala Lys Lys Asn Ile Lys Leu Phe Ile Ile Asp Gly Glu Thr Thr Asn
            500                 505                 510

Asp Glu Ser Lys Leu Ser Leu Phe Ile Gln Ala Val Phe Trp Lys Leu
        515                 520                 525

Ala Phe Gly Leu Asp Val Ala Glu Cys Thr Asn Arg Ile Trp Lys Ser
530                 535                 540

Ile Asp Ser Gly Ala Asp Ile Ser Ala Ala Ser Ile Ser Glu Phe Leu
545                 550                 555                 560

Thr Gly Ala Phe Lys Asn Phe Leu Ser Glu Val Pro Leu Ala Leu Tyr
                565                 570                 575

Thr Lys Phe Ser Glu Ile Asn Ile Glu Lys Lys Glu Asp Glu Glu
            580                 585                 590

Pro Ala Ala Leu Pro Ile Phe Val Asn Glu Thr Ser Phe Leu Pro Asn
        595                 600                 605

Asn Ser Thr Ile Glu Glu Ile Pro Leu Pro Glu Thr Ser Glu Ile Ser
610                 615                 620
```

```
Asp Ile Ala Lys Lys Leu Ser Phe Lys Glu Ala Tyr Glu Val Glu Asn
625                 630                 635                 640

Lys Leu Arg Pro Asp Leu Pro Val Lys Asn Phe Val Lys Val Lys
            645                 650                 655

Glu Asn Arg Arg Val Thr Pro Ala Asp Tyr Asp Arg Tyr Ile Phe His
            660                 665                 670

Ile Glu Phe Asp Ile Ser Gly Thr Gly Met Thr Tyr Asp Ile Gly Glu
            675                 680                 685

Ala Leu Gly Ile His Ala Arg Asn Asn Glu Ser Leu Val Lys Glu Phe
690                 695                 700

Leu Thr Phe Tyr Gly Leu Asn Glu Ser Asp Val Val Leu Val Pro Asn
705                 710                 715                 720

Lys Asp Asn His His Leu Leu Glu Thr Arg Thr Val Leu Gln Ala Phe
                725                 730                 735

Val Glu Asn Leu Asp Ile Phe Gly Lys Pro Lys Arg Phe Tyr Glu
            740                 745                 750

Ser Leu Ile Pro Tyr Ala Ser Asn Glu Glu Lys Lys Lys Leu Glu
        755                 760                 765

Asp Leu Val Thr Pro Ala Gly Ala Val Asp Leu Lys Arg Phe Gln Asp
        770                 775                 780

Val Glu Tyr Tyr Thr Tyr Ala Asp Ile Phe Glu Leu Phe Pro Ser Val
785                 790                 795                 800

Arg Pro Ser Leu Glu Glu Leu Val Thr Ile Ile Glu Pro Leu Lys Arg
                805                 810                 815

Arg Glu Tyr Ser Ile Ala Ser Ser Gln Lys Val His Pro Asn Glu Val
            820                 825                 830

His Leu Leu Ile Val Val Asp Trp Val Asp Asn Lys Gly Arg Lys
        835                 840                 845

Arg Tyr Gly Gln Ala Ser Lys Tyr Ile Ser Asp Leu Ala Val Gly Ser
850                 855                 860

Glu Leu Val Val Ser Val Lys Pro Ser Val Met Lys Leu Pro Pro Ser
865                 870                 875                 880

Pro Lys Gln Pro Val Ile Met Ser Gly Leu Gly Thr Gly Leu Ala Pro
            885                 890                 895

Phe Lys Ala Ile Val Glu Glu Lys Leu Trp Gln Lys Gln Gly Tyr
        900                 905                 910

Glu Ile Gly Glu Val Phe Leu Tyr Leu Gly Ser Arg His Lys Arg Glu
            915                 920                 925

Glu Tyr Leu Tyr Gly Glu Leu Trp Glu Ala Tyr Lys Asp Ala Gly Ile
930                 935                 940

Ile Thr Tyr Ile Gly Ala Ala Phe Ser Arg Asp Gln Pro Gln Lys Ile
945                 950                 955                 960

Tyr Ile Gln Asp Arg Ile Lys Glu Asn Leu Asp Glu Leu Lys Thr Ala
            965                 970                 975

Met Ile Asp Asn Lys Gly Ser Phe Tyr Leu Cys Gly Pro Thr Trp Pro
            980                 985                 990

Val Pro Asp Ile Thr Gln Ala Leu  Gln Asp Ile Leu  Ala Lys Asp Ala
            995                 1000                1005

Glu Glu  Arg Gly Ile Lys Val  Asp Leu Asp Ala Ala  Ile Glu Glu
        1010                1015                1020

Leu Lys  Glu Ala Ser Arg Tyr  Ile Leu Glu Val Tyr
        1025                1030                1035
```

```
<210> SEQ ID NO 22
<211> LENGTH: 1035
<212> TYPE: PRT
<213> ORGANISM: Saccharomyces cerevisiae

<400> SEQUENCE: 22

Met Pro Val Glu Phe Ala Thr Asn Pro Phe Gly Glu Ala Lys Asn Ala
1               5                   10                  15

Thr Ser Leu Pro Lys Tyr Gly Thr Pro Val Thr Ala Ile Ser Ser Val
            20                  25                  30

Leu Phe Asn Asn Val Asp Ser Ile Phe Ala Tyr Lys Ser Phe Ser Gln
        35                  40                  45

Pro Asp Leu Leu His Gln Asp Leu Lys Lys Trp Ser Glu Lys Arg Gly
    50                  55                  60

Asn Glu Ser Arg Gly Lys Pro Phe Phe Gln Glu Leu Asp Ile Arg Ser
65                  70                  75                  80

Gly Ala Gly Leu Ala Pro Leu Gly Phe Ser His Gly Leu Lys Asn Thr
                85                  90                  95

Thr Ala Ile Val Ala Pro Gly Phe Ser Leu Pro Tyr Phe Ile Asn Ser
            100                 105                 110

Leu Lys Thr Val Ser His Asp Gly Lys Phe Leu Leu Asn Val Gly Ala
        115                 120                 125

Leu Asn Tyr Asp Asn Ala Thr Gly Ser Val Thr Asn Asp Tyr Val Thr
    130                 135                 140

Ala Leu Asp Ala Ala Ser Lys Leu Lys Tyr Gly Val Val Thr Pro Ile
145                 150                 155                 160

Ser Ala Asn Glu Val Gln Ser Val Ala Leu Leu Ala Leu Ala Ile Ala
                165                 170                 175

Thr Phe Ser Asn Asn Ser Gly Ala Ile Asn Leu Phe Asp Gly Leu Asn
            180                 185                 190

Tyr Ser Lys Thr Val Leu Pro Leu Val Glu Ser Val Pro Glu Ala Ser
        195                 200                 205

Ile Leu Ala Lys Leu Ser Lys Val Ile Ala Pro Asp Ala Ala Phe Asp
    210                 215                 220

Asp Val Leu Asp Lys Phe Asn Glu Leu Thr Gly Leu Arg Leu His Asn
225                 230                 235                 240

Phe Gln Tyr Phe Gly Ala Gln Asp Ala Glu Thr Val Phe Ile Thr Tyr
                245                 250                 255

Gly Ser Leu Glu Ser Glu Leu Phe Asn Ser Ala Ile Ser Gly Asn Asn
            260                 265                 270

Ser Lys Ile Gly Leu Ile Asn Val Arg Val Pro Leu Pro Phe Asn Val
        275                 280                 285

Ala Lys Phe Val Thr His Val Pro Ser Thr Thr Lys Gln Ile Val Val
    290                 295                 300

Ile Gly Gln Thr Leu Asp Gly Ser Ser Pro Ser Phe Leu Arg Ser Gln
305                 310                 315                 320

Val Ser Ala Ala Leu Phe Tyr His Gly Arg Thr Ser Ile Ser Val Ser
                325                 330                 335

Glu Tyr Ile Tyr Gln Pro Asp Phe Ile Trp Ser Pro Lys Ala Val Lys
            340                 345                 350

Ser Ile Val Ser Phe Ile Pro Glu Phe Thr Tyr Asn Ala Asp Ser
        355                 360                 365

Ser Phe Gly Glu Gly Phe Ile Tyr Trp Ala Ser Asp Lys Ser Ile Asn
    370                 375                 380

Ile Asp Val Ala Ser Lys Leu Val Lys Ala Leu Ser Leu Glu Asp Gly
```

```
                385                 390                 395                 400
Lys Phe Val Ser Leu Arg Thr Lys Phe Asp Asn Leu Ala Asn Ala Gly
                    405                 410                 415

Thr Phe Gln Ala Gln Phe Val Thr Ser Lys Glu Gln Ile Pro Val Ser
                    420                 425                 430

Asn Ile Asp Ser Thr Lys Leu Ser Val Val Glu Asp Val Ser Leu Leu
                    435                 440                 445

Lys His Leu Asp Val Ala Ala Thr Val Thr Glu Gln Gly Ser Ile Ala
                    450                 455                 460

Leu Val Ser Gln Lys Ala Val Lys Asp Leu Asp Leu Asn Ser Val Glu
465                 470                 475                 480

Ser Tyr Val Lys Asn Leu Gly Ile Pro Glu Ser Phe Leu Ile Ser Ile
                    485                 490                 495

Ala Lys Lys Asn Ile Lys Leu Phe Ile Ile Asp Gly Glu Thr Ile Asn
                    500                 505                 510

Asp Glu Ser Lys Leu Ser Leu Phe Ile Gln Ala Val Phe Trp Lys Leu
                    515                 520                 525

Ala Phe Gly Leu Asp Val Ala Glu Cys Thr Asn Arg Ile Trp Lys Ser
                    530                 535                 540

Ile Asp Ser Gly Ala Asp Ile Ser Ala Ala Ser Ile Ser Glu Phe Leu
545                 550                 555                 560

Thr Gly Ala Phe Lys Asn Phe Leu Ser Glu Val Pro Leu Ala Leu Tyr
                    565                 570                 575

Thr Lys Phe Ser Glu Ile Asn Ile Glu Lys Lys Glu Asp Glu Glu Glu
                    580                 585                 590

Pro Ala Ala Leu Pro Ile Phe Val Asn Glu Thr Ser Phe Leu Pro Asn
                    595                 600                 605

Asn Ser Thr Ile Glu Glu Ile Pro Leu Pro Glu Thr Ser Glu Ile Ser
                    610                 615                 620

Asp Ile Ala Lys Lys Leu Ser Phe Lys Glu Ala Tyr Glu Val Glu Asn
625                 630                 635                 640

Lys Leu Arg Pro Asp Leu Pro Val Lys Asn Phe Val Val Lys Val Lys
                    645                 650                 655

Glu Asn Arg Arg Val Thr Pro Ala Asp Tyr Asp Arg Tyr Ile Phe His
                    660                 665                 670

Ile Glu Phe Asp Ile Ser Gly Thr Gly Met Thr Tyr Asp Ile Asp Glu
                    675                 680                 685

Ala Leu Gly Ile His Ala Arg Asn Asn Glu Ser Leu Val Lys Glu Phe
                    690                 695                 700

Leu Thr Phe Tyr Gly Leu Asn Glu Ser Asp Val Val Leu Val Pro Asn
705                 710                 715                 720

Lys Asp Asn His His Leu Leu Glu Thr Arg Thr Val Leu Gln Ala Phe
                    725                 730                 735

Val Glu Asn Leu Asp Ile Phe Gly Lys Pro Pro Lys Arg Phe Tyr Glu
                    740                 745                 750

Ser Leu Ile Pro Tyr Ala Ser Asn Glu Glu Lys Lys Lys Leu Glu
                    755                 760                 765

Asp Leu Val Thr Pro Ala Gly Ala Val Asp Leu Lys Arg Phe Gln Asp
                    770                 775                 780

Val Glu Tyr Tyr Thr Tyr Ala Asp Ile Phe Glu Leu Phe Pro Ser Val
785                 790                 795                 800

Arg Pro Ser Leu Lys Glu Leu Val Thr Ile Ile Glu Pro Leu Lys Arg
                    805                 810                 815
```

```
Arg Glu Tyr Ser Ile Ala Ser Ser Gln Lys Val His Pro Asn Glu Val
            820             825             830
His Leu Leu Ile Val Val Val Asp Trp Val Asp Asn Lys Gly Arg Lys
            835             840             845
Arg Tyr Gly Gln Ala Ser Lys Tyr Ile Ser Asp Leu Ala Val Gly Ser
    850             855             860
Glu Leu Val Val Ser Val Lys Pro Ser Val Met Lys Leu Pro Pro Ser
865             870             875             880
Pro Lys Gln Pro Val Ile Met Ser Gly Leu Gly Thr Gly Leu Ala Pro
                885             890             895
Phe Lys Ala Ile Val Glu Glu Lys Leu Trp Gln Lys Gln Gly Tyr
                900             905             910
Glu Ile Gly Glu Val Phe Leu Tyr Leu Gly Ser Arg His Lys Arg Glu
            915             920             925
Glu Tyr Leu Tyr Gly Glu Leu Trp Glu Ala Tyr Lys Asp Ala Gly Ile
    930             935             940
Ile Thr His Ile Gly Ala Ala Phe Ser Arg Asp Gln Pro Gln Lys Ile
945             950             955             960
Tyr Ile Gln Asp Arg Ile Lys Glu Asn Leu Asp Glu Leu Lys Thr Ala
                965             970             975
Met Ile Asp Asn Lys Gly Ser Phe Tyr Leu Cys Gly Pro Thr Trp Pro
            980             985             990
Val Pro Asp Ile Thr Gln Ala Leu  Gln Asp Ile Leu Ala  Lys Asp Ala
            995             1000            1005
Glu Glu  Arg Gly Ile Lys Val  Asp Leu Asp Ala Ala  Ile Glu Glu
    1010            1015            1020
Leu Lys  Glu Ala Ser Arg Tyr  Ile Leu Glu Val Tyr
    1025            1030            1035
```